(12) United States Patent
Engel et al.

(10) Patent No.: US 8,912,186 B2
(45) Date of Patent: Dec. 16, 2014

(54) ALLOSTERIC PROTEIN KINASE MODULATORS

(75) Inventors: Matthias Engel, Zweibrücken (DE); Wolfgang Fröhner, Saarbrücken (DE); Adriane Stroba, Nohfelden (DE); Ricardo M. Biondi, Frankfurt (DE)

(73) Assignee: Universitaet des Saarlandes, Saarbruecken (DE)

(*) Notice: Subject to any disclaimer, the term of this patent is extended or adjusted under 35 U.S.C. 154(b) by 273 days.

(21) Appl. No.: 13/124,773

(22) PCT Filed: Oct. 16, 2009

(86) PCT No.: PCT/EP2009/063592
§ 371 (c)(1),
(2), (4) Date: Nov. 9, 2011

(87) PCT Pub. No.: WO2010/043711
PCT Pub. Date: Apr. 22, 2010

(65) Prior Publication Data
US 2012/0046307 A1  Feb. 23, 2012

(30) Foreign Application Priority Data
Oct. 17, 2008 (EP) .................................. 081669285

(51) Int. Cl.
| A01N 43/58 | (2006.01) |
| A61K 31/50 | (2006.01) |
| C07C 59/88 | (2006.01) |
| C07C 59/90 | (2006.01) |
| C07D 213/55 | (2006.01) |
| C07D 307/80 | (2006.01) |
| C07D 333/56 | (2006.01) |
| C07D 209/18 | (2006.01) |

(52) U.S. Cl.
CPC .............. *C07D 209/18* (2013.01); *C07C 59/88* (2013.01); *C07C 59/90* (2013.01); *C07D 213/55* (2013.01); *C07D 307/80* (2013.01); *C07D 333/56* (2013.01)

USPC .................. 514/247; 514/252.1; 514/266.1; 514/307; 514/311; 514/367; 514/373; 514/375; 514/394; 514/403; 514/419; 514/532; 514/576; 514/577; 544/224; 544/283; 544/353; 546/139; 546/174; 548/180; 548/207; 548/217; 548/310.1; 548/361.1; 548/491; 560/118; 562/400; 562/490

(58) Field of Classification Search
USPC ................ 544/224, 283, 353; 546/139, 174; 548/180, 207, 217, 310.1, 361.1, 491; 549/569; 560/118; 562/400, 490; 514/247, 252.1, 266.1, 307, 311, 367, 514/373, 375, 394, 403, 419, 532, 576, 577
See application file for complete search history.

(56) References Cited

PUBLICATIONS

M. Engel et al., 25 The EMBO Journal, 5469-5480 (2006).*
International Preliminary Report on Patentability, PCT/US2009/063592 (Apr. 19, 2011).*
R. Sarges, 40 Journal of Organic Chemistry, 1216-1224 (1975).*
P. Gravel et al., 55 Canadian Journal of Chemistry, 2373-2384 (1977).*
Denis Gravel et al., "Synthesis and photochemistry of 4,4-diphenyl-y-pyran. Di-π-methane rearrangement in a new chromophore"; Can J. Chem. (55) 2373-2383 (1977).

* cited by examiner

*Primary Examiner* — James O. Wilson
*Assistant Examiner* — Alexander R Pagano
(74) *Attorney, Agent, or Firm* — Norris McLaughlin & Marus PA

(57) ABSTRACT

The invention provides specific small molecule compounds that allosterically regulate the activity or modulate protein-protein interactions of AGC protein kinases and the Aurora family of protein kinases, methods for their production, pharmaceutical compositions comprising same, and their use for preparing medicaments for the treatment and prevention of diseases related to abnormal activities of AGC protein kinases or of protein kinases of the Aurora family.

5 Claims, 7 Drawing Sheets

ALLOSTERIC PROTEIN KINASE MODULATORS

Figure 1:
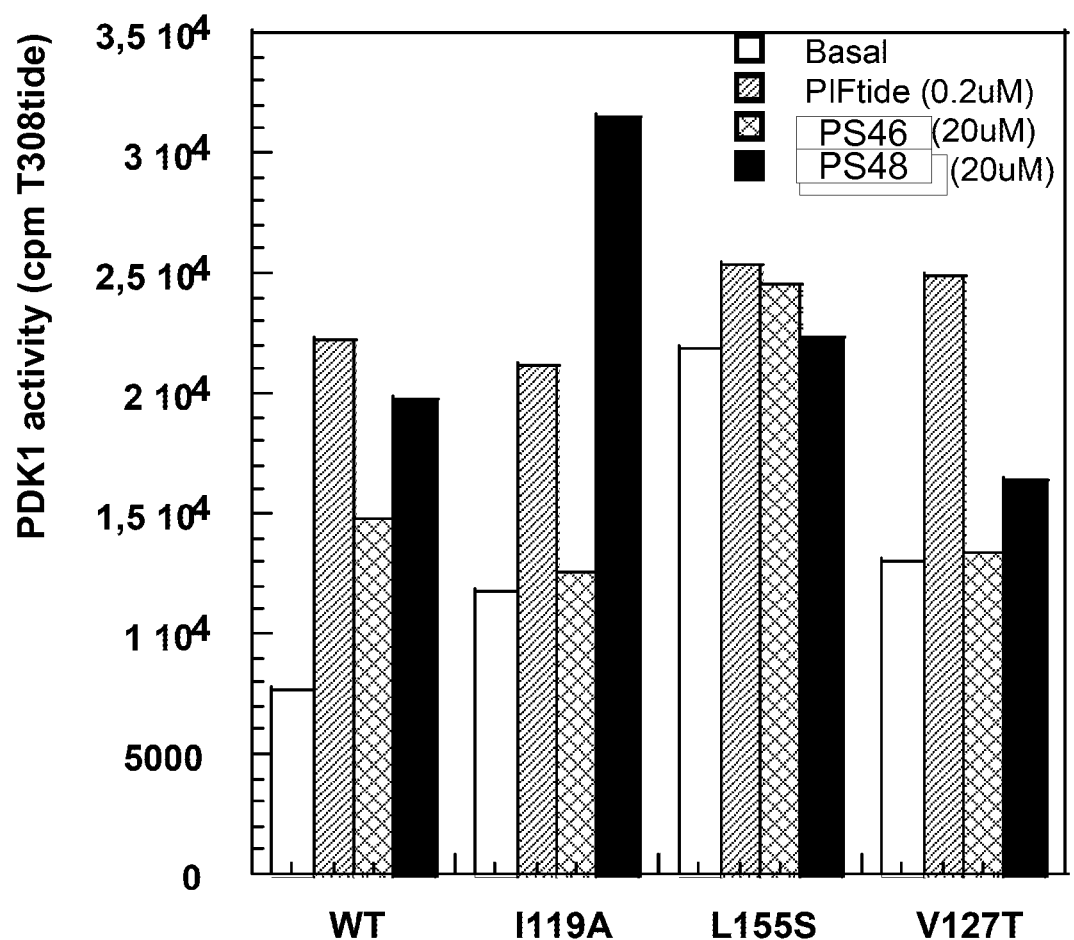
Figure 1:
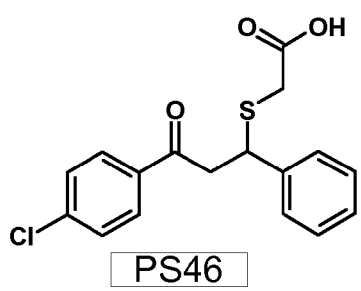
Figure 1:
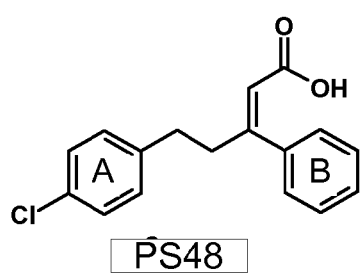

This application is a 371 of PCT/EP2009/063592, filed Oct. 16, 2009, which claims foreign priority benefit under 35 U.S.C. §119 of the German Patent Application No. 08166928.5 filed Oct. 17, 2008.

The invention provides specific small molecule compounds that allosterically regulate the activity or modulate protein-protein interactions of AGC protein kinases and the Aurora family of protein kinases, methods for their production, pharmaceutical compositions comprising same, and their use for preparing medicaments for the treatment and prevention of diseases related to abnormal activities of AGC protein kinases or of protein kinases of the Aurora family.

BACKGROUND OF THE INVENTION

Protein kinases are an important class of enzymes, which are frequently used as targets in drug development. Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, reactive oxygen species like $H_2O_2$), cytokines (e.g. interleukin-1 (IL-1) and tumor necrosis factor.alpha. (TNFα)), and growth factors (e.g. insulin, insulin-like growth factor (IGF1), granulocyte macrophage colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose and lipid metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases, such as diabetes.

Accordingly, there has been a substantial effort in medicinal chemistry to find protein kinase inhibitors that are effective as therapeutic agents. Thus, protein kinases have emerged as one third of all new targets in pharmaceutical industry. The protein kinase ATP binding site is clearly a drugable site and almost all protein kinase inhibitors target this site. Importantly, a similar effort has not been evident for the development of protein kinase non-ATP competitive inhibitors. In addition, the existence of small molecule compounds that target regulatory sites on protein kinase catalytic domains by an allosteric mechanism were for the first time described in Engel et al., EMBO J. 2006, Vol. 25, pp. 5469-5480 and EP-A-1486488. This was surprising as small molecule compounds were generally considered as being not suitable as they cannot promote the required conformational changes. Alternatively, the assays and analysis tools usually performed for screening and analysis of the data may not select for these compounds. Alternatively, compounds might have been disregarded as potential drug molecules, or the regulatory sites disregarded as possible drugable sites. At any rate, the finding and demonstration that small molecule compounds can regulate protein kinase activities by interacting with regulatory sites is not obvious.

Although the ATP binding site is a proven drugable site, small molecule compounds which are directed against the ATP binding site of a given protein kinase, have a high probability to bind to ATP binding site(s) of one or more other protein kinases, or even other ATP binding enzymes such as DNA polymerases or pyruvate kinase. The reason for this is that binding sites for the universal enzymatic co-factor ATP share strong homologies, similar dimensions and shapes, which enable binding of ATP but potentially also ATP-competitive inhibitors, to an undefined number of ATP-binding enzymes. Such non-target related inhibition will inevitably lead to side effects if not amended. The improvement of selectivity while maintaining potency by means of medicinal chemistry can be a difficult, time-consuming process, which in many cases fails in the end.

In addition, ATP-competitive compounds are often found to be considerably less potent in cells and organs due to the high intracellular ATP levels, which are in the range of 1-2 mM, when compared to cell-free assay conditions which usually work with ATP concentrations of 10-20 µM or less. Thus, a drop of IC50 values of up to 100 fold must be expected when compounds are transferred to cell assays.

Up to now, the problem described here was addressed by the extension of merely ATP-competitive compounds, i.e. additional chemical moieties were added to the ATP-competitive scaffolds which were designed to interact with additional, less strongly conserved amino acid residues located at the close environment of the ATP-binding site. Such compounds possess a non-ATP competitive portion but are not truly "allosteric". By doing so, it was possible in some cases to specifically stabilize a catalytically less competent form of the kinase. In this low number of cases, it was possible to develop rather selective compounds. A well known example is imatinib (gleevec) from Novartis, which inhibits, besides the actual target BCR-Abl tyrosin kinase, only a limited number of other tyrosine kinases, such as c-kit and platelet-derived growth factor receptor (PDGFR) (Adrián, F. J. et al., Nature Chemical Biology 2:95-102 (2006)).

Another example for an inhibitor which enganges a binding site adjacent to the ATP binding site, thereby stabilizing an inactive conformation, is the p38 MAP kinase inhibitor BIRB 796 (Pargellis, C. et al., Nature Structural Biology 9:268-272 (2002)). Since the size of orally available compounds is limited to below 500 Da, this strategy can only be successful if differences outside but within reach of the ATP binding site, in particular between close homologs of protein kinases, are big enough to allow for creation of selectivity. This limitation will prevent larger applications of this strategy in the kinase drug discovery field, though it might work for a subset of current kinase targets. However, it is unlikely to work for targeting such closely related isoforms such as the PKC or PKB family of kinases.

However, true allosteric binding at sites remote from the ATP site that affect kinase activity have barely been described (for example, Akt-I-1, a pleckstrin-homology-domain-dependent Akt (PKB) inhibitor (Barnett, S. F. et al., Biochem. J. 38:399-408 (2005)). Review articles summarising the efforts to develop kinase inhibitors termed "allosteric" actually refer to ATP-competitive compounds with a non-ATP-competitive portion of interaction in the majority of cases (see Kiselyov et al., Recent Progress in Development of Non-ATP Competitive Small-Molecule Inhibitors of Protein Kinases, Mini-Reviews in Medicinal Chemistry, 2006, 6, 109-120). Furthermore, Gumireddy et al. (P.N.A.S. USA, 2005, vol. 102, pp. 1992-1997) report a non ATP-competitive BCR-Abl inhibitor which however does not act allosterically but in a substrate competitive manner. The same group also disclosed ON01910, a non ATP-competitive inhibitor of Polo-like kinase-1, which also displayed substrate competitive binding (Gumireddy et al., Cancer Cell. 2005, 7, 275-286). Non ATP-competitive inhibitors have also been described for PKB (AKT), which bind to the kinase in a PH domain-dependent fashion, indicating that they are not only targeting the catalytic domain (reviewed in Martinez et al, Current Topics in Medicinal Chemistry 2005, 5, 109-125). Further non ATP-competitive PKB/AKT inhibitors with unknown binding sites were identified in screening campaigns (reviewed in Martinez et al, Current Topics in Medicinal Chemistry 2005, 5, 109-125, and Amaravadi and Thompson, J. Clin. Invest. 2005, 115, 2618-2624). Furthermore, thiadiazolidinones have been disclosed as non ATP-competitive inhibitors of GSK-3beta; the binding site has not been determined experimentally (Martinez et al., J. Med. Chem. 2002, 45, 1292-1299, and WO/2005/097117)).

An obvious limitation of the vast majority of compounds whose binding sites are at least overlapping with the ATP binding site is that they can usually only inhibit the enzymatic activity but not activate. In the current state of the art, activation of protein kinase regulated signalling pathways is only possible indirectly, e.g. by the following ways:

receptor agonists: in cases where the protein kinase is activated following to receptor stimulation, agonistic compounds can be developed. This route is often employed in drug development but is of course dependent on the expression of the appropriate receptor proteins in the target organs, and is not applicable to cases where the stimulus is not properly propagated from the receptor to the executive protein kinase. The latter situation is encountered e.g. with diabetes type 2, where resistance to insulin is mainly mediated trough inhibitory phosphorylation of the IRS proteins (insulin receptor substrate), which is impairing signal transduction from the insulin receptor.

activation of protein kinases possible in some cases by abolishing the inhibition imposed by regulatory subunits. A known example is cAMP-dependent protein kinase (PKA), which is released in an active state from a complex with regulatory subunits after binding of cAMP to said regulatory proteins. In this case, cAMP mimetics could tigger the same effect. The applicability of such strategies depends on particular regulatory mechanisms reserved to only a few kinases and might provoque another type of selectivity problems since second messengers usually have pleiotropic effects due to affecting several target proteins.

inhibition of negative feedback pathways: a known example herefor is the PDK1/PKB pathway in insulin responsive cells. Via inhibition of ribosomal S6-Kinase the negative feedback inhibition of insulin signalling is abolished, thus effecting enhanced activity of PDK1 and stronger phosphorylation and activity of e.g. PKB, which is a major mediator of insulin signalling. As a consequence, the insulin action is enhanced and prolonged. Therefore, rapamycin and analogous, which cause inhibition of S6Kinase, are also tested for the indication diabetes type 2 as insulin sensitizers. ATP competitive inhibitors of protein kinases such as S6Kinase will show the described selectivity problems again, while in particular rapamycin and analogues, albeit non-ATP competitive, mediate further effects besides inhibition of the S6Kinase resulting in immuno-suppression, which is not favourable during a lifetime treatment of a chronic disease like diabetes type 2.

At any rate, little reports or patents disclose small molecule compounds which are able to incease the catalytic activity of a given protein kinase by binding to the catalytic domain. A rare example is the recent report on an in vitro-activator of Aurora kinase A (Kishore et al., J. Med. Chem. 2008, 51, 792-797). The lack of availability of such compounds and the lack of knowledge of drugable allosteric binding sites allowing the development of such compounds, respectively, have hitherto led to a disregarding of potential applications for such compounds. It is therefore expected that on the basis of our allosterically activating compounds, further indications with a medical need to activate a target kinase will be identified and met by utilising compounds of the present invention. Therefore, the examples 2 and 3 (Tables 2 and 3) in connection with example 6 as described below for the PDK1/PKB pathway are by far not limiting but rather reflect current state of the art which is dominated by concepts for direct inhibition of protein kinase activity rather than activation.

AGC kinases form a group within the protein kinase superfamily (Manning et al., Science 2002, 298, 1912-1934). AGC kinase homologues are found throughout the whole eukaryotic world. The AGC kinase group consist of 63 protein kinase domains from which 6 are predicted to be pseudogenes. AGC kinase group can be divided into several families according to their homology within the catalytic domain. Furthermore, they can be grouped and named according to the most relevant protein kinases members of each group. The AGC kinases can be divided into families according to the Protein kinome, the families are: AKT (PKB), LAT, ROCK, MRCK, DMPK, GRK, MAST, NDR, PDK, PKA, 4 PKC families, PKG, PKN, 4RSK families, RSKL, SGK, YANK. Each one of these families may contain subfamilies. When the tree of AGC kinases is observed, important branches within the AGC group are formed by PKC, PKB (AKT)/SGK, S6K/RSK/MSK, GRK, ROCK/DMPK/LATS/NDR, MAST, and RSKL families.

Another group of kinases, which can also be targeted by the compounds according to the present invention, are the Aurora family of kinases, Aurora-A, -B and -C. Although the Aurora kinases are not directly classified as AGC kinases, they are closely related in sequence homology and moreover, in mechanisms of regulation. This is already reflected by the fact that the Aurora kinases were placed on the same branch of the kinome as the AGC-kinase family. Being key regulators of mitosis, the Aurora kinases are exploited as pharmaceutical targets for the development of anti-cancer drugs (Carvajal et al., Clinical Cancer Research Vol. 12, 2006, pp. 6869-6875).

AGC kinases conservation throughout evolution is reflected by their overall catalytic domain sequence conservation and importantly also by its mode of regulation. Their active conformation is regulated by the state of phosphorylation of their activation loop and to secondary phosphorylations in segments outside the catalytic domain. AGC kinases have phosphorylations within the C-terminal extension to the catalytic core, which interact with the catalytic domain. Most notably is the phosphorylation within a hydrophobic motif C-terminal to the catalytic domain, which also participates in protein kinase activation. The lack of phosphorylation in this site helps to keep the protein kinase inactive in some cases, like S6K members. The mechanism by which the AGC kinases are activated upon hydrophobic motif phosphorylation appears to involve the interaction of the phosphate with a phosphate binding site, while the hydrophobic motif interacts with a hydrophobic PIF pocket (Yang, J. et al., Mol. Cell. 9:1227-40 (2002); Yang, J. et al., Nat. Struct. Biol. 9:940-4

(2002); Biondi, R. M. et al., Embo J. 19:979-88 (2000); Biondi, R. M. et al. Embo J. 21:4219-28 (2002); Frodin, M. et al., Embo J. 21 (2002)). The hydrophobic PIF pocket on its own can modulate protein kinase activity (Biondi, R. M. et al., Embo J. 19:979-88 (2000)). The role in protein kinase activation was first characterised on PDK1, by homology with PKA. By homology modelling it was found to be present and play a role on a number of AGC kinases (Frodin, M. et al., Embo J. 21:5396-407 (2002)). Furthermore, PDK1 and PKB crystal structures support the general existence within AGC kinases of a site homologous to the site in PKA that interacts with its Phe-X—X-PheCOOH C-terminal sequence (Yang, J. et al., Nat. Struct. Biol. 9:940-4 (2002); Biondi, R. M. et al. Embo J. 21:4219-28 (2002)).

A subgroup of the AGC family of protein kinases, here referred to as the "growth factor-activated AGC kinases" is activated by insulin, growth factors, many polypeptide hormones and other extracellular stimuli. This group regulates cellular division, growth, differentiation, survival, metabolism, motility and function and it includes the kinases: protein kinase B (PKBα-γ or AKT1-3), p70 ribosomal S6 kinase (S6K1,2), p90 ribosomal S6 kinase (RSK1-4), mitogen- and stress-activated protein kinase (MSK1,2), serum- and gluticocoid-induced kinase (SGK1-3) and several members of the protein kinase C (PKC).

The regulatory PIF-pocket site of the protein kinase PDK1 is a target site of phosphorylation-dependent conformational changes induced by some of the small compounds described in this application. It is envisaged that the compounds targeting this site on PDK1 may be employed for the treatment of cancers since they are expected to block the activation of protein kinases which are involved in cancers, such as S6K, RSK, SGK, PKCs, etc. It is expected that to achieve such results, the PIF-pocket of PDK1 may require to be blocked in a constitutive manner; for this, it is preferred that small compounds with slow off-rate are selected and developed into drugs. However, it can be envisaged that transient blockage of the pocket, may block transient activation of the substrate S6K and is expected to block a feed-back loop phosphorylation of IRS1; in such scenario, the block of PDK1 PIF-pocket may sensitize cells for insulin signalling. Compounds acting in this way may be selected for treatment of insulin resistance or diabetes. It is further envisaged that such compounds may be of use in other circumstances where blocking of transient PDK1 PIF-pocket-dependent phosphorylations may be required. It is expected that treatment for insulin resistance or diabetes may not require complete blockage of the pocket in a constitutive manner, but rather with a transient pharmacological profile that would favour the action of insulin after food intake.

Growth factor-activated AGC kinases as drug targets. The growth factor-activated AGC kinases are known or assumed to be important in a variety of important human diseases, and several of the kinases are reportedly included in drug development programs (e.g. PKB and PKC isoforms). Cancer: Most of the growth factor-activated AGC kinases are constitutively activated in cancer cells, due to hyperactivation of upstream activating pathways, and are known (PKB, S6K, PKC, RSK) or thought/hypothesized (SGK, MSK) to promote cancer cell growth, survival or metastasis. Drugs that inhibit these kinases may therefore be new anti-cancer drugs. Diabetes mellitus: The activation of PKB, a key mediator of insulin metabolic regulation, is reduced in type-II diabetes due to insulin resistance. Interference with S6K (by gene knockout) protects mice from dietary-induced diabetes. Activators of PKB or inhibitors of S6K may therefore be used as anti-type-II diabetes drugs. Hypertension: Hyperactivation of SGK is thought to promote hypertension. Compounds that inhibit SGK, may be used as anti-hypertensive drugs. Tuberous sclerosis complex syndrome (TSC): Inactivating mutations in the TSC genes results in hyperactivation of S6K, which is likely important in development of TSC. Inhibitors of S6K may therefore be used to treat TSC patients, for which currently no treatment exists. Other diseases in which AGC kinase inhibitors/activators may be used include chronic inflammation/arthritis, cardiac hypertrophy, neurodegenerative disorders, ischaemic conditions, and more.

AGC kinases participate in a number of further signalling pathways, many of which are involved in disease states and conditions that may be improved in patients. A number of non limiting examples of conditions related to the different subfamilies are given below. Furthermore, a large list of conditions where protein kinases are involved are being grouped and continuously updated from available sources, such as the protein kinase resource (PKR) website (http://pkr.sdsc.edu). PKC family member inhibitors as sought after for a number of conditions including the treatment of cancer; virus infections, such as treatments of cytomegalovirus infections, and HIV infections (U.S. Pat. Nos. 6,291,446 and, 6,107,327), asthma (U.S. Pat. No. 6,103,712); pain, for example pain perception and hyperalgesia (CA-A-2,336,709); skin treatments, e.g. to inhibit Langerhans cell migration induced by the presence of an allergenic agent (AU-A-200218371); renal dysfunction, such as for treatment of renal failure, intraglomerular hypertension, inhibiting glomerolosclerosis and inhibiting glomerular intestinal fibrosis (CA-A-2323172); chronic myeloid leukaemia and cute lymphoid leukaemia (CA-A-2311736), treatment of sexual dysfunctions directed to a method for inducing endothelium dependent vasodilation, smooth muscle relaxation, e.g. penile erection, clitoral engorgement and erection (U.S. Pat. No. 6,093,709), etc. Within the subfamily including PKB and SGK, inhibitors are being searched for the treatment of disease states. SGK inhibitors (U.S. Pat. No. 6,416,759) are claimed as an antiproliferative agent, and also for treatment of diseases related to a disturbance of ion channel activity, in particular, sodium and/or potassium channels, e.g. for the regulation of blood pressure (WO02/017893). PKB inhibition is seeked for a number of conditions including the treatment of proliferative diseases and where apoptosis is wanted. PKB inhibitors have also been proposed to inhibiting restenosis after angioplasty (WO03/032809). PKB inhibitors can be used to promote apoptosis of rheumatoid arthritis synovial fibroblasts for the treatment of rheumatoid arthritis (WO02/083075). PKB activators and inhibitors may be used for regulating the level of mucin production; PKB activators can be used to treat mucin overproduction in several diseases including otitis media, chronic obstructive pulmonary disease, asthma and cystic fibrosis, otitis media infections, and chronic obstructive pulmonary disease caused by nontypeable *Haemophilus influenzae* (US-A-2002/0151491); S6K/RSK subfamily can be targeted for diseases where subfamily members act downstream of MAPK signalling, for example in cancer and inflammation. Rapamycin inhibits S6K as a downstream target of mTOR; thus, inhibition of S6K may be wanted to obtain part of the responses obtained with rapamycin, as immunosupressant; also it may be used to treat cancer. The subfamily of G-protein coupled receptor kinases (GRKS) can be targeted to modulate the signal intensity of G-protein coupled receptors, which form the largest family within the human genome and are important targets in drug development and therapies. Disease state and conditions that can be treated with GRKs include neurological disorders, depression, inflammation, central nervous system states, osteoporosis, immunosuppressant, hypertension, infection, hypertension, retinitis pigmentosa, cancer, asthma, cystic fibrosis, arthritis, Alzheimer, Parkinson, rheumatoid arthritis, and in general conditions treated with drugs which target G-protein coupled receptors. Within the ROCK/DMPK/LATS/NDR subfamily, ROCK inhibitors are being developed as therapeutic agents for the treatment of a number of conditions, including cancer, inflammation, as immunosuppressant, a therapeutic agent of autoimmune disease, an hypertension, a therapeutic agent of angina pectoris, a suppressive agent of cerebrovascular contraction, a therapeutic agent of asthma, a prophylactic agent of peripheral circulation disorder, a prophylactic agent of immature birth, a prophylactic agent of digestive tract infection, a therapeutic agent of osteoporosis, a therapeutic agent of retinopathy and a brain function improving drug (U.S. Pat. No. 6,218,410).

PDK1 is being targeted for the treatment of cancer with an ATP competitive inhibitor termed UCN-01.

Activators of AGC kinases could also be used in therapeutics. For example, DMPK activators could be used for treatment of conditions where DMPK activity is reduced, including Myotonic Dystrophy. Furthermore, transient activation of PDK1 or PKB beta could be used to mimic insulin signalling action for the treatment of diabetes and states where GSK3 inhibition is required for treatment or cure of diseases. By inhibiting apoptosis, these activators may be used for treatment of diseases where apoptosis is to be avoided, such as in neurological disorders. Activators of RSK family members may compensate in part the effects in genetic diseases such as Coffin-Lowry syndrome. Therefore, RSK2 activators may be used for treatment of mental retardations or states where neurological performance is to be enhanced. Therefore, compounds that regulate (inhibit or activate) AGC kinases are important for drug development, since they could target conditions where the AGC kinase is required to be inhibited or activated.

Modulators of AGC kinase activities could be used as a therapy for treatment of patients with degrees of mental retardation or to enhance performances where disease states are not involved.

Phosphoinositide dependent protein kinase 1 (PDK1) and Protein kinase B (Akt/PKB) are components of an intracellular signalling pathway of fundamental importance that functions to exert the effects of growth and survival factors, and which mediates the response to insulin and inflammatory signals (Brazil, D. P. & Hemmings, B. A., Trends Biochem. Sci. 26:657-64 (2001)). PKB enzyme is rapidly activated by PDK1 phosphorylation following stimulation of phosphoinositide 3-kinase, and generation of the lipid second messenger phosphatidylinositol-3,4,5-trisphosphate[PtdIns (3,4,5) P3].

Activated PKB phosphorylates numerous cytosolic and nuclear proteins to regulate cell metabolism, growth and survival. In the insulin signalling pathway, PKB phosphorylates GSK-3, PFK2 and mTOR, inducing glycogenesis and protein synthesis, and regulates glucose uptake by promoting the translocation of Glut4 to the plasma membrane. Cell survival and transformation are controlled by phosphorylation of BAD, caspase-9, forkhead transcription factors and IkB kinase, promoting proliferation and suppressing cell apoptosis (Datta, S. R. et al., Genes Dev. 13:2905-27 (1999)). A mechanism by which PKB stimulates cell cycle progression is by phosphorylation of the CDK inhibitors p21wAF1 and p27kiP1, causing their retention in the cytoplasm (Zhou, B. P. et al., Nat. Cell. Biol. 3:245-52 (2001)), whereas in contrast, PKB mediates nuclear localisation of mdm2 and subsequent regulation of the mdm2/p53 pathway (Mayo, L. D. & Donner, D. B., Proc. Natl. Acad. Sci. USA 98:11598-603 (2001)). In humans, the three isoforms of PKB are highly conserved, with a mean sequence identity of 73%, and share the same regulatory phosphorylation sites.

PKB plays an important role in the generation of human malignancy.

The enzyme is the cellular homologue of v-Akt, an oncogene of the transforming murine leukaemia virus PKB8 isolated from a mouse lymphoma (Staal, S. P., Proc. Natl. Acad. Sci. USA 84:5034-7 (1987)). Viral-Akt is a fusion of the viralGag protein with the PKBalpha sequence (Bellacosa, A. et al., Science 254:274-7 (1991)). Myristoylation of the Gag sequence targets v-Akt to the cell membrane, resulting in its constitutive phosphorylation. The genes for several isoforms of PKB are over-expressed and amplified in ovarian, prostate, pancreatic, gastric, and breast tumors (Testa, J. R. & Bellacosa, A., Proc. Natl. Acad. Sci. USA 98:10983-5 (2001)). Compelling evidence linking PKB to oncogenesis stems from the elucidation of the mechanism of the PTEN tumour suppressor gene. PTEN is one of the most commonly mutated genes in human cancer and somatic deletions or mutations of PTEN have been identified in glioblastomas, melanoma and prostate cancers, and are associated with increased susceptibility to breast and thyroid tumours (Cantley, L. C. & Neel, B. G., Proc. Natl. Acad. Sci. USA 96:4240-5 (1999)). PTEN negatively regulates the PI-3 kinase/PKB pathway by dephosphorylating PtdIns (3,4,5) P3 on the D-3 position, and therefore loss of PTEN activity leads to a constitutive cell survival stimulus (Maehama, T. & Dixon, J. E., J. Biol. Chem. 273:13375-8 (1998); Myers, M. P. et al., Proc. Natl. Acad. Sci. USA 95:13513-8 (1998)).

Therefore, modulators (activators or inhibitors) of PDK1 or PKB could be used for treatment of diseases, e.g. the treatment of diabetes, cancer, neurodegeneration and erectile dysfunction.

By modulating PKB activity, the phosphorylation state of Glycogen synthase kinase-3 (GSK3) could be regulated. GSK-3 is a serine/threonine protein kinase comprised of isoforms that are each encoded by distinct genes (Coghlan, M. P. et al., Chem. Biol. 7:793-803 (2000); Kim, L. & Kimmel, A. R., Curr. Opin. Genet. Dev. 10:508-14 (2000)). This enzyme participates in several signalling pathways important in disease and small molecule compounds are being developed as ATP competitive inhibitors. As these inhibitors are ATP competitive inhibitors, they inactivate GSK3 in all different pathways. As will be described below, GSK3 inhibition by compounds may also mimic Wnt signalling and promote proliferative disorders, e.g. colon cancer. As PKB does not affect the activity of GSK3 within Wnt signalling, modulation of PKB activity could be better used for a safer treatment of a number of disorders which require inhibition of GSK3, without affecting Wnt signalling. Therefore, for example, PKB .beta. activators could have the added value that they would inhibit GSK-3 downstream from PKB but not affect Wnt signalling. GSK-3 has been implicated in various diseases including diabetes, Alzheimer's disease, CNS disorders such as manic depressive disorder and neurodegenerative diseases, and cardiomyocyte hypertrophy [WO99/65897; WO00/38675; and Haq et al., J. Cell Biol. (2000) 151, 117-]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the amyloid peptide, the gene transcription factor-catenin, the translation initiation factor elF2B, as well as ATP citrate lyase, axin, heat shock factor-1, c-Jun, c-Myc, c-Myb, CREB, and CEPBa. These diverse protein targets implicate GSK-3 in many aspects of cellular metabolism, proliferation, differentiation and development. In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake (Klein et al., PNAS, 93:8455-9 (1996); Cross et al., Biochem. J., 303:21-26 (1994); Cohen, Biochem. Soc. Trans., 21:555-567 (1993); Massillon et al., Biochem. J. 299:123-128 (1994)). However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO00/38675]. Therefore, inhibition of GSK-3 can mimic insulin action. GSK-3 activity has also been associated with Alzheimer's disease. This disease is characterized by the well-known P-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells (Lovestone et al., Current Biology 4:1077-86 (1994); Brownlees et al., Neuroreport 8:3251-55 (1997)). Therefore, it is believed that GSK-3 activity may promote generation of the neurofibrillary tangles and the progression of Alzheimer's disease. Another substrate of GSK-3 is β-catenin which is degradated after phosphorylation by GSK-3. Reduced levels of β-catenin have been reported in schizophrenic patients and have also been associated with other diseases related to an increase in neuronal cell death (Zhong et al., Nature 395:698-702 (1998); Takashima et al., PNAS 90:7789-93 (1993); Pei et al., J. Neuropathol. Exp. 56:70-78 (1997)). As a result of the biological importance of GSK-3, there is current interest in therapeutically effective GSK-3 inhibitors. Small molecules that inhibit GSK-3 have recently been reported in WO99/65897, WO02/096905 and WO00/38675.

WO 2008/019890 moreover discloses compounds having the following formula,

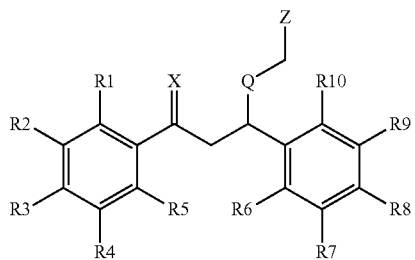

in which
X is selected from O, N—R and NO—R, wherein R is H, $C_{1-4}$-alkyl, or -L-Y (wherein L is a linker and Y is a functional group);
Q is selected from S and $CH_2$;

Z is selected from COOH, tetrazolyl, CN, phosphonic acid, phosphate and COOE (wherein E is $C_{1-5}$-alkanoyloxy-$C_{1-3}$-alkyl or $C_{1-5}$-alkoxycarbonyloxy-$C_{1-3}$-alkyl;
R1, R4-R10 are selected from H, halogen, $C_{1-4}$-alkyl, $C_{2-4}$-alkenyl and $CF_3$; and
R2 and R3 are a member of a benzoanneleted cyclopentane, cyclohexane or benzene, or are selected from H, halogen, $C_{1-4}$-alkyl, $C_{2-4}$-alkenyl and $CF_3$,
as well as its use for modulating the activity of AGC kinases and for target validation studies.

Another signalling pathway in which GSK3 participates is Wnt signalling. Wnt signalling inhibits GSK3, which in turn translates into activation of transcription factors involved in tumor development, e.g. in colon cancers. Thus, GSK3 inhibition by compounds to treat diabetes or neurological disorders, in time, could lead to unwanted side effects. Importantly, PKB phosphorylation does not play a role in Wnt signalling inhibition of GSK3. Therefore, a compound triggering activation of the specific PKB isoform (PKB beta), which in turn phosphorylates and inhibits GSK3 within the insulin signalling pathway may be used to mimic insulin action for the treatment of diabetes, without affecting Wnt signalling.

One object of the invention is to provide compounds that modulate AGC protein kinases and are suitable for the preparation of pharmaceutical compositions for oral, parenteral, topical, rectal, nasal, buccal, vaginal administration or via an implanted reservoir or by inhalation spray. A further object is to provide compounds that modulate AGC protein kinases having a PIF binding pocket in the N-terminal lobe of the catalytic domain, such as PKCzeta and SGK. A further object is to provide compounds which activate PDK1 and inhibit PDK1 and/or PKB. A further object is to provide pharmaceutical compositions suitable for treating diseases associated with protein kinases, in particular AGC kinases, PDK1 signalling and PKB signalling, e.g. cancer or diabetes.

SHORT DESCRIPTION OF THE INVENTION

It was now found that specific low molecular compounds modulate AGC protein kinases. The invention thus provides (1) compound of formula I

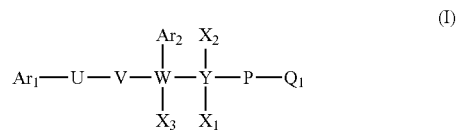

wherein
Y is C;
W is C or N;
$X_1$ is H, or $X_1$, together with $X_2$, forms a carbonyl group, or, if W is C, $X_1$ taken together with $X_3$ forms a double bond between Y and W;
$X_2$ is $Q_2$ or $X_2$, taken together with $X_1$, forms a carbonyl group;
$X_3$, if W is C, is H, or, taken together with $X_1$, forms a double bond between W and Y, or $X_3$, if W is N, is a lone electron pair;
$Q_1$ and $Q_2$ are independently selected from H, $-OR^1$, $-NR^1R^2$, $-NR^1OR^2$, $-SR^1$, $-COOR^1$, $-CONR^1R^2$, $-CONHCN$, $-CONH(SO_2R^1)$, $-CONR^1OR^2$, $-C(O)SR^1$, $-C(S)OR^1$, $-CN$, $-COR^1$, $-COOCHR^1C(O)R^2$, $-COOCH_2C(O)NR^1R^2$, $-CR^1R^2OR^3$, $-CR^1R^2NR^3R^4$, $-CR^1R^2SR^3$, $-CR^1R^2NO_2$, $-SOR^1$, $SO_2R^1$, $-S(O)_2$ $OR^1$, $-SO_2NR^1R^2$, $-SO_2NH(COR^1)$, $-P(O)(OR^1)OR^2$, and a heterocyclic bioisostere of a carboxyl group;

P is selected from a single bond, $-CR^5R^6-$, $-CR^5(OR^6)-$, $-CR^5NR^6R^7-$, $-CR^5COOR^6-$, $-C(OR^5)COOR^6-$, and $-C(NR^5R^6)COOR^7-$ and, if $Q_1$ is H, $-OR^1$, $-NR^1R^2$, $-NR^1OR^2$ or $-SR^1$, P may also be $-CO-$;

V is a single bond, $-CR^8R^9-$, or $-CHNH_2-$, and, if $X_2$ is $Q_2$, V may also be $-CO-$, and, if W is C, P may also be $-NR^8-$;

U is a single bond, or $-CR^{10}R^{11}-$, and, if V is $CR^8R^9$, U may also be $-O-$, $-S-$, $-NR^{10}-$ or $-CO-$;

$R^1$, $R^2$, $R^3$, $R^4$, $R^5$, $R^6$, $R^7$, $R^8$, $R^9$, $R^{10}$ and $R^{11}$ are at each occurrence in the compound of formula I independently selected from H, $C_{1-6}$alkyl, $C_{2-6}$alkenyl, $C_{2-6}$ alkynyl, $C_{3-6}$cycloalkyl, $C_{3-6}$cycloalkenyl, optionally substituted heteroaryl and optionally substituted aryl;

$Ar_1$ and $Ar_2$ are independently selected from an aryl and a heteroaryl ring carrying 0-4 same or different substituents $R^{12}$;

$R^{12}$ is at each occurrence in the compound of formula I independently selected from hydrogen, $C_{1-6}$alkyl, $C_{2-6}$alkenyl, $C_{2-6}$alkynyl, $C_{3-6}$cycloalkyl, $C_{3-6}$cycloalkenyl, optionally substituted heterocyclyl, optionally substituted heteroaryl, optionally substituted aryl, $-F$, $-Cl$, $-Br$, $-I$, $-CF_3$, $-Z-OR^{13}$, $-Z-NO_2$, $-Z-NR^{13}OR^{14}$, $-Z-NR^{13}R^{14}$, $-Z-SR^{13}$, $-Z-COOR^{13}$, $-Z-CONR^{13}R^{14}$, $-Z-C(O)SR^{13}$, $-Z-C(O)NR^{13}OR^{14}$, $-Z-CN$, $-Z-COR^{13}$, $-Z-COOCH_2C(O)R^{13}$, $-Z-COOCH_2C(O)NR^{13}R^{14}$, $-Z-SOR^{13}$, $-Z-SO_2R^{13}$, $-Z-SO_2NR^{13}R^{14}$, $-Z-P(O)(OR^{13})OR^{14}$ and $-Z$-tetrazol-5-yl (wherein Z is a single bond or a bivalent spacer group);

$R^{13}$ and $R^{14}$ are at each occurrence in the compound of formula I independently selected from hydrogen, $C_{1-6}$alkyl, $C_{2-6}$alkenyl, $C_{2-6}$alkynyl, $C_{3-6}$cycloalkyl, $C_{3-6}$ cycloalkenyl, optionally substituted heteroaryl and optionally substituted aryl, and pharmaceutically acceptable salts, solvates, diastereomers, enantiomers, tautomers, and racemates thereof;

(2) a pharmaceutical composition or medicament comprising a compound of (1) above;

(3) the use of a compound of (1) above for the preparation of a medicament for the prevention or treatment of a disease related to an AGC kinase or to an Aurora kinase;

(4) the use of the compound of (1) above for co-crystallization with a protein, for target validation studies, as a lead compound for drug development, including virtual docking to target proteins;

(5) a method for in vitro or in vivo modulating and/or regulating the activity of an AGC kinase containing a PIF pocket homologous site in the small lobe of the kinase domain which comprises applying a compound of (1) above; and (6) a method for preventing or treating a disease related to an AGC kinase in an organism or patient having the risk of obtaining the disease or suffering from said disease, which comprises administering a compound of (1) above or a pharmaceutical composition or medicament of (2) above in a physiologically effective dose to the organism or patient.

SHORT DESCRIPTION OF THE FIGURES

FIG. 1 corroborates that the PIF pocket of PDK1 is the target site of PS48. Mutation of the PIF pocket residue Val127 to threonine abrogates the activation of PDK1 by PS48 but not by the 22 residue peptide PIFtide.

Figure 2:
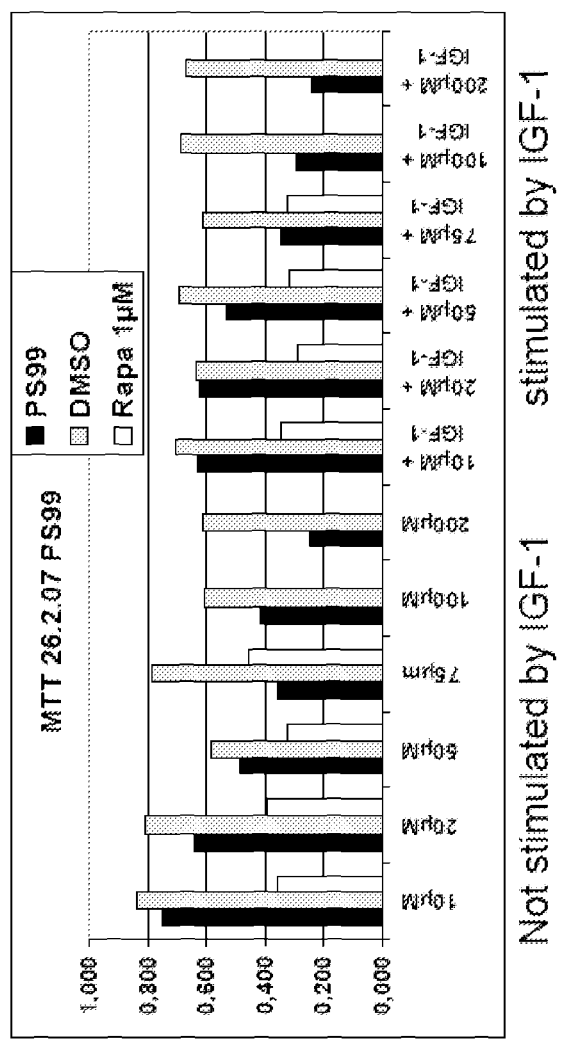
Figure 2:
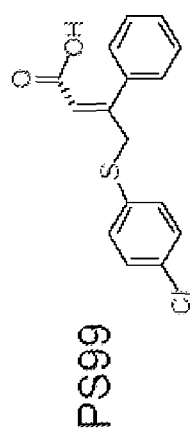

FIG. 2 shows by the example compound PS 99 that compounds according to the invention can inhibit the proliferation of/or induce cell death of cancer cells (here: PC3 prostate carcinoma cells) in comparison to rapamycin. Cells were serum starved overnight and stimulated or not with 50 μg/ml IGF-I, then test compounds and 5% FCS were added, and cells grown for 36 h. A standard MTT assay was then performed to measure the number of living cells.

Figure 3:
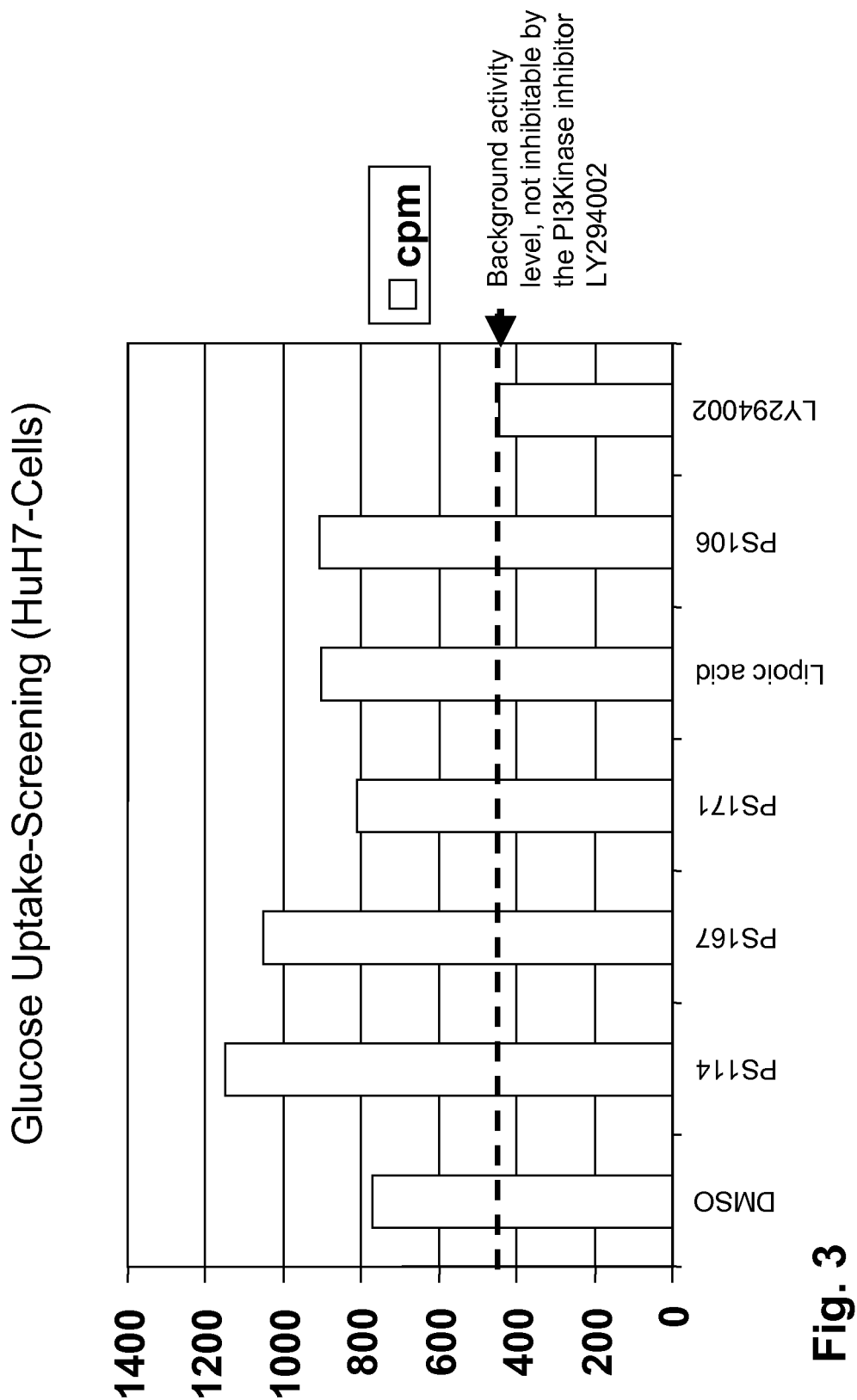

FIG. 3 summarizes the results of the glucose uptake assay of example 6. Principle: cells are deprived of glucose, test compounds or DMSO is added, then $^3$H-labelled 2-Desoxyglucose is added (50 μM) in the presence of buffered saline (including Mg2+, Ca2+), uptake of glucose is triggered by the addition of a suboptimal concentration of insulin (0.3 nM), cells are washed 4 times, the relative amount of 2-DG taken up by the cells is quantified by β-counting (all compounds 50 μM; except LY294002: 10 μM).

Figure 4:
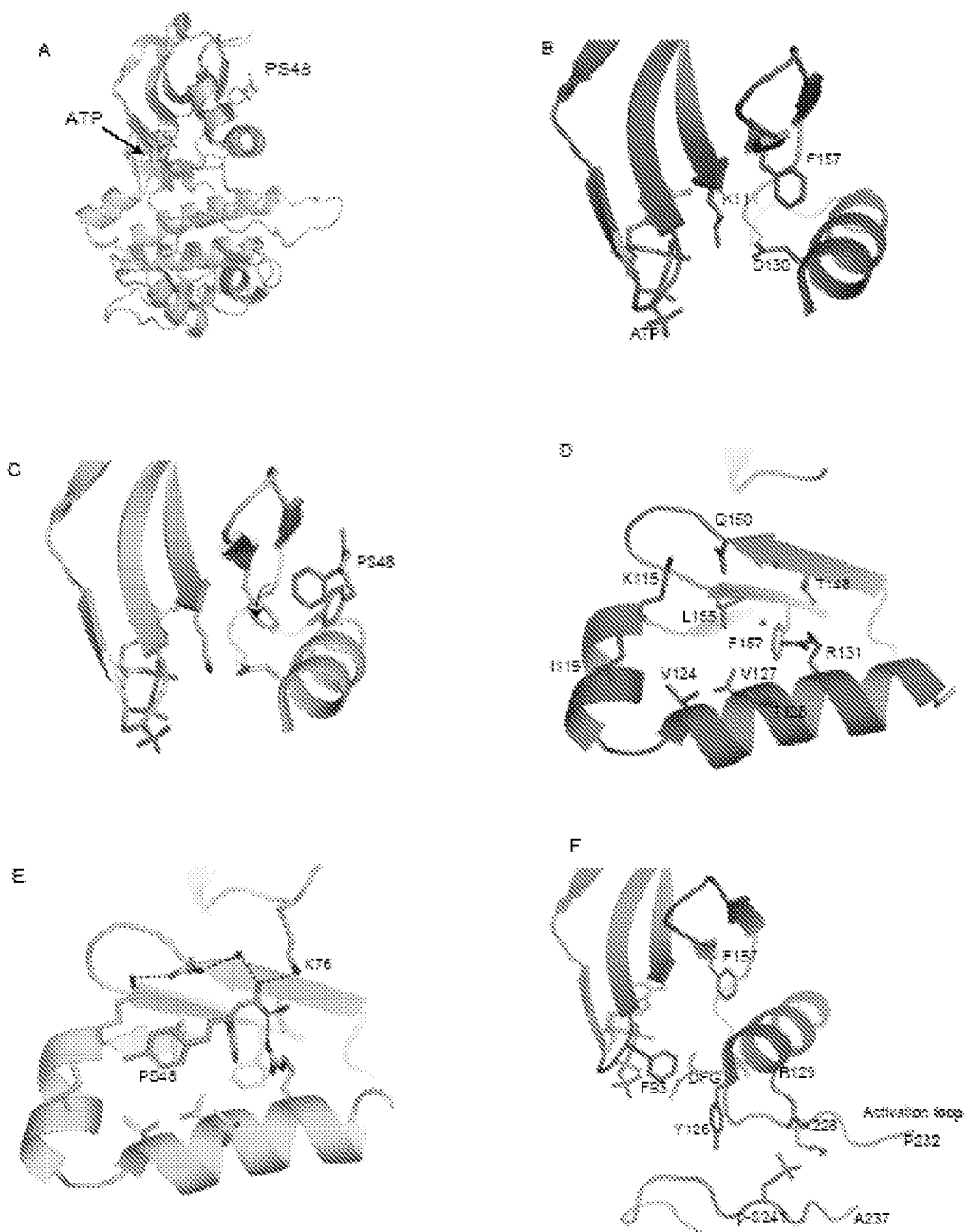
Figure 4:
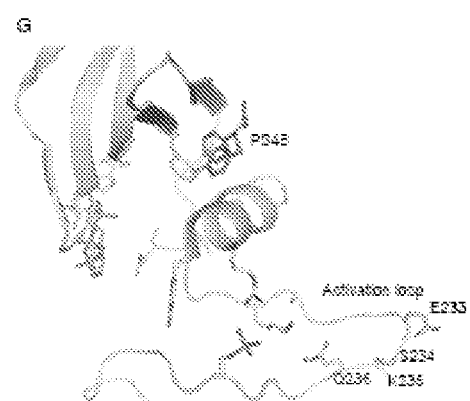

FIG. 4 reveals that in the co-crystal structure of PDK1 bound to PS 48, not only local conformational changes at the PIF pocket site are produced, but also significant changes of key amino acid residues at the top of the ATP binding site.

Figure 5:
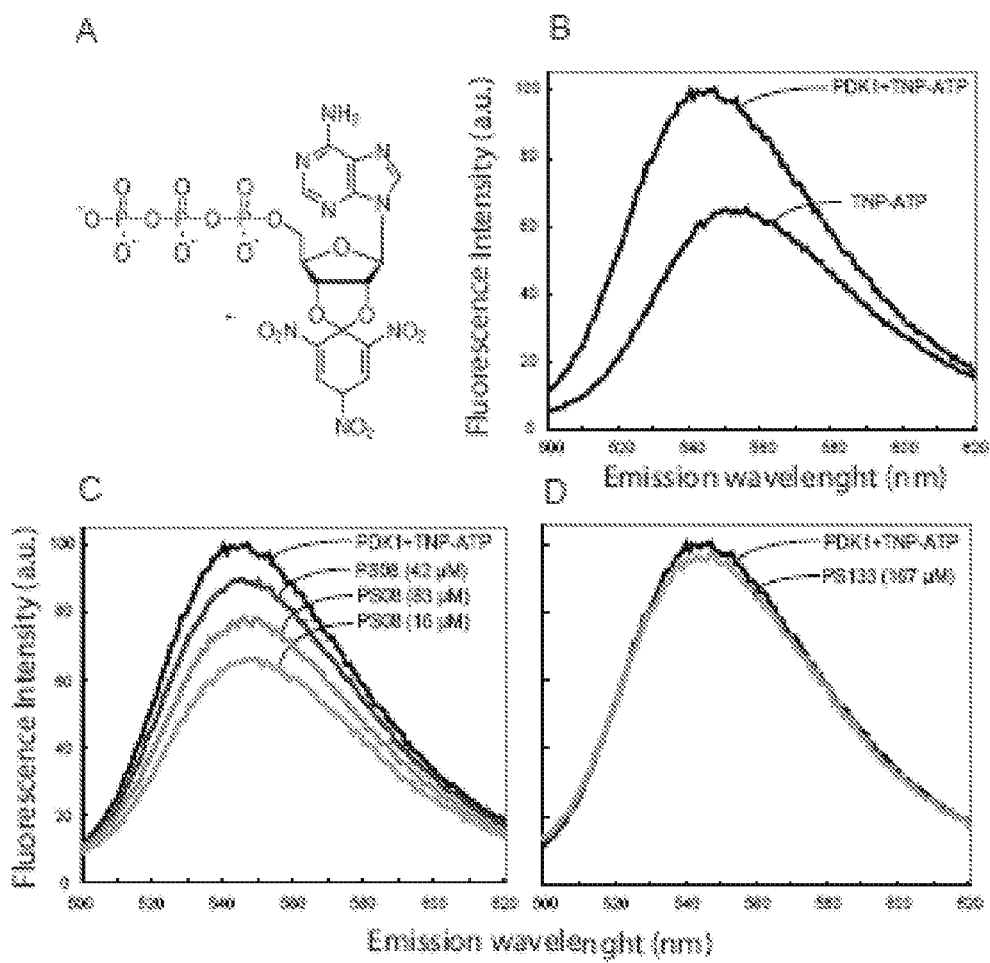

FIG. 5 shows that compound PS-T-8, which targets the PIF-binding pocket of PDK1, produces a significant allosteric effect which could be sensed at the ATP-binding site. A concentration-dependent decrease in fluorescence intensity of the ATP analogue TNP-ATP was observed.

Figure 6:
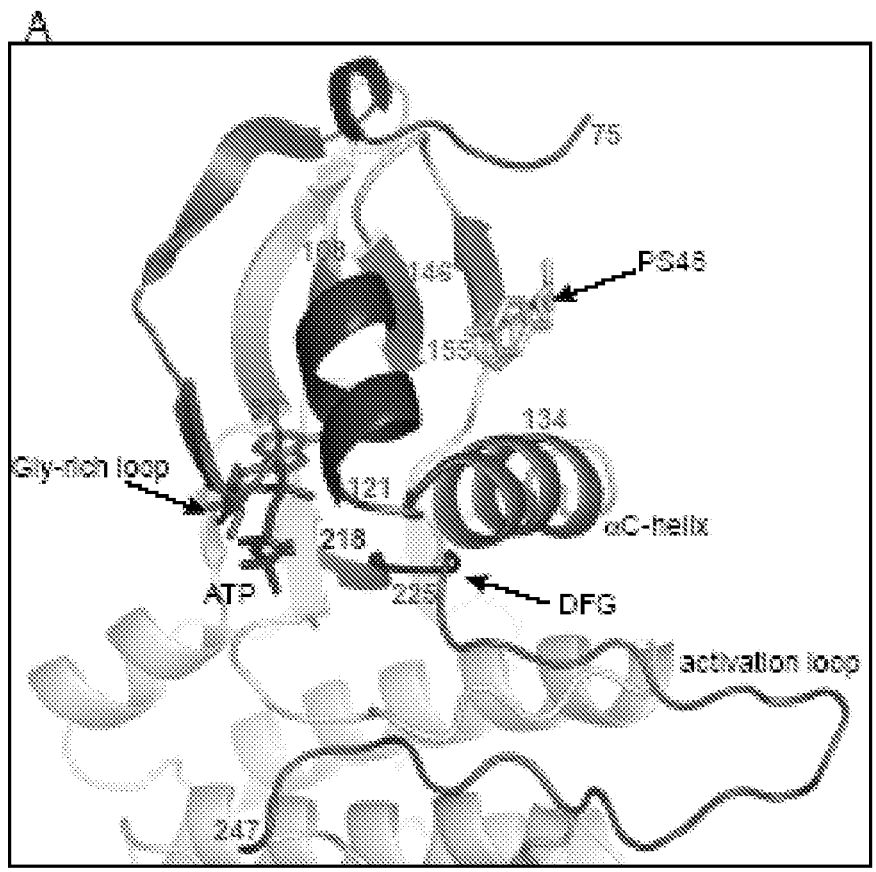
Figure 6:
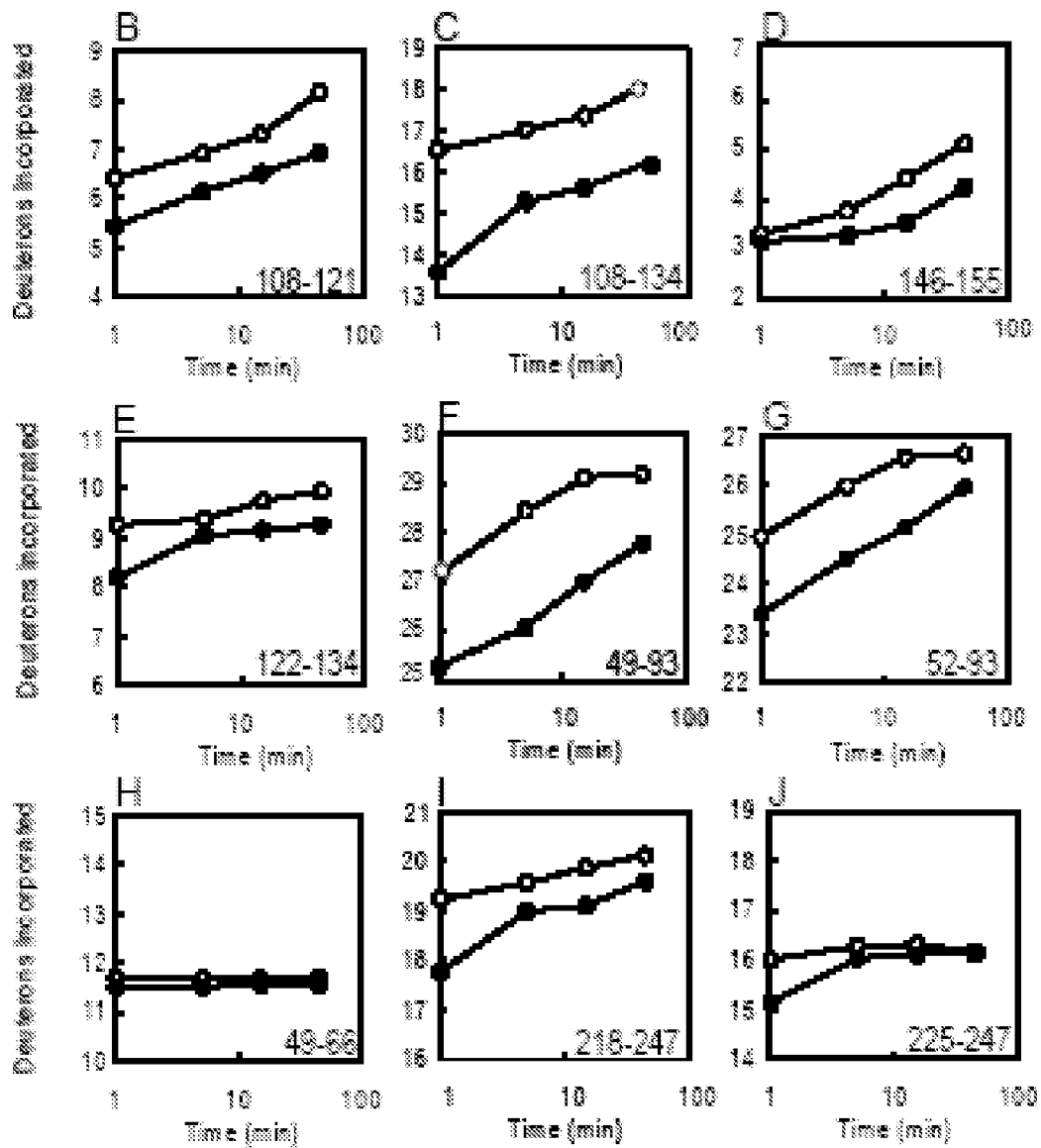

FIG. 6: Peptide regions protected from amide $^1$H/$^2$H exchange experiments in the presence of compound PS-T-8. The observed protections proof that allosteric effects of the compound also extend to the ATP binding site and the α-G-helix on the bottom of the large lobe, some 30 Å away from the allosteric binding site.

SEQUENCE LISTING

Free Text

| SEQ ID NO: | Description |
|---|---|
| 1 | PIF pocket of hPDK1 |
| 2-6 | hydrophobic pockets of protein kinases |
| 7 | catalytic domain of human cAMP dependent protein kinase (PKA) |

DETAILED DESCRIPTION OF THE INVENTION

The invention relates to the general finding that small molecule compounds can be activators or inhibitors of AGC protein kinases, which possess a PIF binding pocket in the N-terminal lobe of the catalytic domain, sometimes also named hydrophobic motif ("HM") binding pocket. The invention describes activators of PDK1 and inhibitors of PDK1 and PKB. The invention also relates to the use of said compounds for treating diseases associated with protein kinases, especially diseases associated with AGC kinases, PDK1 signalling and PKB signalling such as cancer, diabetes or chronic inflammation.

The present invention is, in particular, based on the finding that small molecule compounds, of less than 500 of molecular weight (MW) can regulate the activity of AGC kinases containing a PIF pocket homologous site in the small lobe of the kinase domain. In addition, compounds are described that can activate or inhibit AGC protein kinases, for example, PDK1, PKB, PKCzeta, RSK-2, and S6K. In addition, members of the Aurora kinase family are also inhibited or activated. The compounds described have overall good pharmacological properties. Potentially unfavourable carboxyl groups can be replaced, or modified in pro-drug strategies well known to those skilled in the art (reviewed in Rautio et al., Nature Reviews Drug Discovery, 2008, 7, 255-270). The compounds presented, or its derivatives can be used for treatment of conditions where there is need for activating or inhibiting protein kinases of the AGC family.

Aspect (1) of the invention relates to compounds having the formula (I):

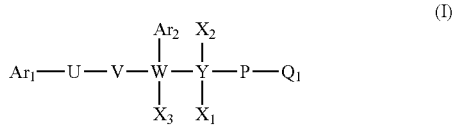

wherein
Y is carbon;
W is selected from carbon and nitrogen, provided that when W is carbon, then $X_3$ is either hydrogen or taken together with $X_1$ to complete a double valence bond between W and Y, and provided that when W is nitrogen, then $X_3$ represents a lone electron pair;
$X_1$ either completes a carbonyl group together with $X_2$ and Y, or, provided that W is C, is taken together with $X_3$ to complete a double valence bond between Y and W, or $X_1$ represents hydrogen;
$X_2$ is either $Q_2$, or taken together with $X_1$ and Y to complete a carbonyl group;
$Q_1$ and $Q_2$ are independently selected from hydrogen, —OR$^1$, —NR$^1$R$^2$, —NR$^1$OR$^2$, —SR$^1$, —COOR$^1$, —CONR$^1$R$^2$, —CONHCN, —CONH(SO$_2$R$^1$), —CONR$^1$OR$^2$, —C(O)SR$^1$, —C(S)OR$^1$, —CN, —COR$^1$, —COOCHR$^1$C(O)R$^2$, —COOCH$_2$C(O)NR$^1$R$^2$, —CR$^1$R$^2$OR$^3$, —CR$^1$R$^2$NR$^3$R$^4$, —CR$^1$R$^2$SR$^3$, —CR$^1$R$^2$NO$_2$, —SOR$^1$, SO$_2$R$^1$, —S(O)$_2$OR$^1$, —SO$_2$NR$^1$R$^2$, —SO$_2$NH(COR$^1$), —P(O)(OR$^1$)OR$^2$, and a heterocyclic bioisostere of the carboxyl group including tetrazol-5-yl, 5-hydroxy-1,2,4-oxadiazol-3-yl, 5-hydroxy-1,2,4-thiadiazol-3-yl, 2-oxo-1,2,3,5-oxathiadiazoline-4-yl, 5-thioxo-1,2,4-oxadiazoline-3-yl, 3,5-dioxo-1,2,4-oxadiazolidine-2-yl, 5-hydroxyisoxazol-4-yl, 3-hydroxyisothiazol-4-yl, 1-hydroxypyrazol-5-yl, 1-hydroxy-1,2,3-triazol-5-yl, 1-hydroxyimidazol-2-yl, 1-hydroxyimidazol-5-yl, 3-hydroxy-1,2,5-oxadiazol-4-yl and 3-hydroxy-1,2,5-thiadiazol-4-yl;
P is a single bond, —CR$^5$R$^6$—, —CR$^5$(OR$^6$)—, —CR$^5$NR$^6$R$^7$—, —CR$^5$COOR$^6$—, —C(OR$^5$)COOR$^6$—, —C(NR$^5$R$^6$)COOR$^7$—, or, if $Q_1$ is selected from —H, —OR$^1$, —NR$^1$R$^2$, —NR$^1$OR$^2$, —SR$^1$, then P is —CO—;
V is selected from a single bond, —CR$^8$R$^9$—, or —CHNH$_2$—, or, if $X_2$ is $Q_2$, from —CO—, or, if W is carbon, from —NR$^8$—;
U is selected from a single bond, —CR$^{10}$R$^{11}$—, or, if V is CR$^8$R$^9$, from —O—, —S—, —NR$^{10}$—, and —CO—;
R$^1$, R$^2$, R$^3$, R$^4$, R$^5$, R$^6$, R$^7$, R$^8$, R$^9$, R$^{10}$, and R$^{11}$ can be the same or different if occurring more than once in the compound of Formula I, and are each independently selected from hydrogen, branched or linear C$_{1-6}$alkyl, branched or linear C$_{2-6}$alkenyl, branched or linear C$_{2-6}$alkynyl, C$_{3-6}$cycloalkyl, C$_{3-6}$cycloalkenyl, substituted or unsubstituted heteroaryl, substituted or unsubstituted aryl;
Ar$_1$ and Ar$_2$ are independently selected from
1. an aryl ring, wherein the aryl ring is selected from a phenyl ring, a naphthyl ring, and an indenyl ring;
2. a heteroaryl ring, wherein the heteroaryl ring is selected from a) a benzo- or a naphtho-annelated 5-membered unsaturated, partly unsaturated, or saturated monocyclic ring with 1 or 2 heteroatom ring atoms selected from N, O and S, and
b) a benzo- or a naphtho-annelated 6-membered unsaturated, partly unsaturated, or saturated monocyclic ring with 1, 2, or 3 heteroatom ring atoms selected from N, O and S,
wherein said aryl and heteroaryl ring is unsubstituted, monosubstituted with R$^{12}$, disubstituted with groups independently selected from R$^{12}$, trisubstituted with groups independently selected from R$^{12}$, or tetrasubstituted with groups independently selected from R$^{12}$, and wherein any stable S and N heteroaryl or heterocyclic ring atom is unsubstituted or substituted with oxo, said heteroaryl R$^{12}$-substitutions being on one or more heteroaryl ring carbon atoms;
R$^{12}$ can be the same or different if occurring more than once in the compound of Formula I, and is at each occurrence independently selected from hydrogen, C$_{1-6}$alkyl, C$_{2-6}$alkenyl, C$_{2-6}$alkynyl, C$_{3-6}$cycloalkyl, C$_{3-6}$cycloalkenyl, substituted or unsubstituted heterocyclyl, substituted or unsubstituted heteroaryl, substituted or unsubstituted aryl, —F, —Cl, —Br, —I, —CF$_3$, —Z—OR$^{13}$, —Z—NO$_2$, —Z—NR$^{13}$OR$^{14}$, —Z—NR$^{13}$R$^{14}$, —Z—SR$^{13}$, —Z—COOR$^{13}$, —Z—CONR$^{13}$R$^{14}$, —Z—C(O)SR$^{13}$, —Z—C(O)NR$^{13}$OR$^{14}$, —Z—CN, —Z—COR$^{13}$, —Z—COOCH$_2$C(O)R$^{13}$, —Z—COOCH$_2$C(O)NR$^{13}$R$^{14}$, —Z—SOR$^{13}$, —Z—SO$_2$R$^{13}$, —Z—SO$_2$NR$^{13}$R$^{14}$, —Z—P(O)(OR$^{13}$)OR$^{14}$, and —Z-tetrazol-5-yl (wherein Z is selected from a valence bond or a bivalent spacer group, said bivalent spacer including an optionally substituted methylene optionally substituted ethylene, an optionally substituted ethenylene, and an ethinylene group, and wherein the number of substituents of the optionally substituted methylene, optionally substituted ethylene, and optionally substituted ethenylene is 1 to 10, preferably 1 to 4, and/or the substituents of the optionally substituted methylene, optionally substituted ethylene, and optionally substituted ethenylene are independently selected from —F, CF$_3$, NO$_2$, —COOR$^{17}$, —CONR$^{17}$R$^{18}$, —CN, —COR$^{17}$, —SOR$^{17}$, —SO$_2$R$^{17}$, —SO$_2$NR$^{17}$R$^{18}$, and —P(O)(OR$^{17}$)OR$^{18}$, wherein R$^{17}$ and R$^{18}$ can be the same or different if occurring more than once in the compound of Formula I, and are each independently selected from hydrogen, branched or linear C$_{1-6}$alkyl, branched or linear C$_{2-6}$alkenyl, branched or linear C$_{2-6}$alkynyl, C$_{3-6}$cycloalkyl, and C$_{3-6}$cycloalkenyl); and
R$^{13}$ and R$^{14}$ can be the same or different if occurring more than once in the compound of Formula I, and are each independently selected from H, branched or linear C$_{1-6}$alkyl, branched or linear C$_{2-6}$alkenyl, branched or linear C$_{2-6}$alkynyl, C$_{3-6}$cycloalkyl, C$_{3-6}$cycloalkenyl, substituted or unsubstituted heteroaryl, and substituted or unsubstituted aryl.

In the above definition of the compound of formula I the heterocyclic bioisostere of the carboxyl group is selected from tetrazol-5-yl, 5-hydroxy-1,2,4-oxadiazol-3-yl, 5-hydroxy-1,2,4-thiadiazol-3-yl, 2-oxo-1,2,3,5-oxathiadiazoline-4-yl, 5-thioxo-1,2,4-oxadiazoline-3-yl, 3,5-dioxo-1,2,4-oxadiazolidine-2-yl, 5-hydroxyisoxazol-4-yl, 3-hydroxyisothiazol-4-yl, 1-hydroxypyrazol-5-yl, 1-hydroxy-1,2,3-triazol-5-yl, 1-hydroxyimidazol-2-yl, 1-hydroxyimidazol-5-yl, 3-hydroxy-1,2,5-oxadiazol-4-yl, and 3-hydroxy-1,2,5-thiadiazol-4-yl.

Further, in the above definition of the compound of formula I, the C$_{1-6}$alkyl, C$_{2-6}$alkenyl or C$_{2-6}$alkynyl groups may be branched or linear.

Further, in the above definition of the compound of formula I, in Ar$_1$ and Ar$_2$ the aryl rings are independently selected from a phenyl ring, a naphthyl ring and an indenyl ring; and/or the heteroaryl rings are independently selected from a benzo- or naphtho-annelated 5-membered unsaturated, partly unsaturated, or saturated monocyclic ring with 1 or 2 hetero ring atoms selected from N, O and S, or a benzo- or a naphtho-annelated 6-membered unsaturated, partly unsaturated, or saturated monocyclic ring with 1 to 3 hetero ring atoms selected from N, O and S, wherein any stable S and N ring atom may be substituted with oxo.

Further, in the above definition of the compound of formula I, in $R^{12}$ the heterocyclyl group of the optionally substituted heterocyclyl is a 5-membered unsaturated, partly unsaturated, or saturated monocyclic ring with 1 or 2 hetero ring atoms selected from N, O and S, or a 6-membered unsaturated, partly unsaturated, or saturated monocyclic ring with 1 to 3 hetero ring atoms selected from N, O and S.

Further, in the above definition of the compound of formula I, the number of substituents of the optionally substituted heterocyclyl, optionally substituted heteroaryl, and optionally substituted aryl is 1 to 10, preferably 1 to 4, and/or said substituents are at each occurrence in the compound of formula I independently selected from —F, —Cl, —Br, —I, —CF$_3$, —OR$^{15}$, —NO$_2$, —NR$^{15}$OR$^{16}$, —SR$^{15}$, —CH$_2$OR$^{15}$, —CH$_2$NR$^{15}$R$^{16}$, —COOR$^{15}$, —CONR$^{15}$R$^{16}$, —C(O)SR$^{15}$, —C(O)NR$^{15}$OR$^{16}$, —CN, —COR$^{15}$, —SOR$^{15}$, —SO$_2$R$^{15}$, and —SO$_2$NR$^{15}$R$^{16}$, wherein R$^{15}$ and R$^{16}$ can be the same or different and are at each occurrence in the compound of formula I independently selected from hydrogen, branched or linear $C_{1-6}$alkyl, branched or linear $C_{2-6}$alkenyl, branched or linear $C_{2-6}$alkynyl, $C_{3-6}$cycloalkyl, and $C_{3-6}$cycloalkenyl.

Preferred embodiments of aspect (1) of the invention are compounds according to formula (I) characterised in that: W is carbon, $X_2$ is $Q_2$, P is a single valence bond, $X_1$ and $X_3$ are taken together to complete a double valence bond between Y and W, V is a single valence bond or —CR$^8$R$^9$—, and U is either not present, or —CR$^{10}$R$^{11}$—, or, provided that V=—CR$^8$R$^9$, U is selected from —O—, —S—, or —NR$^{10}$—.

More preferred compounds selected from the previous embodiment are characterised in that $Q_2$ is hydrogen, V is —CR$^8$R$^9$—, U is —CR$^{10}$R$^{11}$—, and $Q_1$ is selected from —COOR$^1$, —CONR$^1$R$^2$, —CONHCN, —CONH(SO$_2$R$^1$), —CONR$^1$OR$^2$, —C(O)SR$^1$, —C(S)OR$^1$, —CN, —COOCHR$^1$C(O)R$^2$, —COOCH$_2$C(O)NR$^1$R$^2$, or tetrazol-5-yl.

Another preferred embodiment of aspect (1) of the invention is a compound according to formula (I) characterised in that W is carbon, $X_2$ is $Q_2$, P is a single valence bond, $X_1$ and $X_3$ are taken together to complete a double valence bond between Y and W, V is a single valence bond, U is not present, Ar$_2$ is a phenyl ring, a naphthyl ring, or an indenyl ring carrying 0-4 substituents R$^{12}$ as defined above, and Ar$_1$ is selected from indol-2-yl, indol-3-yl, benzofuran-2-yl, benzofuran-3-yl, benzothiophen-2-yl, benzothiophen-3-yl, benzimidazol-2-yl, benzoxazol-2-yl, benzothiazol-2-yl, isoquinolin-3-yl, quinolin-2-yl, quinolin-3-yl, quinoxalin-2-yl, quinazolin-2-yl, cinnolin-3-yl, or naphthoimidazol-2-yl, wherein the hetaryl moieties are optionally substituted by 1-4 groups independently selected from R$^{12}$, and wherein any stable S and N heteroaryl or heterocyclic ring atom is unsubstituted or substituted with oxo, said heteroaryl R$^{12}$-substitutions being on one or more heteroaryl ring carbon atoms.

Another preferred embodiment of aspect (1) of the invention is a compound according to formula (I) characterised in that W is carbon, $X_2$ is $Q_2$, and $X_1$ as well as $X_3$ are hydrogen.

More preferred compounds selected from the previous embodiment are characterised in that V is —CR$^8$R$^9$—, and U is —CO—.

Even more preferred compounds selected from the previous embodiment are characterised in that P is a single valence bond.

Another preferred embodiment of aspect (1) of the invention is a compound according to formula (I) characterised in that W is carbon, $X_2$ is $Q_2$, and $X_1$ as well as $X_3$ are hydrogen, V is a single valence bond or —CR$^8$R$^9$—, and U is either not present or —CR$^{10}$R$^{11}$—.

More preferred compounds selected from the previous embodiment are characterised in that V is —CR$^8$R$^9$— and U is not present.

Even more preferred compounds selected from the previous embodiment are characterised in that P is a single valence bond.

Still more preferred compounds selected from the previous embodiment are characterised in that Ar$_2$ is a phenyl ring, a naphthyl ring, or an indenyl ring carrying 0-4 substituents R$^{12}$ as defined above, and Ar$_1$ is selected from phenyl, naphthyl, indolyl, benzofuranyl, benzothiophenyl, isoindolyl, indazolyl, benzo[d]isothiazolyl, benzimidazolyl, benzoxazolyl, benzothiazolyl, isoquinolinyl, quinolinyl, phthalazinyl, quinoxalinyl, quinazolinyl, cinnolinyl, or naphthoimidazolyl, wherein the aryl moieties are optionally substituted by 1-4 groups independently selected from R$^{12}$, and wherein any stable S and N heteroaryl or heterocyclic ring atom is unsubstituted or substituted with oxo, said heteroaryl R$^{12}$-substitutions being on one or more heteroaryl ring carbon atoms.

Yet more preferred compounds selected from the previous embodiment are characterised in that Ar$_1$ is selected from benzimidazol-2-yl, benzothiazolyl, N-hydroxybenzimidazol-2-yl-, or N-hydroxy-N'-oxido-benzimidazol-2-yl-, wherein the hetaryl moieties are optionally substituted by 1-4 groups independently selected from R$^{12}$.

Another preferred embodiment of the invention is a compound according to formula (I) characterised in that W is carbon, $X_2$ completes a carbonyl group together with $X_1$ and Y, $X_3$ is hydrogen, P≠single valence bond, V is either a single valence bond or —CR$^8$R$^9$—, U is either not present, —CO—, or —CR$^{10}$R$^{11}$—.

Another preferred embodiment of aspect (1) of the invention is a compound according to formula (I) characterised in that W is nitrogen, $X_2$ is $Q_2$, $X_1$ is hydrogen, $X_3$ represents a lone electron pair, V is —CO— or —CR$^8$R$^9$—, and U is either not present, —CO—, or —CR$^{10}$R$^{11}$—.

Another preferred embodiment of the invention is a compound according to formula (I) characterised in that W is nitrogen, $X_2$ completes a carbonyl group together with $X_1$ and Y, $X_3$ represents a lone electron pair, V is either a single valence bond or —CR$^8$R$^9$—, U is either not present, —CO—, or —CR$^{10}$R$^{11}$—, and P≠single valence bond.

Another preferred embodiment of the invention is the use of a compound according to formula (I) to modulate and/or regulate in vitro and/or in vivo the activity of an AGC kinase containing a PIF pocket homologous site in the small lobe of the kinase domain.

Aspect (2) of the invention relates to a pharmaceutical composition or medicament comprising a therapeutically effective amount of a compound of formula (I) and optionally a pharmaceutically acceptable carrier.

Another aspect of the invention, namely aspect (3) is the use of a compound of formula (I) for the prevention or treatment of a disease related to an AGC kinase, comprising PDK1, PKB, p70S6Kinase, p90RSK or PKCzeta having an abnormal high or low activity.

A preferred embodiment of aspect (3) of the invention is the use of a compound according to formula (I) for the production of a pharmaceutical preparation for the treatment of cancer, insulin resistance, diabetes, inflammation, autoimmune diseases, neurodegenerative disorders, infections, hypertension and so on).

Aspect (6) of the invention relates to a method for preventing or treating a disease related to an AGC kinase, comprising PDK1, PKB, p70S6Kinase, p90RSK or PKCzeta having an abnormal high or low activity, wherein a compound according to formula (I) or a pharmaceutical composition comprising a therapeutically effective amount of a compound of formula (I) and a pharmaceutically acceptable carrier is administered in a physiologically effective dose to an organism having the risk of obtaining the disease or suffering from the disease.

Unless otherwise stated, structures depicted herein are also meant to include compounds which differ only in the presence of one or more isotopically enriched atoms. For example, compounds according to formula (I) except for the replacement of one or several hydrogen atoms by deuterium or tritium atoms, or the replacement of one or several carbon atoms by $^{13}C$ or $^{14}C$, are within the scope of this invention.

This invention also envisions the quaternization of any basic nitrogen-containing groups of the compounds disclosed herein. Water or oil-soluble or dispersible products may be obtained by such quaternization.

The present invention includes within its scope prodrugs of the compounds of this invention. Any compound corresponding to formula (I), having one or more prodrug moieties as part of the molecule, can be converted under physiological conditions to the biologically active drug by a number of chemical and biological mechanisms. In general terms, these prodrug conversion mechanisms are hydrolysis, reduction, oxidation, and elimination. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In general, such prodrugs will be functional derivatives of the compounds of this invention which are readily convertible in vivo into the required compound. For example, prodrugs of a carboxylic acid include an ester, an amide, or an ortho-ester. Thus, in the methods of treatment of the present invention, the term "administering" shall encompass the treatment of the various conditions described with the compound specifically disclosed or with a compound which may not be specifically disclosed, but which converts to the compound of formula (I) in vivo after administration to the patient. Conventional procedures for the selection and preparation of suitable prodrug derivatives are described, for example, in "Design of Prodrugs," ed. H. Bundgaard, Elsevier, 1985, and in Rautio et al., Nature Reviews Drug Discovery, 2008, 7, 255-270. Metabolites of these compounds include active species produced upon introduction of compounds of this invention into the biological milieu.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Any compound of the present invention corresponding to formula (I) may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention; further included are all mixtures of the enantiomers or diastereomers. The compounds of the present invention can so exist in tautomeric, geometric, or stereoisomeric forms. The present invention contemplates all such compounds, including cis- and trans-geometric isomers, E- and Z-geometric isomers, (R)- and (S)-enantiomers, diastereomers, d-isomers, l-isomers, the racemic mixtures thereof and other mixtures thereof, as falling within the scope of compounds having formula (I). The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures or R and S forms for each stereocenter present. Also included within the scope of the invention are polymorphs, or hydrates or other modifiers of the compounds of invention.

Moreover, the family of compounds or isomers having formula (I)) also include the pharmaceutically acceptable salts thereof. Pharmaceutically acceptable salts of such tautomeric, geometric or stereoisomeric forms are also included within the invention. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, butyric, pivalic, succinic, glycolic, gluconic, lactic, malic, tartaric, citric, ascorbic, glucoronic, maleic, fumaric, malonic, pyruvic, aspartic, adipic, glutamic, benzoic, anthranilic, salicylic, p-hydroxybenzoic, phenylacetic, mandelic, methanesulfonic, ethylsulfonic, benzenesulfonic, toluenesulfonic, sulfanilic, stearic, cyclohexylamino sulfonic, algenic, pectinic, and galacturonic acid. Suitable pharmaceutically-acceptable base addition salts of the compounds include metallic salts made from aluminum, calcium, lithium, magnesium, potassium, sodium and zinc or organic salts made from N,N'-dibenzylethylene diamine, choline, chloroprocaine, diethanolamine, ethylenediamine, meglumine (N-methylglucamine), Tris (Tromethamine) and procain. All of these salts may be prepared by conventional means from the corresponding compound by reacting, for example, the appropriate acid or base with the selected compound of formula (I).

The present invention also comprises a pharmaceutical composition comprising a therapeutically effective amount of the compound of the invention in association with at least one pharmaceutically acceptable carrier, adjuvant, vehicle, or diluent. Pharmaceutical compositions of the present invention can comprise the active compound of formula (I) in association with one or more non-toxic, pharmaceutically-acceptable carriers and/or diluents and/or adjuvants and/or vehicle (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

Pharmaceutically acceptable carriers that may be used in these pharmaceutical compositions are generally known in the art. They include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, cyclodextrins, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable nonirritating excipient which is solid at room temperature but liquid at rectal temperature and therefore will melt in the rectum to release the drug. Such materials include cocoa butter, beeswax and polyethylene glycols. The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. For ophthalmic use, the pharmaceutical compositions may be formulated as micronised suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilising or dispersing agents.

The amount of the protein kinase inhibitor/activator that may be combined with the carrier materials to produce a single dosage form will vary depending upon the patient treated and the particular mode of administration. Preferably, the compositions should be formulated so that a dosage of between 0.01-100, preferably 0.1-20, mg/kg body weight/day of the inhibitor or activator can be administered to a patient receiving these compositions. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase mediated condition to be treated or prevented, additional therapeutic agents, which are normally administered to treat or prevent that condition, may be administered together with the inhibitors or activators of this invention. For example, in the treatment of cancer other chemotherapeutic agents or other antiproliferative agents may be combined with the present compounds to treat cancer. These agents include, without limitation, adriamycin, dexamethasone, vincristine, cyclophosphamide, fluorouracil, topotecan, taxol, interferons, and platinum derivatives. Other examples of agents the inhibitors of this invention may also be combined with including, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti convulsants, ion channel blockers, riluzole, and anti Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin. Those additional agents may be administered separately from the protein kinase inhibitor/activator-containing composition, as part of a multiple dosage regimen. Alternatively, those agents may be part of a single dosage form, mixed together with the protein kinase inhibitor or activator of this invention in a single composition.

The general synthetic sequences for preparing compounds useful in the present invention are outlined in the following schemes and are intended to be merely illustrative of the present invention, and not limiting thereof in either scope or spirit. Those with skill in the art will readily understand that known variations of the conditions and processes described in the schemes can be used to synthesise the compounds of the present invention.

A great variety of 1,3-diaryl- and mixed 1,3-(hetaryl/aryl)-prop-2-en-1-ones (chalcones) $A_3$ and $A_9$ (scheme A) are available by classical aldol condensation of benzaldehydes or hetarylcarbaldehydes with acetophenones or hetaryl methyl ketones ($Ar_1$ and $Ar_2$ are as previously defined). Michael addition of CH-acidic compounds like malonates, cyanoacetates, nitroacetates, or alkyl/aryl-sulfonoacetates to chalcones $A_3$ leads to 2-substituted 5-oxo-5-(aryl/hetaryl)-3-arylpentanoates $A_4$, hydrolysis of which affords the corresponding free acids $A_5$. Pyrolytic decarboxylation of $A_5$ provides 1-functionalised 4-oxo-4-(aryl/hetaryl)-2-arylbutanes $A_6$.

Chemoselective reduction of the double bond of chalcones $A_9$ affords 1,3-diaryl- or 1-aryl-3-hetaryl-propan-1-ones (hydrochalcones) $A_{10}$. Horner-Wittig-Emmons reactions of $A_{10}$ with phosphonoacetates or phosphonoacetonitriles leads to E/Z-mixtures of 5-(aryl/hetaryl)-3-arylpent-2-enoates or -nitriles, separable by chromatography. The pure geometric isomers can be further processed to give a variety of 5-(aryl/hetaryl)-3-arylpent-2-enoic acid derivatives. Alternatively, classical Cope-Knoevenagel reactions of $A_{10}$ with strongly CH-acidic compound like malononitrile, cyanoacetates, nitroacetates, or rhodanine provides access to 2-substituted 5-(aryl/hetaryl)-3-arylpent-2-enoic acid derivatives $A_{11}$.

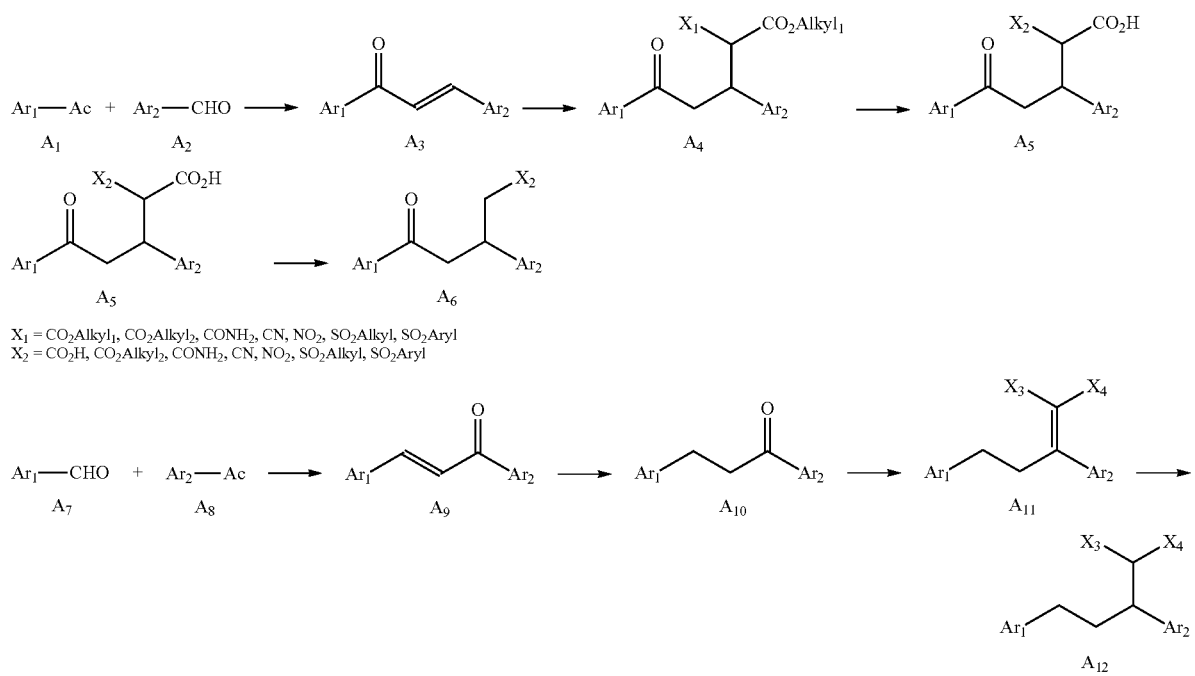

Scheme A

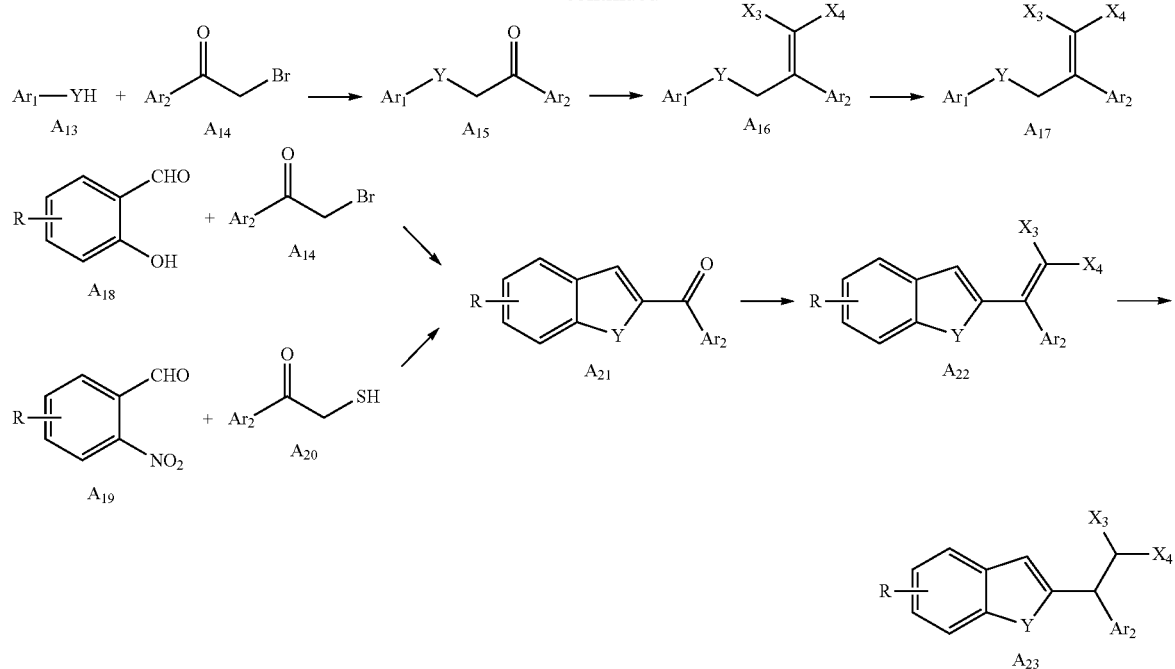

Y = O, S

The corresponding saturated derivatives $A_{12}$ are available from $A_{11}$ by standard reduction procedures. Nucleophilic substitution of phenacyl bromides $A_{14}$ with phenols or thiophenols $A_{13}$ gives oxa- and thia-anlogues of $A_{10}$, which are further reacted the same way as already described to afford oxa- and thia-analogues $A_{16}$ and $A_{17}$ of 5-(aryl/hetaryl)-3-arylpent-2-enoates and -pentanoates $A_{11}$ and $A_{12}$. Well-established Rap-Störmer reaction leads to 2-aroylbenzofurans while a mechanistically related reaction between 2-nitrobenzaldehydes $A_{19}$ and phenacyl thiols $A_{20}$ gives 2-aroylbenzothiophenes. The 2-aroylated heterocycles $A_{21}$ are subjected to C—C-bond formation at the carbonyl group as already described to give 3-(2-benzofuranyl)- and 3-(2-benzothiophenyl)-3-arylacrylic acid derivatives $A_{22}$ as well as 3-(2-benzofuranyl)- and 3-(2-benzothiophenyl)-3-phenylpropanoic acid derivatives $A_{23}$.

It is well known to those skilled in the art that a plethora of differently substituted 3-arylglutaric acids $B_2$ can be easily prepared from arylcarbaldehydes $A_2$ by piperidine-catalysed double acetoacetylation (scheme B) followed by double acid cleavage of intermediates $B_1$ with strong alkali hydroxide solution under reflux ($Ar_2$ as previously defined). Treatment of acids $B_2$ with acetyl chloride leads to 3-arylglutaric anhydrides $B_3$., which serve as starting material for the synthesis of 4-(benzimidazol-2-yl)-3-arylbutanoic acids $B_{10}$ and compounds derived thereof.

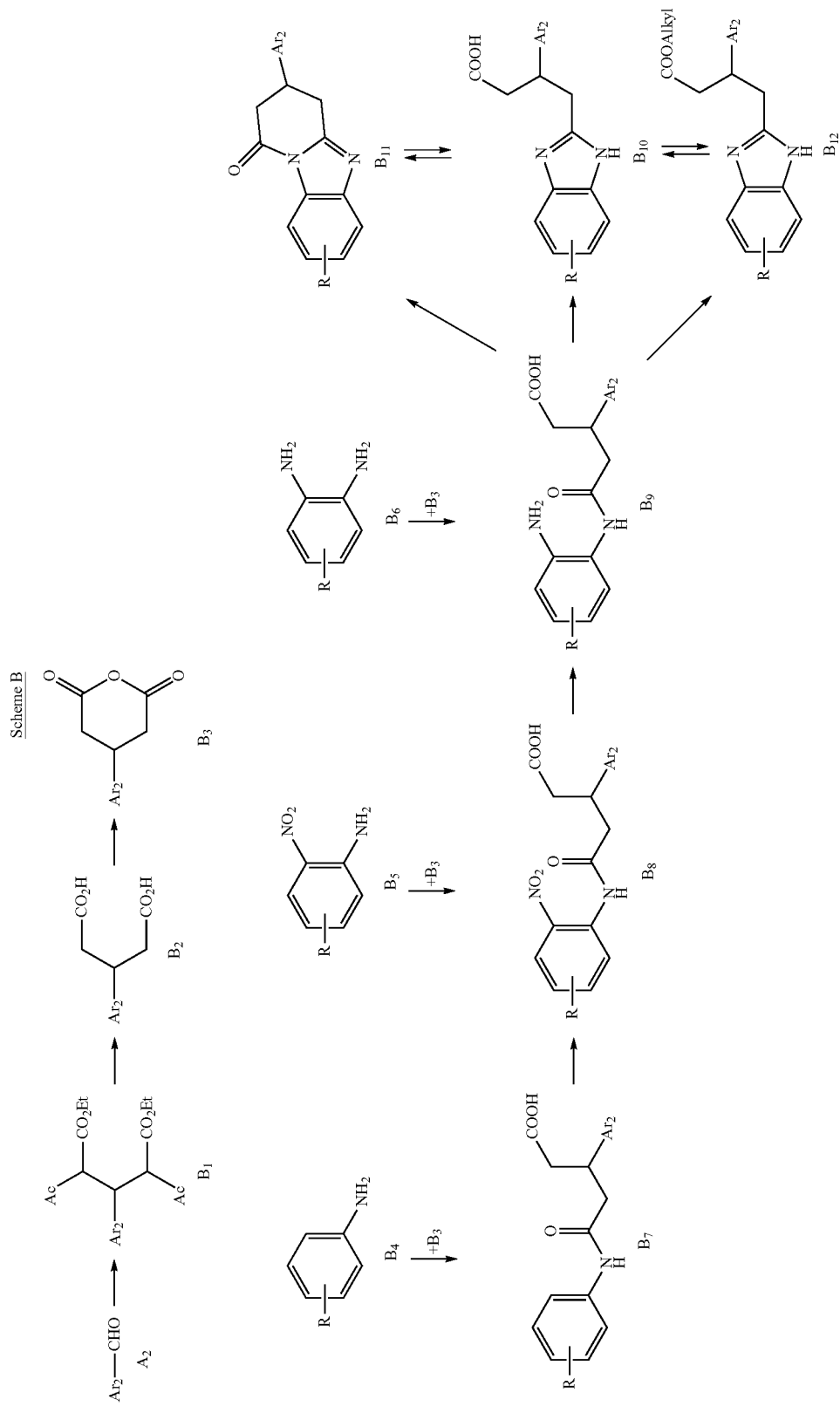

-continued
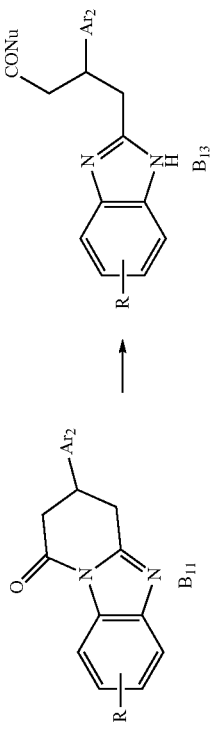
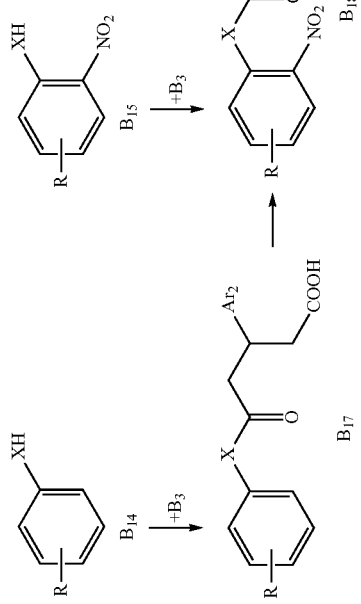
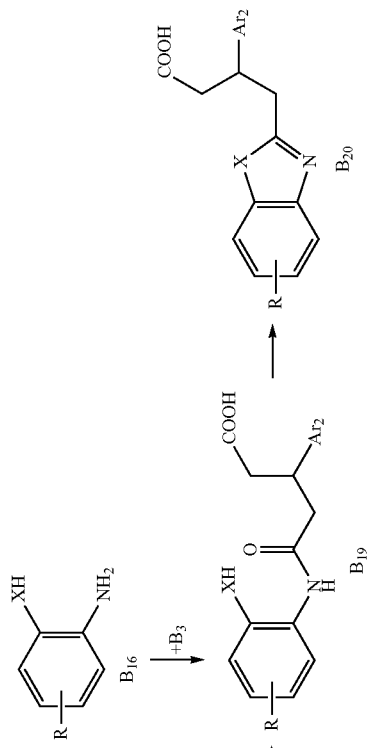
X = O, S

By standard amidation techniques $B_3$ is reacted with different o-phenylenediamines $B_6$ to give N-(o-aminophenyl)-glutaramates $B_9$. In case the appropriate diamine $B_6$ is not commercial derivatives $B_9$ are available from N-(o-nitrophenyl)-glutaramates $B_8$ which in turn are prepared either from commercial o-nitroanilines $B_5$ and anhydrides $B_3$ or by nitration of appropriately substituted 3-arylglutaric monoanilides $B_7$ (from anilines $B_4$ with ortho-amino-directing substituents and anhydrides $B_3$) with fuming nitric acid.

Depending on conditions cyclisation of glutaramates $B_9$ provides access to different derivatives of 4-(benzimidazol-2-yl)-3-arylbutanoic acids $B_{10}$. With 1,4-dioxane or acetic acid solutions of HCl under reflux the HCl-salts of $B_{10}$ are isolated from which the free bases can be liberated with alkaline washings. With mixtures of concentrated HCl and alkanols (cf. methanol, ethanol) under reflux the corresponding alkyl 4-(benzimidazol-2-yl)-3-arylbutanoates $B_{12}$ are formed. Extensive reflux of glutaramates $B_9$ in solvents like acetic acid or 1,4-dioxane solution affords the inner amides of the 4-(benzimidazol-2-yl)-3-arylbutanoic acids: the 3-aryl-3,4-dihydropyrido[1,2-a]benzimidazol-1(2H)-ones $B_{11}$. Interconversion of $B_{10}$ to $B_{11}$ (acetic anhydride, reflux) and $B_{11}$ to $B_{10}$ (acetic acid, conc. HCl, reflux) as well as interconversion of $B_{10}$ to $B_{12}$ (alkanol, catalytic HCl, reflux) and $B_{12}$ to $B_{10}$ (acetic acid, conc. HCl, reflux) is possible. Finally, additional derivatives $B_{13}$ of the 4-(benzimidazol-2-yl)-3-arylbutanoic acids $B_{10}$ are available from the corresponding inner amides $B_{11}$ by nucleophilic ring opening with oxygen, nitrogen, sulfur, and carbon nucleophiles.

Similar synthetic sequences as outlined above—starting from o-aminophenols or o-aminothiophenols $B_{16}$ and 3-arylglutaric anhydrides $B_3$—are leading to 4-(benzoxazol-2-yl)-3-arylbutanoic acids and 4-(benzothiazol-2-yl)-3-arylbutanoic acids $B_{20}$. Due to the high nucleophilicity of the sulfur atom the intermediate N-(o-mercaptophenyl)-glutaramates $B_{19}$ are often not isolable but cyclise directly to the benzothiazoles $B_{20}$. Conversely, the low nucleophilicity of the oxygen atom often demands for rather drastic conditions during the cyclisation of N-(o-hydroxyphenyl)-glutaramates $B_{19}$ to benzoxazoles $B_{20}$: neat melt, T>200° C., vacuum).

Arylmaleic acids $C_3$ are obtained by potassium carbonate mediated aldol condensation between arylacetonitriles $C_1$ and glyoxylic acid (scheme C) and subsequent hydrolysis of the intermediate β-cyanocinnamic acids $C_2$ with conc. HCl under reflux ($Ar_2$ as previously defined). Treatment of diacids $C_3$ leads to arylmaleic anhydrides $C_4$.

Scheme C

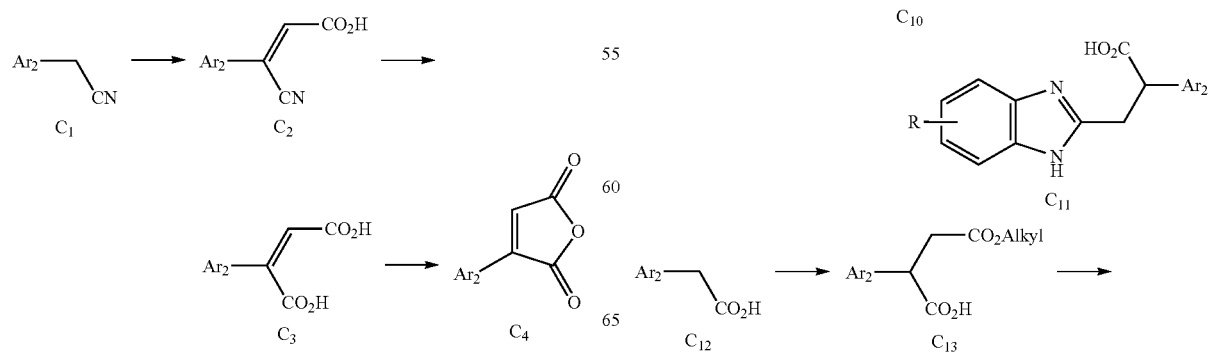

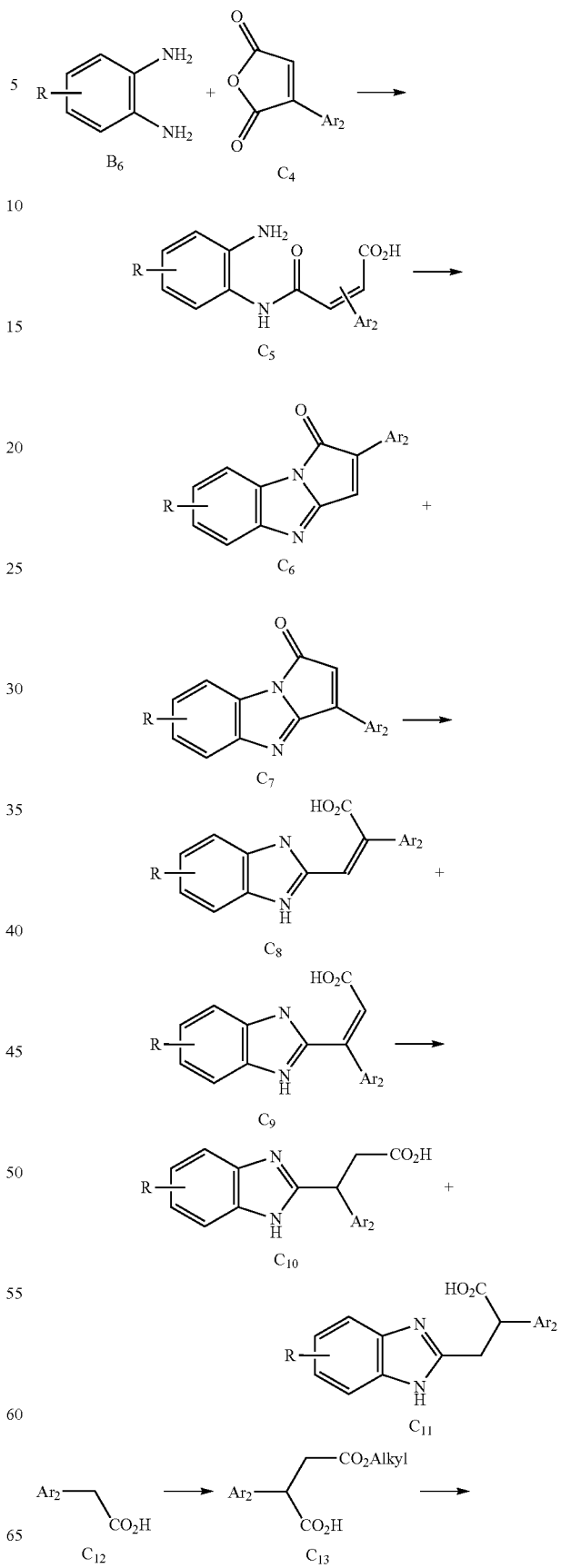

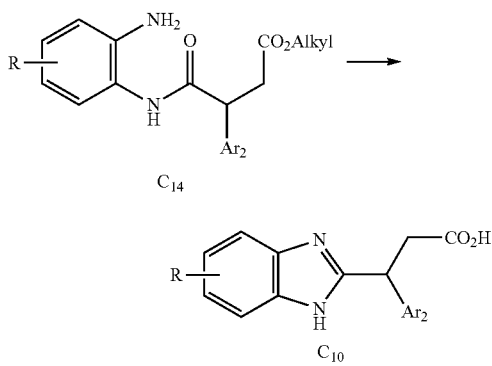

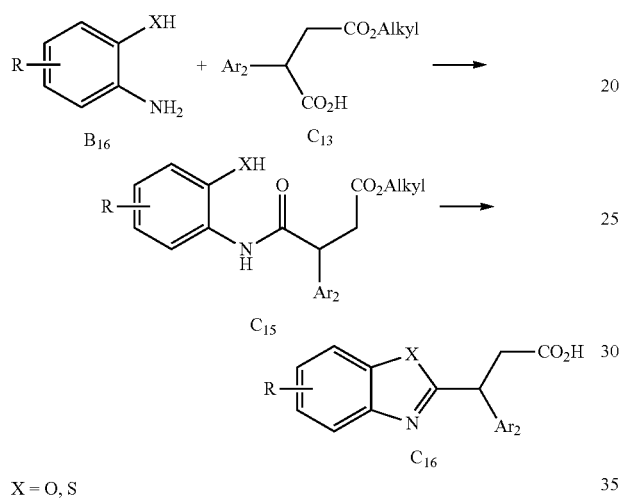

X = O, S

Reaction of anhydrides C₄ with o-phenylenediamines B₆ affords mixtures of the regioisomeric (Z)-2-aryl- and (Z)-3-aryl-4-(o-aminophenylamino)-4-oxobut-2-enoic acids C₅. These mixtures are subjected to HCl-mediated cyclisation in refluxing acetic acid to provide again regioisomeric mixtures of 2-arylpyrrolo[1,2-a]benzimidazol-1(1H)-ones C₆ and 3-arylpyrrolo[1,2-a]benzimidazol-1(1H)-ones C₇. Both isomers can be separated by fractional crystallisation and the isolated heterocycles are hydrolysed with alkali hydroxides in water/alkanol mixtures to give (Z)-2-aryl-3-benzimidazolyl-acrylic acids C₈ and (Z)-3-aryl-3-benzimidazolylacrylic acids C₉. Selective reduction of the double bonds of acids C₈ and C₉ gives access to 3-aryl-3-benzimidazolylpropanoic acids C₁₀ and 2-aryl-3-benzimidazolylpropanoic acids C₁₁.

The assignment of structures for the separated regioisomers C₆ and C₇ and compounds derived thereof is established by independent synthesis of 3-aryl-3-benzimidazolylpropanoic acids C₁₀. Therefor arylacetic acids C₁₂ are doubly deprotonated (lithium diisopropyl amide, tetrahydrofuran, −78° C.) and α-alkylated with alkyl bromoacetate to provide 2-aryl-4-alkoxy-4-oxobutanoic acids C₁₃. After conversion of acids C₁₃ to the corresponding acid chlorides (oxalyl chloride, dichloromethane) and reaction with o-phenylenediamines B₆ the corresponding 3-aryl-4-(o-aminophenylamino)-4-oxobutanoic acids C₁₄ are isolated, which are cyclised to 3-aryl-3-benzimidazolylpropanoic acids C₁₀ (acetic acid, conc. HCl, reflux).

Finally, 3-aryl-3-benzofuranylpropanoic acids and 3-aryl-3-benzothiophenyl-propanoic acids C₁₆ are accessible from o-aminophenols or o-aminothiophenols B₁₆ and 2-aryl-4-alkoxy-4-oxobutanoic acids C₁₃ in a similar way as described above. For those skilled in the art it is well known that the Rodionov variation of the Knoevenagel cinnamic acid synthesis (scheme D) offers a versatile approach to 3-amino-3-arylpropanoic acids D₁ from arylaldehydes A₂ (Ar₂ as previously defined). The homologous 4-amino-3-arylbutanoic acids D₅ are accessible by base-catalysed nitromethane addition to cinnamates D₂, subsequent reduction of the resulting adducts D₃ to give pyrrolidones D₄, and finally hydrolysis of D₄. Both amino acids D₁ and D₅ serve as starting materials for the syntheses of a number of related, benzo-annelated, 5-ring heterocycles with acidic moieties attached in 2-positions.

Scheme D

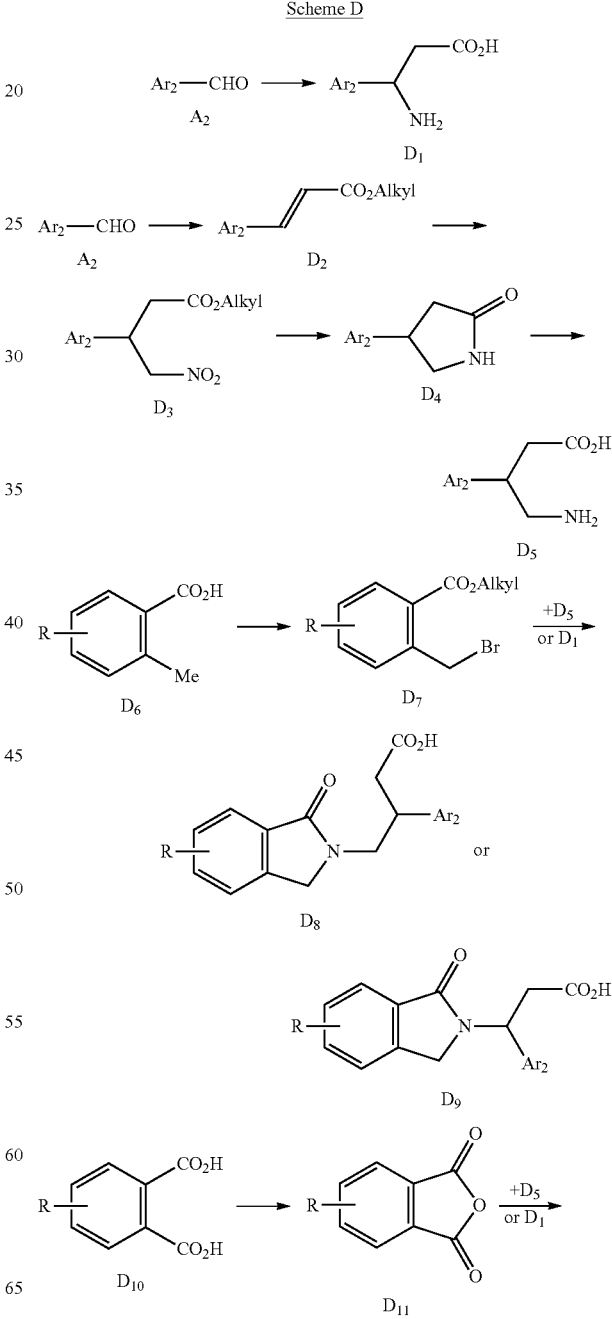

33
-continued

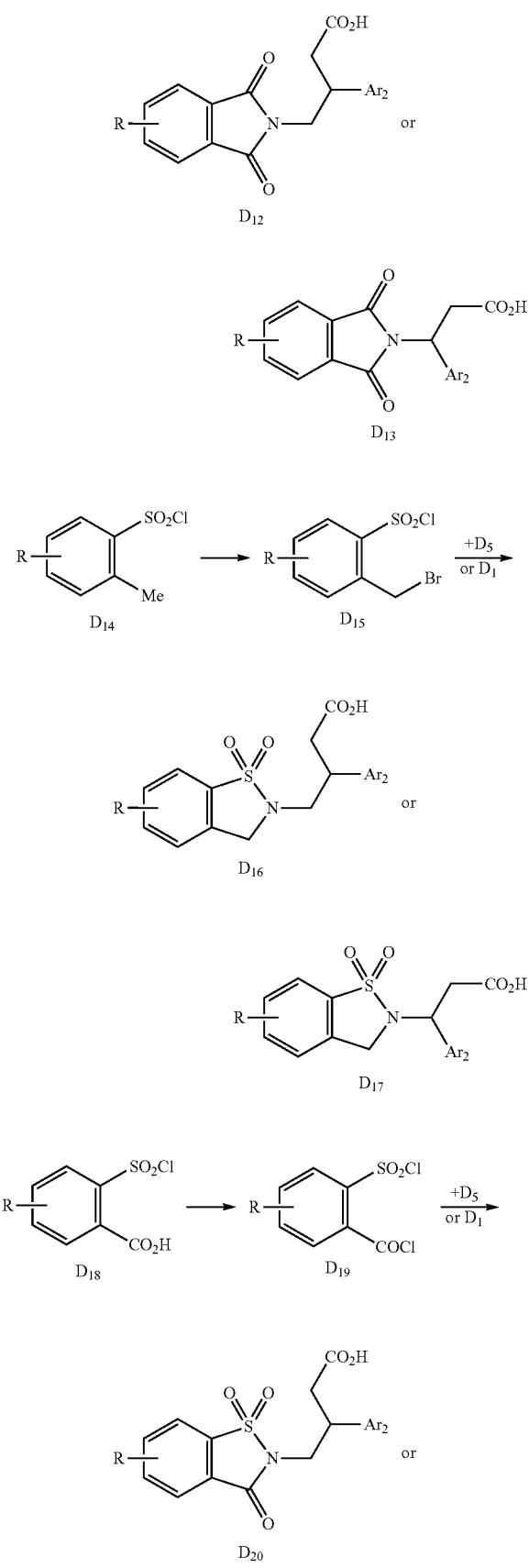

34
-continued

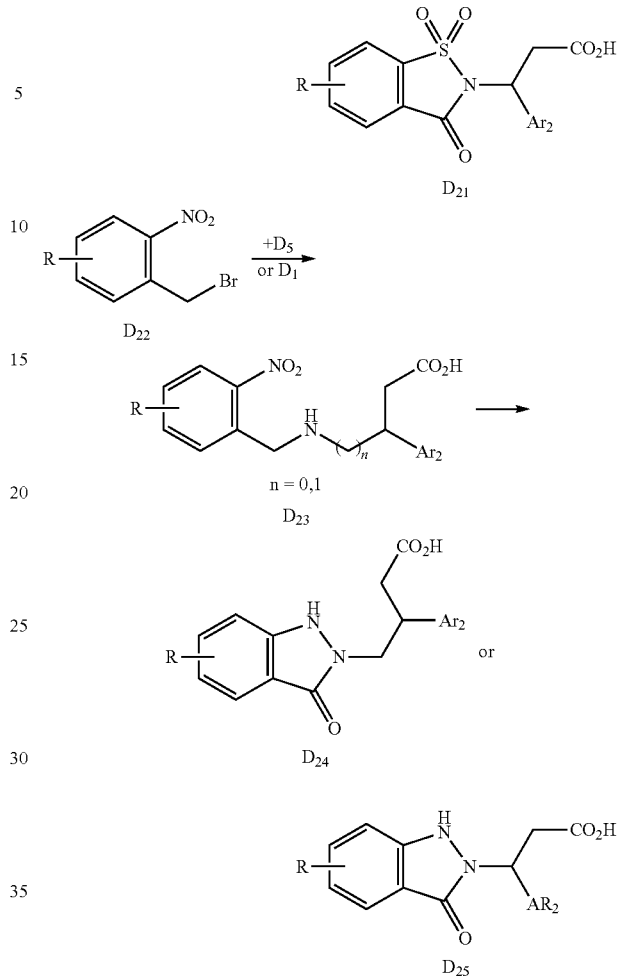

Syntheses of isoindolones $D_8$ and $D_9$ or phthalimides $D_{12}$ and $D_{13}$ can be effected by refluxing a mixture of the corresponding o-bromomethylbenzoates $D_7$ or phthalic anhydrides $D_{11}$ with the amino acids and sodium acetate in acetic acid. Benzo[d]isothiazole-1,1-dioxides $D_{16}$ and $D_{17}$ and 3-oxobenzo[d]isothiazole-1,1-dioxides $D_{20}$ and $D_{21}$ are obtainable by heating a mixture of the corresponding o-bromomethyl-benzenesulfonyl chlorides $D_{15}$ or o-chlorosulfonylbenzoyl chlorides $D_{19}$ with the amino acids in pyridine. N-Alkylation of amino acids $D_1$ or $D_5$ with o-nitrobenzyl bromides $D_{22}$ provides intermediates $D_{23}$, which cyclise on treatment with alkali hydroxides in alkanol/water mixtures to indazolones $D_{24}$ and $D_{25}$. N-Alkylation of arylamine derivatives can be effected either by nucleophilic substitution with α-haloalkanoic, halomalonic or halosuccinic acid derivatives, or by Michael addition to acrylic acid derivatives to afford compounds $E_1$ depicted in scheme E. Intermediates $E_1$ are further functionalised by N-acylation with arylacetic or arylpyruvic acids $E_2$ following established amidation techniques (cf. use of peptide coupling reagents or activation of the carboxylic acid by conversion into its acid chloride). On N-alkylation of intermediates $E_1$ with phenacylbromides $E_4$ 3-aza-3,5-diaryl-5-oxopentanoates $E_5$ are obtained, hydrolysis of which affords the corresponding free acids. A variety of N-acylated 2- or 3-arylamino-acetic or -propionic acid $E_3$ derivatives are obtained by this route.

Scheme E

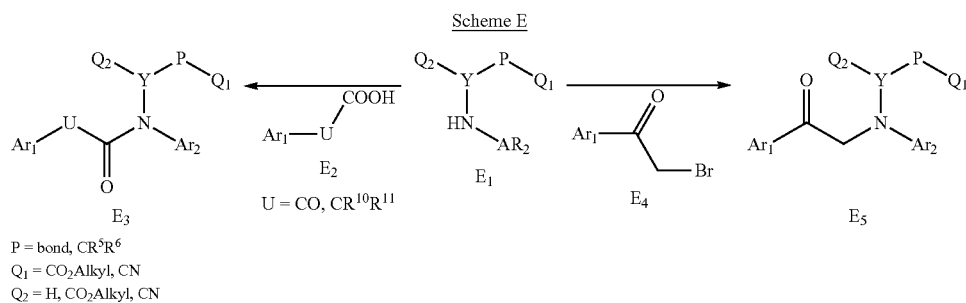

P = bond, CR$^5$R$^6$
Q$_1$ = CO$_2$Alkyl, CN
Q$_2$ = H, CO$_2$Alkyl, CN

In the following text by "binding site" a site (such as an atom, a functional group of an amino acid residue or a plurality of such atoms and/or groups) in a protein kinase binding cavity is meant, which may bind to an agent compound such as a candidate modulator (e.g. inhibitor). Depending on the particular molecule in the cavity, sites may exhibit attractive or repulsive binding interactions, brought about by charge, steric considerations and the like.

By "AGC kinases" is meant any protein kinase comprising a sequence which has a sequence identity of equal to or greater than 35% at the amino acid level within residues 37-350 of the catalytic subunit of PKA (Shoji et al., 1983). Determination of percentage sequence identity may be performed with the AMPS package as described by Barton (1994). AGC kinases are also described in detail by Hanks and Hunter, FASEB J. 9:576 (1995), and in Hanks S K, Hunter T. The eukaryotic protein kinase superfamily. In: Hardie G, Hanks S, eds. The Protein Kinase Facts Book. San Diego, Academic Press, I:7-47; 1995).

A PIF binding pocket or PIF pocket, as an example of hPDK1, is represented by the following sequence: . . . KILE K(115) RHI I(119) KENK V(124) PY V(127) T(128) RE R(131) D(132) VMSRLDHPFFVKLYF T(148) F Q(150) DDEK L(155) Y F(157) GLS . . . (SEQ ID NO:1).

In this sequence, amino acid residues defining the PIF pocket binding site in PDK1 are marked by their respective position numbers in the primary sequence of PDK1 (right of the amino acid symbol in brackets), starting with Lys-115. It includes the residues defining a phosphate binding site, here R131, T148 and Q150 (K76 is not shown).

In general, the following may be stated with respect to the pocket and the target proteins. The compounds of the invention may activate or inhibit a group of protein kinases having a hydrophobic pocket in the position equivalent to the hydrophobic pocket of mouse Protein Kinase A (PKA) that is defined by residues including Lys76, Leu116, Val80 and/or Lys111 of full-length mouse PKA.

The hydrophobic pocket-containing protein kinase may be the protein kinase termed 3-phosphoinositide-dependent protein kinase 1 (PDK1). Alternatively, it may be Serum and Glucocorticoid stimulated protein kinase (SGK), Protein Kinase B (PKB), Protein Kinase A (PKA), p70 S6 kinase, p90 RSK, PKC isoforms (for example PKCalpha, PKCbeta, PKCgamma, PKCzeta, PKCiota, PRK1, PRK1, PRK2, MSK1 or MSK2). Hydrophobic pocket-containing protein kinases include those forming part of the AGC protein kinase group, as described by Rhodopsin and G-protein coupled receptor protein kinases, for example, also have a hydrophobic pocket as defined above and the residue equivalent to Lys76 of mouse PKA is a lysine residue. Furthermore, an included family of kinases are the Aurora kinases A, B and C, which are not belonging to the AGC kinase family but are closely related and posses a hydrophobic binding pocket on the surface of the catalytic domain, which has a shape and dimension similar to the PIF binding pocket. This Aurora kinase hydrophobic pocket has been described in patents U.S. Pat. No. 7,214,518 and EP1522580, and is defined by the amino acid residues Leu164, Leu169, Leu178, Arg179, Val182, Glu183, Tyr199, His201, Val206, and Leu208 in Aurora-A kinase. Like the PIF pocket, the Aurora kinase hydrophobic pocket is about 13.6 Å in length and 8.8 Å in width, where Val206 and Leu178 side chains protrude slightly into the pocket thus forming two subpockets similar to the PIF pocket in AGC kinases, where a Leu residue (e.g., Leu155 in PDK1) serves to this purpose. As can be seen in EP1522580, the human TPX2 protein is binding with two tyrosine residues into said Aurora kinase pocket; the hydroxyl function of the serine side chain between the two tyrosine residues is interacting with Arg179 on Aurora kinase. This set of interactions can be mimicked with compounds according to the present invention as well, since in the Aurora kinase crystal structure, Arg179 and His201 appear in positions very similar to Arg131 and Gln150, respectively, in PDK1.

By "protein kinase having a hydrophobic pocket in the position equivalent to the hydrophobic pocket of mouse Protein Kinase A (PKA) that is defined by residues including Lys76, Leu116, Val80 and/or Lys111 of full-length mouse PKA" is meant a polypeptide having an amino acid sequence identifiable as that of a protein kinase catalytic domain, and further having a predicted or determined three-dimensional structure that includes a hydrophobic pocket corresponding to the region indicated in Knighton et al (1991) Science 253, 407-414 for PKA as interacting with C-terminal amino acids of full-length PKA, for example Phe348 and/or Phe351. Therefore for a subgroup of protein kinases containing the said hydrophobic pocket, it is also preferred that the said protein kinase would interact with a polypeptide containing the amino acid sequence motif Phe/Tyr-Xaa-Xaa-Phe/Tyr-Zaa, preferably Phe-Xaa-Xaa-Phe/Tyr-Zaa, more preferably Phe-Xaa-Xaa-Phe-Zaa (SEQ ID NOs:2-5), still more preferably Phe/Tyr-Xaa-Xaa-Phe/Tyr-Zaa-Phe/Tyr (SEQ ID NO:6) or Phe/Tyr-Xaa-Xaa-Phe/Tyr-COOH, where Xaa is any amino acid and Zaa is an acidic amino acid (e.g. Glu or Asp) or a phosphorylated Ser or Thr.

It is preferred that the hydrophobic pocket containing protein kinase is an AGC kinase or an Aurora kinase. AGC kinase family members can be identified by performing a BLASTP search according to Altschul S. F., et al., Nucleic Acids Res. 25:3389-3402 (1997). The search sequence to be used is the prototype of the AGC kinase group, cAMP dependent protein kinase (PKA) from human origin containing the residues corresponding to the catalytic domain:

(SEQ ID NO: 7)
FERIKTLGTGSFGRVMLVKHKETGNHYAMKILDKQKVVKLKQIEHTLNEK

RILQAVNFPFLVKLEFSFKDNSNLYMVMEYVPGGEMFSHLRRIGRFSEPH

ARFYAAQIVLTFEYLHSLDLIYRDLKPENLLIDQQGYIQVTDFGFAKRVK

GRTWTLCGTPEYLAPEIILSKGYNKAVDWWALGVLIYEMAAGYPPFFADQ

PIQIYEKIVSGKVRFPSHFSSDLKDLLRNLLQVDLTKRFGNLKNGVNDIK

NHKWF.

NCBI BLAST program reference [PMID:9254694]: Altschul S. F et al., Nucleic Acids Res. 25:3389-3402 (1997). Query length: 255 AA. Date run: 2003 Jun. 4 12:31:58 UTC+0100 on sib-blast.unil.ch. Program: NCBI BLASTP 2.2.5 [Nov. 16, 2002], Database: tremblnew; trembl; swissprot, 1,132,117 sequences; 360,517,447 total letters, Swiss-Prot Release 41.10 of 30 May 2003, TrEMBL Release23.14 of 30 May 2003, TrEMBL_new of 30 May 2003

Performing a BLASTP search in this way, proteins containing similar sequences of amino acids are retrieved and characterized by a Score (bits) and an E value. It is preferred that the protein kinases with a hydrophobic motif homologous to that which interacts with the C-terminal Phe residues contains a Score higher than 140 with an E value less than 2e−33. It is further preferred that the Score is higher than 150 with an E value less than 2e−35. It is more preferred that the Score is higher than 190 and the E value less than 5e−40. It should be noted that most of AGC kinases present in databases from different organisms will be selected using this procedure. In addition, when the score value is lower, the parameters may select for protein kinases that may not be of the AGC kinase group but closely related families, like the above mentioned Aurora protein kinases, or Ca-Calmodulin dependent protein kinases, which, because of evolutionary conservations, may contain features or regulatory mechanisms (hydrophobic PIF pocket like sites in the small lobe of the catalytic domain), similar to AGC protein kinases, and which can also be targets for the compounds according to the present invention.

It is preferred that the protein kinase has identical or conserved residues that are equivalent to Lys76, Val80, Lys111 and/or Leu116 of mouse PKA, more preferably at least Lys76 and Leu116 of mouse PKA, most preferably an identical residue equivalent to Lys76. Thus, for example, the protein kinase may have a Lys residue at the position equivalent to Lys76 of PKA and/or a Leu residue at the position equivalent to Leu116 of PKA. Lys115 and Leu155 of PDK1, for example, are equivalent to Lys76 and Leu116, respectively, of PKA. It is preferred that the protein kinase does not have an Ala at the position equivalent to Lys76 and/or a Ser, Asp or Glu at the position equivalent to Leu116 of PKA. The protein kinase may have a Val residue at the position equivalent to Leu116 of PKA, as in PRK1 and PRK2 or an Ile residue. The protein kinase may have a nonconserved residue at the position equivalent to Lys111, for example a glutamine residue and/or at the position equivalent to Val80.

The human protein kinases have been organised and tabulated. In particular, human AGC kinase group of protein kinases members has been identified from the human genome sequencing analysis (Manning G, Whyte D B, Martinez R, Hunter T, Sudarsanam S. The protein kinase complement of the human genome. Science. 2002 Dec. 6; 298(5600):1912-34. Review). The information is also available at http://www.kinase.com.

Protein kinases show a conserved catalytic core, as reviewed in Johnson et al (1996) Cell, 85, 149-158 and Taylor & Radzio-Andzelm (1994) Structure 2, 345-355. This core folds into a small N-terminal lobe largely comprising antiparallel .beta.-sheet, and a large C-terminal lobe which is mostly alpha-helical. A deep cleft at the interface between these lobes is the site of ATP binding, with the phosphate groups near the opening of the cleft.

Protein kinases also show conserved sequences within this catalytic core, and the residue equivalent to a given residue of, for example, PKA, may be identified by alignment of the sequence of the kinase with that of known kinases in such a way as to maximize the match between the sequences. The alignment may be carried out by visual inspection and/or by the use of suitable computer programs, for example the GAP program of the University of Wisconsin Genetic Computing Group, which will also allow the percent identity of the polypeptides to be calculated. The Align program (Pearson (1994) in: Methods in Molecular Biology, Computer Analysis of Sequence Data, Part II (Griffin, A M and Griffin, H G eds) pp 365-389, Humana Press, Clifton) may also be used.

Small molecule compounds are naturally occurring or synthetically accessible chemical structures having a molecular weight less than 1000, preferably less than 700, most preferably less than 550. The compounds typically have a molecular weight above 250.

The invention relates to the general finding that small molecule compounds can be activators or inhibitors of AGC protein kinases and of Aurora kinases, which possess a hydrophobic surface pocket (termed e.g. HM/PIF binding pocket for an AGC kinase) in the N-terminal lobe of the catalytic domain. The patent describes activators of PDK1 and inhibitors of PDK1, PKB, SGK, PKCzeta, PKCiota, Aurora kinases and further AGC kinases. The invention also relates to methods of treating diseases associated with protein kinases, especially diseases associated with AGC kinases, PDK1 signalling and PKB signalling such as cancer, or diabetes. The present invention relates, in particular, to the discovery that small molecule compounds, of less than 500 of molecular weight (MW) can regulate the activity of AGC kinases containing a PIF pocket homologous site in the small lobe of the kinase domain. In addition, compounds are described that can activate or inhibit AGC protein kinases, for example, PDK1 and PKB. The compounds described have overall good pharmacological properties. The compounds presented, or derivatives of these can be used for treatment of conditions where there is need for activating or inhibiting protein kinases of the AGC family.

The term "alkylidene chain" refers to an optionally substituted, straight or branched carbon chain that may be fully saturated or have one or more units of unsaturation. A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week. Unless otherwise stated, structures depicted herein are also meant to include all stereochemical forms of the structure; i.e., the R and S configurations for each asymmetric center. Therefore, single isolated stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of one or several hydrogen atoms by deuterium or tritium atoms, or the replacement of one or several carbon atoms by $^{13}C$ or $^{14}C$ are within the scope of this invention.

Compounds of formula I or salts thereof may be formulated into compositions. In a preferred embodiment, the composition is a pharmaceutical composition (aspect (2) of the invention). In one embodiment, the composition comprises an amount of the protein kinase inhibitor effective to inhibit a protein kinase, particularly an AGC kinase or Aurora kinase, in a biological sample or in a patient. Compounds of this invention and pharmaceutical compositions thereof, which comprise an amount of the protein kinase inhibitor effective to treat or prevent an AGC or Aurora kinase-mediated condition and a pharmaceutically acceptable carrier, adjuvant, or vehicle, may be formulated for administration to a patient. The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

Aspect (6) of this invention relates to a method of treating or preventing an AGC kinase mediated disease with an AGC kinase inhibitor, which method comprises administering to a patient in need of such a treatment a therapeutically effective amount of a compound of formula I or a pharmaceutical composition thereof. Another aspect of this invention relates to a method of treating or preventing an AGC kinase mediated disease with an AGC kinase activator, which method comprises administering to a patient in need of such a treatment a therapeutically effective amount of a compound of formula I or a pharmaceutical composition thereof.

Aspect (2) of this invention provides a composition comprising a compound of formula I and a pharmaceutically acceptable carrier.

Aspect (6) of this invention relates to a method of treating or preventing an AGC kinase mediated disease with an AGC kinase inhibitor, which method comprises administering to a patient in need of such a treatment a therapeutically effective amount of a compound of formula I or a pharmaceutical composition thereof.

A preferred embodiment of aspect (6) of the invention relates to a method of inhibiting an AGC kinase activity in a patient, which method comprises administering to the patient a compound of formula I or a composition comprising said compound.

A further preferred embodiment of aspect (6) of the invention relates to a method of treating or preventing an PDK1-mediated diseases with a PDK1 inhibitor, which method comprises administering to a patient in need of such a treatment a therapeutically effective amount of a compound of formula I or a pharmaceutical composition thereof. The terms "PDK1-mediated disease" or "PDK1-mediated condition", as used herein, mean any disease or other deleterious condition in which PDK1 is known to play a role. The terms "PDK1-mediated disease" or "PDK1-mediated condition" also mean those diseases or conditions that are alleviated by treatment with a PDK1 inhibitor or activator. PDK1-mediated diseases or conditions include, but are not limited to, proliferative disorders, cancer, and neurodegenerative disorders, diabetes. Another aspect of the invention relates to inhibiting PDK1 activity in a biological sample or a patient, which method comprises administering to the patient a compound of formula I or a composition comprising said compound.

A further aspect of the invention relates to activating PDK1 activity in a biological sample or a patient, which method comprises administering to the patient a compound of formula I or a composition comprising said compound.

Another aspect of this invention relates to a method of treating or preventing a PKB-mediated diseases with a PKB inhibitor, which method comprises administering to a patient in need of such a treatment a therapeutically effective amount of a compound of formula I or a pharmaceutical composition thereof. The terms "PKB-mediated disease" or "PKB-mediated condition", as used herein, mean any disease or other deleterious condition in which PKB is known to play a role. The terms "PKB-mediated disease" or "PKB-mediated condition" also mean those diseases or conditions that are alleviated by treatment with a PKB inhibitor.

PKB-mediated diseases or conditions include, but are not limited to, proliferative disorders, cancer, and neurodegenerative disorders. The association of PKB, also known as protein kinase AKT, with various diseases has been described [Khwaja, A., Nature, pp. 33-34, 1990; Zang, Q. Y., et al, Oncogene, 19 2000; Kazuhiko, N., et al, The Journal of Neuroscience, 20 2000]. Another aspect of the invention relates to inhibiting PKB activity in a biological sample or a patient, which method comprises administering to the patient a compound of formula I or a composition comprising said compound.

Another aspect of this invention relates to a method of treating or preventing a GSK-3-mediated disease with a PKB activator, which method comprises administering to a patient in need of such a treatment a therapeutically effective amount of a compound of formula I or a pharmaceutical composition thereof.

Another aspect of this invention relates to a method of treating or preventing a GSK-3-mediated disease with a PDK1 activator, which method comprises administering to a patient in need of such a treatment a therapeutically effective amount of a compound of formula I or a pharmaceutical composition thereof. One aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients.

Another aspect of this invention relates to inhibiting the production of hyperphosphorylated Tau protein, which is useful in halting or slowing the progression of Alzheimer's disease.

Another aspect of this invention relates to a method of inhibiting GSK-3 activity in a patient, which method comprises administering to the patient a compound of formula I or a composition comprising said compound.

Another aspect relates to inhibiting GSK-3 activity in a biological sample, which method comprises contacting the biological sample with the PKB activator of formula I, or a pharmaceutical composition thereof, in an amount effective to inhibit GSK-3.

Another aspect relates to inhibiting GSK-3 activity in a biological sample, which method comprises contacting the biological sample with the PDK1 activator of formula I, or a pharmaceutical composition thereof, in an amount effective to inhibit GSK-3.

Each of the aforementioned methods directed to the inhibition of GSK-3, or the treatment of a disease alleviated thereby, is preferably carried out with a preferred compound of formula I. The terms "GSK-3-mediated disease" or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS associated dementia, amyotrophic lateral sclerosis (AML), multiple sclerosis (MS), schizophrenia, cardiomycete hypertrophy, reperfusion/ischemia, and baldness.

Another aspect of the invention relates to inhibiting GSK-3 activity in a biological sample, which method comprises contacting the biological sample with a PKB or PDK1 activator of formula I. Another aspect of this invention relates to a method of inhibiting GSK-3 activity in a patient, which method comprises administering to the patient a compound of formula I or a composition comprising said compound. Example 7 provides crystallographic evidence for allosteric changes induced by low molecular weight compound binding to the PIF-binding pocket on PDK1. In particular, PS48 induced changes at Phe93 within the Gly rich loop at the top of the ATP binding site. A polypeptide comprising this region of the protein was also found to be protected from deuterium exchange upon incubation of the PDK1 protein with PS48 and PS08 (=PS-T8) low molecular weight compounds. Furthermore, using a fluorescent probe as a third independent method, we also verified that there was an allosteric change on the ATP binding site upon interaction of low molecular weight compound activators onto the PIF-binding pocket of PDK1.

The allosteric communication between the PIF-binding pocket and PDK1 brings about a means of inhibiting the activity of kinases having an allosteric regulatory site with similar characteristics to the PIF-binding pocket on PDK1. The method involves the use of two compounds, one binding to the regulatory site and a second, which binds to the ATP binding site. Since both sites will, together, stabilize a particular conformation of the kinase, compounds do not need to be specific for one kinase in order to stabilize, for example inhibit, a given protein kinase specifically.

The method of the invention uses two compounds, one binding to the regulatory site, the PIF-binding pocket, and a second, which binds to the ATP binding site. Since both sites will, together, stabilize a particular conformation of the kinase, compounds do not need to be specific for one kinase in order to stabilize, for example inhibit, a given protein kinase specifically.

Thus, in aspects (2) to (6) if the invention the compounds of aspect (1) of the invention can be used in combination with a second compound, ATP competitor compound identified with the method of the invention, for co-administration into assays or kits of parts or, within a pharmacologically appropriate form, into organisms, including human beings, for inhibition of kinases having a site to bind to the allosteric compound which stabilizes the ATP binding site into a conformation suitable for binding of the second ATP competitive compound.

The present invention also comprises the use of a compound of the invention in the screening for ATP competitive compounds which bind to the form of the ATP binding site stabilized by the compound of the invention.

Alternatively, a linker could bring together into one molecule the two individually identified PIF-binding pocket compound and ATP competitive compound.

An assay of the invention makes use of a compound of the invention, together with a protein kinase having an appropriate allosteric regulatory site together with a test compound, in order to identify if the given test compound binds to the ATP binding site, in the form stabilized by allosteric compound of the invention.

The method of the invention can use an allosteric compound of the invention which stabilizes the active conformation of the kinase or, alternatively, one that stabilizes an inactive conformation. In both cases, when the two compounds are used in a combined manner, they will both lead to inhibition of the target kinase, with higher potency than each of the compounds on its own. This embodiment of the invention will have two major advantages: Firstly, the occurrence of point mutations leading to resistance against a single small molecule inhibitor will be substantially reduced since inhibition is achieved by binding of two small molecules to two different, non overlapping binding sites of the same protein. In this case, resistance can only effectively occur if two appropriate point mutations are generated in the cell at the same time which simultaneously affect binding of the two compounds two either binding site. The probability of such an event is very low. Secondly, a compound identified and optimized to bind to an the ATP binding site in another than the basal conformation will have good chances to be more selective per se, because particular conformations and constellations of amino acid residues can be exploited which are more restricted to only a family or some individual protein kinases. A good example was provided by the inhibitor gleevec (imatinib mesylate), which was found to bind to the inactive conformation of the Bcr-Abl tyrosine kinase, thus achieving relative selectivity due to the fact that the inactive conformations of human protein kinases are significantly diverse whereas the more commonly targeted active conformations are highly conserved (Nagar, B. et al. Cancer Res. 2002, 62, 4236-4243).

Therefore, one preferred embodiment for the method of the invention requires the use of a protein kinase having a HM/PIF-binding pocket regulatory site in the presence of a compound of the invention that binds to the HM/PIF-binding pocket and further testing of a second type of compound for its binding to the ATP binding site in the conformation stabilized by the allosterically acting compound of the invention and selecting for compounds which binds to the ATP binding site in the presence of the allosteric compound of the invention.

The test can be an in silico tested for the interaction, using structural information, as can be derived from crystallography work as presented in Example 7. It is preferred that the structural evaluation is performed with the support of suitable software, such as software suitable for evaluating and ranking compounds according to their potential to dock to the site. The structural data used for the in silico screening can be that derived from the crystallography of the protein kinase target in complex with the allosteric compound. Alternatively, the structural coordinates may be derived from models obtained from comparing the experimentally obtained data from similar protein kinases.

Alternatively, the test of the invention can be any suitable in vitro test, which identifies compounds which bind to the ATP binding site. The in vitro suitable tests are for example those that can measure the displacement of a labelled compound known to bind to the ATP binding site. The assay of the invention can be made into high throughput format (HTS), for the screening of libraries of compounds. The libraries can be those already available to be enriched in compounds capable of binding to the active site of protein kinases or, alternatively, unbiased libraries of compounds. When the test is performed in HTS format, an homogeneous assay is preferred. Furthermore, a fluorescent or luminescent read-out is also preferred for HTS formats. The assay of the invention may use TNP-ATP, as described in Example 7, or similarly fluorescent analogues, to probe the conformation of the ATP binding site. Alternatively, the assay of the invention may use staurosporine or any other suitable ATP competitive compound which can be labelled without completely disrupting its binding to the kinase target. The kinabeads technology as published by Bantscheff et al. (Nature Biotechnology 25, 1035-1044 (2007)) is also appropriate to identify compounds which competitively bind to the ATP binding site of an AGC or Aurora kinase in the presence of an allosteric effector according to our invention. The readout for the assay of this aspect of our invention can be based on luminescence, fluorescence intensity, fluorescence polarization, alpha screen, and on further techniques well known to experts skilled in the art.

The term "patient" includes human and veterinary subjects. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof. An amount effective to inhibit or activate a protein kinase, for example PDK1, PKB, or GSK3, is an amount that causes measurable inhibition or activation of the kinase activity when compared to the activity of the enzyme in the absence of a compound. Any method may be used to determine inhibition, such as, for example, the Biological Testing Examples described below.

Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene-polyoxypropylene-block polymers, polyethylene glycol and wool fat. The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable nonirritating excipient which is solid at room temperature but liquid at rectal temperature and therefore will melt in the rectum to release the drug. Such materials include cocoa butter, beeswax and polyethylene glycols. The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. In addition to the compounds of this invention, pharmaceutically acceptable derivatives or prodrugs of the compounds of this invention may also be employed in compositions to treat or prevent the above-identified diseases or disorders. A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitory active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species. Pharmaceutically acceptable prodrugs of the compounds of this invention include, without limitation, the following derivatives of the present compounds: esters, amino acid esters, phosphate esters, metal salts sulfonate esters, carbamates, and amides. Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleat, malonate, methanesulfonate, 2naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N+ (C14 alkyl)4 salts. This invention also envisions the quaternization of any basic nitrogen-containing groups of the compounds disclosed herein. Water or oil-soluble or dispersible products may be obtained by such quaternization. The amount of the protein kinase inhibitor/activator that may be combined with the carrier materials to produce a single dosage form will vary depending upon the patient treated and the particular mode of administration. Preferably, the compositions should be formulated so that a dosage of between 0.01-100, preferably 0.1-20, mg/kg body weight/day of the inhibitor or activator can be administered to a patient receiving these compositions. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition. Depending upon the particular protein kinase mediated condition to be treated or prevented, additional therapeutic agents, which are normally administered to treat or prevent that condition, may be administered together with the inhibitors or activators of this invention. For example, in the treatment of cancer other chemotherapeutic agents or other antiproliferative agents may be combined with the present compounds to treat cancer. These agents include, without limitation, adriamycin, dexamethasone, vincristine, cyclophosphamide, fluorouracil, topotecan, taxol, interferons, and platinum derivatives. Other examples of agents the inhibitors of this invention may also be combined with including, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti convulsants, ion channel blockers, riluzole, and anti Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin. Those additional agents may be administered separately from the protein kinase inhibitor/activator-containing composition, as part of a multiple dosage regimen. Alternatively, those agents may be part of a single dosage form, mixed together with the protein kinase inhibitor or activator of this invention in a single composition. Compounds of this invention may exist in alternative tautomeric forms. Unless otherwise indicated, the representation of either tautomer is meant to include the other.

The invention is further explained by means of the following non-limiting examples.

EXAMPLES

Example 1

Preparation of AGC Kinase and Aurora Kinase Modulators 1.1. 4-(2-Benzimidazolyl)-3-(4-chlorophenyl)butanoic acid•HCl (PS 153)

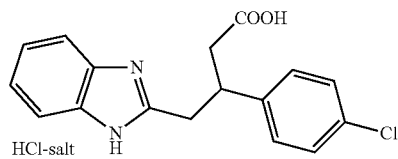 [SMILES: O=C(O)CC(Cc1nc2ccccc2[nH]1)c1ccc(Cl)cc1]

1) 3-(4-Chlorophenyl)glutaric anhydride

The suspension of commercial 3-(4-chlorophenyl)glutaric acid (15 g) in acetyl chloride (20 ml) was heated to reflux for 2 h. Then precipitation of the product is completed by addition of petrol ether (50 ml) and cooling to rt. The precipitate is isolated by suction filtration, washed with petrol ether, and dried in vacuo to give 3-(4-chlorophenyl)glutaric anhydride (13.3 g) as colourless crystals.

2) N-(2-Aminophenyl)-3-(4-chlorophenyl)glutaramic acid

The solution of commercial 1,2-phenylenediamine (1.08 g) and 3-(4-chlorophenyl)glutaric anhydride (2.25 g) in 1,4-dioxane (7 ml) was stirred at rt for 10 min. A voluminous precipitate is formed which is kept at rt for further 50 min. The thick slurry is heated to reflux with methanol, cooled to rt, isolated by suction filtration, and washed with methanol. After drying in vacuo N-(2-aminophenyl)-3-(4-chlorophenyl)glutaramic acid (2.1 g) is obtained as off-white solid.

3) Ethyl 4-(2-benzimidazolyl)-3-(4-chlorophenyl)butanoate

N-(2-Aminophenyl)-3-(4-chlorophenyl)glutaramic acid (2.04 g) is dissolved in a mixture of ethanol (20 ml) and conc. HCl (5 ml) and heated to reflux overnight. The ethanol is removed in vacuo and the aqueous layer is neutralised with 10M NaOH. Saturated sodium bicarbonate solution (40 ml) is added and the aqueous layer is extracted twice with dichloromethane (50 ml). The combined organic layers are dried (sodium sulfate) and concentrated. The residue is purified by flash chromatography (dichloromethane/3% methanol/1% triethyl amine) on silica gel to afford ethyl 4-(2-benzimidazolyl)-3-(4-chlorophenyl)butanoate (1.39 g) as yellowish solid.

4) 4-(2-Benzimidazolyl)-3-(4-chlorophenyl)butanoic acid•HCl

The solution of ethyl 4-(2-benzimidazolyl)-3-(4-chlorophenyl)butanoate (200 mg) in a mixture of acetic acid (1 ml) and conc. HCl (0.25 ml) was heated at 100° C. for 1 h. Then toluene (30 ml) was added and all volatiles were removed by distillation. Distillation was repeated with further toluene (30 ml). The oily residue is treated with diethyl ether to induce crystallisation, triturated with acetone, and dried in vacuo to leave 4-(2-benzimidazolyl)-3-(4-chlorophenyl)butanoic acid•HCl (208 mg) as light red solid.

$^{1}$H-NMR (500 MHz, DMSO-d$_{6}$): δ (ppm)=2.73 (dd, J=16.2, 8.6 Hz, 1H), 2.83 (dd, J=16.2, 6.1 Hz, 1H), 3.46 (dd, J=15.0, 9.4 Hz, 1H), 3.58 (dd, J=15.0, 6.7 Hz, 1H), 3.89 (m, 1H), 7.30 (d, J=8.5 Hz, 2H), 7.37 (d, J=8.5 Hz, 2H), 7.47 (m, 2H), 7.71 (m, 2H).

$^{13}$C-NMR and DEPT (125 MHz, DMSO-d$_{6}$): δ (ppm)= 32.43 (CH$_{2}$), 39.16 (CH), 39.69 (CH$_{2}$), 113.62 (2CH), 125.34 (2CH), 128.33 (2CH), 129.14 (2CH), 130.61 (2C), 131.42 (C), 140.65 (C), 151.78 (C), 172.08 (CO).

MS (+ESI): m/z=315 (M+H).

1.2. 4-(2-Benzimidazolyl)-3-phenylbutanoic acid•HCl (PS 155)

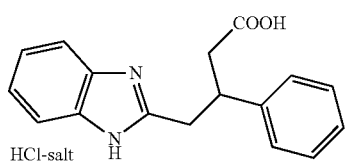 [SMILES: O=C(O)CC(Cc1nc2ccccc2[nH]1)c1ccccc1]

1) 3-Phenylglutaric anhydride

The mixture of benzaldehyde (21.22 g) and ethyl acetoacetate (52.06 g) was cooled in an ice bath. Piperidine (3.3 ml) was added with stirring. The resulting mixture was kept at rt for 3 days whereupon it solidifies. The solid was recrystallised from ethanol (100 ml) to give a light yellowish solid (the bis-adduct of acetoacetate to benzaldehyde). The powdered solid was added in portions to 50% NaOH (200 ml) with stirring. The resulting yellow slurry was diluted with ethanol (70 ml) and stirred at reflux for 2 h. After addition of ice water (100 ml) and cooling in an ice bath the mixture was acidified with conc. HCl to give a white precipitate. The solid was collected by suction filtration and washed with water. After drying in vacuo 3-phenylglutaric acid (16.4 g) was obtained as colourless crystals.

The suspension of 3-phenylglutaric acid (16.39 g) in acetyl chloride (28.6 ml) was heated to reflux with stirring for 2 h. Then precipitation of the product is completed by addition of petrol ether (70 ml) and cooling to rt. The precipitate is isolated by suction filtration, washed with petrol ether, and dried in vacuo to give 3-phenylglutaric anhydride (13.24 g) as colourless crystals.

2) 4-(2-Benzimidazolyl)-3-phenylbutanoic acid HCl

By a procedure similar to that of example 1.1, starting from 1,2-phenylenediamine and 3-phenylglutaric anhydride, 4-(2-benzimidazolyl)-3-phenylbutanoic acid•HCl was obtained as colourless solid in three steps.

$^{1}$H-NMR (500 MHz, DMSO-d$_{6}$): δ (ppm)=2.72 (dd, J=16.1, 8.3 Hz, 1H), 2.82 (dd, J=16.1, 6.4 Hz, 1H), 3.47 (dd, J=14.9, 9.4 Hz, 1H), 3.59 (dd, J=14.9, 7.0 Hz, 1H), 3.88 (m, 1H), 7.14 (t, J=7.3 Hz, 1H), 7.24 (t, J=7.6 Hz, 2H), 7.33 (d, J=7.6 Hz, 2H), 7.46 (m, 2H), 7.71 (m, 2H).

$^{13}$C-NMR and DEPT (125 MHz, DMSO-d$_{6}$): δ (ppm)= 32.59 (CH$_{2}$), 39.73 (CH), 39.94 (CH$_{2}$), 113.58 (2CH), 125.32 (2CH), 126.87 (CH), 127.13 (2CH), 128.39 (2CH), 130.57 (2C), 141.65 (C), 152.03 (C), 172.22 (CO).

MS (+ESI): m/z=281 (M+H).

1.3. 4-(5-Chloro-2-benzimidazolyl)-3-phenylbutanoic acid•HCl (PS 154)

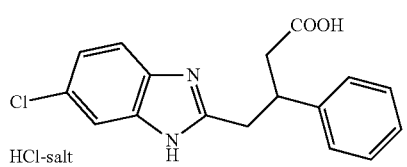 [SMILES: O=C(O)CC(Cc1nc2ccc(Cl)cc2[nH]1)c1ccccc1]

By a procedure similar to that of example 1.1, starting from commercial 4-chloro-1,2-phenylenediamine and 3-phenylglutaric anhydride, 4-(5-chloro-2-benzimidazolyl)-3-phenylbutanoic acid•HCl was obtained as light red solid in three steps.

$^{1}$H-NMR (500 MHz, DMSO-d$_{6}$): δ (ppm)=2.71 (dd, J=16.1, 8.3 Hz, 1H), 2.82 (dd, J=16.1, 6.4 Hz, 1H), 3.44 (dd, J=14.9, 9.1 Hz, 1H), 3.55 (dd, J=14.9, 7.1 Hz, 1H), 3.84 (m, 1H), 7.15 (t, J=7.3 Hz, 1H), 7.24 (t, J=7.4 Hz, 2H), 7.32 (d, J=7.4 Hz, 2H), 7.48 (dd, J=8.7, 1.9 Hz, 1H), 7.72 (d, J=8.7 Hz, 1H), 7.81 (d, J=1.9 Hz, 1H).

$^{13}$C-NMR and DEPT (125 MHz, DMSO-d$_{6}$): δ (ppm)= 32.87 (CH$_{2}$), 39.77 (CH), 39.81 (CH$_{2}$), 113.50 (CH), 115.20 (CH), 125.43 (CH), 126.87 (CH), 127.11 (2CH), 128.39 (2CH), 129.48 (C), 129.99 (C), 131.96 (C), 141.72 (C), 153.52 (C), 172.25 (CO).

MS (+ESI): m/z=315 (M+H).

1.4. 4-(5-Chloro-2-benzimidazolyl)-3-(4-chlorophenyl)butanoic acid•HCl (PS 114)

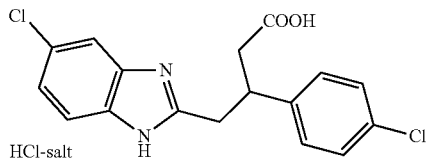 [SMILES: O=C(O)CC(Cc1nc2cc(Cl)ccc2[nH]1)c1ccc(Cl)cc1]

The solution of 4-chloro-1,2-phenylenediamine (2.85 g) and 3-(4-chlorophenyl)-glutaric anhydride (4.49 g) in 1,4-dioxane (7 ml) was stirred at rt for 1 h. The precipitate is collected by suction filtration, washed with 1,4-dioxane, and dried in vacuo to provide a mixture of regioisomeric amides (5.37 g) as beige coloured solid.

This solid is dissolved in acetic acid (10 ml) with heating. Conc. HCl (4 ml) is added and the resulting solution is heated to reflux for 2 h. Then all volatiles are removed at the water aspirator and the still hot residue is suspended in acetone (20 ml). The suspension is cooled to rt with stirring and the solid is isolated by filtration. After washings with acetone the off-white solid is dried in vacuo to yield the hydrochloride salt of 4-(5-chloro-2-benzimidazolyl)-3-(4-chlorophenyl)butanoic acid (4.66 g).

$^1$H-NMR (500 MHz, DMSO-d$_6$): δ (ppm)=2.72 (dd, J=16.2, 8.6 Hz, 1H), 2.83 (dd, J=16.2, 6.2 Hz, 1H), 3.43 (dd, J=14.9, 9.2 Hz, 1H), 3.55 (dd, J=14.9, 6.9 Hz, 1H), 3.86 (m, 1H), 7.30 (d, J=8.5 Hz, 2H), 7.36 (d, J=8.5 Hz, 1H), 7.48 (dd, J=8.8, 1.9 Hz, 1H), 7.73 (d, J=8.8 Hz, 1H), 7.81 (d, J=1.8 Hz, 1H).

$^{13}$C-NMR and DEPT (125 MHz, DMSO-d$_6$): δ (ppm)= 32.67 (CH$_2$), 39.19 (CH), 39.60 (CH$_2$), 113.55 (CH), 115.25 (CH), 125.51 (CH), 128.34 (2CH), 129.14 (2CH), 129.56 (C), 129.96 (C), 131.43 (C), 131.92 (C), 140.70 (C), 153.27 (C), 172.11 (CO).

MS (+ESI): m/z=349 (M+H).

1.5. 3-(4-Chlorophenyl)-4-(5-fluoro-2-benzimidazolyl)butanoic acid•HCl (PS 170)

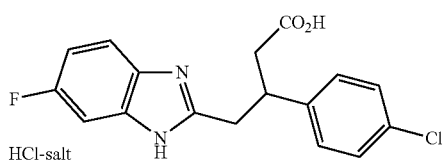 [SMILES: O=C(O)CC(Cc1nc2ccc(F)cc2[nH]1)c1ccc(Cl)cc1]

By a procedure similar to that of 1.4, starting from commercial 4-fluoro-1,2-phenylenediamine and 3-(4-chlorophenyl)glutaric anhydride, 3-(4-chlorophenyl)-4-(5-fluoro-2-benzimidazolyl)butanoic acid•HCl was obtained as colourless solid.

$^1$H-NMR (500 MHz, DMSO-d$_6$): δ (ppm)=2.72 (dd, J=16.2, 8.6 Hz, 1H), 2.82 (dd, J=16.2, 6.1 Hz, 1H), 3.44 (dd, J=15.0, 9.2 Hz, 1H), 3.55 (dd, J=15.0, 6.9 Hz, 1H), 3.87 (m, 1H), 7.27-7.39 (m, 5H), 7.59 (dd, J=8.5, 2.4 Hz, 1H), 7.74 (dd, J=9.0, 4.5 Hz, 1H).

$^{13}$C-NMR and DEPT (125 MHz, DMSO-d$_6$): δ (ppm)= 32.61 (CH$_2$), 39.17 (CH), 39.64 (CH$_2$), 100.40 (CH, $^2J_{C-F}$=27.8 Hz), 113.65 (CH, $^2J_{C-F}$=25.7 Hz), 115.20 (CH, $^3J_{C-F}$=10.5 Hz), 127.66 (C), 128.33 (2CH), 129.15 (2CH), 131.38 (C, $^3J_{C-F}$=10.0 Hz), 131.45 (C), 140.71 (C), 153.18 (C), 159.64 (C, $^1J_{C-F}$=241.1 Hz), 172.09 (CO).

MS (+ESI): m/z=333 (M+H).

1.6. 4-(5-Bromo-2-benzimidazolyl)-3-(4-chlorophenyl)butanoic acid•HCl (PS 169)

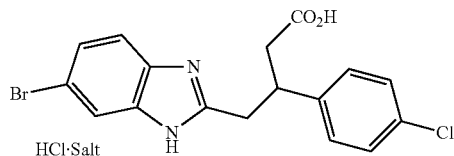 [SMILES: O=C(O)CC(Cc1nc2ccc(Br)cc2[nH]1)c1ccc(Cl)cc1]

Commercial 4-bromo-1,2-phenylenediamine (561 mg) and 3-(4-chlorophenyl)-glutaric anhydride (674 mg) were dissolved in THF (1 ml) with heating. The dark solution was stirred at rt for 1 h. Then the solution was decolorized with activated carbon and filtered. The filtrate was concentrated and the solid residue dried in vacuo. The solid was dissolved in a mixture of acetic acid (4 ml) and conc. HCl (2 ml) and stirred under reflux for 3 h. All volatiles were removed at the water aspirator and the residue was recrystallised from ethanol/EtOAc 1:3 to give a crude (0.47 g). The impure crude was again refluxed with acetic acid/conc. HCl 2:1 for 1 h to leave after concentration and acetone trituration 4-(5-bromo-2-benzimidazolyl)-3-(4-chlorophenyl)butanoic acid•HCl (0.3 g) as light greyish solid.

$^1$H-NMR (500 MHz, DMSO-d$_6$): δ (ppm)=2.72 (dd, J=16.2, 8.6 Hz, 1H), 2.83 (dd, J=16.3, 8.2 Hz, 1H), 3.43 (dd, J=14.9, 9.2 Hz, 1H), 3.55 (dd, J=14.9, 6.9 Hz, 1H), 3.85 (m, 1H), 7.30 (d, J=8.5 Hz, 2H), 7.35 (d, J=8.5 Hz, 1H), 7.60 (dd, J=8.7, 1.7 Hz, 1H), 7.67 (d, J=8.7 Hz, 1H), 7.94 (d, J=1.7 Hz, 1H).

$^{13}$C-NMR and DEPT (125 MHz, DMSO-d$_6$): δ (ppm)= 32.66 (CH$_2$), 39.19 (CH), 39.60 (CH$_2$), 115.57 (CH), 116.42 (CH), 117.34 (C), 128.14 (CH), 128.34 (2CH), 129.14 (2CH), 130.26 (C), 131.44 (C), 132.32 (C), 140.69 (C), 153.07 (C), 172.12 (CO).

MS (+ESI): m/z=393 (M+H).

1.7. 3-(4-Chlorophenyl)-4-(5-iodo-2-benzimidazolyl)butanoic acid•HCl (PS 181)

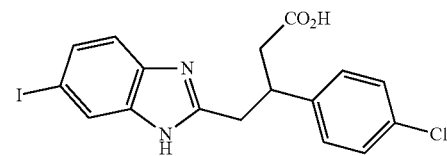

1) 4-Iodo-1,2-phenylenediamine

Commercial 4-iodo-2-nitroaniline was reduced with 5 eq tin dichloride dihydrate in ethanol solution (75° C., 2 h) to give 92% 4-iodo-1,2-phenylenediamine as light red solid.

2) 3-(4-Chlorophenyl)-4-(5-iodo-2-benzimidazolyl)butanoic acid•HCl

By a procedure similar to that of example 1.4, starting from 4-iodo-1,2-phenylenediamine and 3-(4-chlorophenyl)glutaric anhydride, 3-(4-chlorophenyl)-4-(5-iodo-2-benzimidazolyl)butanoic acid•HCl was obtained as light red solid.
$^1$H-NMR (500 MHz, DMSO-d$_6$): δ (ppm)=2.72 (dd, J=16.3, 8.6 Hz, 1H), 2.83 (dd, J=16.3, 6.2 Hz, 1H), 3.43 (dd, J=14.9, 9.3 Hz, 1H), 3.55 (dd, J=14.9, 6.9 Hz, 1H), 3.86 (m, 1H), 7.29 (d, J=8.5 Hz, 2H), 7.35 (d, J=8.5 Hz, 2H), 7.53 (d, J=8.6 Hz, 1H), 7.74 (dd, J=8.6, 1.4 Hz, 1H), 8.07 (d, J=1.3 Hz, 1H).
$^{13}$C-NMR and DEPT (125 MHz, DMSO-d$_6$): δ (ppm)= 32.55 (CH$_2$), 39.17 (CH), 39.61 (CH$_2$), 89.49 (C), 115.68 (CH), 122.02 (CH), 128.34 (2CH), 129.13 (2CH), 130.49 (C), 131.44 (C), 132.56 (C), 133.71 (CH), 140.66 (C), 152.47 (C), 172.10 (CO).
MS (+ESI): m/z=441 (M+H).

1.8. 4-(5-Chloro-6-fluoro-2-benzimidazolyl)-3-(4-chlorophenyl)butanoic acid•HCl (PS 175)

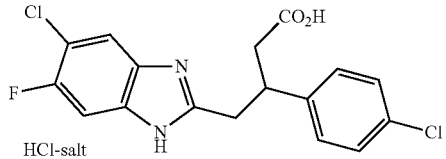 [SMILES: O=C(O)CC(Cc1nc2cc(Cl)c(F)cc2[nH]1)c1ccc(Cl)cc1]

By a procedure similar to that of example 1.4, starting from commercial 4-chloro-5-fluoro-1,2-phenylenediamine and 3-(4-chlorophenyl)glutaric anhydride, 4-(5-chloro-6-fluoro-2-benzimidazolyl)-3-(4-chlorophenyl)butanoic acid•HCl was obtained as light greyish solid.
$^1$H-NMR (500 MHz, DMSO-d$_6$): δ (ppm)=2.70 (dd, J=16.3, 8.7 Hz, 1H), 2.81 (dd, J=16.3, 6.1 Hz, 1H), 3.39 (dd, J=14.9, 9.1 Hz, 1H), 3.51 (dd, J=14.9, 7.0 Hz, 1H), 3.80 (m, 1H), 7.29 (d, J=8.6 Hz, 2H), 7.33 (dd, J=8.6 Hz, 2H), 7.82 (d, $^3J_{H\text{-}F}$=8.8 Hz, 1H), 7.98 (d, $^4J_{H\text{-}F}$=6.4 Hz, 1H).
$^{13}$C-NMR and DEPT (125 MHz, DMSO-d$_6$): δ (ppm)= 33.01 (CH$_2$), 39.44 (CH), 39.70 (CH$_2$), 102.11 (CH, $^2J_{C\text{-}F}$=27.6 Hz), 115.42 (CH), 117.66 (C, $^2J_{C\text{-}F}$=20.6 Hz), 128.49 (2CH), 128.57 (C), 129.26 (2CH), 130.82 (C, $^3J_{C\text{-}F}$=12.6 Hz), 131.57 (C), 140.81 (C), 154.52 (C), 154.78 (C, $^1J_{C\text{-}F}$=243.4 Hz), 172.30 (CO).
MS (+ESI): m/z=367 (M+H).

1.9. 3-(4-Chlorophenyl)-4-(5-trifluoromethyl-2-benzimidazolyl)butanoic acid•HCl (PS 176)

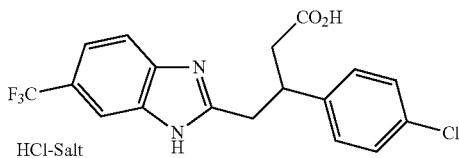 [SMILES: O=C(O)CC(Cc1nc2ccc(C(F)(F)F)cc2[nH]1)c1ccc(Cl)cc1]

By a procedure similar to that of example 1.4, starting from commercial 4-trifluoromethyl-1,2-phenylenediamine and 3-(4-chlorophenyl)glutaric anhydride, 3-(4-chlorophenyl)-4-(5-trifluoromethyl-2-benzimidazolyl)butanoic acid•HCl was obtained as colourless solid.
$^1$H-NMR (500 MHz, DMSO-d$_6$): δ (ppm)=2.73 (dd, J=16.3, 8.6 Hz, 1H), 2.85 (dd, J=16.3, 6.2 Hz, 1H), 3.46 (dd, J=14.9, 9.0 Hz, 1H), 3.57 (dd, J=14.9, 7.0 Hz, 1H), 3.88 (m, 1H), 7.31 (d, J=8.5 Hz, 2H), 7.37 (d, J=8.5 Hz, 2H), 7.76 (dd, J=8.6, 1.2 Hz, 1H), 7.92 (d, J=8.6 Hz, 1H), 8.08 (s, 1H).
$^{13}$C-NMR and DEPT (125 MHz, DMSO-d$_6$): δ (ppm)= 32.96 (CH$_2$), 39.24 (CH), 39.59 (CH$_2$), 111.70 (CH, $^3J_{C\text{-}F}$=4.0 Hz), 115.0 (CH), 121.59 (CH, $^3J_{C\text{-}F}$=3.7 Hz), 122.96 (C), 128.35 (2CH), 129.16 (2CH), 131.41 (C), 131.48 (br, C), 133.98 (br, C), 140.80 (C), 154.89 (C), 172.16 (CO).
MS (+ESI): m/z=383 (M+H).

1.10. 3-(4-Chlorophenyl)-4-(5,6-difluoro-2-benzimidazolyl)butanoic acid•HCl (PS 177)

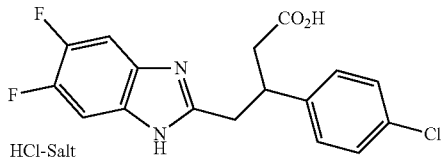 [SMILES: O=C(O)CC(Cc1nc2cc(F)c(F)cc2[nH]1)c1ccc(Cl)cc1]

By a procedure similar to that of example 1.4, starting from commercial 4,5-difluoro-1,2-phenylenediamine and 3-(4-chlorophenyl)glutaric anhydride, 3-(4-chlorophenyl)-4-(5,6-difluoro-2-benzimidazolyl)butanoic acid•HCl was obtained as light greyish solid.
$^1$H-NMR (500 MHz, DMSO-d$_6$): δ (ppm)=2.70 (dd, J=16.2, 8.8 Hz, 1H), 2.79 (dd, J=16.2, 6.0 Hz, 1H), 3.39 (dd, J=14.9, 8.9 Hz, 1H), 3.49 (dd, J=14.9, 7.1 Hz, 1H), 3.84 (m, 1H), 7.30 (d, J=8.5 Hz, 2H), 7.35 (d, J=8.5 Hz, 2H), 7.82 (t, $^3J_{H\text{-}F}$=8.5 Hz, 2H).
$^{13}$C-NMR and DEPT (125 MHz, DMSO-d$_6$): δ (ppm)= 32.95 (CH$_2$), 39.25 (CH), 39.64 (CH$_2$), 102.48 (m, 2CH), 127.77 (br, 2C), 128.29 (2CH), 129.18 (2CH), 131.33 (C), 140.95 (C), 147.93 (dd, $^2J_{C\text{-}F}$=245 Hz, $^3J_{C\text{-}F}$=17 Hz, 2C), 154.03 (C), 172.14 (CO).
MS (+ESI): m/z=351 (M+H).

1.11. 3-(4-Chlorophenyl)-4-(1H-naphtho[2,3-a]benzimidazol-2-yl)butanoic acid•HCl (PS 167)

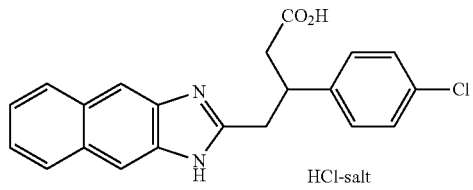 [SMILES: O=C(O)CC(Cc1nc2cc3ccccc3cc2[nH]1)c1ccc(Cl)cc1]

By a procedure similar to that of example 1.4, starting from commercial 2,3-diamino-naphthalene and 3-(4-chlorophenyl)glutaric anhydride, 3-(4-chlorophenyl)-4-(1H-naphtho[2,3-a]benzimidazol-2-yl)-butanoic acid•HCl was obtained as light yellow crystals.
$^1$H-NMR (500 MHz, DMSO-d$_6$): δ (ppm)=2.77 (dd, J=16.2, 8.5 Hz, 1H), 2.89 (dd, J=16.3, 6.2 Hz, 1H), 3.53 (dd, J=14.9, 9.4 Hz, 1H), 3.67 (dd, J=14.9, 6.8 Hz, 1H), 3.97 (m, 1H), 7.29 (d, J=8.5 Hz, 2H), 7.40 (d, J=8.5 Hz, 2H), 7.54 (m, 2H), 8.13 (m, 2H), 8.27 (s, 2H).
$^{13}$C-NMR and DEPT (125 MHz, DMSO-d$_6$): δ (ppm)= 32.96 (CH$_2$), 39.13 (CH), 39.69 (CH$_2$), 110.40 (2CH), 125.50 (2CH), 127.95 (2CH), 128.34 (2CH), 129.17 (2CH), 130.33 (2C), 130.56 (2C), 131.46 (C), 140.66 (C), 156.45 (C), 172.11 (CO).
MS (+ESI): m/z=365 (M+H).

1.12. 3-(4-Chlorophenyl)-4-(5-cyano-2-benzimidazolyl)butanoic acid•HCl (PS 218)

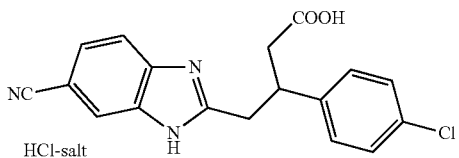 [SMILES: N#Cc1ccc2nc(CC(CC(=O)O)c3ccc(Cl)cc3)[nH]c2c1]

By a procedure similar to that of example 1.4, starting from commercial 3,4-diaminobenzonitrile and 3-(4-chlorophenyl) glutaric anhydride, 3-(4-chlorophenyl)-4-(5-cyano-2-benzimidazolyl)-butanoic acid•HCl was obtained as light beige solid.

$^1$H-NMR (500 MHz, DMSO-d$_6$): δ (ppm)=2.72 (dd, J=16.3, 8.7 Hz, 1H), 2.83 (dd, J=16.3, 6.1 Hz, 1H), 3.43 (dd, J=14.9, 8.9 Hz, 1H), 3.53 (dd, J=14.9, 7.1 Hz, 1H), 3.85 (m, 1H), 7.30 (d, J=8.5 Hz, 2H), 7.35 (d, J=8.5 Hz, 2H), 7.81 (dd, J=8.5, 1.3 Hz, 1H), 7.86 (d, J=8.5 Hz, 1H), 8.28 (br s, 1H).

$^{13}$C-NMR and DEPT (125 MHz, DMSO-d$_6$): δ (ppm)= 33.11 (CH$_2$), 39.23 (CH), 39.58 (CH$_2$), 106.79 (CH), 115.16 (CH), 118.58 (C), 119.14 (CH), 128.02 (CH), 128.33 (2CH), 129.15 (2CH), 131.39 (C), 132.14 (br, C), 134.93 (br, C), 140.90 (C), 155.45 (C), 172.19 (CO).

MS (+ESI): m/z=340 (M+H).

1.13. 4-(5-Carboxy-2-benzimidazolyl)-3-(4-chlorophenyl)butanoic acid•HCl (PS 165)

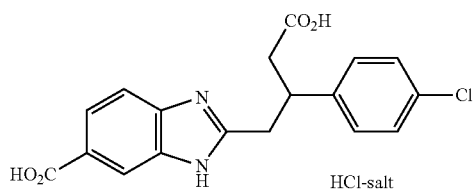 [SMILES: O=C(O)CC(Cc1nc2ccc(C(=O)O)cc2[nH]1)c1ccc(Cl)cc1]

1) Methyl 3,4-diaminobenzoate

To the stirred suspension of commercial 3,4-diaminobenzoic acid (10.3 g) in methanol (150 ml) conc. sulphuric acid (5 ml) was added cautiously. The mixture was stirred under reflux for 3 h. About half of the solvent is removed by distillation and dichloromethane (150 ml) is added. The organic layer was poured in ice water (300 ml) and with vigorous stirring the pH was adjusted to 11 with 10M NaOH. The organic layer was separated and the aqueous layer extracted with dichloromethane (150 ml). The combined organic layers were dried over sodium sulfate and concentrated. The residue was purified by fractional crystallisation from dichloromethane to give methyl 3,4-diaminobenzoate (7.05 g) as beige coloured solid.

2) 4-(5-Carboxy-2-benzimidazolyl)-3-(4-chlorophenyl)butanoic acid•HCl

By a procedure similar to that of example 1.4, starting from methyl 3,4-diaminobenzoate and 3-(4-chlorophenyl)glutaric anhydride, 4-(5-carboxy-2-benzimidazolyl)-3-(4-chlorophenyl)butanoic acid•HCl was obtained as colourless solid.

$^1$H-NMR (500 MHz, DMSO-d$_6$): δ (ppm)=2.74 (dd, J=16.3, 8.6 Hz, 1H), 2.85 (dd, J=16.2, 6.1 Hz, 1H), 3.47 (dd, J=15.0, 9.2 Hz, 1H), 3.59 (dd, J=15.0, 6.9 Hz, 1H), 3.89 (m, 1H), 7.30 (d, J=8.5 Hz, 2H), 7.37 (d, J=8.5 Hz, 2H), 7.79 (d, J=8.6 Hz, 1H), 8.02 (dd, J=8.6, 1.5 Hz, 1H), 8.22 (d, J=1.5 Hz, 1H).

$^{13}$C-NMR and DEPT (125 MHz, DMSO-d$_6$): δ (ppm)= 32.79 (CH$_2$), 39.18 (CH), 39.62 (CH$_2$), 113.78 (CH), 115.20 (CH), 126.07 (CH), 127.72 (C), 128.36 (2CH), 129.16 (2CH), 131.00 (C), 131.45 (C), 133.93 (C), 140.69 (C), 154.16 (C), 166.46 (CO), 172.13 (CO).

MS (+ESI): m/z=359 (M+H).

1.14. 4-(5-Benzoyl-2-benzimidazolyl)-3-(4-chlorophenyl)butanoic acid•HCl (PS 241)

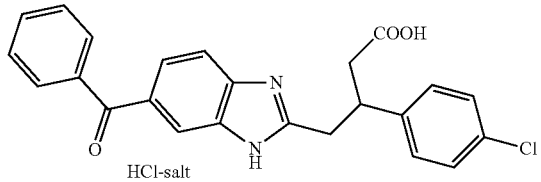 [SMILES: O=C(O)CC(Cc1nc2ccc(C(=O)c3ccccc3)cc2[nH]1)c1ccc(Cl)cc1]

The solution of commercial 3,4-diaminobenzophenone (0.43 g) and 3-(4-chlorophenyl)glutaric anhydride (0.45 g) in 1,4-dioxane (3 ml) was stirred under reflux for 0.5 h. 4M HCl in 1,4-dioxane (3 ml) was added and the solution is further heated to reflux for 2.5 h. After cooling to rt the precipitate is collected by suction filtration and washed with 1,4-dioxane and diethyl ether. The crude is recrystallised from acetic acid to give 4-(5-benzoyl-2-benzimidazolyl)-3-(4-chlorophenyl) butanoic acid HCl (0.64 g) as light brown solid.

$^1$H-NMR (500 MHz, DMSO-d$_6$)): δ (ppm)=2.74 (dd, J=16.2, 8.6 Hz, 1H), 2.85 (dd, J=16.2, 6.1 Hz, 1H), 3.50 (dd, J=15.0, 9.1 Hz, 1H), 3.60 (dd, J=15.0, 6.9 Hz, 1H), 3.91 (m, 1H), 7.32 (d, J=8.5 Hz, 2H), 7.39 (d, J=8.5 Hz, 2H), 7.58 (t, J=7.6 Hz, 2H), 7.70 (t, J=7.4 Hz, 1H), 7.75 (dd, J=8.3, 1.3 Hz, 2H), 7.83 (dd, J=8.6, 1.5 Hz, 1H), 7.86 (d, J=8.6 Hz, 1H), 8.01 (d, J=1.4 Hz, 1H).

$^{13}$C-NMR and DEPT (125 MHz, DMSO-d$_6$): δ (ppm)= 32.83 (CH$_2$), 39.17 (CH), 39.67 (CH$_2$), 113.91 (CH), 115.78 (CH), 126.51 (CH), 128.37 (2CH), 128.52 (2CH), 129.19 (2CH), 129.54 (2CH), 131.02 (C), 131.46 (C), 132.70 (CH), 133.79 (C), 133.95 (C), 136.90 (C), 140.75 (C), 154.47 (C), 172.14 (CO), 194.71 (CO).

1.15. 3-(4-Chlorophenyl)-4-(5-nitro-2-benzimidazolyl)butanoic acid•HCl (PS 242)

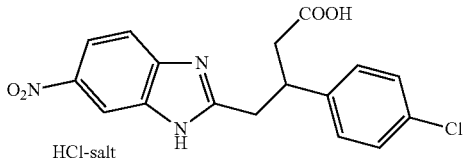 [SMILES: O=C(O)CC(Cc1nc2ccc([N+](=O)[O-])cc2[nH]1)c1ccc(Cl)cc1]

The solution of commercial 4-nitro-1,2-phenylenediamine (0.31 g) and 3-(4-chlorophenyl)glutaric anhydride (0.45 g) in 1,4-dioxane (3 ml) was stirred under reflux for 0.75 h. 4M HCl in 1,4-dioxane (3 ml) was added and the solution is further heated to reflux for 1 h. After cooling to rt the precipitate is collected by suction filtration and washed with 1,4-dioxane and diethyl ether. The crude is recrystallised from acetic acid to give 4-(5-benzoyl-2-benzimidazolyl)-3-(4-chlorophenyl)butanoic acid•HCl (0.59 g) as beige coloured solid.

$^1$H-NMR (500 MHz, DMSO-d$_6$): δ (ppm)=2.72 (dd, J=16.2, 8.7 Hz, 1H), 2.84 (dd, J=16.2, 6.1 Hz, 1H), 3.41 (dd, J=14.9, 8.9 Hz, 1H), 3.52 (dd, J=14.9, 7.0 Hz, 1H), 3.85 (m, 1H), 7.30 (d, J=8.5 Hz, 2H), 7.36 (d, J=8.5 Hz, 2H), 7.85 (d, J=9.0 Hz, 1H), 8.23 (dd, J=9.0, 2.2 Hz, 1H), 8.51 (d, J=2.1 Hz, 1H).

$^{13}$C-NMR and DEPT (125 MHz, DMSO-d$_6$): δ (ppm)= 33.46 (CH$_2$), 39.28 (CH), 39.64 (CH$_2$), 110.68 (CH), 114.50 (CH), 119.70 (CH), 128.31 (2CH), 129.19 (2CH), 131.36 (C), 132.76 (C), 136.93 (C), 140.97 (C), 144.01 (C), 156.90 (C), 172.23 (CO).

1.16. 3-(4-Chlorophenyl)-4-(5-methoxycarbonyl-2-benzimidazolyl)butanoic acid•HCl (PS 219)

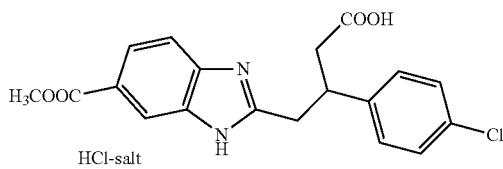

By a procedure similar to that of example 1.4, starting from methyl 3,4-diaminobenzoate and 3-(4-chlorophenyl)glutaric anhydride, 3-(4-chlorophenyl)-4-(5-methoxycarbonyl-2-benzimidazolyl)-butanoic acid•HCl was obtained as light tan solid, provided that cyclisation of the crude glutaramic acid was carried out in commercial 4M HCl in 1,4-dioxane at reflux for 0.5 h.

$^1$H-NMR (500 MHz, DMSO-d$_6$): δ (ppm)=2.74 (dd, J=16.3, 8.6 Hz, 1H), 2.85 (dd, J=16.3, 6.2 Hz, 1H), 3.46 (dd, J=15.0, 9.2 Hz, 1H), 3.58 (dd, J=15.0, 6.9 Hz, 1H), 3.88 (m, 1H), 3.89 (s, 3H), 7.30 (d, J=8.5 Hz, 2H), 7.37 (d, J=8.5 Hz, 2H), 7.81 (d, J=8.5 Hz, 1H), 8.02 (dd, J=8.6, 1.5 Hz, 1H), 8.23 (d, J=1.1 Hz, 1H).

$^{13}$C-NMR and DEPT (125 MHz, DMSO-d$_6$): δ (ppm)= 34.87 (CH$_2$), 39.18 (CH), 39.61 (CH$_2$), 52.39 (CH$_3$), 114.04 (CH), 115.19 (CH), 125.76 (CH), 126.31 (C), 128.34 (2CH), 129.16 (2CH), 131.24 (br, C), 131.44 (C), 134.39 (br, C), 140.71 (C), 154.49 (C), 165.52 (CO), 172.15CO).

MS (+ESI): m/z=373 (M+H).

1.17. 3-(4-Chlorophenyl)-4-(5-methoxy-2-benzimidazolyl)butanoic acid•HCl (PS 223)

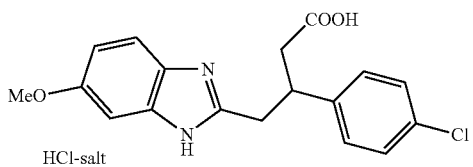 [SMILES: COc1ccc2nc(CC(CC(=O)O)c3ccc(Cl)cc3)[nH]c2c1]

By a procedure similar to that of example 1.4, starting from commercial 4-methoxy-1,2-phenylenediamine and 3-(4-chlorophenyl)glutaric anhydride, 3-(4-chlorophenyl)-4-(5-methoxy-2-benzimidazolyl)butanoic acid•HCl was obtained as light red solid, provided that cyclisation of the crude glutaramic acid was carried out with HCl in 1,4-dioxane at reflux for 1.5 h.

$^1$H-NMR (500 MHz, DMSO-d$_6$): δ (ppm)=2.72 (dd, J=16.3, 8.6 Hz, 1H), 2.81 (dd, J=16.3, 6.1 Hz, 1H), 3.43 (dd, J=14.9, 9.5 Hz, 1H), 3.54 (dd, J=14.9, 6.7 Hz, 1H), 3.82 (s, 3H), 3.86 (m, 1H), 7.07 (dd, J=9.0, 2.3 Hz, 1H), 7.15 (d, J=2.3 Hz, 1H), 7.30 (d, J=8.5 Hz, 2H), 7.36 (d, J=8.5 Hz, 2H), 7.59 (d, J=9.0 Hz, 1H).

$^{13}$C-NMR and DEPT (125 MHz, DMSO-d$_6$): δ (ppm)= 32.37 (CH$_2$), 39.22 (CH), 39.72 (CH$_2$), 55.75 (CH$_3$), 96.05 (CH), 114.40 (CH), 115.11 (CH), 124.80 (C), 128.33 (2CH), 129.16 (2CH), 131.41 (C), 131.60 (C), 140.67 (C), 150.99 (C), 157.60 (C), 172.09 (CO).

MS (+ESI): m/z=345 (M+H).

1.18. 3-(4-Chlorophenyl)-4-(5-phenoxy-2-benzimidazolyl)butanoic acid•HCl (PS 111)

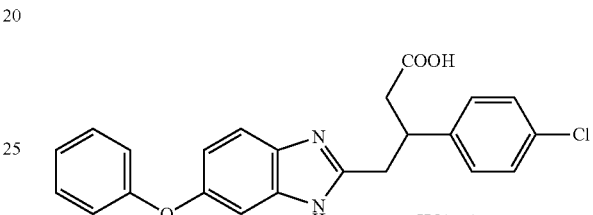

1) N-(4-Phenoxyphenyl)-3-(4-chlorophenyl)glutaramic acid

A solution of triethyl amine (1.5 ml) in 1,4-dioxane (5 ml) was added to a mixture of commercial 4-phenoxyaniline (1.85 g) and 3-(4-chlorophenyl)glutaric anhydride. The resulting solution was stirred at rt for 0.5 h and at 40° C. for 2 h. Under cooling with ice conc. HCl (2 ml) and water (10 ml) was added. A gummy precipitate is formed from which the aqueous layer is removed by decantation. Crystallisation was induced by heating with methanol (5 ml). After cooling in the refrigerator the precipitate was isolated by filtration, washed with methanol and diethyl ether, and dried in vacuo to give colourless, powdery crystals (3 g) of N-(4-phenoxyphenyl)-3-(4-chlorophenyl)-glutaramic acid.

2) N-(2-Nitro-4-phenoxyphenyl)-3-(4-chlorophenyl)glutaramic acid

N-(4-Phenoxyphenyl)-3-(4-chlorophenyl)glutaramic acid (1.41 g) was dissolved in acetic acid (3 ml) with heating. The solution was allowed to cool to 30° C. With vigorous stirring fuming nitric acid (0.7 ml) was rapidly added in portions. The resulting hot, orange coloured solution was stirred at rt for 0.5 h. With ice cooling water (15 ml) was added slowly. From the gummy, yellow precipitate the aqueous layer is removed by decantation. Crystallisation is induced by heating with methanol (4 ml). After cooling to rt the precipitate is isolated by filtration, washed with methanol, and dried in vacuo to yield bright yellow crystals (1.21 g) of N-(2-nitro-4-phenoxyphenyl)-3-(4-chlorophenyl)glutaramic acid.

3) Methyl 3-(4-chlorophenyl)-4-(5-phenoxy-2-benzimidazolyl)butanoate

N-(2-Nitro-4-phenoxyphenyl)-3-(4-chlorophenyl)glutaramic acid (0.72 g) is dissolved in methanol (8 ml). Iron powder (0.88 g) is added and the suspension is heated to reflux. Conc. HCl (10 drops) was added carefully and refluxing was continued for 1 h. Then further conc. HCl (4 ml) was added and the greenish-yellow solution was stirred at reflux for additional 20 h. After cooling to rt the solution was poured into a mixture of sat. NaHCO$_3$ solution (60 ml) and ethyl acetate (50 ml). The inorganic precipitates were removed by suction filtration and subsequently washed with ethyl acetate. From the filtrate the organic layer was separated and the aqueous layer extracted with ethyl acetate (50 ml). The combined organic layers were dried (sodium sulfate), concentrated and dried in vacuo. The residue (0.61 g of brownish oil) was purified by flash chromatography (dichloromethane/2% methanol/1% triethyl amine) on silica gel to give methyl 3-(4-chlorophenyl)-4-(5-phenoxy-2-benzimidazolyl)butanoate (0.46 g) as a colourless solid.

4) 3-(4-Chlorophenyl)-4-(5-phenoxy-2-benzimidazolyl)butanoic acid•HCl

Methyl 3-(4-chlorophenyl)-4-(5-phenoxy-2-benzimidazolyl)butanoate (0.44 g) is dissolved in a mixture of acetic acid (3 ml) and conc. HCl (1 ml). The solution is stirred at 100° C. for 1 h. All volatiles are removed at the water aspirator and the solid residue was precipitated with toluene from acetone solution to give 0.19 g of the hydrochloride salt of 3-(4-chlorophenyl)-4-(5-phenoxy-2-benzimidazolyl)butanoic acid as a yellowish solid.

$^1$H-NMR (500 MHz, DMSO-d$_6$): δ (ppm)=2.72 (dd, J=16.2, 8.7 Hz, 1H), 2.81 (dd, J=16.2, 6.1 Hz, 1H), 3.44 (dd, J=15.0, 9.2 Hz, 1H), 3.54 (dd, J=15.0, 6.8 Hz, 1H), 3.86 (m, 1H), 7.04 (dd, J=8.6, 1.1 Hz, 2H), 7.18 (m, 2H), 7.24 (d, J=2.2 Hz, 1H), 7.32 (d, J=8.5 Hz, 2H), 7.37 (d, J=8.5 Hz, 2H), 7.42 (dt, J=7.5, 1.0 Hz, 2H), 7.73 (d, J=8.9 Hz, 1H).

$^{13}$C-NMR and DEPT (125 MHz, DMSO-d$_6$): δ (ppm)= 32.48 (CH$_2$), 39.14 (CH), 39.69 (CH$_2$), 102.73 (CH), 115.08 (CH), 117.51 (CH), 118.69 (2CH), 123.85 (CH), 126.96 (C), 128.36 (2CH), 129.16 (2CH), 130.10 (2CH), 131.45 (C), 131.66 (C), 140.69 (C), 152.26 (C), 154.61 (C), 156.47 (C), 172.09 (CO).

MS (+ESI): m/z=407 (M+H).

1.19. 3-(4-Chlorophenyl)-4-(5-phenyl-2-benzimidazolyl)butanoic acid•HCl (PS 168)

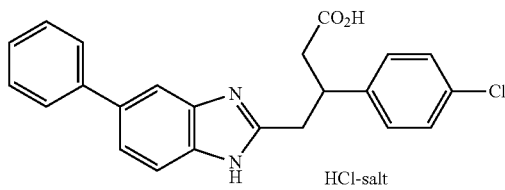 [SMILES: O=C(O)CC(Cc1nc2cc(-c3ccccc3)ccc2[nH]1)c1ccc(Cl)cc1]

1) 3-(4-Chlorophenyl)-N-(3-nitro-[1,1'-biphenyl]-4-yl)glutaramic acid

By a procedure similar to that of example 1.18, starting from commercial 4-aminobiphenyl and 3-(4-chlorophenyl) glutaric anhydride, 3-(4-chlorophenyl)-N-(3-nitro-[1,1'-biphenyl]-4-yl)glutaramic acid was prepared in 2 steps.

2) 3-(4-Chlorophenyl)-4-(5-phenyl-2-benzimidazolyl)butanoic acid•HCl

To a solution of 3-(4-chlorophenyl)-N-(3-nitro-[1,1'-biphenyl]-4-yl)glutaramic acid (0.52 g) in acetic acid (3 ml) iron powder (0.34 g) was added. The mixture was stirred vigorously at under reflux for 0.5 h. Then conc. HCl (2 ml) was added with caution. The resulting solution was stirred at reflux temperature for further 2 h. All volatiles were removed at the water aspirator and the residue was dissolved in acetic acid/conc. HCl 2:1 (3 ml). Water (3 ml) was added at reflux temperature and the mixture was left standing at rt overnight. The precipitate was collected by suction filtration and washed well with 1M HCl and water. After drying in vacuo 3-(4-chlorophenyl)-4-(5-phenyl-2-benzimidazolyl)butanoic acid•HCl (0.36 g) was obtained as beige coloured solid.

$^1$H-NMR (500 MHz, DMSO-d$_6$): δ (ppm)=2.74 (dd, J=16.2, 8.5 Hz, 1H), 2.85 (dd, J=16.2, 6.0 Hz, 1H), 3.47 (dd, J=14.8, 9.3 Hz, 1H), 3.58 (dd, J=14.8, 6.7 Hz, 1H), 3.90 (m, 1H), 7.32 (d, J=8.3 Hz, 1H), 7.38 (d, J=8.3 Hz, 2H), 7.40 (t, J=7.5 Hz, 1H), 7.49 (t, J=7.5 Hz, 2H), 7.70 (d, J=7.5 Hz, 2H), 7.75 (d, J=8.5 Hz, 1H), 7.78 (d, J=8.5 Hz, 1H), 7.89 (s, 1H).

$^{13}$C-NMR and DEPT (125 MHz, DMSO-d$_6$): δ (ppm)= 32.64 (CH$_2$), 39, 23 (CH), 39.69 (CH$_2$), 111.35 (CH), 114.09 (CH), 124.52 (CH), 127.07 (2CH), 127.64 (CH), 128.35 (2CH), 128.94 (2CH), 129.15 (2CH), 130.49 (C), 131.42 (C), 131.73 (C), 137.77 (C), 139.34 (C), 140.74 (C), 152.49 (C), 172.13 (CO).

MS (+ESI): m/z=391 (M+H).

1.20. 3-(4-Chlorophenyl)-4-(5-ethyl-2-benzimidazolyl)butanoic acid•HCl (PS 187)

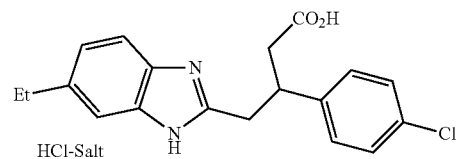 [SMILES: CCc1ccc2nc(CC(CC(=O)O)c3ccc(Cl)cc3)[nH]c2c1]

By a procedure similar to that of example 1.18, starting from commercial 4-ethylaniline and 3-(4-chlorophenyl)glutaric anhydride, 3-(4-chlorophenyl)-4-(5-ethyl-2-benzimidazolyl)butanoic acid•HCl was prepared in 4 steps without characterisation of the intermediates.

$^1$H-NMR (500 MHz, DMSO-d$_6$): δ (ppm)=1.19 (t, J=6.3 Hz, 3H), 2.66-2.86 (m, 4H), 3.46 (m, 1H), 3.55 (m, 1H), 3.88 (m, 1H), 7.24-7.40 (m, 5H), 7.50 (s, 1H), 7.60 (d, J=7.3 Hz, 1H), 15.2 (br s, 2H).

$^{13}$C-NMR and DEPT (125 MHz, DMSO-d$_6$): δ (ppm)= 15.71 (CH$_3$), 27.96 (CH$_2$), 32.23 (CH$_2$), 39.04 (CH), 39.66 (CH$_2$), 111.81 (CH), 113.23 (CH), 125.77 (CH), 128.25 (2CH), 128.56 (C), 129.07 (2CH), 130.61 (C), 131.32 (C), 140.52 (C), 141.69 (C), 151.21 (C), 171.96 (CO).

MS (+ESI): m/z=343 (M+H).

1.21. 4-(5-$^t$Butyl-2-benzimidazolyl)-3-(4-chlorophenyl)butanoic acid•HCl (PS 244)

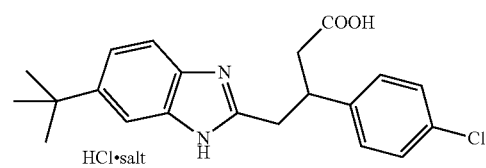 [SMILES: CC(C)(C)c1ccc2nc(CC(CC(=O)O)c3ccc(Cl)cc3)[nH]c2c1]

3-(4-Chlorophenyl)glutaric anhydride (0.45 g) was added with stirring at rt to the solution of commercial 4-ᵗbutyl-1,2-phenylenediamine (0.33 g) in dichloromethane (3 ml). After 1 h at rt the precipitate is collected by suction filtration, washed with dichloromethane, and dried in vacuo to give a mixture of regioisomeric amides (0.63 g) as light grey solid. The solid was suspended in 1,4-dioxane (2 ml) and 4M HCl in 1,4-dioxane (3 ml) was added. The solution is heated to reflux for 1.5 h. From the solution all volatiles are removed at the water aspirator and the residue is recrystallised from acetone/ethyl acetate to give 4-(5-ᵗbutyl-2-benzimidazolyl)-3-(4-chlorophenyl)butanoic acid HCl (0.45 g) as light grey solid.

$^1$H-NMR (500 MHz, DMSO-d$_6$)): δ (ppm)=1.32 (s, 9H), 2.71 (dd, J=16.2, 8.6 Hz, 1H), 2.81 (dd, J=16.2, 6.1 Hz, 1H), 3.47 (dd, J=15.0, 9.4 Hz, 1H), 3.56 (dd, J=15.0, 6.7 Hz, 1H), 3.89 (m, 1H), 7.30 (d, J=8.5 Hz, 2H), 7.38 (d, J=8.5 Hz, 2H), 7.56 (dd, J=8.7, 1.7 Hz, 1H), 7.59 (d, J=1.0 Hz, 1H), 7.63 (d, J=8.7 Hz, 1H).

$^{13}$C-NMR and DEPT (125 MHz, DMSO-d$_6$): δ (ppm)= 31.11 (3CH$_3$), 32.31 (CH$_2$), 34.74 (C), 39.15 (CH), 109.32 (CH), 113.12 (CH), 123.56 (CH), 128.35 (2CH), 128.51 (C), 129.18 (2CH), 130.64 (C), 131.43 (C), 140.67 (C), 148.65 (C), 151.53 (C), 172.09 (CO). One carbon signal missing.

1.22. 7,8-Dichloro-3-phenyl-3,4-dihydropyrido[1,2-a]benzimidazol-1(2H)-one (PS 162) and 4-(5,6-Dichloro-2-benzimidazolyl)-3-phenylbutanoic acid•HCl (PS 163)

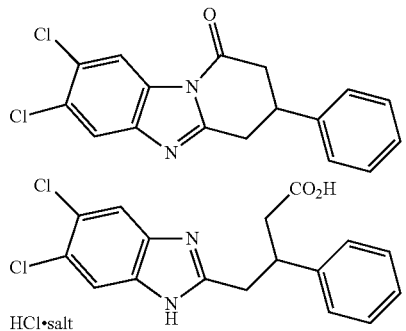

1) 7,8-Dichloro-3-phenyl-3,4-dihydropyrido[1,2-a]benzimidazol-1(2H)-one

The solution of commercial 4,5-dichloro-1,2-phenylenediamine (0.38 g) and 3-phenylglutaric anhydride (0.4 g) in THF (1 ml) was heated shortly and kept at rt for 0.5 h. The solvent was removed in vacuo and the residue redissolved in acetic acid (3 ml). The dark solution was heated to reflux overnight. Then all volatiles were removed in vacuo and the residue was heated with ethanol (5 ml). After reccoling to rt the precipitate was collected by filtration, washed with ethanol, and dried to give a crude (0.39 g). The crude was decolorized in boiling acetone solution with activated carbon and filtered over Celite. Concentration of the filtrate and drying of the residue afforded 7,8-dichloro-3-phenyl-3,4-dihydropyrido[1,2-a]benzimidazol-1(2H)-one (0.13 g) as colourless crystals.

2) 4-(5,6-Dichloro-2-benzimidazolyl)-3-phenylbutanoic acid•HCl

The solution of 7,8-dichloro-3-phenyl-3,4-dihydropyrido[1,2-a]benzimidazol-1(2H)-one (96 mg) in a mixture of acetic acid (2 ml) and conc. HCl (1 ml) was heated to reflux shortly and then stirred at rt for 1 h. All volatiles were removed at the water aspirator at elevated temperature and the residue was dried by azeotropic distillation with toluene. The crude was triturated with chloroform (5 ml) to give 4-(5,6-dichloro-2-benzimidazolyl)-3-phenylbutanoic acid•HCl (102 mg) as colourless solid.

$^1$H-NMR (500 MHz, DMSO-d$_6$): δ (ppm)=2.70 (dd, J=16.1, 8.4 Hz, 1H), 2.81 (dd, J=16.1, 6.4 Hz, 1H), 3.40 (dd, J=14.8, 8.8 Hz, 1H), 3.51 (dd, J=14.8, 7.3 Hz, 1H), 3.81 (m, 1H), 7.16 (t, J=7.3 Hz, 1H), 7.24 (t, J=7.6 Hz, 2H), 7.31 (d, J=7.2 Hz, 2H), 8.01 (s, 2H).

$^{13}$C-NMR (125 MHz, DMSO-d$_6$): δ (ppm)=33.18 (CH2), 39.83 (CH2), 115.40 (CH), 126.84 (CH), 127.11 (2CH), 127.47 (CH), 128.39 (2CH), 131.45 (C), 141.84 (C), 154.96 (C), 172.29 (CO).

MS (+ESI): m/z=349 (M+H).

1.23. 3-(4-Chlorophenyl)-7(8)-methyl-3,4-dihydropyrido[1,2-a]benzimidazol-1(2H)-one and 3-(4-Chlorophenyl)-4-(5-methyl-2-benzimidazolyl)butanoic acid•HCl (PS 166)

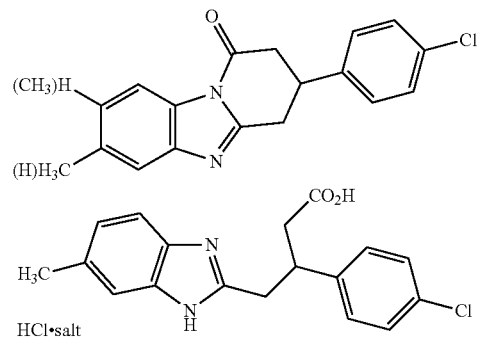

1) 7-Methyl-3-phenyl-3,4-dihydropyrido[1,2-a]benzimidazol-1(2H)-one and 8-methyl-3-phenyl-3,4-dihydropyrido[1,2-a]benzimidazol-1(2H)-one By a procedure similar to that of example 1.22.1, starting from commercial 4-methyl-1,2-phenylenediamine and 3-(4-chlorophenyl)glutaric anhydride, a 1:1-mixture of the regioisomers 7-methyl-3-phenyl-3,4-dihydropyrido[1,2-a]benzimidazol-1(2H)-one and 8-methyl-3-phenyl-3,4-dihydropyrido[1,2-a]benzimidazol-1(2H)-one was obtained.

2) 3-(4-Chlorophenyl)-4-(5-methyl-2-benzimidazolyl)butanoic acid•HCl

Above mixture was converted to 3-(4-chlorophenyl)-4-(5-methyl-2-benzimidazolyl) butanoic acid•HCl with acetic acid and conc. HCl at reflux temperature as described in example 1.22.2.

$^1$H-NMR (500 MHz, DMSO-d$_6$): δ (ppm)=2.43 (s, 3H), 2.72 (dd, J=16.2, 8.6 Hz, 1H), 2.82 (dd, J=16.2, 6.2 Hz, 1H), 3.43 (dd, J=15.0, 9.6 Hz, 1H), 3.56 (dd, J=15.0, 6.7 Hz, 1H), 3.87 (m, 1H), 7.28 (m, 1H), 7.29 (d, J=8.5 Hz, 2H), 7.35 (d, J=8.5 Hz, 2H), 7.50 (s, 1H), 7.58 (d, J=8.4 Hz, 1H).

$^{13}$C-NMR and DEPT (125 MHz, DMSO-d$_6$): δ (ppm)= 20.91 (CH$_3$), 32.39 (CH$_2$), 39.20 (CH), 39.70 (CH$_2$), 113.05

(CH), 113.17 (CH), 126.77 (CH), 128.32 (2CH), 128.63 (C), 129.14 (2CH), 130.84 (C), 131.41 (C), 135.33 (C), 140.63 (C), 151.26 (C), 172.08 (CO).
MS (+ESI): m/z=329 (M+H).

1.24. 4-(5,6-Dichloro-2-benzimidazolyl)-3-(4-chlorophenyl)butanoic acid•HCl (PS 150)

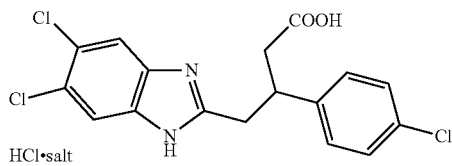 [SMILES: O=C(O)CC(Cc1nc2cc(Cl)c(Cl)cc2[nH]1)c1ccc(Cl)cc1]

1) Ethyl 4-(5,6-dichloro-2-benzimidazolyl)-3-(4-chlorophenyl)butanoate

The solution of commercial 4,5-dichloro-1,2-phenylenediamine (0.36 g) and triethyl amine (0.32 ml) in 1,4-dioxane (1.5 ml) was added to a solution of 3-(4-chlorophenyl)glutaric anhydride (0.45 g) in 1,4-dioxane (1 ml) with ice cooling. The resulting mixture was stirred at rt for 0.5 h and at 40° C. for 0.5 h. Again under ice cooling 1M HCl (3 ml) was added dropwise. A gummy precipitate is formed. After 0.5 h of cooling the aqueous layer is removed by decantation and the residue is dissolved in methanol. The dark solution is decolorized with activated carbon, filtered, and the filtrate concentrated in vacuo. The amorphous solid is redissolved in ethanol (6 ml) and conc. HCl (2 ml) and stirred at reflux for 16 h. After cooling to rt the pH is adjusted to 8 by addition of first NaOH solution, then sat. sodium bicarbonate solution. The aqueous layer is extracted with dichloromethane (40 ml) and the organic layer is washed with sat. sodium chloride solution and dried (sodium sulfate). After concentration the crude (0.46 g) is purified by flash chromatography ((dichloromethane/2% methanol/1% triethyl amine) on silica gel to afford ethyl 4-(5,6-dichloro-2-benzimidazolyl)-3-(4-chlorophenyl)butanoate (0.33 g) as yellowish, amorphous solid.

2) 4-(5,6-Dichloro-2-benzimidazolyl)-3-(4-chlorophenyl)butanoic acid•HCl

The solution of ethyl 4-(5,6-dichloro-2-benzimidazolyl)-3-(4-chlorophenyl)butanoate (0.31 g) in a mixture of acetic acid (2 ml) and conc. HCl (0.5 ml) was heated to reflux for 1 h. Then all volatiles are removed at the water aspirator. The residue is dried by distillation with toluene (50 ml) and triturated with boiling acetone (5 ml). The precipitate is collected by filtration, washed with acetone and dried in vacuo to yield 4-(5,6-dichloro-2-benzimidazolyl)-3-(4-chlorophenyl)butanoic acid•HCl (0.26 g) as colourless solid.

$^1$H-NMR (500 MHz, DMSO-$d_6$): δ (ppm)=2.71 (dd, J=16.2, 8.6 Hz, 1H), 2.82 (dd, J=16.2, 6.1 Hz, 1H), 3.40 (dd, J=14.9, 9.0 Hz, 1H), 3.51 (dd, J=14.9, 7.0 Hz, 1H), 3.83 (m, 1H), 7.30 (d, J=8.6 Hz, 2H), 7.34 (d, J=8.6 Hz, 2H), 8.01 (s, 2H).

$^{13}$C-NMR and DEPT (125 MHz, DMSO-$d_6$): δ (ppm)= 32.97 ($CH_2$), 39.26 (CH), 39.54 ($CH_2$), 115.43 (CH), 127.52 (C), 128.33 (2CH), 129.14 (2CH), 131.41 (C), 140.81 (C), 154.68 (C), 172.15 (CO). Four carbon signals are not visible.
MS (+ESI): m/z=383 (M+H).

1.25. 4-(5,7-Dichloro-2-benzimidazolyl)-3-(4-chlorophenyl)butanoic acid•HCl (PS 171)

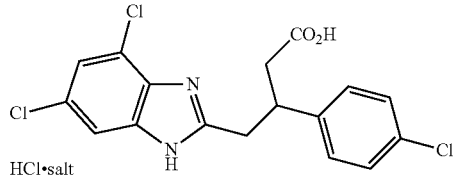 [SMILES: O=C(O)CC(Cc1nc2c(Cl)cc(Cl)cc2[nH]1)c1ccc(Cl)cc1]

The solution of commercial 2,4-dichloro-6-nitroaniline (621 mg) and 3-(4-chlorophenyl)glutaric anhydride (674 mg) in 1,4-dioxane (2 ml) was heated to reflux shortly and stirred at rt for 1 h. The solvent was removed by distillation and the residue dried in vacuo. The oily residue was dissolved in acetic acid (6 ml) and heated to reflux. Iron powder (1.01 g) was added and the mixture stirred under reflux for 1 h. Then conc. HCl (6 ml) was added cautiously and the green-yellow solution was refluxed for additional 2 h. All volatiles were removed at the water aspirator and the residue precipitated from acetic acid/conc. HCl solution with water. The solid was collected by suction filtration and washed well with 1M HCl and water. The crude was recrystallised from acetic acid to give 4-(5,7-dichloro-2-benzimidazolyl)-3-(4-chlorophenyl)butanoic acid•HCl (325 mg) as colourless crystals.

$^1$H-NMR (500 MHz, DMSO-$d_6$): δ (ppm)=2.70 (dd, J=16.2, 8.9 Hz, 1H), 2.79 (dd, J=16.2, 5.9 Hz, 1H), 3.35 (dd, J=14.7, 8.3 Hz, 1H), 3.43 (dd, J=14.7, 7.6 Hz, 1H), 3.83 (m, 1H), 7.33 (q, J=8.6 Hz, 4H), 7.59 (d, J=1.6 Hz, 1H), 7.73 (d, J=1.6 Hz, 1H).

$^{13}$C-NMR and DEPT (125 MHz, DMSO-$d_6$): δ (ppm)= 33.39 ($CH_2$), 39.39 (CH), 39.46 ($CH_2$), 112.58 (CH), 119.26 (C), 123.64 (CH), 128.28 (2CH), 128.63 (C), 129.14 (2CH), 131.1 (br, C), 131.29 (C), 134.40 (C), 141.22 (C), 154.96 (C), 172.24 (CO).
MS (+ESI): m/z=383 (M+H).

1.26. 4-(5-Chloro-7-methyl-2-benzimidazolyl)-3-(4-chlorophenyl)butanoic acid•HCl (PS 172)

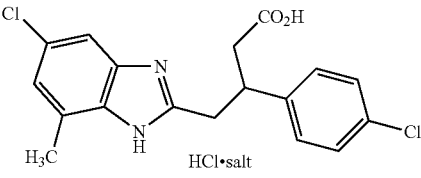 [SMILES: Cc1cc(Cl)cc2nc(CC(CC(=O)O)c3ccc(Cl)cc3)[nH]c12]

By a procedure similar to that of example 1.25, starting from commercial 4-chloro-2-methyl-6-nitroaniline and 3-(4-chlorophenyl)glutaric anhydride, 4-(5-chloro-7-methyl-2-benzimidazolyl)-3-(4-chlorophenyl)butanoic acid•HCl was prepared as colourless solid.

$^1$H-NMR (500 MHz, DMSO-$d_6$): δ (ppm)=2.56 (s, 3H), 2.72 (dd, J=16.2, 8.7 Hz, 1H), 2.81 (dd, J=16.2, 6.1 Hz, 1H), 3.43 (dd, J=14.8, 8.8 Hz, 1H), 3.53 (dd, J=14.8, 7.3 Hz, 1H), 3.89 (m, 1H), 7.23-7.40 (m, 5H), 7.61 (d, J=1.0 Hz, 1H).

$^{13}$C-NMR and DEPT (125 MHz, DMSO-$d_6$): δ (ppm)= 32.61 ($CH_2$), 39.22 (CH), 39.53 ($CH_2$), 110.74 (CH), 125.66 (CH), 126.08 (C), 128.33 (2CH), 129.12 (2CH), 129.39 (C), 129.85 (br, C), 131.41 (C), 131.59 (br, C), 140.79 (C), 152.91 (C), 172.11 (CO).
MS (+ESI): m/z=363 (M+H).

1.27. 7(8)-Chloro-3-phenyl-3,4-dihydropyrido[1,2-a]benzimidazol-1(2H)-one and 4-(5-Chloro-2-benzimidazolyl)-3-(4-chlorophenyl)butyrohydroxamic acid (PS 173)

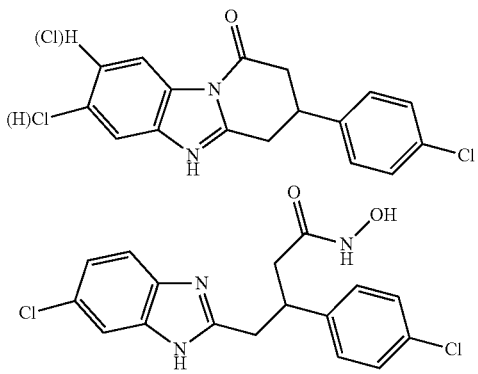

1) 7-Chloro-3-phenyl-3,4-dihydropyrido[1,2-a]benzimidazol-1(2H)-one and 8-chloro-3-phenyl-3,4-dihydropyrido[1,2-a]benzimidazol-1(2H)-one A 1:1-mixture of the regioisomeric dihydropyridobenzimidazolones was obtained as light red solid in 78-86% yield by cyclisation of crude 4-(5-chloro-2-benzimidazolyl)-3-(4-chlorophenyl)butanoic acid•HCl (see example 1.4) with acetic anhydride under reflux for 1 h.

2) 4-(5-Chloro-2-benzimidazolyl)-3-(4-chlorophenyl)butyrohydroxamic acid

The above mentioned regioisomeric mixture of 7-chloro-3-phenyl-3,4-dihydropyrido[1,2-a]benzimidazol-1(2H)-one and 8-chloro-3-phenyl-3,4-dihydropyrido[1,2-a]benzimidazol-1(2H)-one (331 mg) and hydroxylamine•HCl (83 mg) in ethanol (2 ml) was heated to reflux with stirring. Sodium ethanolate (82 mg) was added to give a clear solution. Refluxing was continued for 1 h whereupon a new precipitate is formed. Water (2 ml) was added and the mixture was kept at rt overnight. The solid was isolated by suction filtration and washed with water. After drying in vacuo 4-(5-chloro-2-benzimidazolyl)-3-(4-chlorophenyl)butyrohydroxamic acid (242 mg) is obtained as light red solid.

$^1$H-NMR (500 MHz, DMSO-$d_6$): δ (ppm)=2.40 (m, 2H), 3.11 (dd, J=14.8, 8.8 Hz, 1H), 3.21 (dd, J=14.8, 6.8 Hz, 1H), 3.77 (m, 1H), 7.15 (dd, J=8.5, 1.9 Hz, 1H), 7.23 (d, J=8.5 Hz, 2H), 7.27 (d, J=8.5 Hz, 2H), 7.46 (d, J=8.5 Hz, 1H), 7.53 (d, J=1.9 Hz, 1H), 10.38 (br s, 1H).

$^{13}$C-NMR and DEPT (125 MHz, DMSO-$d_6$): δ (ppm)= 34.69 (CH$_2$), 38.26 (CH$_2$), 39.78 (CH), 114.25 (br, C), 115.29 (br, C), 121.78 (CH), 125.99 (C), 128.06 (2CH), 128.55 (CH), 128.71 (CH), 129.17 (2CH), 130.91 (C), 141.80 (C), 154.73 (C), 166.89 (CO).

MS (+ESI): m/z=364 (M+H).

1.28. 4-(5-Chloro-2-benzimidazolyl)-3-(4-chlorophenyl)butyramide (PS 174)

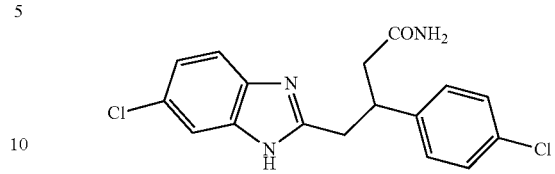

A 1:1-mixture of 7-chloro-3-phenyl-3,4-dihydropyrido[1,2-a]-benzimidazol-1(2H)-one and 8-chloro-3-phenyl-3,4-dihydropyrido[1,2-a]benzimidazol-1(2H)-one (222 mg)—see example 1.27.1—was dissolved in 1,4-dioxane (3 ml) at reflux temperature. A 25% solution of ammonia in water (2 ml) was added to give a light red solution. Refluxing was continued for 1 h. All volatiles were removed at the water aspirator to leave a light red oil, which was dissolved in acetone (3 ml). Soon precipitation occurs and the solid is isolated by suction filtration and washed with acetone. After drying in vacuo 4-(5-chloro-2-benzimidazolyl)-3-(4-chlorophenyl)-butyramide (120 mg) is obtained as colourless solid.

$^1$H-NMR (500 MHz, DMSO-$d_6$): δ (ppm)=2.47 (br d, J=7.5 Hz, 2H), 3.06 (dd, J=14.7, 8.6 Hz, 1H), 3.16 (dd, J=14.7, 6.9 Hz, 1H), 3.73 (m, 1H), 6.72 (br s, 1H), 7.10 (dd, J=8.5, 2.0 Hz, 1H), 7.26 (q, J=8.6 Hz, 5H), 7.43 (d, J=8.5 Hz, 1H), 7.49 (br s, 1H), 12.4 (br s, 1H).

$^{13}$C-NMR and DEPT (125 MHz, DMSO-$d_6$): δ (ppm)= 34.96 (CH$_2$), 39.88 (CH), 41.06 (CH$_2$), 110.52 (CH), 111.95 (CH), 117.49 (CH), 119.21 (CH), 121.00 (CH), 121.38 (CH), 125.16 (C), 127.94 (2CH), 129.16 (2CH), 130.68 (C), 132.85 (C), 134.78 (C), 142.48 (C), 144.11 (C), 154.36 (C), 154.83 (C), 172.15 (CO).

MS (+ESI): m/z=348 (M+H).

1.29. 3-(4-Fluorophenyl)-4-(5-iodo-2-benzimidazolyl)butanoic acid•HCl (PS 236)

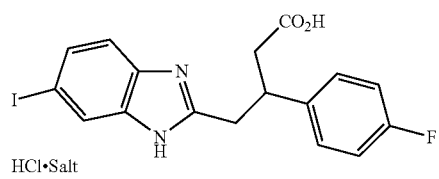 [SMILES: O=C(O)CC(Cc1nc2ccc(I)cc2[nH]1)c1ccc(F)cc1]

1) 3-(4-Fluorophenyl)glutaric anhydride

To a solution of commercial 4-fluorobenzaldehyde (12.4 g) in ethyl acetoacetate (25.3 ml) piperidine (2 ml) was added with stirring at rt. The cloudy solution solidifies within 3 h. The yellow solid was crushed, slurried with ethanol (20 ml), collected by suction filtration, and washed with ethanol. After drying in vacuo 27 g of a faint yellowish solid (the bis-adduct of acetoacetate to the benzaldehyde) was isolated. The powdered solid was added in portions to 40% NaOH (400 g) with stirring. The resulting yellow slurry was stirred at reflux for 2 h. After cooling in an ice bath the mixture was acidified by portionwise addition of conc. HCl (370 ml) to give a colourless precipitate. The solid was collected by suction filtration and washed with water. After drying in vacuo 3-(4-fluorophenyl)glutaric acid (12.3 g) was obtained. The suspension of finely divided 3-(4-fluorophenyl)glutaric acid in acetyl chloride (20 ml) was heated to reflux with stirring for 1 h. After cooling to rt precipitation of the product is completed by addition of petrol ether (150 ml). The precipitate is isolated by suction filtration, washed with petrol ether, and dried in vacuo to give 3-(4-fluorophenyl)glutaric anhydride (9.4 g) as colourless crystals.

2) 3-(4-Fluorophenyl)-4-(5-iodo-2-benzimidazolyl) butanoic acid•HCl

To a solution of 4-iodo-1,2-phenylenediamine (0.47 g) in dichloromethane (3 ml) 3-(4-fluorophenyl)glutaric anhydride (0.42 g) was added with stirring at rt. After 1 h at rt the voluminous precipitate was collected by suction filtration, washed with dichloromethane, and dried at the air to give a mixture of regioisomeric amides (0.84 g) as light red solid. This solid was dissolved in 1,4-dioxane (1 ml) with heating. 4M HCl in 1,4-dioxane (3 ml) was added and the solution was heated to reflux for 1 h to give a precipitate. After cooling to rt the precipitate is collected by suction filtration, washed with 1,4-dioxane and diethyl ether, and dried in vacuo to provide 3-(4-fluorophenyl)-4-(5-iodo-2-benzimidazolyl)butanoic acid HCl (0.65 g) as light red solid.

$^1$H-NMR (500 MHz, DMSO-$d_6$)): δ (ppm)=2.71 (dd, J=16.2, 8.5 Hz, 1H), 2.82 (dd, J=16.2, 6.3 Hz, 1H), 3.42 (dd, J=14.9, 9.3 Hz, 1H), 3.54 (dd, J=14.9, 6.9 Hz, 1H), 3.86 (m, 1H), 7.06 (t, $^3J_{H-H}$=8.9 Hz, $^3J_{H-F}$=8.9 Hz, 2H), 7.36 (m, 2H), 7.53 (d, J=8.5 Hz, 1H), 7.74 (dd, J=8.6, 1.5 Hz, 1H), 8.07 (d, J=1.2 Hz, 1H).

$^{13}$C-NMR and DEPT (125 MHz, DMSO-$d_6$): δ (ppm)= 32.76 (CH$_2$), 39.07 (CH), 39.81 (CH$_2$), 89.48 (C), 115.13 (d, $^2J_{C-F}$=21 Hz, 2CH), 115.67 (CH), 122.00 (CH), 129.12 (d, $^3J_{C-F}$=8.1 Hz, 2CH), 130.48 (C), 132.55 (C), 133.71 (CH), 137.78 (C), 152.59 (C), 160.93 (d, $^1J_{C-F}$=241.3 Hz, C), 172.18 (CO).

1.30. 3-(4-Bromophenyl)-4-(5-chloro-2-benzimidazolyl)butanoic acid•HCl (PS 253)

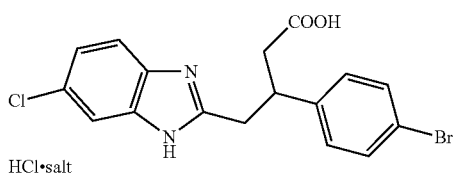 [SMILES: O=C(O)CC(Cc1nc2ccc(Cl)cc2[nH]1)c1ccc(Br)cc1]

1) 3-(4-Bromophenyl)glutaric anhydride

To a solution of commercial 4-bromobenzaldehyde (23.4 g) in ethyl acetoacetate (32.9 g) piperidine (3 ml) was added with stirring at rt. The yellowish solution slowly evolves strong heat. Ethanol (40 ml) was added to induce crystallisation and the mixture was kept at rt for 2 h. The precipitate was collected by suction filtration, washed with ethanol, and dried in vacuo to give 29.5 g of a faint yellowish solid (the bis-adduct of acetoacetate to the benzaldehyde). The powdered solid was added in portions to 50% NaOH (500 g) with stirring. The resulting yellow slurry was stirred at reflux for 2 h. After cooling in an ice bath the mixture was acidified by portionwise addition of conc. HCl (450 ml) to give a white, partly resinous precipitate. The solid was collected by suction filtration and washed with water. After drying in vacuo 3-(4-bromophenyl)glutaric acid (16.7 g) was obtained. The suspension of finely divided 3-(4-bromophenyl)-glutaric acid in acetyl chloride (20 ml) was heated to reflux with stirring for 1 h. After cooling to rt precipitation of the product is completed by addition of petrol ether (100 ml). The precipitate is isolated by suction filtration, washed with acetyl chloride (2×6 ml) and petrol ether, and dried in vacuo to give 3-(4-bromophenyl)-glutaric anhydride (12.3 g) as colourless crystals.

2) 3-(4-Bromophenyl)-4-(5-chloro-2-benzimidazolyl)butanoic acid•HCl

To a solution of 4-chloro-1,2-phenylenediamine (1.43 g) in dichloromethane (10 ml) 3-(4-bromophenyl)glutaric anhydride (2.69 g) was added with stirring at rt. Almost instantaneously an oily precipitate is formed, which solidifies after 0.5 h at rt. The solid is collected by suction filtration, mechanically divided, and washed with dichloromethane. After drying in vacuo a mixture of regioisomeric amides (3.8 g) is provided as greyish solid. This solid is dissolved in acetic acid (10 ml) with heating. Conc. HCl (4 ml) is added and the resulting dark solution is heated to reflux for 1.5 h. The still hot solution is decolorized with activated carbon and filtered over Celite. From the filtrate all volatiles are removed at the water aspirator and the residue is triturated with acetone (5 ml) to leave 3-(4-bromophenyl)-4-(5-chloro-2-benzimidazolyl)butanoic acid HCl (2.8 g) as colourless solid after drying in vacuo.

$^1$H-NMR (500 MHz, DMSO-$d_6$)): δ (ppm)=2.72 (dd, J=16.2, 8.6 Hz, 1H), 2.83 (dd, J=16.3, 6.2 Hz, 1H), 3.43 (dd, J=14.9, 9.2 Hz, 1H), 3.54 (dd, J=15.0, 6.9 Hz, 1H), 3.84 (m, 1H), 7.30 (d, J=8.5 Hz, 2H), 7.44 (d, J=8.5 Hz, 2H), 7.48 (dd, J=8.7, 1.9 Hz, 1H), 7.73 (d, J=8.7 Hz, 1H), 7.81 (d, J=1.9 Hz, 1H).

$^{13}$C-NMR and DEPT (125 MHz, DMSO-$d_6$): δ (ppm)= 32.66 (CH$_2$), 39.26 (CH), 39.55 (CH$_2$), 113.57 (CH), 115.25 (CH), 119.97 (C), 125.40 (CH), 129.46 (C), 129.51 (2CH), 130.14 (C), 131.25 (2CH), 132.12 (C), 141.17 (C), 153.28 (C), 172.11 (CO).

1.31. 4-(5-Chloro-2-benzimidazolyl)-3-(2,4-dichlorophenyl)butanoic acid•HCl (PS 178)

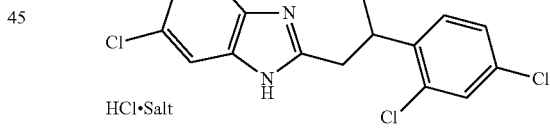

1) 3-(2,4-Dichlorophenyl)glutaric anhydride

By a procedure similar to that of example 1.2.1, starting from commercial 2,4-dichlorobenzaldehyde and ethyl acetoacetate, 3-(2,4-dichlorophenyl)glutaric anhydride was obtained in three steps with an overall yield of 41% as colourless crystals.

2) 4-(5-Chloro-2-benzimidazolyl)-3-(2,4-dichlorophenyl)butanoic acid•HCl

By a procedure similar to that of example 1.4, starting from 4-chloro-1,2-phenylenediamine and 3-(2,4-dichlorophenyl) glutaric anhydride, 4-(5-chloro-2-benzimidazolyl)-3-(2,4-dichlorophenyl)butanoic acid•HCl was obtained as light greyish solid.

¹H-NMR (500 MHz, DMSO-d₆): δ (ppm)=2.84 (m, 2H), 3.36 (dd, J=14.6, 8.1 Hz, 1H), 3.45 (dd, J=14.6, 7.1 Hz, 1H), 4.16 (m, 1H), 7.39 (dt, J=8.4, 2.4 Hz, 2H), 7.48 (d, J=2.2 Hz, 1H), 7.55 (d, J=8.5 Hz, 1H), 7.66 (d, J=8.7 Hz, 1H), 7.74 (d, J=1.7 Hz, 1H).
¹³C-NMR and DEPT (125 MHz, DMSO-d₆): δ (ppm)= 31.94 ($CH_2$), 36.20 (CH), 38.29 ($CH_2$), 113.81 (CH), 115.37 (CH), 124.45 (CH), 127.62 (2CH), 128.52 (C), 128.71 (2CH), 129.82 (CH), 131.97 (C), 133.79 (C), 138.40 (C), 152.94 (C), 171.99 (CO).
MS (+ESI): m/z=383 (M+H).

1.32. 4-(5-Chloro-2-benzimidazolyl)-3-(3,4-dichlorophenyl)butanoic acid•HCl (PS 179)

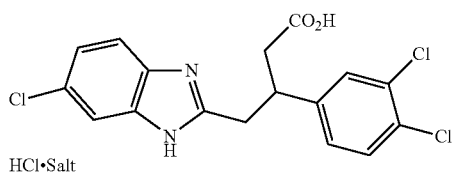 [SMILES: O=C(O)CC(Cc1nc2ccc(Cl)cc2[nH]1)c1ccc(Cl)c(Cl)c1]

1) 3-(3,4-Dichlorophenyl)glutaric anhydride

By a procedure similar to that of example 1.2.1, starting from commercial 3,4-dichlorobenzaldehyde and ethyl acetoacetate, 3-(3,4-dichlorophenyl)glutaric anhydride was obtained in three steps with an overall yield of 49% as off-white crystals.

2) 4-(5-Chloro-2-benzimidazolyl)-3-(3,4-dichlorophenyl)butanoic acid•HCl

By a procedure similar to that of example 1.4, starting from 4-chloro-1,2-phenylenediamine and 3-(3,4-dichlorophenyl) glutaric anhydride, 4-(5-chloro-2-benzimidazolyl)-3-(3,4-dichlorophenyl)butanoic acid•HCl was obtained as off-white solid.

¹H-NMR (500 MHz, DMSO-d₆): δ (ppm)=2.78 (dd, J=16.4, 8.7 Hz, 1H), 2.86 (dd, J=16.4, 6.1 Hz, 1H), 3.45 (dd, J=15.0, 9.0 Hz, 1H), 3.55 (dd, J=15.0, 6.8 Hz, 1H), 3.87 (m, 1H), 7.32 (dd, J=8.3, 2.0 Hz, 1H), 7.46-7.52 (m, 2H), 7.66 (d, J=2.0 Hz, 1H), 7.74 (d, J=8.8 Hz, 1H), 7.82 (d, J=1.8 Hz, 1H).
¹³C-NMR and DEPT (125 MHz, DMSO-d₆): δ (ppm)= 32.52 ($CH_2$), 38.99 (CH), 39.21 ($CH_2$), 113.61 (CH), 115.29 (CH), 125.48 (CH), 127.83 (CH), 129.44 (C), 129.49 (C), 129.53 (C), 130.06 (C), 130.46 (CH), 130.98 (C), 132.03 (C), 142.97 (C), 153.04 (C), 172.05 (CO).
MS (+ESI): m/z=383 (M+H).

1.33. 4-(5-Chloro-2-benzimidazolyl)-3-(3-chlorophenyl)butanoic acid•HCl (PS 186)

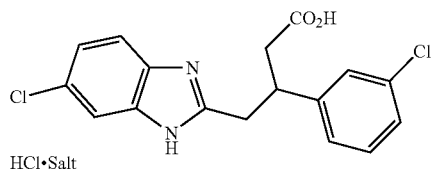 [SMILES: O=C(O)CC(Cc1nc2ccc(Cl)cc2[nH]1)c1cccc(Cl)c1]

1) 3-(3-Chlorophenyl)glutaric anhydride

By a procedure similar to that of example 1.2.1, starting from commercial 3-chlorobenzaldehyde and ethyl acetoacetate, 3-(3-chlorophenyl)glutaric anhydride was obtained in three steps with an overall yield of 38% as colourless crystals.

2) 4-(5-Chloro-2-benzimidazolyl)-3-(3-chlorophenyl)butanoic acid•HCl

By a procedure similar to that of example 1.4, starting from 4-chloro-1,2-phenylenediamine and 3-(3-chlorophenyl)glutaric anhydride, 4-(5-chloro-2-benzimidazolyl)-3-(3-chlorophenyl)butanoic acid•HCl was obtained as light greyish solid.

¹H-NMR (500 MHz, DMSO-d₆): δ (ppm)=2.75 (dd, J=16.3, 8.7 Hz, 1H), 2.82 (dd, J=16.3, 6.1 Hz, 1H), 3.46 (dd, J=14.9, 8.8 Hz, 1H), 3.55 (dd, J=14.9, 7.3 Hz, 1H), 3.90 (m, 1H), 7.21 (dt, J=7.8, 1.4 Hz, 1H), 7.26 (t, J=7.7 Hz, 1H), 7.31 (d, J=7.7 Hz, 1H), 7.44 (t, J=1.6 Hz, 1H), 7.47 (dd, J=8.7, 1.8 Hz, 1H), 7.72 (d, J=8.7 Hz, 1H), 7.80 (d, J=1.8 Hz, 1H).
¹³C-NMR and DEPT (125 MHz, DMSO-d₆): δ (ppm)= 32.64 ($CH_2$), 39.40 (CH), 39.44 ($CH_2$), 113.55 (CH), 115.26 (CH), 125.39 (CH), 126.01 (CH), 126.92 (CH), 127.25 (CH), 129.41 (C), 130.18 (C), 130.22 (CH), 132.16 (br, C), 132.95 (C), 144.43 (C), 153.17 (C), 172.08 (CO).
MS (+ESI): m/z=349 (M+H).

1.34. 4-(5-Chloro-2-benzimidazolyl)-3-(4-chloro-3-fluorophenyl)butanoic acid•HCl (PS 188)

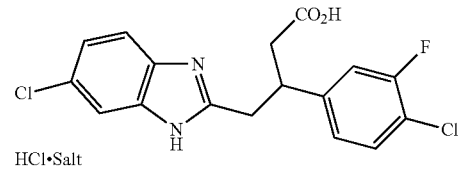 [SMILES: O=C(O)CC(Cc1nc2ccc(Cl)cc2[nH]1)c1ccc(Cl)c(F)c1]

1) 3-(4-Chloro-3-fluorophenyl)glutaric anhydride

By a procedure similar to that of example 1.2.1, starting from commercial 4-chloro-3-fluoro-benzaldehyde and ethyl acetoacetate, 3-(4-chloro-4-fluorophenyl)glutaric anhydride was obtained in three steps with an overall yield of 51% as colourless crystals.

2) 4-(5-Chloro-2-benzimidazolyl)-3-(4-chloro-3-fluorophenyl)butanoic acid•HCl By a procedure similar to that of example 1.4, starting from 4-chloro-1,2-phenylenediamine and 3-(4-chloro-3-fluorophenyl)glutaric anhydride, 4-(5-chloro-2-benzimidazolyl)-3-(4-chloro-3-fluorophenyl)butanoic acid•HCl was obtained as light red solid.

¹H-NMR (500 MHz, DMSO-d₆): δ (ppm)=2.75 (dd, J=16.3, 8.8 Hz, 1H), 2.83 (dd, J=16.3, 6.0 Hz, 1H), 3.45 (dd, J=14.9, 9.1 Hz, 1H), 3.53 (dd, J=14.9, 6.9 Hz, 1H), 3.92 (m, 1H), 7.19 (dd, J=8.3, 1.7 Hz, 1H), 7.42 (t, J=8.1 Hz, 1H), 7.43-7.49 (m, 2H), 7.70 (d, J=8.7 Hz, 1H), 7.76 (d, J=1.7 Hz, 1H).
¹³C-NMR and DEPT (125 MHz, DMSO-d₆): δ (ppm)= 32.64 ($CH_2$), 39.13 (CH), 39.41 ($CH_2$), 113.61 (CH), 115.30 (CH), 115.88 (CH), 117.71 (C), 124.89 (CH), 125.14

1.35. 4-(5-Chloro-2-benzimidazolyl)-3-(4-chloro-3-trifluoromethylphenyl)butanoic acid•HCl (PS 189)

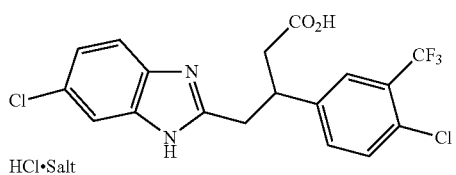 [SMILES: O=C(O)CC(Cc1nc2ccc(Cl)cc2[nH]1)c1ccc(Cl)c(C(F)(F)F)c1]

HCl•Salt

1) 3-(4-Chloro-3-trifluoromethylphenyl)glutaric anhydride

By a procedure similar to that of example 1.2.1, starting from commercial 4-chloro-3-trifluoromethylbenzaldehyde and ethyl acetoacetate, 3-(4-chloro-4-trifluoromethylphenyl) glutaric anhydride was obtained in three steps with an overall yield of 47% as colourless crystals.

2) 4-(5-Chloro-2-benzimidazolyl)-3-(4-chloro-3-trifluoromethylphenyl)butanoic acid •HCl By a procedure similar to that of example 1.4, starting from 4-chloro-1,2-phenylenediamine and 3-(4-chloro-3-trifluoromethylphenyl)glutaric anhydride, 4-(5-chloro-2-benzimidazolyl)-3-(4-chloro-3-trifluoromethylphenyl)butanoic acid•HCl was obtained as light greyish solid.

$^1$H-NMR (500 MHz, DMSO-d$_6$): δ (ppm)=2.79-2.93 (m, 2H), 3.48 (dd, J=15.0, 8.6 Hz, 1H), 3.57 (dd, J=15.0, 7.1 Hz, 1H), 3.99 (m, 1H), 7.48 (dd, J=8.7, 1.9 Hz, 1H), 7.62 (d, J=8.3 Hz, 1H), 7.68 (dd, J=8.3, 1.9 Hz, 1H), 7.73 (d, J=8.7 Hz, 1H), 7.82 (dd, J=10.8, 1.9 Hz, 2H).

$^{13}$C-NMR and DEPT (125 MHz, DMSO-d$_6$): δ (ppm)= 32.47 (CH$_2$), 39.00 (CH$_2$), 39.33 (CH), 113.56 (CH), 115.26 (CH), 122.63 (C, $^1$J$_{C\text{-}F}$=270.3 Hz), 125.35 (CH), 126.31 (C), 126.55 (C), 126.98 (CH, $^3$J$_{C\text{-}F}$=4.9 Hz), 129.03 (C), 129.39 (C), 130.28 (C), 131.59 (CH), 132.25 (C), 133.04 (CH), 142.01 (C), 152.94 (C), 172.03 (CO).

MS (+ESI): m/z=417 (M+H).

1.36. 4-(5-Iodo-2-benzimidazolyl)-3-phenylbutanoic acid•HCl (PS 235)

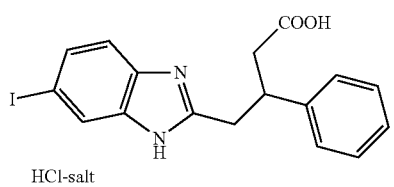 [SMILES: O=C(O)CC(Cc1nc2ccc(I)cc2[nH]1)c1ccccc1]

HCl-salt

To a solution of 4-iodo-1,2-phenylenediamine (0.47 g) in dichloromethane (3 ml) 3-phenylglutaric anhydride (0.38 g) was added with stirring at rt. After 2 h at rt the precipitate is collected by suction filtration, washed with dichloromethane, and dried in vacuo to give a mixture of regioisomeric amides (0.23 g) as colourless solid. This solid is dissolved in 4M HCl in 1,4-dioxane (3 ml) and the solution is heated to reflux for 1.5 h. From the solution all volatiles are removed at the water aspirator and the still hot oily residue is dissolved in acetone (2 ml). After cooling to rt the precipitate is collected by filtration, washed with acetone, and dried in vacuo to provide 4-(5-iodo-2-benzimidazolyl)-3-phenylbutanoic acid HCl (0.08 g) as beige coloured solid.

$^1$H-NMR (500 MHz, DMSO-d$_6$)): δ (ppm)=2.71 (dd, J=16.1, 8.2 Hz, 1H), 2.81 (dd, J=16.1, 6.4 Hz, 1H), 3.43 (dd, J=14.9, 9.2 Hz, 1H), 3.55 (dd, J=14.9, 7.1 Hz, 1H), 3.84 (m, 1H), 7.15 (t, J=7.3 Hz, 1H), 7.24 (m, 2H), 7.31 (d, J=7.2 Hz, 2H), 7.53 (d, J=8.6 Hz, 1H), 7.74 (dd, J=8.6, 1.5 Hz, 1H), 8.07 (d, J=1.3 Hz, 1H).

$^{13}$C-NMR and DEPT (125 MHz, DMSO-d$_6$): δ (ppm)= 32.73 (CH$_2$), 39.76 (CH), 39.83 (CH$_2$), 89.47 (C), 115.65 (CH), 121.99 (CH), 126.89 (CH), 127.12 (2CH), 128.41 (2CH), 130.47 (C), 132.54 (C), 133.70 (CH), 141.67 (C), 152.74 (C), 172.25 (CO).

1.37. 3-(3-Chlorophenyl)4-(5-iodo-2-benzimidazolyl)butanoic acid•HCl (PS 194)

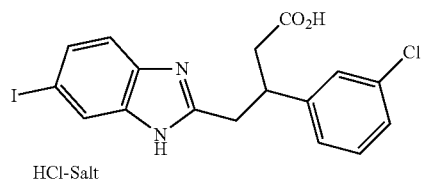 [SMILES: O=C(O)CC(Cc1nc2ccc(I)cc2[nH]1)c1cccc(Cl)c1]

HCl-Salt

By a procedure similar to that of example 1.4, starting from 4-iodo-1,2-phenylenediamine and 3-(3-chlorophenyl)glutaric anhydride, 3-(3-chlorophenyl)-4-(5-iodo-2-benzimidazolyl)butanoic acid•HCl was obtained as light beige solid.

$^1$H-NMR (500 MHz, DMSO-d$_6$): δ (ppm)=2.72 (dd, J=16.2, 8.8 Hz, 1H), 2.80 (dd, J=16.2, 6.0 Hz, 1H), 3.33 (dd, J=14.9, 8.6 Hz, 1H), 3.41 (dd, J=14.9, 7.2 Hz, 1H), 3.82 (m, 1H), 7.20 (dt, J=7.0, 2.0 Hz, 1H), 7.23-7.29 (m, 2H), 7.41 (br s, 1H), 7.44 (d, J=8.5 Hz, 1H), 7.60 (dd, J=8.5, 1.3 Hz, 1H), 7.97 (d, J=1.0 Hz, 1H).

$^{13}$C-NMR and DEPT (125 MHz, DMSO-d$_6$): δ (ppm)= 33.34 (CH$_2$), 39.50 (CH$_2$), 39.62 (CH), 87.64 (C), 115.98 (CH), 122.43 (CH), 126.06 (CH), 126.73 (CH), 127.23 (CH), 130.11 (CH), 132.09 (CH), 132.87 (C), 133.27 (br, C), 135.68 (br, C), 144.91 (C), 152.91 (C), 172.25 (CO).

MS (+ESI): m/z=441 (M+H).

1.38. 3-(3,4-Dichlorophenyl)-4-(5-iodo-2-benzimidazolyl)butanoic acid•HCl (PS 185)

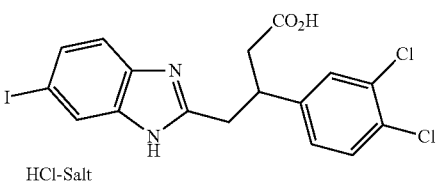 [SMILES: O=C(O)CC(Cc1nc2ccc(I)cc2[nH]1)c1ccc(Cl)c(Cl)c1]

HCl-Salt

By a procedure similar to that of example 1.4, starting from 4-iodo-1,2-phenylenediamine and 3-(3,4-dichlorophenyl)

glutaric anhydride, 3-(3,4-dichlorophenyl)-4-(5-iodo-2-benzimidazolyl)butanoic acid•HCl was obtained as off-white solid.

$^1$H-NMR (500 MHz, DMSO-$d_6$): δ (ppm)=2.78 (dd, J=16.4, 8.7 Hz, 1H), 2.85 (dd, J=16.4, 6.1 Hz, 1H), 3.44 (dd, J=15.0, 9.1 Hz, 1H), 3.54 (dd, J=15.0, 6.8 Hz, 1H), 3.87 (m, 1H), 7.31 (dd, J=8.35, 2.07 Hz, 1H), 7.50 (d, J=8.3 Hz, 1H), 7.54 (d, J=8.6 Hz, 1H), 7.66 (d, J=2.1 Hz, 1H), 7.75 (dd, J=8.6, 1.5 Hz, 1H), 8.08 (d, J=1.4 Hz, 1H).

$^{13}$C-NMR and DEPT (125 MHz, DMSO-$d_6$): δ (ppm)= 32.40 ($CH_2$), 38.97 (CH), 39.22 ($CH_2$), 89.43 (C), 115.73 (CH), 122.09 (CH), 127.82 (CH), 129.43 (CH), 129.49 (C), 130.46 (CH), 130.67 (C), 130.97 (C), 132.75 (C), 133.66 (CH), 142.93 (C), 152.25 (C), 172.04 (CO).

MS (+ESI): m/z=475 (M+H).

1.39. 4-(5-Iodo-2-benzimidazolyl)-3-(2-methylphenyl)butanoic acid•HCl (PS 226)

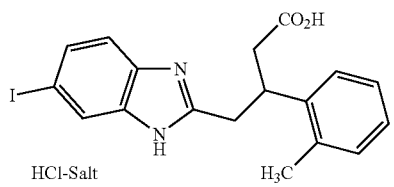 [SMILES: Cc1ccccc1C(CC(=O)O)Cc1nc2ccc(I)cc2[nH]1]

1) 3-(2-Methylphenyl)glutaric anhydride

To a solution of commercial 2-methylbenzaldehyde (18 g) and ethyl acetoacetate (39 g) in ethanol (30 ml) piperidine (3 ml) was added with stirring at rt. The mixture was kept at rt for 2 d. The precipitate was collected by suction filtration, washed with ethanol, and dried in vacuo to give 25.66 g of a yellowish solid (the bis-adduct of acetoacetate to the benzaldehyde). The powdered solid was added in portions to 40% NaOH (300 g) with stirring. The resulting yellow slurry was stirred at reflux for 2 h. After cooling in an ice bath the mixture was acidified by portionwise addition of conc. HCl (280 ml) to give a colourless precipitate. The solid was collected by suction filtration and washed with water. After drying in vacuo 3-(2-methylphenyl)glutaric acid (9.01 g) was obtained. The suspension of finely divided 3-(2-methylphenyl)glutaric acid in acetyl chloride (14.4 ml) was heated to reflux with stirring for 2 h. After cooling to rt petrol ether (50 ml) is added and the mixture is kept in the refrigerator for 12 h. The precipitate is isolated by suction filtration, washed with petrol ether, and dried in vacuo to give a crude which is dissolved in dichloromethane (400 ml). Insolubles are removed by filtration and the filtrate is concentrated in vacuo to provide 3-(2-methylphenyl)glutaric anhydride (6.79 g) as colourless solid.

2) 4-(5-Iodo-2-benzimidazolyl)-3-(2-methylphenyl)butanoic acid•HCl

To a solution of 4-iodo-1,2-phenylenediamine (0.47 g) in dichloromethane (3 ml) the solution of 3-(2-methylphenyl)glutaric anhydride (0.41 g) in dichloromethane (4 ml) was added with stirring at rt. Almost instantaneously an resinous precipitate is formed. After 1 h at rt all volatiles are removed in vacuo and the residue is taken up in 1,4-dioxane (2 ml). 4M HCl in 1,4-dioxane (3 ml) is added and the resulting dark solution is heated to reflux for 1 h. Again all volatiles are removed at the water aspirator and the residue is recrystallised from EtOAc/methanol to give 4-(5-iodo-2-benzimidazolyl)-3-(2-methylphenyl)butanoic acid•HCl (0.49 g) as light brown solid.

$^1$H-NMR (500 MHz, DMSO-$d_6$): δ (ppm)=2.71 (m, 2H), 3.42 (dd, J=14.6, 8.2 Hz, 1H), 3.49 (dd, J=14.6, 7.9 Hz, 1H), 4.02 (m, 1H), 7.05 (m, 2H), 7.16 (m, 1H), 7.36 (d, J=7.7 Hz, 1H), 7.54 (d, J=8.6 Hz, 1H), 7.75 (dd, J=8.6, 1.5 Hz, 1H), 8.09 (d, J=1.3 Hz, 1H).

$^{13}$C-NMR and DEPT (125 MHz, DMSO-$d_6$): δ (ppm)= 19.14 ($CH_3$), 32.06 ($CH_2$), 35.29 (CH), 39.66 ($CH_2$), 89.32 (C), 115.69 (CH), 122.04 (CH), 125.68 (CH), 126.21 (CH), 126.49 (CH), 130.20 (CH), 130.75 (C), 132.86 (C), 133.56 (CH), 135.56 (C), 140.08 (C), 152.78 (C), 172.35 (CO).

1.40. 3-(4-Chloro-2-methylphenyl)-4-(5-iodo-2-benzimidazolyl)butanoic acid•HCl (PS 227)

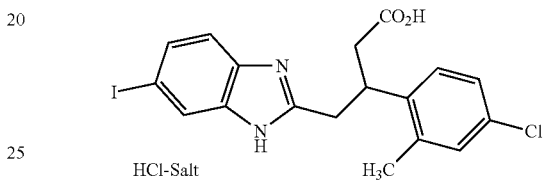

1) 3-(4-Chloro-2-methylphenyl)glutaric anhydride

To a solution of commercial 4-chloro-2-methylbenzaldehyde (5.16 g) and ethyl acetoacetate (8.69 g) in ethanol (10 ml) piperidine (1 ml) was added with stirring at rt. The mixture was kept at rt for 4 d. The precipitate was collected by suction filtration, washed with ethanol, and dried in vacuo to give 4.5 g of a light yellow solid (the bis-adduct of acetoacetate to the benzaldehyde). The powdered solid was added in portions to 40% NaOH (50 g) with stirring. The resulting yellow slurry was stirred at reflux for 2 h. After cooling in an ice bath the mixture was acidified by portionwise addition of conc. HCl (30 ml) to give a yellow resinous precipitate. The aqueous layer was extracted with ethyl acetate, the organic layer dried (sodium sulphate), and filtered. After evaporation of the solvent a crude was obtained which was recrystallised from benzene to afford 3-(4-chloro-2-methylphenyl)glutaric acid (1.43 g). The suspension of finely divided 3-(4-chloro-2-methylphenyl)glutaric acid in acetyl chloride (4 ml) was heated to reflux with stirring for 1 h. Further acetyl chloride (15 ml) was added and reflux continued for another hour. Then the excess of acetyl chloride is removed by distillation, petrol ether (55 ml) is added to the residue, and the solution is kept in the refrigerator. The precipitate is isolated by suction filtration, washed with petrol ether, and dried in vacuo to give 3-(4-chloro-2-methylphenyl)glutaric anhydride (0.9 g) as colourless solid.

2) 3-(4-Chloro-2-methylphenyl)-4-(5-iodo-2-benzimidazolyl)butanoic acid•HCl To a solution of 4-iodo-1,2-phenylenediamine (0.47 g) in dichloromethane (2 ml) the solution of 3-(4-chloro-2-methylphenyl)glutaric anhydride (0.48 g) in dichloromethane (2 ml) was added with stirring at rt. Almost instantaneously an resinous precipitate is formed. After 1 h the mixture was cooled in an ice bath and the solvent was removed by decantation. The residue is dissolved in acetic acid (3 ml). Conc. HCl (1 ml) is added and the resulting solution is heated to reflux for 1 h. All volatiles are removed at the water aspirator and the residue is triturated with acetic acid and acetone to leave 3-(4-chloro-2-methylphenyl)-4-(5-iodo-2-benzimidazolyl)butanoic acid HCl (0.62 g) as light brown solid.

$^1$H-NMR (500 MHz, DMSO-$d_6$)): δ (ppm)=2.73 (m, 2H), 3.40 (dd, J=14.6, 8.3 Hz, 1H), 3.48 (dd, J=14.6, 7.7 Hz, 1H), 3.98 (m, 1H), 7.15 (d, J=2.1 Hz, 1H), 7.22 (dd, J=8.4, 2.3 Hz, 1H), 7.39 (d, J=8.4 Hz, 1H), 7.55 (d, J=8.6 Hz, 1H), 7.75 (dd, J=8.6, 1.5 Hz, 1H), 8.09 (d, J=1.2 Hz, 1H).

$^{13}$C-NMR and DEPT (125 MHz, DMSO-$d_6$): δ (ppm)= 18.85 ($CH_3$), 31.92 ($CH_2$), 34.91 (CH), 39.47 ($CH_2$), 89.41 (C), 115.72 (CH), 122.09 (CH), 126.03 (CH), 127.76 (CH), 129.64 (CH), 130.71 (C), 130.80 (C), 132.80 (C), 133.65 (CH), 138.34 (C), 139.15 (C), 152.55 (C), 172.23 (CO).

1.41. 3-(2-Bromophenyl)-4-(5-iodo-2-benzimidazolyl)butanoic acid•HCl (PS 237)

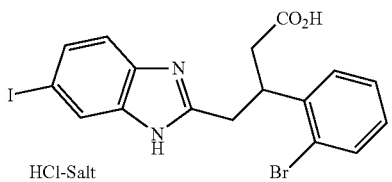 [SMILES: O=C(O)CC(Cc1nc2ccc(I)cc2[nH]1)c1ccccc1Br]

1) 3-(2-Bromophenyl)glutaric anhydride

To a solution of commercial 2-bromobenzaldehyde (5 g) in ethyl acetoacetate (7 g) piperidine (0.5 ml) was added with stirring at rt. The cloudy solution was kept at rt for 3 d. The yellowish amorphous solid (the bis-adduct of acetoacetate to the benzaldehyde) was dissolved in ethanol (20 ml). This solution was added in portions to 40% NaOH (150 g) with stirring. The resulting orange slurry was stirred at reflux for 2 h. After cooling in an ice bath the now yellowish mixture was acidified by portionwise addition of conc. HCl (150 ml) to give a white, partly resinous precipitate. The solid was collected by suction filtration and washed with water. After drying in vacuo 3-(2-bromophenyl)glutaric acid (5.7 g) was obtained. The suspension of finely divided 3-(2-bromophenyl)glutaric acid in acetyl chloride (7 ml) was heated to reflux with stirring for 1 h. After cooling to rt precipitation was induced by addition of petrol ether (50 ml). From the oily precipitate the mother liquor was removed by decantation and the residue was dried in vacuo to afford 3-(2-bromophenyl)glutaric anhydride (4.6 g) as light yellow solid in sufficient purity.

2) 3-(2-Bromophenyl)-4-(5-iodo-2-benzimidazolyl)butanoic acid HCl

To a solution of 4-iodo-1,2-phenylenediamine (0.47 g) in dichloromethane (3 ml) 3-(2-bromophenyl)glutaric anhydride (0.54 g) was added with stirring at rt. Almost instantaneously an resinous precipitate is formed. After 1 h at rt the solvent was removed by decantation and the residue dried in vacuo to give an amorphous solid (0.52 g). The solid is dissolved in 1,4-dioxane (1 ml) and 4M HCl in 1,4-dioxane (3 ml) is added. The resulting dark solution is heated to reflux for 1 h whereupon a precipitate is formed. After cooling to rt the precipitate is collected by suction filtration, washed with 1,4-dioxane and diethyl ether, and dried in vacuo to give 3-(2-bromophenyl)-4-(5-iodo-2-benzimidazolyl)butanoic acid•HCl (0.27 g) as light grey solid.

$^1$H-NMR (500 MHz, DMSO-$d_6$)): δ (ppm)=2.81 (dd, J=16.4, 7.4 Hz, 1H), 2.88 (dd, J=16.6, 7.0 Hz, 1H), 3.44 (dd, J=14.5, 8.4 Hz, 1H), 3.54 (dd, J=14.6, 7.0 Hz, 1H), 4.16 (m, 1H), 7.14 (dt, J=7.8, 1.6 Hz, 1H), 7.37 (dt, J=7.7, 1.1 Hz, 1H), 7.51 (dd, J=8.0, 1.2 Hz, 1H), 7.54 (m, 2H), 7.75 (dd, J=8.6, 1.5 Hz, 1H), 8.08 (d, J=1.3 Hz, 1H).

$^{13}$C-NMR and DEPT (125 MHz, DMSO-$d_6$): δ (ppm)= 31.60 ($CH_2$), 38.67 ($CH_2$), 39.01 (CH), 89.46 (C), 115.75 (CH), 122.07 (CH), 123.60 (C), 128.20 (CH), 128.34 (br, CH), 128.89 (CH), 130.78 (C), 132.71 (CH), 132.86 (br, C), 133.67 (CH), 140.36 (C), 152.04 (C), 171.97 (CO).

1.42. 4-(5-Iodo-2-benzimidazolyl)-3-(4-propylphenyl)butanoic acid (PS 233)

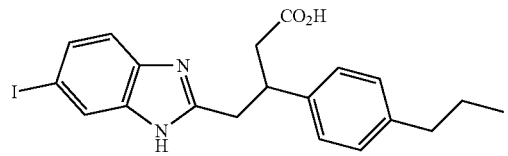 [SMILES: CCCc1ccc(C(CC(=O)O)Cc2nc3ccc(I)cc3[nH]2)cc1]

1) 3-(4-Propylphenyl)glutaric anhydride

To a solution of commercial 4-propyl-benzaldehyde (5 g) and ethyl acetoacetate (8.77 g) in ethanol (10 ml) piperidine (1 ml) was added with stirring at rt. The yellow solution was kept at rt overnight. The precipitate was collected by suction filtration and washed with ethanol. After drying in vacuo 8.75 g of a faint yellowish solid (the bis-adduct of acetoacetate to the benzaldehyde) was isolated. The finely divided solid was added in portions to 40% NaOH (120 g) with stirring. The resulting yellow slurry was stirred at reflux for 2 h. After cooling in an ice bath the mixture was acidified by portionwise addition of conc. HCl (110 ml) to give a precipitate. The solid was collected by suction filtration and washed with water. After drying in vacuo 3-(4-propylphenyl)glutaric acid (4.89 g) was obtained. The suspension of finely divided 3-(4-propylphenyl)glutaric acid in acetyl chloride (7 ml) was heated to reflux with stirring for 1 h. After cooling to rt precipitation of the product is completed by addition of petrol ether (50 ml). The precipitate is isolated by suction filtration, washed with petrol ether, and recrystallised to give 3-(4-propylphenyl)glutaric anhydride (2.5 g) as colourless crystals.

2) 4-(5-Iodo-2-benzimidazolyl)-3-(4-propylphenyl)butanoic acid

To a solution of 4-iodo-1,2-phenylenediamine (0.47 g) in dichloromethane (3 ml) 3-(4-fluorophenyl) glutaric anhydride (0.46 g) was added with stirring at rt. After 1 h at rt the precipitate was collected by suction filtration, washed with dichloromethane, and dried in vacuo to give a mixture of regioisomeric amides (0.78 g) as light yellowish solid. This solid was dissolved in 1,4-dioxane (1 ml) with heating. 4M HCl in 1,4-dioxane (3 ml) was added and the solution was heated to reflux for 1.5 h. All volatiles were removed at the water aspirator and the crude product is liberated from HCl by treatment with propene oxide in methanolic solution at rt for 2 h. Again all volatiles were removed in vacuo and the residue was crystallised from acetone to provide 4-(5-iodo-2-benzimidazolyl)-3-(4-propylphenyl)butanoic acid (0.47 g) as light beige solid.

$^1$H-NMR (500 MHz, DMSO-$d_6$)): δ (ppm)=0.85 (t, J=7.4 Hz, 3H), 1.52 (m, 2H), 2.45 (m, 2H), 2.60 (dd, J=15.8, 9.1 Hz, 1H), 2.69 (dd, J=15.8, 5.7 Hz, 1H), 3.07 (dd, J=14.7, 7.8 Hz, 1H), 3.14 (dd, J=14.7, 7.6 Hz, 1H), 3.66 (m, 1H), 7.04 (d, J=8.1 Hz, 2H), 7.16 (d, J=8.1 Hz, 2H), 7.28 (d, J=8.4 Hz, 1H), 7.38 (dd, J=8.4, 1.6 Hz, 1H), 7.80 (br s, 1H).

$^{13}$C-NMR and DEPT (125 MHz, DMSO-$d_6$): δ (ppm)= 13.62 (CH$_3$), 23.84 (CH$_2$), 35.19 (CH$_2$), 36.76 (CH$_2$), 39.81 (CH), 39.98 (CH$_2$), 84.56 (C), 127.01 (2CH), 128.06 (2CH), 129.43 (CH), 140.00 (C), 140.46 (C), 154.15 (C), 172.76 (CO). Four carbon signals missing.

1.43. 3-(4-$^t$Butylphenyl)-4-(5-iodo-2-benzimidazolyl)butanoic acid•HCl (PS 231)

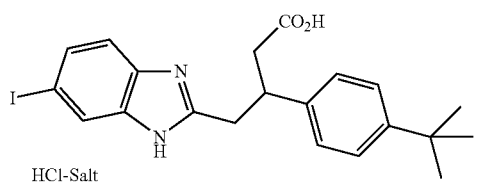 [SMILES: CC(C)(C)c1ccc(C(CC(=O)O)Cc2nc3ccc(I)cc3[nH]2)cc1]

HCl-Salt

1) 3-(4-$^t$Butylphenyl)glutaric anhydride

To a solution of commercial 4-$^t$butyl-benzaldehyde (5.43 g) and ethyl acetoacetate (8.71 g) in ethanol (10 ml) piperidine (1 ml) was added with stirring at rt. The yellow solution was kept at rt for 24 h. The precipitate was collected by suction filtration and washed with ethanol. After drying in vacuo 8.44 g of a faint yellowish solid (the bis-adduct of acetoacetate to the benzaldehyde) was isolated. The finely divided solid was added in portions to 40% NaOH (120 g) with stirring. The resulting yellow slurry was stirred at reflux for 2 h. After cooling in an ice bath conc. HCl (70 ml) was added with stirring to give a yellowish precipitate. The solid (sodium salt of 3-(4-$^t$butylphenyl)glutaric acid) was collected by suction filtration and slurried in ice-cold water (100 ml). Conc. HCl (20 ml) was added with stirring. The now colourless solid is isolated by suction filtration, washed with water, and dried in vacuo to give a crude. The crude was recrystallised from benzene to provide 3-(4-$^t$butylphenyl)-glutaric acid (2.83 g) as colourless crystals. The suspension of finely divided 3-(4-$^t$butylphenyl)glutaric acid in acetyl chloride (5 ml) was heated to reflux with stirring for 1 h. After cooling to rt precipitation of the product is completed by addition of petrol ether (50 ml). The precipitate is isolated by suction filtration, washed with petrol ether, and dried in vacuo to give 3-(4-propylphenyl)glutaric anhydride (2.3 g) as colourless crystals.

2) 3-(4-$^t$Butylphenyl)-4-(5-iodo-2-benzimidazolyl)butanoic acid•HCl

To a solution of 4-iodo-1,2-phenylenediamine (0.47 g) in dichloromethane (3 ml) 3-(4-$^t$butylphenyl)glutaric anhydride (0.49 g) was added with stirring at rt. After 1 h at rt the precipitate was collected by suction filtration, washed with dichloromethane, and dried in vacuo to give a mixture of regioisomeric amides (0.82 g) as light yellowish solid. This solid was slurried in 1,4-dioxane (1 ml) with heating. 4M HCl in 1,4-dioxane (3 ml) was added and the solution was heated to reflux for 1.5 h. All volatiles were removed at the water aspirator and the amorphous residue is crystallised from acetone to afford 3-(4-$^t$butylphenyl)-4-(5-iodo-2-benzimidazolyl)-butanoic acid HCl (0.62 g) as light grey solid.

$^1$H-NMR (500 MHz, DMSO-$d_6$): δ (ppm)=1.20 (s, 9H), 2.68 (dd, J=16.1, 8.2 Hz, 1H), 2.75 (dd, J=16.1, 6.4 Hz, 1H), 3.43 (dd, J=14.9, 8.5 Hz, 1H), 3.50 (dd, J=14.9, 7.5 Hz, 1H), 3.81 (m, 1H), 7.26 (dd, J=8.7, 4.9 Hz, 4H), 7.54 (d, J=8.6 Hz, 1H), 7.75 (dd, J=8.6, 1.5 Hz, 1H), 8.08 (d, J=1.3 Hz, 1H).

$^{13}$C-NMR and DEPT (125 MHz, DMSO-$d_6$): δ (ppm)= 30.97 (3CH$_3$), 32.74 (CH$_2$), 33.99 (C), 39.14 (CH), 39.81 (CH$_2$), 89.43 (C), 115.66 (CH), 121.99 (CH), 125.15 (2CH), 126.71 (2CH), 130.52 (C), 132.61 (C), 133.66 (CH), 138.83 (C), 149.04 (C), 152.79 (C), 172.27 (CO).

1.44. 3-(Biphenyl-4-yl)-4-(5-iodo-2-benzimidazolyl)butanoic acid•HCl (PS 229)

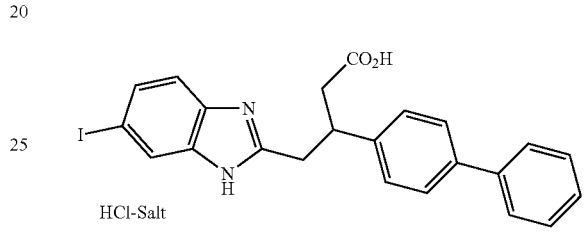

HCl-Salt

1) 3-(Biphenyl-4-yl)glutaric anhydride

To a solution of commercial 4-biphenylcarboxaldehyde (5.37 g) and ethyl acetoacetate (7.68 g) in ethanol (10 ml) piperidine (1 ml) was added with stirring at rt. The yellow solution was kept at rt overnight. The precipitate was collected by suction filtration and washed with ethanol. After drying in vacuo 10.2 g of a faint yellowish solid (the bis-adduct of acetoacetate to the aldehyde) was isolated. The finely divided solid was added in portions to 40% NaOH (120 g) with stirring. The resulting yellow slurry was stirred at reflux for 2 h. After cooling in an ice bath the mixture was acidified by portionwise addition of conc. HCl (110 ml) to give a yellowish precipitate. The solid was collected by suction filtration and washed with water. After drying in vacuo slightly impure 3-(4-biphenyl-4-yl)glutaric acid (8.1 g) was obtained. The suspension of finely divided 3-(4-biphenyl-4-yl)glutaric acid in acetyl chloride (28 ml) was heated to reflux with stirring for 2 h. After cooling to rt precipitation of the product is completed by addition of petrol ether (100 ml). The precipitate is isolated by suction filtration, washed with petrol ether, and dried at the air to give a crude (4.39 g). The crude was dissolved in dichloromethane (110 ml), filtered, and the filtrate concentrated in vacuo to afford 3-(biphenyl-4-yl)glutaric anhydride (3.37 g) as colourless solid.

2) 3-(Biphenyl-4-yl)-4-(5-iodo-2-benzimidazolyl)butanoic acid•HCl

4-Iodo-1,2-phenylenediamine (0.47 g) and 3-(biphenyl-4-yl)glutaric anhydride (0.53 g) were dissolved in dichloromethane (5 ml) with heating. The dark solution was stirred at rt for 1 h. The precipitate formed was collected by suction filtration, washed with dichloromethane, and dried in vacuo to give a mixture of regioisomeric amides (0.74 g) as light brown solid. This solid was dissolved in 1,4-dioxane (1 ml) with heating. 4M HCl in 1,4-dioxane (3 ml) was added and the solution was heated to reflux for 1 h. All volatiles were removed at the water aspirator and the amorphous residue is fractionally crystallised to provide 3-(biphenyl-4-yl)-4-(5-iodo-2-benzimidazolyl)butanoic acid HCl (0.43 g) as off-white solid.

$^1$H-NMR (500 MHz, DMSO-$d_6$)): δ (ppm)=2.76 (dd, J=16.2, 8.3 Hz, 1H), 2.85 (dd, J=16.2, 6.3 Hz, 1H), 3.47 (dd, J=14.9, 9.0 Hz, 1H), 3.56 (dd, J=14.9, 7.0 Hz, 1H), 3.88 (m, 1H), 7.33 (t, J=7.3 Hz, 1H), 7.42 (m, 4H), 7.55 (m, 3H), 7.60 (dd, J=8.0, 1.0 Hz, 2H), 7.75 (dd, J=8.6, 1.5 Hz, 1H), 8.09 (d, J=1.3 Hz, 1H).

1.45. 3-(Biphenyl-4-yl)-7(8)-iodo-3,4-dihydropyrido[1,2-a]benzimidazol-1(2H)-one and 3-(Biphenyl-4-yl)-4-(5-iodo-2-benzimidazolyl)butyramide (PS 243)

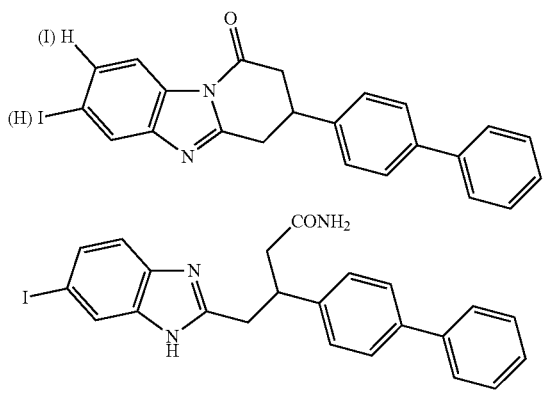

1) 3-(Biphenyl-4-yl)-7-iodo-3,4-dihydropyrido[1,2-a]benzimidazol-1(2H)-one and 3-(Biphenyl-4-yl)-8-iodo-3,4-dihydropyrido[1,2-a]benzimidazol-1(2H)-one A 1:1-mixture of the regioisomeric dihydropyridobenzimidazolones was obtained as light yellow solid by cyclisation of crude 3-(biphenyl-4-yl)-4-(5-iodo-2-benzimidazolyl)butanoic acid HCl with acetic anhydride under reflux for 0.5 h.

2) 3-(Biphenyl-4-yl)-4-(5-iodo-2-benzimidazolyl)butyramide

The 1:1-mixture of 3-(biphenyl-4-yl)-7-iodo-3,4-dihydropyrido[1,2-a]benzimidazol-1(2H)-one and 3-(biphenyl-4-yl)-8-iodo-3,4-dihydropyrido[1,2-a]benzimidazol-1(2H)-one (140 mg) was dissolved in 1,4-dioxane (2 ml) at reflux temperature. A 25% solution of ammonia in water (1 ml) was added and refluxing was continued for 2 h while addition of 25% ammonia solution in 1 ml portions was repeated every half an hour (3 times). Then all volatiles were removed at the water aspirator and the residue was triturated with acetone to leave 3-(biphenyl-4-yl)-4-(5-iodo-2-benzimidazolyl)-butyramide (85 mg) as light colourless solid.

$^1$H-NMR (500 MHz, DMSO-$d_6$)): δ (ppm)=2.51 (m, 2H), 3.12 (dd, J=14.7, 8.3 Hz, 1H), 3.19 (dd, J=14.7, 7.0 Hz, 1H), 3.79 (m, 1H), 6.72 (s, 1H), 7.24-7.43 (m, 8H), 7.52 (d, J=8.3 Hz, 2H), 7.60 (dd, J=8.4, 1.2 Hz, 2H), 7.80 (br d, 1H), 12.4 (br d, 1H).

Due to tautomerism a double set of all benzimidazole C-signals is exhibited.

$^{13}$C-NMR and DEPT (125 MHz, DMSO-$d_6$)): δ (ppm)= 35.07 ($CH_2$), 40.06 (CH), 41.17 ($CH_2$), 84.20 (C), 84.94 (C), 113.04 (CH), 119.21 (CH), 120.24 (CH), 126.33 (2CH), 126.39 (2CH), 126.46 (CH), 127.09 (CH), 127.84 (2CH), 128.75 (2CH), 129.29 (CH), 129.52 (CH), 133.62 (C), 136.02 (C), 138.00 (C), 139.79 (C), 142.72 (C), 142.86 (C), 145.36 (C), 154.10 (C), 154.40 (C), 172.36 (CO).

1.46. 3-(Biphenyl-4-yl)-4-(5-chloro-2-benzimidazolyl)butanoic acid•HCl (PS 245)

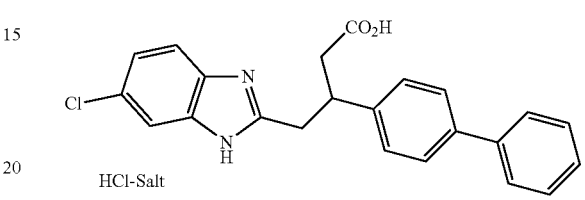

HCl-Salt

Commercial 4-chloro-1,2-phenylenediamine (214 mg) and 3-(biphenyl-4-yl)glutaric anhydride (399 mg) were dissolved in dichloromethane (5 ml) with heating. The dark solution was stirred at rt for 1 h. The precipitate formed was collected by suction filtration, washed with dichloromethane, and dried in vacuo to give a mixture of regioisomeric amides (0.48 g) as light brown solid. This solid was dissolved in 1,4-dioxane (1 ml) with heating. 4M HCl in 1,4-dioxane (3 ml) was added and the solution was heated to reflux for 1.5 h. The precipitate formed is isolated by suction filtration and washed with 1,4-dioxane and diethyl ether. The crude (0.4 g) is crystallised from acetic acid to provide 3-(biphenyl-4-yl)-4-(5-chloro-2-benzimidazolyl)butanoic acid HCl (0.27 g) as light brown crystals.

$^1$H-NMR (500 MHz, DMSO-$d_6$)): δ (ppm)=2.76 (dd, J=16.2, 8.4 Hz, 1H), 2.85 (dd, J=16.2, 6.3 Hz, 1H), 3.50 (dd, J=14.9, 8.9 Hz, 1H), 3.59 (dd, J=14.9, 7.1 Hz, 1H), 3.91 (m, 1H), 7.32 (t, J=7.3 Hz, 1H), 7.42 (m, 4H), 7.49 (dd, J=8.8, 2.0 Hz, 1H), 7.56 (d, J=8.3 Hz, 2H), 7.59 (dd, J=7.2, 1.2 Hz, 2H), 7.74 (d, J=8.8 Hz, 1H), 7.83 (d, J=1.8 Hz, 1H).

$^{13}$C-NMR and DEPT (125 MHz, DMSO-$d_6$)): δ (ppm)= 32.80 ($CH_2$), 39.41 (CH), 39.76 ($CH_2$), 113.55 (CH), 115.25 (CH), 125.52 (CH), 126.39 (2CH), 126.64 (2CH), 127.27 (CH), 127.76 (2CH), 128.77 (2CH), 129.58 (C), 129.96 (C), 131.91 (C), 138.63 (C), 139.47 (C), 141.00 (C), 153.50 (C), 172.26 (CO).

1.47. 3-(Biphenyl-4-yl)-7(8)-chloro-3,4-dihydropyrido[1,2-a]benzimidazol-1(2H)-one and 3-(Biphenyl-4-yl)-4-(5-chloro-2-benzimidazolyl)butyramide (PS 252)

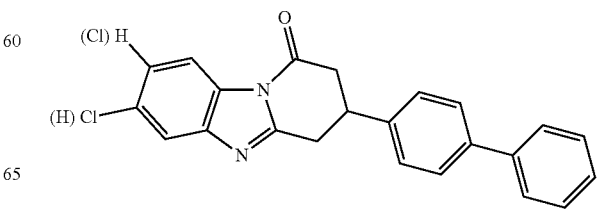

-continued

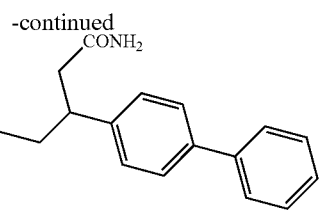

1) 3-(Biphenyl-4-yl)-7-chloro-3,4-dihydropyrido[1,2-a]benzimidazol-1(2H)-one and 3-(Biphenyl-4-yl)-8-chloro-3,4-dihydropyrido[1,2-a]benzimidazol-1(2H)-one A 1:1-mixture of the regioisomeric dihydropyridobenzimidazolones was obtained as light yellow solid in >55% yield by cyclisation of crude 3-(biphenyl-4-yl)-4-(5-chloro-2-benzimidazolyl)butanoic acid HCl with acetic anhydride under reflux for 1.5 h.

2) 3-(Biphenyl-4-yl)-4-(5-chloro-2-benzimidazolyl)butyramide

The 1:1-mixture of 3-(biphenyl-4-yl)-7-chloro-3,4-dihydropyrido[1,2-a]benzimidazol-1(2H)-one and 3-(biphenyl-4-yl)-8-chloro-3,4-dihydropyrido[1,2-a]benzimidazol-1(2H)-one (200 mg) was dissolved in 1,4-dioxane (3 ml) at reflux temperature. A 25% solution of ammonia in water (1 ml) was added to give a light red solution. Refluxing was continued for 2 h while addition of 25% ammonia solution in 1 ml portions was repeated every half an hour (3 times). Then all volatiles were removed at the water aspirator and the residue was triturated with acetone to leave 3-(biphenyl-4-yl)-4-(5-chloro-2-benzimidazolyl)butyramide (165 mg) as light yellowish solid.

$^1$H-NMR (500 MHz, DMSO-$d_6$)): δ (ppm)=2.51 (m, 2H), 3.13 (dd, J=14.7, 8.3 Hz, 1H), 3.19 (dd, J=14.7, 6.9 Hz, 1H), 3.80 (m, 1H), 6.72 (br s, 1H), 7.11 (t, J=7.6 Hz, 1H), 7.30-7.36 (m, 4H), 7.38-7.44 (m, 3H), 7.49-7.54 (m, 3H), 7.60 (d, J=8.3 Hz, 2H), 12.4 (br d, 1H).

Due to tautomerism a double set of all benzimidazole C-signals is exhibited.

$^{13}$C-NMR and DEPT (125 MHz, DMSO-$d_6$): δ (ppm)= 35.13 ($CH_2$), 40.03 (CH), 41.16 ($CH_2$), 110.51 (CH), 111.96 (CH), 117.49 (CH), 119.22 (CH), 120.99 (CH), 121.35 (CH), 126.32 (2CH), 126.36 (2CH), 127.08 (CH), 127.83 (2CH), 128.73 (2CH), 132.88 (C), 134.84 (C), 137.99 (C), 139.79 (C), 141.99 (C), 142.88 (C), 144.17 (C), 154.60 (C), 155.10 (C), 172.34 (CO).

1.48. 4-(5-Iodo-2-benzimidazolyl)-3-(1-naphthyl)butanoic acid•HCl (PS 228)

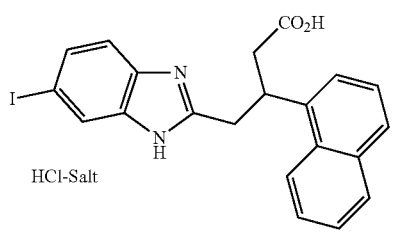 [SMILES: O=C(O)CC(Cc1nc2ccc(I)cc2[nH]1)c1cccc2ccccc12]

1) 3-(1-Naphthyl)glutaric anhydride

To a solution of commercial 1-naphthaldehyde (25 g) and ethyl acetoacetate (40.5 ml) in ethanol (30 ml) piperidine (3 ml) was added with stirring at rt. The orange coloured solution was kept at rt for a week. The viscous orange oil (the bis-adduct of acetoacetate to the aldehyde) was not further purified but used directly for the next step. The oil was added in portions to 40% NaOH (500 g) with stirring and rinsed with ethanol. The resulting orange slurry was stirred at reflux for 2 h. After cooling to rt the mixture was filtered and washed with water to give an orange coloured, partly resinous solid (sodium salt of 3-(1-naphthyl)glutaric acid). The salt was slurried in conc. HCl/water 1:1 (300 ml) and kept at rt for 3 d. The remaining solid was isolated by suction filtration and washed with water. The still wet filter cake was taken up in acetone (200 ml) and the organic layer was dried by addition of sodium sulfate. After filtration the solvent was removed by distillation and the residue (32.1 g amorphous orange solid) was triturated with ethyl acetate (40 ml) to leave a light yellowish powder (11.6 g) which was identified by NMR as the desired 3-(1-naphthyl)glutaric acid. The suspension of 3-(1-naphthyl)glutaric acid in acetyl chloride (16 ml) was heated to reflux with stirring for 1.5 h. After cooling to rt precipitation of the product is completed by addition of petrol ether (100 ml). The precipitate is isolated by suction filtration, washed with petrol ether, and dried in vacuo to provide 3-(1-naphthyl)glutaric anhydride (10.54 g) as light beige solid.

2) 4-(5-Iodo-2-benzimidazolyl)-3-(1-naphthyl)butanoic acid•HCl

4-Iodo-1,2-phenylenediamine (0.47 g) and 3-(1-naphthyl) glutaric anhydride (0.48 g) were dissolved in dichloromethane (6 ml) with heating. The dark solution was stirred at rt for 1 h. The precipitate formed was collected by suction filtration, washed with dichloromethane, and dried in vacuo to give a mixture of regioisomeric amides (0.69 g) as beige coloured solid. This solid was dissolved in 4M HCl in 1,4-dioxane (3 ml) and the dark solution was heated to reflux for 1 h. All volatiles were removed at the water aspirator and the amorphous residue is crystallised from acetone/methanol to provide 4-(5-iodo-2-benzimidazolyl)-3-(1-naphthyl)butanoic acid HCl (0.54 g) as light grey solid.

$^1$H-NMR (500 MHz, DMSO-$d_6$)): δ (ppm)=2.89 (m, 2H), 3.61 (m, 2H), 4.72 (m, 1H), 7.49 (td, J=7.7, 3.8 Hz, 2H), 7.53-7.58 (m, 2H), 7.60 (d, J=7.2 Hz, 1H), 7.74 (dd, J=8.6, 1.3 Hz, 1H), 7.80 (d, J=8.1 Hz, 1H), 7.89 (d, J=8.0 Hz, 1H), 8.08 (d, J=1.0 Hz, 1H), 8.41 (d, J=8.6 Hz, 1H).

$^{13}$C-NMR and DEPT (125 MHz, DMSO-$d_6$): δ (ppm)= 32.38 ($CH_2$), 34.09 (br, CH), 39.42 ($CH_2$), 89.40 (C), 115.66 (CH), 122.00 (CH), 123.09 (CH), 123.34 (br, CH), 125.46 (CH), 125.61 (CH), 126.15 (CH), 127.31 (CH), 128.59 (CH), 130.61 (C), 132.67 (C), 133.36 (CH), 133.65 (C), 138.01 (C), 152.60 (C), 172.30 (CO).

1.49. 4-(5-Iodo-2-benzimidazolyl)-3-(2-naphthyl)butanoic acid•HCl (PS 238) $CO_2H$

1) 3-(2-Naphthyl)glutaric anhydride

To a solution of commercial 2-naphthaldehyde (7.81 g) and ethyl acetoacetate (13 g) in ethanol (15 ml) piperidine (1 ml) was added with stirring at rt. The yellowish solution was kept at rt for 20 h. The precipitate was isolated by suction filtration, washed with ethanol, and dried in vacuo to give 14.7 g light yellow crystals (the bis-adduct of acetoacetate to the aldehyde). The crystals were added in portions to 40% NaOH (400 g) with stirring and the resulting yellow slurry was stirred at reflux for 2 h. After cooling in an ice bath the mixture was acidified by portionwise addition of conc. HCl (360 ml). A resinous precipitate is formed. The aqueous layer was extracted with ethyl acetate (3×100 ml) and the combined organic layers dried (sodium sulfate). After filtration and evaporation of the solvent the crude (8.5 g) was triturated with ethyl acetate to leave 3-(2-naphthyl)glutaric acid (3.6 g) as colourless solid. The suspension of 3-(2-naphthyl)glutaric acid in acetyl chloride (10 ml) was heated to reflux with stirring for 1 h. After cooling to rt the precipitate is isolated by suction filtration, washed with acetyl chloride (4×3 ml) and petrol ether, and dried in vacuo to provide 3-(2-naphthyl)glutaric anhydride (2.88 g) as colourless powdery solid.

2) 4-(5-Iodo-2-benzimidazolyl)-3-(2-naphthyl)butanoic acid•HCl

4-Iodo-1,2-phenylenediamine (0.47 g) and 3-(2-naphthyl)glutaric anhydride (0.48 g) were dissolved in dichloromethane (6 ml) with heating. The dark solution was stirred at rt for 1 h. The precipitate formed was collected by suction filtration, washed with dichloromethane, and dried in vacuo to give a mixture of regioisomeric amides (0.82 g) as light red solid. This solid was dissolved in 4M HCl in 1,4-dioxane (3 ml) and the dark solution was heated to reflux for 1 h. The precipitate formed is isolated by suction filtration of the still hot mixture and washed with 1,4-dioxane, hot acetic acid, and finally diethyl ether to provide 4-(5-iodo-2-benzimidazolyl)-3-(2-naphthyl)butanoic acid HCl (0.71 g) as light red solid.

$^1$H-NMR (500 MHz, DMSO-d$_6$)): δ (ppm)=2.83 (dd, J=16.1, 8.3 Hz, 1H), 2.91 (dd, J=16.1, 6.4 Hz, 1H), 3.57 (dd, J=14.9, 9.1 Hz, 1H), 3.64 (dd, J=14.9, 7.0 Hz, 1H), 4.02 (m, 1H), 7.45 (m, 2H), 7.51 (dd, J=8.6, 2.4 Hz, 2H), 7.72 (dd, J=8.6, 1.5 Hz, 1H), 7.82 (m, 4H), 8.06 (d, J=1.4 Hz, 1H).

$^{13}$C-NMR and DEPT (125 MHz, DMSO-d$_6$): δ (ppm)= 32.64 (CH$_2$), 39.93 (CH$_2$), 39.96 (CH), 89.44 (C), 115.64 (CH), 121.99 (CH), 125.53 (CH), 125.60 (CH), 125.70 (CH), 126.06 (CH), 127.34 (CH), 127.48 (CH), 128.01 (CH), 130.49 (C), 131.96 (C), 132.57 (C), 132.75 (C), 133.67 (CH), 139.23 (C), 152.73 (C), 172.25 (CO).

1.50. 4-(5-Iodo-2-benzimidazolyl)-3-(2-thienyl)butanoic acid (PS 234)

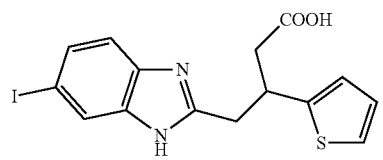 [SMILES: O=C(O)CC(Cc1nc2ccc(I)cc2[nH]1)c1cccs1]

1) 3-(2-Thienyl)glutaric anhydride

To a solution of commercial 2-thiophen-carboxaldehyde (22.4 g) and ethyl acetoacetate (50.5 ml) in ethanol (40 ml) piperidine (4 ml) was added with stirring at rt. The solution was kept at rt for 3 d to form a precipitate. After cooling in the refrigerator the yellow solid was crushed, collected by suction filtration, and washed with ethanol. Drying in vacuo affords 31 g of a faint yellowish solid (the bis-adduct of acetoacetate to the aldehyde). The powdered solid was added in portions to 40% NaOH (500 g) with stirring. The resulting orange coloured slurry was stirred at reflux for 2 h. After cooling in an ice bath the mixture was acidified by portionwise addition of conc. HCl (440 ml) to give a colourless precipitate. The solid was collected by suction filtration and washed with water. After drying in vacuo 3-(2-thienyl)glutaric acid (9.7 g) was obtained. The suspension of finely divided 3-(2-thienyl)glutaric acid in acetyl chloride (17 ml) was heated to reflux with stirring for 1 h. After cooling to rt precipitation of the product is induced by addition of petrol ether (100 ml). The precipitate is isolated by suction filtration, washed with petrol ether, and dried in vacuo to give 3-(2-thienyl)glutaric anhydride (8.2 g) as colourless crystals.

2) 4-(5-Iodo-2-benzimidazolyl)-3-(2-thienyl)butanoic acid

To a solution of 4-iodo-1,2-phenylenediamine (0.47 g) in dichloromethane (3 ml) 3-(2-thienyl)glutaric anhydride (0.39 g) was added with stirring at rt. After 1 h at rt the precipitate is collected by suction filtration, washed with dichloromethane, and dried in vacuo to give a mixture of regioisomeric amides (0.75 g) as light red solid. This solid is suspended in 1,4-dioxane (2 ml) and 4M HCl in 1,4-dioxane (3 ml) is added. The dark solution is heated to reflux for 1 h. From the solution all volatiles are removed at the water aspirator and the crude product is liberated from HCl by treatment with propene oxide in methanolic solution at rt for 2 h. Again all volatiles were removed in vacuo and the residue was crystallised from acetone/ethyl acetate to provide 4-(5-iodo-2-benzimidazolyl)-3-(2-thienyl)butanoic acid (0.4 g) as beige coloured solid.

$^1$H-NMR (500 MHz, DMSO-d$_6$)): δ (ppm)=2.65 (dd, J=16.0, 8.9 Hz, 1H), 2.79 (dd, J=16.0, 5.5 Hz, 1H), 3.13 (dd, J=14.7, 7.9 Hz, 1H), 3.21 (dd, J=14.7, 7.2 Hz, 1H), 4.01 (m, 1H), 6.88 (m, 2H), 7.26 (dd, J=4.9, 1.3 Hz, 1H), 7.31 (br m, 1H), 7.39 (dd, J=8.3, 1.6 Hz, 1H), 7.82 (br s, 1H).

$^{13}$C-NMR and DEPT (125 MHz, DMSO-d$_6$): δ (ppm)= 35.60 (CH), 35.91 (CH$_2$), 40.79 (CH$_2$), 84.70 (C), 123.66 (CH), 123.86 (CH), 126.50 (CH), 129.53 (CH), 146.42 (C), 153.63 (C), 172.40 (CO). Four carbon signals missing.

1.51. 3-Amino-N-(5-chloro-2-benzimidazolyl)-3-(4-chlorophenyl)propanoic acid•HCl (PS 180)

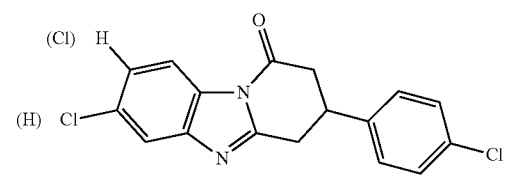

-continued

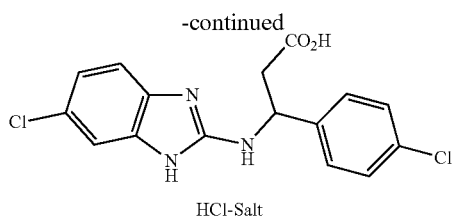

HCl-Salt

1) 2-Amino-5-chlorobenzimidazole

Commercial 2-aminobenzimidazole was chlorinated with a mixture of hydrogen peroxide and HCl in aqueous solution at rt for 1.5 h. After removal of all volatiles the residue was dissolved in water and the product precipitated by addition of ammonia solution to give a 72% yield of 2-amino-5-chlorobenzimidazole as beige coloured solid.

2) 5-(p-Chlorobenzyliden)-2,2-dimethyl-1,3-dioxane-4,6-dione

Prepared from Meldrum's acid and 4-chlorobenzaldehyde by Cope-Knoevenagel reaction.

3) 6-Chloro-2-(4-chlorophenyl)-1,2,3,4-tetrahydropyrimido[1,2-a]benzimidazol-4-one and 7-Chloro-2-(4-chlorophenyl)-1,2,3,4-tetrahydropyrimido[1,2-a]benzimidazol-4-one A mixture of 2-amino-5-chlorobenzimidazole (1.68 g) and 5-(p-chlorobenzyliden)-2,2-dimethyl-1,3-dioxane-4,6-dione (2.67 g) in N,N-dimethyl formamide (2 ml) was heated to reflux for 10 min. After cooling to rt the crude was precipitated by addition of iso-propanol (5 ml). The precipitate was isolated by suction filtration, washed with iso-propanol, dried, and recrystallised from N,N-dimethylformamide/ethanol to give 1.3 g of a mixture of the regioisomers 6-chloro-2-(4-chlorophenyl)-1,2,3,4-tetrahydropyrimido[1,2-a]benzimidazol-4-one and 7-chloro-2-(4-chlorophenyl)-1,2,3,4-tetrahydropyrimido[1,2-a]benzimidazol-4-one as almost colourless crystals.

4) 3-Amino-N-(5-chloro-2-benzimidazolyl)-3-(4-chlorophenyl)propanoic acid•HCl To the above mixture of 6-chloro-2-(4-chlorophenyl)-1,2,3,4-tetrahydropyrimido-[1,2-a]benzimidazol-4-one and 7-chloro-2-(4-chlorophenyl)-1,2,3,4-tetrahydropyrimido[1,2-a]benzimidazol-4-one (0.66 g) in glacial acetic acid (4 ml) conc. HCl (2 ml) was added. The resulting solution was heated to reflux for 1.5 h. Then all volatiles were removed at the water aspirator. Crystallisation of the amorphous residue was induced by treatment with boiling acetone. The precipitate was collected by suction filtration, washed with acetone, and dried in vacuo to afford 3-amino-N-(5-chloro-2-benzimidazolyl)-3-(4-chlorophenyl)propanoic acid•HCl (0.64 g) as colourless solid.

$^1$H-NMR (500 MHz, DMSO-$d_6$): δ (ppm)=2.89-2.98 (m, 1H), 3.06 (dd, J=16.7, 9.1 Hz, 1H), 5.35 (dt, J=9.0, 5.2 Hz, 1H), 7.24 (dd, J=8.5, 2.0 Hz, 1H), 7.40 (d, J=8.5 Hz, 1H), 7.42-7.46 (m, 3H), 7.58-7.65 (m, 3H), 10.24 (d, J=9.06 Hz, 1H), 10.2-10.4 (br m, 1H), 12-14 (br m, 2H).

$^{13}$C-NMR and DEPT (125 MHz, DMSO-$d_6$): δ (ppm)= 40.46 (CH$_2$), 53.19 (CH), 111.26 (CH), 112.62 (CH), 123.01 (CH), 127.10 (C), 128.41 (2CH), 128.59 (2CH), 128.69 (C), 130.76 (C), 132.40 (C), 139.06 (C), 149.56 (C), 171.09 (CO). MS (+ESI): m/z=350 (M+H).

1.52. N-[(5-Chloro-2-benzimidazolyl)methyl]-N-(4-chlorophenyl)glycine (PS 128)

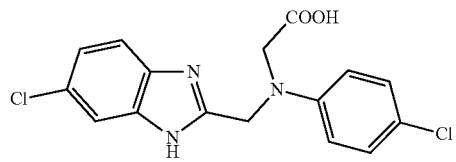 [SMILES: O=C(O)CN(Cc1nc2ccc(Cl)cc2[nH]1)c1ccc(Cl)cc1]

1) Ethyl N-(4-chlorophenyl)glycinate

Sodium acetate trihydrate (6 g) was added to a solution of commercial ethyl chloroacetate (6.2 g) and commercial 4-chloroaniline (6.4 g) in ethanol (5 ml). The mixture was heated to reflux for 5 h. After cooling in an ice bath the product precipitates. The solid was collected by suction filtration and washed with water. The still wet product was recrystallised from ethanol to give ethyl N-(4-chlorophenyl) glycinate (5.99 g) as greyish crystals.

2) 5-Chloro-2-chloromethylbenzimidazole

The solution of 4-chloro-1,2-phenylenediamine (1.43 g) and chloroacetic acid (1.43 g) in 4M HCl (10 ml) was heated to reflux for 1 h. After cooling to rt overnight the mixture was filtered and the filtrate was cooled in an ice bath. With stirring the solution was adjusted to pH 8 with 25% ammonia solution. A gummy precipitate is formed which is cooled for 1 h. The aqueous layer is removed by decantation and the residue crystallised from acetone/water to yield 5-chloro-2-chloromethylbenzimidazole (1.4 g) as brownish solid.

3) Ethyl N-[(5-chloro-2-benzimidazolyl)methyl]-N-(4-chlorophenyl)glycinate

The mixture of ethyl N-(4-chlorophenyl)glycinate (0.43 g), 5-chloro-2-chloromethylbenzimidazole (0.4 g), and sodium bicarbonate (0.17 g) in N,N-dimethylformamide (2 ml) was stirred at 150° C. for 0.5 h. After cooling to rt the mixture was poured into saturated sodium bicarbonate solution (50 ml) and extracted twice with EtOAc (40 ml). The combined organic layers were washed with 10% sodium carbonate solution (40 ml) and water (40 ml) and dried (sodium sulfate). After concentration the crude (0.66 g) was purified by flash chromatography (dichloromethane/1% methanol) on silica gel to provide an orange solid. The solid was further purified by trituration with diethyl ether to give ethyl N-[(5-chloro-2-benzimidazolyl)methyl]-N-(4-chlorophenyl)glycinate (0.17 g) as a light orange crystals.

4) N-[(5-Chloro-2-benzimidazolyl)methyl]-N-(4-chlorophenyl)glycine

Ethyl N-[(5-chloro-2-benzimidazolyl)methyl]-N-(4-chlorophenyl)glycinate (0.15 g) was dissolved in methanol (3 ml). A solution of LiOH monohydrate (92 mg) in water (0.5 ml) was added and the cloudy mixture was stirred at rt for 2 h. Water (25 ml) was added and the aqueous layer was washed with EtOAc (20 ml) and diethyl ether (20 ml). By addition of 1M HCl a pH of 5 was adjusted. The white precipitate was extracted with EtOAc (4×50 ml). The combined organic layers were dried (sodium sulfate) and concentrated to give a yellowish solid which was further purified by trituration with acetone to provide N-[(5-chloro-2-benzimidazolyl)methyl]-N-(4-chlorophenyl)glycine (43 mg) as colourless crystals.

$^1$H-NMR (500 MHz, DMSO-d$_6$:): δ (ppm)=4.34 (s, 2H), 4.87 (s, 2H), 6.66 (d, J=9.1 Hz, 2H), 7.18 (d, J=9.1 Hz, 2H), 7.22 (dd, J=8.6, 2.0 Hz, 1H), 7.54 (d, J=8.6 Hz, 1H), 7.61 (d, J=2.0 Hz, 1H).

1.53. 4-(5-Chloro-2-benzoxazolyl)-3-(4-chlorophenyl)butanoic acid (PS 215)

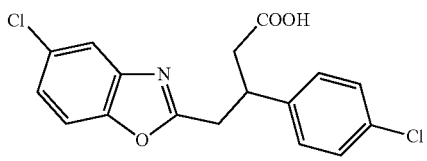 [SMILES: O=C(O)CC(Cc1nc2cc(Cl)ccc2o1)c1ccc(Cl)cc1]

1) N-(2-Hydroxy-5-chlorophenyl)-3-(4-chlorophenyl)glutaramic acid

Prepared by dissolving an equimolar mixture of 3-(4-chlorophenyl)glutaric anhydride and commercial 5-chloro-2-hydroxyaniline in boiling dichloromethane. Upon cooling to rt product precipitates and yields after isolation 87% of N-(2-hydroxy-5-chlorophenyl)-3-(4-chlorophenyl)glutaramic acid as colourless crystals.

2) 4-(5-Chloro-2-benzoxazolyl)-3-(4-chlorophenyl)butanoic acid

Neat N-(2-hydroxy-5-chlorophenyl)-3-(4-chlorophenyl)glutaramic acid (1.5 g) was kept under vacuum (membrane pump) and placed in a preheated (230° C.) oil bath. The resulting melt was stirred at this temperature under vacuum for 1 h. The melt was cooled and close to the point of solidification diethyl ether was added to give a cloudy solution. The traces of solid were removed by filtration and the filtrate was shaken with 20% NaOH solution (20 ml). The sodium salt of the product separates as ether and water insoluble brownish oil. The neat oil is isolated and treated with 10% HCl (2 ml). The desired product separates as slowly solidifying oil which is triturated with methanol/water 1:2 and with acetone to afford 0.16 g of 4-(5-chloro-2-benzoxazolyl)-3-(4-chlorophenyl)butanoic acid as almost colourless solid.

$^1$H-NMR (500 MHz, DMSO-d$_6$): δ (ppm)=2.67 (dd, J=16.2, 8.4 Hz, 1H), 2.83 (dd, J=16.2, 6.4 Hz, 1H), 3.27 (dd, J=15.5, 8.7 Hz, 1H), 3.38 (dd, J=15.5, 6.5 Hz, 1H), 3.69 (m, 1H), 7.30 (q, J=8.6 Hz, 4H), 7.36 (dd, J=8.6, 2.1 Hz, 1H), 7.66 (d, J=8.6 Hz, 1H), 7.74 (d, J=2.0 Hz, 1H), 12.2 (br s, 1H).

$^{13}$C-NMR and DEPT (125 MHz, DMSO-d$_6$): δ (ppm)= 34.06 (CH$_2$), 38.87 (CH), 39.65 (CH$_2$), 111.75 (CH), 119.00 (CH), 124.68 (CH), 128.14 (2CH), 128.39 (C), 129.22 (2CH), 131.14 (C), 141.55 (C), 141.93 (C), 148.79 (C), 166.57 (C), 172.40CO).

MS (+ESI): m/z=350 (M+H).

1.54. 4-(6-Chloro-2-benzoxazolyl)-3-(4-chlorophenyl)butanoic acid (PS 216)

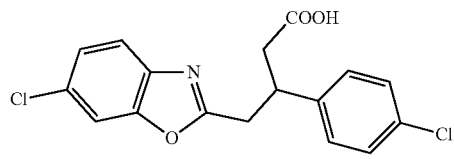 [SMILES: O=C(O)CC(Cc1nc2ccc(Cl)cc2o1)c1ccc(Cl)cc1]

1) N-(2-Hydroxy-4-chlorophenyl)-3-(4-chlorophenyl)glutaramic acid

Prepared by refluxing an equimolar mixture of 3-(4-chlorophenyl)glutaric anhydride and commercial 4-chloro-2-hydroxyaniline in dichloromethane for 0.5 h. After cooling to rt the precipitated product is isolated by suction filtration, washed, and dried to provide 90% of N-(2-hydroxy-4-chlorophenyl)-3-(4-chlorophenyl)glutaramic acid as light red crystals.

2) 4-(6-Chloro-2-benzoxazolyl)-3-(4-chlorophenyl)butanoic acid

By a procedure similar to that of example 1.53.2, starting from N-(2-hydroxy-4-chlorophenyl)-3-(4-chlorophenyl)glutaramic acid, 4-(6-chloro-2-benzoxazolyl)-3-(4-chlorophenyl)-butanoic acid was obtained as light beige solid.

$^1$H-NMR (500 MHz, DMSO-d$_6$): δ (ppm)=2.67 (dd, J=16.2, 8.4 Hz, 1H), 2.83 (dd, J=16.2, 6.4 Hz, 1H), 3.26 (dd, J=15.5, 8.7 Hz, 1H), 3.37 (dd, J=15.5, 6.4 Hz, 1H), 3.68 (m, 1H), 7.31 (q, J=8.6 Hz, 4H), 7.35 (dd, J=8.5, 2.0 Hz, 1H), 7.64 (d, J=8.5 Hz, 1H), 7.83 (d, J=1.9 Hz, 1H), 12.2 (br s, 1H).

$^{13}$C-NMR and DEPT (125 MHz, DMSO-d$_6$): δ (ppm)= 34.00 (CH$_2$), 38.87 (CH), 39.64 (CH$_2$), 111.02 (CH), 120.19 (CH), 124.55 (CH), 128.13 (2CH), 128.94 (C), 129.23 (2CH), 131.13 (C), 139.60 (C), 141.56 (C), 150.32 (C), 165.79 (C), 172.39CO).

MS (+ESI): m/z=350 (M+H).

1.55. 4-(5-Chloro-2-benzothiazolyl)-3-(4-chlorophenyl)butanoic acid (PS 221)

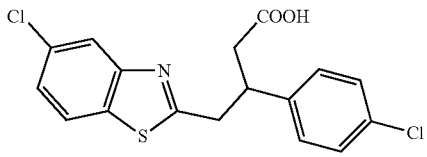 [SMILES: O=C(O)CC(Cc1nc2cc(Cl)ccc2s1)c1ccc(Cl)cc1]

A mixture of 3-(4-chlorophenyl)glutaric anhydride (0.5 g) and commercial 2-amino-4-chlorothiophenol (0.37 g) is dissolved in boiling dichloromethane (3 ml). The solution is stirred overnight at rt. The precipitate is isolated by suction filtration, washed with dichloromethane, and dried in vacuo. The crude product is recrystallised from acetone to give 0.3 g of 4-(5-chloro-2-benzothiazolyl)-3-(4-chlorophenyl)butanoic acid as colourless crystals.

$^1$H-NMR (500 MHz, DMSO-d$_6$): δ (ppm)=2.08 (s, 3H), 2.65 (dd, J=16.0, 8.6 Hz, 1H), 2.79 (dd, J=16.0, 6.2 Hz, 1H), 3.45 (dd, J=14.8, 9.3 Hz, 1H), 3.53 (dd, J=14.8, 5.9 Hz, 1H), 3.63 (m, 1H), 7.29 (d, J=8.7 Hz, 2H), 7.33 (d, J=8.7 Hz, 2H), 7.42 (dd, J=8.6, 2.0 Hz, 1H), 7.99 (d, J=2.0 Hz, 1H), 8.02 (d, J=8.6 Hz, 1H), 12.17 (br s, 1H).
$^{13}$C-NMR and DEPT (125 MHz, DMSO-d$_6$): δ (ppm)= 39.27 (CH$_2$), 40.02 (CH$_2$), 41.17 (CH), 121.59 (CH), 123.42 (CH), 124.84 (CH), 128.11 (2CH), 129.54 (2CH), 130.70 (C), 131.12 (C), 133.35 (C), 141.45 (C), 153.38 (C), 171.82 (C), 172.42 (CO).
MS (+ESI): m/z=366 (M+H).

1.56. 4-(5-Chloro-1,3-dioxo-2-isondolinyl)-3-(4-chlorophenyl)butanoic acid (PS 147)

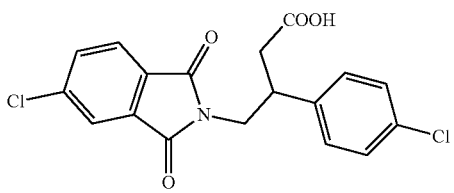 [SMILES: O=C(O)CC(CN1C(=O)c2ccc(Cl)cc2C1=O)c1ccc(Cl)cc1]

1)-4-Chlorophthalic anhydride

The mixture of commercial 4-chlorophthalic acid monosodium salt (40 g) and thionyl chloride (50 ml) was stirred under reflux for 2 h. From the resulting viscous mass all volatiles were removed at the water aspirator. The residue was heated with benzene (150 ml) and the still hot slurry was filtered by suction. The filter cake was washed twice with benzene (50 ml) and the filtrate was concentrated in vacuo to give a yellowish solid. The crude was recrystallised from n-hexane/benzene 3:1 (filtration of the boiling solution needed) to yield 4-chlorophthalic anhydride (21.1 g) as colourless crystals.

2) 4-Amino-3-(4-chlorophenyl)butanoic acid•HCl

The solution of ethyl 4-chlorocinnamate (12.6 g) and N,N,N',N'-tetramethylguanidine (1.2 g) in nitromethane (36.6 g) was kept at rt for three days. The excess of nitromethane was evaporated and the residue dissolved in diethyl ether (250 ml). The organic layer was washed with 2M HCl (2×150 ml), dried (sodium sulfate), and evaporated. The residue was subjected to purification by flash chromatography on silica gel (petrol ether/ethyl acetate 10:1) to give ethyl 3-(4-chlorophenyl)-4-nitrobutanoate (15.1 g) as yellowish oil.

The solution of ethyl 3-(4-chlorophenyl)-4-nitrobutanoate (2.33 g) in acetic acid (18 ml) was stirred vigorously while iron powder (5.7 g) was added. The suspension was stirred at reflux temperature for 1.5 h. The resulting thick slurry was pored into a mixture of conc. HCl (30 ml) and ice (30 g). The aqueous layer was extracted with dichloromethane (2×50 ml) and the combined organic layers washed with water and dried (sodium sulfate). After evaporation of the solvent the oily residue was distilled with toluene to remove acetic acid whereupon crystallisation took place. The crude was washed with diethyl ether (3×2 ml) and dried in vacuo to afford 4-(4-chlorophenyl)-2-pyrrolidone (0.86 g) as colourless crystals.

The suspension of 4-(4-chlorophenyl)-2-pyrrolidone (0.86 g) in conc. HCl (20 ml) was stirred under reflux for 2 h. From the clear solution all volatiles were removed at the water aspirator and from the residue, toluene (2×50 ml) was distilled to remove traces of water. The crude was slurried in boiling toluene (5 ml), filtered while hot, washed with diethyl ether, and dried in vacuo to afford 4-amino-3-(4-chlorophenyl)butanoic acid•HCl (1.01 g) as colourless solid.

3) 4-(5-Chloro-1,3-dioxo-2-isondolinyl)-3-(4-chlorophenyl)butanoic acid

The mixture of 4-chlorophthalic anhydride (0.25 g), 4-amino-3-(4-chlorophenyl)-butanoic acid•HCl salt (0.25 g), and dry sodium acetate (0.1 g) in acetic acid (3 ml) was heated under reflux with stirring for 20 h. The still hot, cloudy solution was filtered over a plug of cotton. To the filtrate water (3 ml) was added. A gummy precipitate is formed which solidifies quickly. The aqueous layer was removed by decantation and the residue recrystallised from ethanol/water to give 4-(5-chloro-1,3-dioxo-2-isondolinyl)-3-(4-chlorophenyl)butanoic acid (0.28 g) as beige coloured solid.
$^1$H-NMR (500 MHz, DMSO-d$_6$): δ (ppm)=2.57-2.65 (m, 1H), 2.75-2.83 (m, 1H), 3.52 (m, 1H), 3.71-3.80 (m, 2H), 7.24-7.34 (m, 4H), 7.76-8.15 (m, 3H), 12.10 (br s, 1H).
$^{13}$C-NMR and DEPT (125 MHz, DMSO-d$_6$): δ (ppm)= 37.46 (CH$_2$), 39.55 (CH), 42.79 (CH$_2$), 123.08 (CH), 124.68 (CH), 128.13 (2CH), 129.51 (2CH), 129.82 (C), 131.29 (C), 133.28 (C), 134.05 (CH), 139.13 (C), 139.99 (C), 166.35 (CO), 166.69 (CO), 172.42 (CO).
MS (APCI): m/z=378 (M+H).

1.57. N-[(5-chloro-1,3-dioxo-2-isondolinyl)methyl]-N-(4-chlorophenyl)glycine (PS 148)

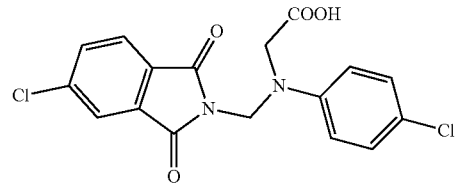 [SMILES: O=C(O)CN(CN1C(=O)c2ccc(Cl)cc2C1=O)c1ccc(Cl)cc1]

1) N-(4-Chlorophenyl)glycine

To the suspension of ethyl N-(4-chlorophenyl)-glycinate (10.4 g) in ethanol (4 ml) the solution of NaOH (4 g) in water (40 ml) was added. Upon heating a clear solution is formed, which is refuxed for 0.5 h. The solution is decolorized with activated carbon and filtered while hot. The filtrate is cooled in an ice bath and conc. HCl (5 ml) is added dropwise with stirring (pH 1-2). The precipitate formed is collected by suction filtration and washed with water. After drying in vacuo N-(4-chlorophenyl)-glycine (6.51 g) is obtained as colourless crystals.

2) 4-Chlorophthalimide

The suspension of 4-chlorophthalic anhydride (3 g) in formamide (15 ml) was heated with stirring to 150° C. for 1 h. The resulting yellowish solution was cooled to rt and the product was fractionally precipitated by addition of water to yield 4-chlorophthalimide (1.91 g) as colourless crystals.

3) N-[(5-chloro-1,3-dioxo-2-isondolinyl)methyl]-N-(4-chlorophenyl)glycine

4-Chlorophthalimide (273 mg) is dissolved in a minimum of boiling ethanol (ca. 2.5 ml). 37% formaldehyde solution (0.15 ml) is added to the still hot solution followed by N-(4- chlorophenyl)glycine (279 mg). Reflux is continued for 3 h. The yellow solution is kept in the refrigerator overnight. The yellow precipitate is collected by suction filtration, washed with ethanol, and dried in vacuo. The crude is recrystallised from ethanol to provide N-[(5-chloro-1,3-dioxo-2-isondolinyl)methyl]-N-(4-chlorophenyl)glycine (135 mg) as light yellow crystals.

$^1$H-NMR (500 MHz, DMSO-d$_6$): δ (ppm)=4.26 (s, 2H), 5.24 (s, 2H), 6.97 (d, J=9.1 Hz, 2H), 7.22 (d, J=9.1 Hz, 2H), 7.90 (d, J=1.2 Hz, 2H), 7.97 (t, J=1.2 Hz, 1H), 12.71 (br s, 1H).

$^{13}$C-NMR and DEPT (125 MHz, DMSO-d$_6$): δ (ppm)= 51.77 (CH$_2$), 54.72 (CH$_2$), 114.39 (2CH), 121.70 (C), 123.35 (CH), 124.99 (CH), 128.39 (2CH), 129.97 (C), 133.41 (C), 134.38 (CH), 139.41 (C), 145.34 (C), 167.01 (CO), 167.35 (CO), 171.48 (CO).

MS (+ESI): m/z=379 (M+H).

1.58. 4-(5-Chloro-2-isoindolinyl)-3-(4-chlorophenyl)-4-oxobutanoic acid (PS 112)

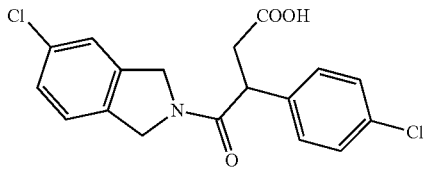 [SMILES: O=C(O)CC(C(=O)N1Cc2ccc(Cl)cc2C1)c1ccc(Cl)cc1]

1) 5-Chloroisoindoline

Prepared according to EP 0343560 A2, page 92.

2) 2-(4-Chlorophenyl)succinic acid 4-monoethylester

Prepared by double deprotonation of 4-chlorophenylacetic acid with LDA and subsequent alkylation with ethyl bromoacetate.

3) Ethyl 4-(5-chloro-2-isoindolinyl)-3-(4-chlorophenyl)-4-oxobutanoate 2-(4-Chlorophenyl)succinic acid 4-monoethylester (1.11 g) was converted to the corresponding acid chloride by treatment with oxalyl chloride (0.7 ml) in dichloromethane (3 ml) and catalytic amounts of N,N-dimethylformamide (0.5 h at rt, then 0.5 h reflux). All volatiles were removed in vacuo and the crude acid chloride dissolved in dichloromethane (4 ml). This solution was added dropwise to a stirred, ice-cold solution of 5-chloroisoindoline (0.86 g) and triethyl amine (1.7 ml) in dichloromethane (6 ml). After the addition the cooling bath was removed and the solution stirred at rt for 1.5 h. Then the organic layer was diluted with dichloromethane (50 ml), extracted two times with 1M HCl (50 ml), and dried (sodium sulfate). After removal of the solvent the crude was purified by flash chromatography on silica gel (petrol ether/ethyl acetate 2:1) to afford ethyl 4-(5-chloro-2-isoindolinyl)-3-(4-chlorophenyl)-4-oxobutanoate (1.13 g) as amorphous, colourless solid.

4) 4-(5-Chloro-2-isoindolinyl)-3-(4-chlorophenyl)-4-oxobutanoic acid

With stirring at rt the solution of lithium hydroxide monohydrate (0.29 g) in water (1.5 ml) was added to the solution of ethyl 4-(5-chloro-2-isoindolinyl)-3-(4-chlorophenyl)-4-oxobutanoate (0.64 g) in methanol (10 ml). The cloudy solution was stirred at rt for 2 h. Then the methanol was removed by distillation and the residue was diluted with water (3 ml). With ice-cooling conc. HCl (1 ml) was added dropwise to the stirred solution. The precipitate formed is kept at 0° C. for 0.5 h and collected by suction filtration. After washings with 1M HCl and water the solid is dried in vacuo to provide 4-(5-chloro-2-isoindolinyl)-3-(4-chlorophenyl)-4-oxobutanoic acid (0.56 g) as colourless solid.

$^1$H-NMR (500 MHz, DMSO-d$_6$): δ (ppm)=2.55 (ddd, J=16.8, 4.9, 1.8 Hz, 1H), 3.02 (dd, J=16.8, 9 Hz, 1H), 4.26 (td, J=9.9, 5.00, 5.00 Hz, 1H), 4.42-4.62 (m, 2H), 4.68 (dd, J=16.1, 11.3 Hz, 1H), 4.97-5.13 (m, 1H), 7.26-7.34 (m, 2H), 7.34-7.44 (m, 5H), 12.24 (br s, 1H).

$^{13}$C-NMR and DEPT (125 MHz, DMSO-d$_6$): δ (ppm)= 38.56 (CH$_2$), 44.33 (CH), 51.26 (CH$_2$), 51.43 (CH$_2$), 51.50 (CH$_2$), 51.73 (CH$_2$), 122.84 (CH), 123.05 (CH), 124.48 (CH), 124.64 (CH), 127.32 (CH), 127.44 (CH), 128.61 (2CH), 129.70 (2CH), 131.77 (C), 131.84 (C), 131.98 (C), 134.89 (C), 135.31 (C), 137.20 (C), 137.22 (C), 138.29 (C), 138.69 (C), 170.22 (CO), 170.26 (CO), 172.47 (CO).

MS (+ESI): m/z=364 (M+H).

1.59. 2-[3-(4-Chlorophenyl)-3-oxo-1-phenylpropyl]malonic acid (PS 182)

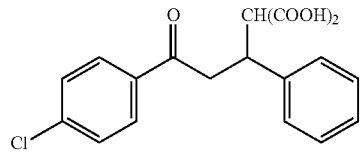

1) 1-(4-Chlorophenyl)-3-phenylprop-2-en-1-one

To a solution of benzaldehyde (2 g) in EtOH (40 ml) 3 M NaOH solution (3 eq) and 4-chloroacetophenone (2.91 g) were added. The resulting mixture was stirred at rt for 2 h forming a yellow precipitate. The solid was separated by suction filtration and washed with water. The crude was purified by recrystallisation from methanol to give 1-(4-chlorophenyl)-3-phenylprop-2-en-1-one (4.2 g) as pale yellow crystals.

2) Diethyl 2-[3-(4-chlorophenyl)-3-oxo-1-phenylpropyl]malonate

To a solution of 1-(4-chlorophenyl)-3-phenylprop-2-en-1-one (1 g) in toluene (10 ml) magnesium oxide (0.41 g) and diethyl malonate (0.62 ml) were added. The slurry was stirred at rt for 2 h. The inorganics were removed by suction filtration and washed with dichloromethane. The filtrate was concentrated in vacuo and the residue was recrystallised from diethyl ether/hexanes to provide diethyl 2-[3-(4-chlorophenyl)-3-oxo-1-phenylpropyl]malonate (1.5 g) as colourless solid.

$^1$H-NMR (500 MHz, CDCl$_3$): δ (ppm)=1.01 (t, J=7.2 Hz, 3H), 1.23 (t, J=7.2 Hz, 3H), 3.36-3.42 (m, 1H), 3.53 (dd, J=4.4, 4.4 Hz, 1H), 3.80 (d, J=9.7 Hz, 1H), 3.95 (q, J=7.2 Hz, 2H), 4.12-4.25 (m, 3H), 7.14-7.19 (m, 1H), 7.22-7.25 (m, 4H), 7.39 (d, J=8.8 Hz, 2H), 7.83 (d, J=8.8 Hz, 2H).

$^{13}$C-NMR (125 MHz, CDCl$_3$): δ (ppm)=13.7, 14.0, 40.9, 42.6, 57.5, 61.4, 61.7, 127.2, 128.2, 128.4, 128.8, 129.5, 135.1, 139.4, 140.2, 167.6 (CO), 168.3 (CO), 196.4 (CO).

3) 2-[3-(4-Chlorophenyl)-3-oxo-1-phenylpropyl]malonic acid

The solution of diethyl 2-[3-(4-chlorophenyl)-3-oxo-1-phenylpropyl]malonate (0.9 g) and 3M NaOH (7.5 ml) in ethanol (30 ml) was heated to reflux for 4 h. The mixture was cooled to rt, poured into water (30 ml), and acidified with 10% HCl. The aqueous layer was extracted three times with ethyl acetate (20 ml) and the combined organic layers were washed with brine and dried (magnesium sulfate). After evaporation of the solvent the residue was recrystallised from benzene to give 2-[3-(4-chlorophenyl)-3-oxo-1-phenylpropyl]malonic acid (0.5 g) as colourless solid.

$^1$H-NMR (500 MHz, CD$_3$OD): δ (ppm)=3.33 (dd, J=3.5, 16.7 Hz, 1H), 3.60 (dd, J=10.1, 10.1 Hz, 1H), 3.73 (d, J=3.5, 16.7 Hz, 1H), 3.87 (dt, J=3.8, 10.4 Hz, 1H), 7.11 (t, J=7.2 Hz, 1H), 7.19 (t, J=7.2 Hz, 2H), 7.27 (d, J=7.2 Hz, 2H), 7.54 (d, J=8.5 Hz, 2H), 7.87 (d, J=8.5 Hz, 2H), 12.67 (s, 2H).

$^{13}$C-NMR (125 MHz, CD$_3$OD): δ (ppm)=40.4, 42.4, 57.2, 126.4, 127.8, 128.3, 128.7, 129.6, 135.2, 137.9, 141.0, 169.0, 169.6, 196.4.

MS (+ESI): m/z=347 (M+H).

1.60. 5-(4-Chlorophenyl)-5-oxo-3-phenylpentanoic acid (PS 193)

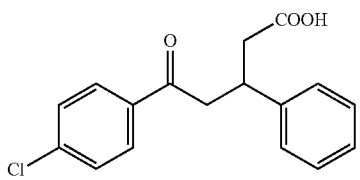 [SMILES: O=C(O)CC(CC(=O)c1ccc(Cl)cc1)c1ccccc1]

Neat 2-[3-(4-chlorophenyl)-3-oxo-1-phenylpropyl]malonic acid (0.3 g) was heated to 160° C. with stirring for 1 h. After cooling to rt the crude was dissolved in acetone/methanol. Precipitation of product was effected by addition of dichloromethane. The precipitate was collected to afford 5-(4-chlorophenyl)-5-oxo-3-phenylpentanoic acid (0.19 g) as colourless crystals.

$^1$H-NMR (500 MHz, CDCl$_3$): δ (ppm)=2.73 (dd, J=7.6, 7.6 Hz, 1H), 2.85 (dd, J=6.9, 6.9 Hz, 1H), 3.28-3.37 (m, 2H), 3.81-3.87 (m, 1H), 7.18-7.22 (m, 1H), 7.24-7.31 (m, 4H), 7.39 (d, J=8.8 Hz, 2H), 7.82 (d, J=8.8 Hz, 2H).

$^{13}$C-NMR (125 MHz, CDCl$_3$): δ (ppm)=37.2, 40.1, 44.5, 127.0, 127.3, 128.7, 128.9, 129.5, 135.1, 139.6, 142.8, 176.9, 196.9.

MS (+ESI): m/z=303 (M+H).

1.61. 5-(4-Chlorophenyl)-2-ethoxycarbonyl-5-oxo-3-phenylpentanoic acid (PS 197)

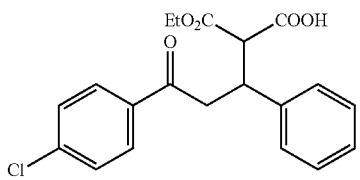 [SMILES: CCOC(=O)C(C(=O)O)C(CC(=O)c1ccc(Cl)cc1)c1ccccc1]

1) 1-tert-Butyl 3-ethyl 2-[3-(4-chlorophenyl)-3-oxo-1-phenylpropyl]malonate

By a procedure similar to that of example 1.59.2, starting from 1-(4-chlorophenyl)-3-phenylprop-2-en-1-one and tert-butyl ethyl malonate, a diastereomeric mixture of 1-tert-butyl 3-ethyl 2-[3-(4-chlorophenyl)-3-oxo-1-phenylpropyl]malonate was obtained as colourless solid.

2) 5-(4-Chlorophenyl)-2-ethoxycarbonyl-5-oxo-3-phenylpentanoic acid

The solution of 1-tert-butyl 3-ethyl 2-[3-(4-chlorophenyl)-3-oxo-1-phenylpropyl]malonate (1 g) and trifluoroacetic acid (10 ml) in dichloromethane (10 ml) was stirred at rt for 1 h. An excess of saturated sodium bicarbonate solution was added carefully and the resultant mixture extracted with ethyl acetate (3×20 ml). The combined extracts were dried over MgSO$_4$ and the solvent removed in vacuo. The residue was purified by crystallisation from benzene to give a diastereomeric mixture of 5-(4-chlorophenyl)-2-ethoxycarbonyl-5-oxo-3-phenylpentanoic acid (0.52 g) as colourless solid.

1H-NMR (500 MHz, CDCl$_3$): δ (ppm)=0.93 (t, J=7.2 Hz, 3H), 3.45-3.50 (m, 2H), 3.84-3.88 (m 3H), 4.00-4.04 (m, 1H), 7.14 (t, J=6.9 Hz, 1H), 7.19-7.26 (m, 4H), 7.44 (d, J=8.5 Hz, 2H), 7.87 (d, J=8.5 Hz, 2H).

13C-NMR (125 MHz, CDCl$_3$): δ (ppm)=14.0, 42.8, 44.2, 58.7, 62.3, 128.2, 129.3, 129.7, 129.9, 130.9, 136.9, 140.5, 141.8, 169.9 (CO), 171.3 (CO), 189.9 (CO).

MS (+ESI): m/z=375 (M+H).

1.62. Bis(acetoxymethyl)2-[3-(4-chlorophenyl)-3-oxo-1-phenylpropyl]malonate

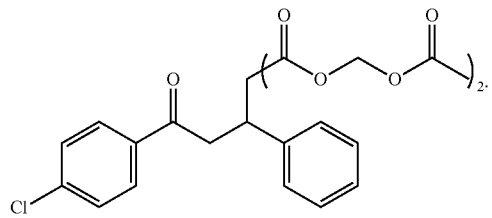

To a stirred solution of 2-[3-(4-chlorophenyl)-3-oxo-1-phenylpropyl]malonic acid (0.5 g) and triethyl amine (1 ml) in anhydrous N,N-dimethyl formamide (5 ml) bromomethyl acetate (0.42 ml) was added at rt. After being stirred for 4 h at rt, the mixture was hydrolised, extracted with ethyl acetate, washed with brine, dried over MgSO$_4$, filtered and concentrated. The residue was purified by flash chromatography on silica gel (petrol ether/ethyl acetate) to provide bis(acetoxymethyl) 2-(3-[4-chlorophenyl)-3-oxo-1-phenylpropyl]malonate (0.46 g) as colourless solid.

$^1$H-NMR (500 MHz, CD$_3$OD): δ (ppm)=1.99 (s, 3H), 2.10 (s, 3H), 3.47 (dd, J=8.9 Hz, 1H), 3.54 (dd, J=4.72 Hz, 1H), 3.96 (d, J=9.1 Hz, 1H), 4.17-4.21 (m, 1H), 5.67 (q, J=5.7 Hz, 2H), 5.76 (q, J=5.7 Hz, 2H), 7.19-7.23 (m, 1H), 7.25-7.28 (m, 4H), 7.41 (d, J=8.5 Hz, 2H), 7.83 (d, J=8.5 Hz, 2H).

$^{13}$C-NMR (125 MHz, CD$_3$OD): δ (ppm)=20.5, 20.53, 40.42, 42.1, 56.3, 79.4, 79.8, 127.5, 128.1, 128.6, 128.9, 129.5, 134.9, 139.6, 139.64, 166.0, 166.5, 169.1, 169.3, 196.0.

MS (+ESI): m/z=491 (M+H).

1.63. 2-[1,3-Bis(4-chlorophenyl)-3-oxopropyl]malonic acid (PS 190)

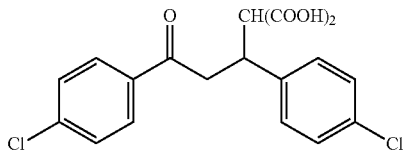

1) 1,3-Bis(4-chlorophenyl)-prop-2-en-1-one

By a procedure similar to that of example 1.59.1, starting from 4-chlorobenzaldehyde and 4-chloroacetophenone, 1,3-bis(4-chlorophenyl)-prop-2-en-1-one was obtained as yellowish solid.

2) Diethyl 2-[1,3-bis(4-chlorophenyl)-3-oxopropyl]malonate

By a procedure similar to that of example 1.59.2, starting from 1,3-bis(4-chlorophenyl)-prop-2-en-1-one and diethyl malonate, diethyl 2-[1,3-bis(4-chlorophenyl)-3-oxopropyl]malonate was obtained as colourless solid.

$^1$H-NMR (500 MHz, CDCl$_3$): δ (ppm)=3.53 (d, J=6.9 Hz, 2H), 3.84 (d, J=10.4 Hz, 1H), 4.03-4.07 (m, 1H), 7.24 (d, J=8.5 Hz, 2H), 7.30 (d, J=8.5 Hz, 2H), 7.49 (d, J=8.8 Hz, 2H), 7.92 (d, J=8.8 Hz, 2H).

3) 2-[1,3-Bis(4-chlorophenyl)-3-oxopropyl]malonic acid

By a procedure similar to that of example 1.59.3, starting from diethyl 2-[1,3-bis(4-chlorophenyl)-3-oxopropyl]malonate, 2-[1,3-bis(4-chlorophenyl)-3-oxopropyl]malonic acid was obtained as colourless solid.

$^1$H-NMR (500 MHz, CD$_3$OD): δ (ppm)=3.53 (d, J=6.9 Hz, 2H), 3.84 (d, J=10.4 Hz, 1H), 4.03-4.07 (m, 1H), 7.24 (d, J=8.5 Hz, 2H), 7.30 (d, J=8.5 Hz, 2H), 7.49 (d, J=8.8 Hz, 2H), 7.92 (d, J=8.8 Hz, 2H).

$^{13}$C-NMR (125 MHz, CD$_3$OD): δ (ppm)=42.0, 43.8, 58.6, 129.3, 130.0, 130.9, 131.3, 133.8, 136.8, 140.6, 141.0, 171.3 (CO), 171.6 (CO), 198.8 (CO).

MS (+ESI): m/z=383 (M+H).

1.64. 3,5-Bis(4-chlorophenyl)-3-oxopentanoic acid (PS 195)

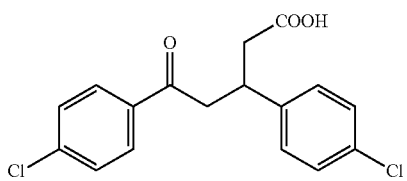 [SMILES: O=C(O)CC(CC(=O)c1ccc(Cl)cc1)c1ccc(Cl)cc1]

By a procedure similar to that of example 1.60, starting from 2-[1,3-bis(4-chlorophenyl)-3-oxopropyl]malonic acid, 3,5-bis(4-chlorophenyl)-3-oxopentanoic acid was obtained as colourless solid.

$^1$H-NMR (500 MHz, CDCl$_3$): δ (ppm)=2.68 (dd, J=7.9 Hz, 1H), 2.83 (dd, J=6.9 Hz, 1H), 3.24-3.35 (m, 2H), 3.79-3.85 (m, 1H), 7.18 (d, J=8.5 Hz, 2H), 7.25 (d, J=8.5 Hz, 2H), 7.40 (d, J=8.8 Hz, 2H), 7.81 (d, J=8.8 Hz, 2H).

$^{13}$C-NMR (125 MHz, CDCl$_3$): δ (ppm)=36.5, 40.0, 44.3, 128.7, 128.8, 129.0, 129.4, 132.7, 135.0, 139.8, 141.3, 176.7 (CO), 196.4 (CO).

MS (+ESI): m/z=339 (M+H).

1.65. 2-[1-(4-Chlorophenyl)-3-(4-iodophenyl)-3-oxopropyl]malonic acid (PS 230)

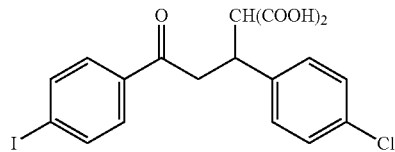

1) 3-(4-Chlorophenyl)-1-(4-iodophenyl)prop-2-en-1-one

By a procedure similar to that of example 1.59.1, starting from 4-chlorobenzaldehyde and 4-iodoacetophenone, 3-(4-chlorophenyl)-1-(4-iodophenyl)prop-2-en-1-one was obtained as beige coloured solid.

$^1$H-NMR (500 MHz, CDCl$_3$): δ (ppm)=7.39 (d, J=8.5 Hz, 2H), 7.42 (d, J=15.8 Hz, 1H), 7.57 (d, J=8.5 Hz, 2H), 7.71 (d, J=8.5 Hz, 2H), 7.77 (d, J=15.8 Hz, 1H), 7.85 (d, J=8.5 Hz, 2H).

$^{13}$C-NMR (125 MHz, CDCl$_3$): δ (ppm)=100.8, 121.8, 129.2, 129.6, 129.9, 133.2, 136.7, 137.3, 138.0, 143.8, 189.3 (CO).

2) Diethyl 2-(1-(4-chlorophenyl)-3-(4-iodophenyl)-3-oxopropyl)malonate

By a procedure similar to that of example 1.59.2, starting from 3-(4-chlorophenyl)-1-(4-iodophenyl)prop-2-en-1-one and diethyl malonate, diethyl 2-(1-(4-chlorophenyl)-3-(4-iodophenyl)-3-oxopropyl)malonate was obtained as beige coloured solid.

$^1$H-NMR (500 MHz, CDCl$_3$): δ (ppm)=1.05 (t, J=7.2 Hz, 3H), 1.25 (t, J=7.2 Hz, 3H), 3.35 (dd, J=9.5 Hz, 1H), 3.49 (dd, J=4.1 Hz, 1H), 3.76 (d, J=9.8 Hz, 1H), 3.98 (q, J=7.2 Hz, 2H), 4.09-4.25 (m, 3H), 7.18 (d, J=8.8 Hz, 2H), 7.22 (d, J=8.8 Hz, 2H), 7.59 (d, J=8.8 Hz, 2H), 7.79 (d, J=8.8 Hz, 2H).

$^{13}$C-NMR (125 MHz, CDCl$_3$): δ (ppm)=13.8, 14.0, 40.1, 42.3, 57.2, 61.5, 61.8, 101.2, 128.6, 129.5, 129.6, 133.0, 133.9, 138.0, 138.8, 167.5 (CO), 168.1 (CO), 196.6 (CO).

3) 2-[1-(4-Chlorophenyl)-3-(4-iodophenyl)-3-oxopropyl]malonic acid

By a procedure similar to that of example 1.59.3, starting from diethyl 2-(1-(4-chlorophenyl)-3-(4-iodophenyl)-3-oxopropyl)malonate, 2-[1-(4-chlorophenyl)-3-(4-iodophenyl)-3-oxopropyl]malonic acid was obtained as yellowish solid.

$^1$H-NMR (500 MHz, DMSO-d$_6$): δ (ppm)=3.31 (dd, J=3.5, 17.0 Hz, 1H), 3.59 (dd, J=9.9 Hz, 1H), 3.73 (d, J=10.8 Hz, 1H), 3.82 (dt, J=3.5, 10.42 Hz, 1H), 7.26 (d, J=8.5 Hz, 2H), 7.29 (d, J=8.5 Hz, 2H), 7.62 (d, J=8.5 Hz, 2H), 7.88 (d, J=8.5 Hz, 2H), 12.62 (s, OH), 12.89 (s, OH).

¹³C-NMR (125 MHz, DMSO-d₆): δ (ppm)=39.8, 42.1, 57.0, 101.8, 127.8, 129.4, 130.3, 131.0, 135.6, 137.5, 140.1, 168.9 (CO), 169.5 (CO), 197.3 (CO).

1.66. 3-(4-Chlorophenyl)-5-(4-iodophenyl)-5-oxopentanoic acid (PS 254)

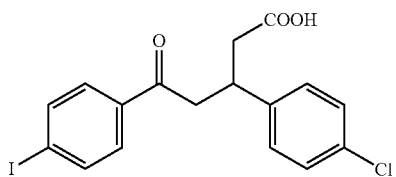 [SMILES: O=C(O)CC(CC(=O)c1ccc(I)cc1)c1ccc(Cl)cc1]

By a procedure similar to that of example 1.60, starting from 2-[1-(4-chlorophenyl)-3-(4-iodophenyl)-3-oxopropyl]malonic acid, 3-(4-chlorophenyl)-5-(4-iodophenyl)-5-oxopentanoic acid was obtained as colourless solid.

¹H-NMR (500 MHz, CDCl₃): δ (ppm)=2.67 (dd, J=7.9 Hz, 1H), 2.82 (dd, J=6.6 Hz, 1H), 3.25 (dd, J=7.2 Hz, 1H), 3.32 (dd, J=6.6 Hz, 1H), 3.79-3.85 (m, 1H), 7.18 (d, J=8.4 Hz, 2H), 7.25 (d, J=8.4 Hz, 2H), 7.59 (d, J=8.8 Hz, 2H), 7.80 (d, J=8.8 Hz, 2H).

¹³C-NMR (125 MHz, CDCl₃): δ (ppm)=36.5, 40.0, 44.2, 101.3, 128.7, 128.8, 129.4, 132.7, 135.9, 138.0, 141.3, 176.2 (CO), 197.0 (CO).

1.67. 2-[3-(4-Bromophenyl)-3-oxo-1-phenylpropyl]malonic acid (PS 206)

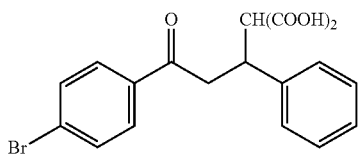

1) 1-(4-Bromophenyl)-3-phenylprop-2-en-1-one

By a procedure similar to that of example 1.59.1, starting from benzaldehyde and 4-bromoacetophenone, 1-(4-bromophenyl)-3-phenylprop-2-en-1-one was obtained as yellowish solid.

2) Diethyl 2-[3-(4-bromophenyl)-3-oxo-1-phenylpropyl]malonate

By a procedure similar to that of example 1.59.2, starting from 1-(4-bromophenyl)-3-phenylprop-2-en-1-one and diethyl malonate, diethyl 2-[3-(4-bromophenyl)-3-oxo-1-phenylpropyl]malonate was obtained as colourless solid.

¹H-NMR (500 MHz, CDCl₃): δ (ppm)=1.01 (t, J=7.2 Hz, 3H), 1.23 (t, J=7.2 Hz, 3H), 3.39 (dd, J=9.2, 9.2 Hz, 1H), 3.52 (dd, J=4.4, 4.4 Hz, 1H), 3.94 (d, J=9.5 Hz, 1H), 3.95 (q, J=7.2 Hz, 2H), 4.11-4.25 (m, 3H), 7.15-7.19 (m, 1H), 7.22-7.25 (m, 4H), 7.56 (d, J=8.8 Hz, 2H), 7.75 (d, J=8.8 Hz, 2H).

¹³C-NMR (125 MHz, CDCl₃): δ (ppm)=13.7, 14.0, 40.9, 42.6, 57.5, 61.4, 61.7, 127.2, 128.2, 128.4, 129.6, 131.8, 135.5, 140.2, 167.6 (CO), 168.3 (CO), 190.6, 196.6 (CO).

3) 2-[3-(4-Bromophenyl)-3-oxo-1-phenylpropyl]malonic acid

By a procedure similar to that of example 1.59.3, starting from diethyl 2-[3-(4-bromophenyl)-3-oxo-1-phenylpropyl]malonate, 2-[3-(4-bromophenyl)-3-oxo-1-phenylpropyl]malonic acid was obtained as colourless solid.

¹H-NMR (500 MHz, DMSO-d₆): δ (ppm)=3.29-3.33 (m, 1H), 3.59 (dd, J=10.1. 10.1 Hz, 1H), 3.74 (d, J=10.7 Hz, 1H), 3.83-3.88 (m, 1H), 7.11 (t, J=7.2 Hz, 1H), 7.18 (t, J=7.2 Hz, 2H), 7.26 (d, J=7.2 Hz, 2H), 7.70 (d, J=86 Hz, 2H), 7.78 (d, J=8.6 Hz, 2H).

¹³C-NMR (125 MHz, DMSO-d₆): δ (ppm)=40.4, 42.3, 57.2, 126.4, 127.1, 127.8, 128.3, 129.7, 131.6, 135.5, 141.0, 168.9 (CO), 169.9 (CO), 197.1 (CO).

MS (+ESI): m/z=393 (M+H).

1.68. 5-(4-Bromophenyl)-5-oxo-3-phenylpentanoic acid (PS 196)

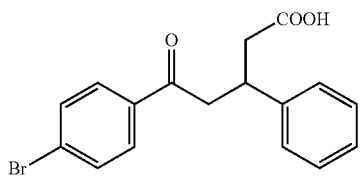

By a procedure similar to that of example 1.60, starting from 2-[3-(4-bromophenyl)-3-oxo-1-phenylpropyl]malonic acid, 5-(4-bromophenyl)-5-oxo-3-phenylpentanoic acid was obtained as colourless solid.

¹H-NMR (500 MHz, CD₃OD): δ (ppm)=2.64-2.71 (m, 1H), 2.78-2.85 (m, 1H), 3.39 (d, J=6.9 Hz, 2H), 3.75-3.81 (m, 1H), 7.16 (t, J=6.9 Hz, 1H), 7.23-7.29 (m, 4H), 7.63 (d, J=8.8 Hz, 2H), 7.83 (d, J=8.8 Hz, 2H).

¹³C-NMR (125 MHz, CD₃OD): δ (ppm)=37.2, 40.1, 44.4, 127.0, 127.3, 128.3, 128.7, 129.6, 131.9, 135.5, 142.8, 176.8 (CO), 197.1 (CO).

1.69. 2-[3-(3-Chlorophenyl)-3-oxo-1-phenylpropyl]malonic acid (PS 198)

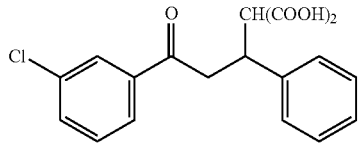

1) 1-(3-Chlorophenyl)-3-phenylprop-2-en-1-one

By a procedure similar to that of example 1.59.1, starting from benzaldehyde and 3-chloroacetophenone, 1-(3-chlorophenyl)-3-phenylprop-2-en-1-one was obtained as yellowish solid.

2) Diethyl 2-[3-(3-chlorophenyl)-3-oxo-1-phenylpropyl]malonate

By a procedure similar to that of example 1.59.2, starting from 1-(3-chlorophenyl)-3-phenylprop-2-en-1-one and diethyl malonate, diethyl 2-[3-(3-chlorophenyl)-3-oxo-1-phenylpropyl]malonate was obtained as colourless solid.

¹H-NMR (500 MHz, CDCl₃): δ (ppm)=1.02 (t, J=7.2 Hz, 3H), 1.25 (t, J=7.2 Hz, 3H), 3.43 (dd, J=9.1, 9.4 Hz, 1H), 3.53 (dd, J=4.4, 4.7 Hz, 1H), 3.80 (d, J=9.5 Hz, 1H), 3.97 (q, J=7.2 Hz, 2H), 4.13-4.24 (m, 3H), 7.16-7.19 (m, 1H), 7.24-7.27 (m, 4H), 7.36 (t, J=8.2 Hz, 1H), 7.48-7.50 (m, 1H), 7.77-7.79 (m, 1H), 7.84 (t, J=1.6 Hz, 1H).

¹³C-NMR (125 MHz, CDCl₃): δ (ppm)=13.8, 14.0, 40.7, 42.7, 57.4, 61.4, 61.7, 126.2, 127.2, 128.2, 128.4, 129.9, 132.9, 134.9, 138.4, 167.7 (CO), 168.3 (CO), 182.9 (CO).

3) 2-[3-(3-Chlorophenyl)-3-oxo-1-phenylpropyl]malonic acid

By a procedure similar to that of example 1.59.3, starting from diethyl 2-[3-(3-chlorophenyl)-3-oxo-1-phenylpropyl]malonate, 2-[3-(3-chlorophenyl)-3-oxo-1-phenylpropyl]malonic acid was obtained as colourless solid.

¹H-NMR (500 MHz, CD₃OD): δ (ppm)=3.50 (d, J=7.6 Hz, 2H), 3.84 (d, J=10.4 Hz, 1H), 4.00-4.05 (m, 1H), 7.14 (t, J=7.2 Hz, 1H), 7.21 (t, J=7.6 Hz, 2H), 7.27 (d, J=7.2 Hz, 2H), 7.44 (t, J=7.9 Hz, 1H), 7.55 (d, J=8.8 Hz, 1H), 7.8-7.83 (m, 2H).

¹³C-NMR (125 MHz, CD₃OD): δ (ppm)=42.7, 44.1, 58.8, 127.6, 128.1, 128.6, 129.0, 129.3, 129.6, 131.4, 134.0, 140.1, 142.1, 171.4 (CO), 171.8 (CO), 199.0 (CO).

MS (+ESI): m/z=341 (M+H).

1.70. 5-(3-Chlorophenyl)-5-oxo-3-phenylpentanoic acid (PS 204)

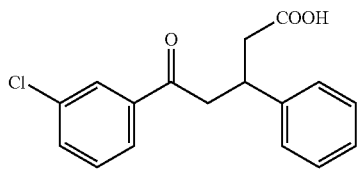 [SMILES: O=C(O)CC(CC(=O)c1cccc(Cl)c1)c1ccccc1]

By a procedure similar to that of example 1.60, starting from 2-[3-(3-chlorophenyl)-3-oxo-1-phenylpropyl]malonic acid, 5-(3-chlorophenyl)-5-oxo-3-phenylpentanoic acid was obtained as colourless solid.

¹H-NMR (500 MHz, CDCl₃): δ (ppm)=2.73 (dd, J=7.6, 7.6 Hz, 1H), 2.85 (dd, J=7.2, 7.2 Hz, 1H), 3.29-3.38 (m, 2H), 3.82-3.88 (m, 1H), 7.21 (t, J=6.9 Hz, 1H), 7.25-7.31 (m, 3H), 7.37 (t, J=7.6 Hz, 1H), 7.50-7.52 (m, 2H), 7.76 (d, J=8.8 Hz, 1H), 7.84-7.86 (t, J=1.6 Hz, 1H).

¹³C-NMR (125 MHz, CDCl₃): δ (ppm)=37.1, 39.9, 44.0, 126.2, 126.4, 127.4, 127.5, 128.0, 130.6, 132.7, 133.5, 138.4, 143.6, 156.9 (CO), 190.2 (CO).

MS (+ESI): m/z=303 (M+H).

1.71. 2-[3-Oxo-1-phenylpropyl-3-(4-trifluoromethylphenyl)]malonic acid (PS 210)

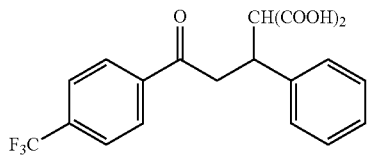

1) 3-Phenyl-1-(4-trifluoromethylphenyl)-prop-2-en-1-one

By a procedure similar to that of example 1.59.1, starting from benzaldehyde and 3-trifluoromethyl-acetophenone, 3-phenyl-1-(4-trifluoromethylphenyl)-prop-2-en-1-one was obtained as yellowish solid.

2) Diethyl 2-[3-oxo-1-phenylpropyl-3-(4-trifluoromethylphenyl)]malonate

By a procedure similar to that of example 1.59.2, starting from 3-phenyl-1-(4-trifluoro-methylphenyl)-prop-2-en-1-one and diethyl malonate, diethyl 2-[3-oxo-1-phenylpropyl-3-(4-trifluoromethylphenyl)]-malonate was obtained as colourless solid.

¹H-NMR (500 MHz, CDCl₃): δ (ppm)=1.01 (t, J=7.2 Hz, 3H), 1.23 (t, J=7.2 Hz, 3H), 3.39 (dd, J=9.2, 9.2 Hz, 1H), 3.52 (dd, J=4.4, 4.4 Hz, 1H), 3.94 (d, J=9.5 Hz, 1H), 3.95 (q, J=7.2 Hz, 2H), 4.11-4.25 (m, 3H), 7.15-7.19 (m, 1H), 7.22-7.25 (m, 4H), 7.56 (d, J=8.8 Hz, 2H), 7.75 (d, J=8.8 Hz, 2H).

¹³C-NMR (125 MHz, CDCl₃): δ (ppm)=13.7, 14.0, 40.9, 42.6, 57.5, 61.4, 61.7, 127.2, 128.2, 128.4, 129.6, 131.8, 135.5, 140.2, 167.6 (CO), 168.3 (CO), 190.6, 196.6 (CO).

3) 2-[3-Oxo-1-phenylpropyl-3-(4-trifluoromethylphenyl)]malonic acid

By a procedure similar to that of example 1.59.3, starting from diethyl 2-[3-oxo-1-phenylpropyl-3-(4-trifluoromethylphenyl)]malonate, 2-[3-oxo-1-phenylpropyl-3-(4-trifluoromethylphenyl)]malonic acid was obtained as colourless solid.

¹H-NMR (500 MHz, DMSO-d₆): δ (ppm)=3.42 (dd, J=3.8, 17.0 Hz 1H), 3.66 (dd, J=9.8, 9.8 Hz, 1H), 3.75 (d, J=10.7 Hz, 1H), 3.85-3.90 (m, 1H), 7.12 (t, J=7.2 Hz, 1H), 7.20 (t, J=7.9 Hz, 2H), 7.28 (d, J=7.2 Hz, 2H), 7.85 (d, J=8.2 Hz, 2H), 8.04 (d, J=8.2 Hz, 2H).

¹³C-NMR (125 MHz, DMSO-d₆): δ (ppm)=40.4, 42.7, 54.8, 57.2, 125.6, 126.5, 127.8, 128.3, 128.5, 139.5, 141.0, 168.9 (CO), 169.6 (CO), 197.4 (CO).

MS (+ESI): m/z=381 (M+H).

1.72. 2-[3-(4-Ethylphenyl)-3-oxo-1-phenylpropyl]malonic acid (PS 211)

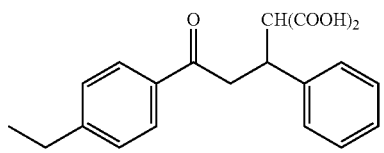

1) 1-(4-Ethylphenyl)-3-phenylprop-2-en-1-one

By a procedure similar to that of example 1.59.1, starting from benzaldehyde and 4-ethylacetophenone, 1-(4-ethylphenyl)-3-phenylprop-2-en-1-one was obtained as yellowish solid.

2) Diethyl 2-[3-(4-ethylphenyl)-3-oxo-1-phenylpropyl]malonate

By a procedure similar to that of example 1.59.2, starting from 1-(4-ethylphenyl)-3-phenylprop-2-en-1-one and diethyl malonate, diethyl 2-[3-(4-ethylphenyl)-3-oxo-1-phenylpropyl]malonate was obtained as colourless solid.

$^1$H-NMR (500 MHz, CDCl$_3$): δ (ppm)=1.01 (t, J=7.2 Hz, 3H), 1.24 (t, J=7.2 Hz, 6H), 2.69 (q, J=7.6 Hz, 2H), 3.42-3.52 (m, 2H), 3.82 (d, J=9.5 Hz, 1H), 3.95 (q, J=7.2 Hz, 2H), 4.18-4.25 (m, 3H), 7.16 (t, J=7.2 Hz, 1H), 7.21-7.27 (m, 6H), 7.82 (d, J=8.2 Hz, 2H).

$^{13}$C-NMR (125 MHz, CDCl$_3$): δ (ppm)=13.7, 14.1, 15.1, 28.9, 40.8, 42.5, 57.6, 61.3, 61.6, 127.1, 128.0, 128.2, 128.3, 128.3, 134.6, 140.6, 149.9, 167.7 (CO), 168.4 (CO), 197.1 (CO).

3) 2-[3-(4-Ethylphenyl)-3-oxo-1-phenylpropyl]malonic acid

By a procedure similar to that of example 1.59.3, starting from diethyl 2-[3-(4-ethylphenyl)-3-oxo-1-phenylpropyl]malonate, 2-[3-(4-ethylphenyl)-3-oxo-1-phenylpropyl]malonic acid was obtained as colourless solid.

$^1$H-NMR (500 MHz, DMSO-d$_6$): δ (ppm)=1.17 (t, J=7.6 Hz, 3H), 2.64 (q, J=7.6 Hz, 2H), 3.27 (q, J=3.5, 16.7 Hz, 1H), 3.59 (dd, J=10.4. 10.4 Hz, 1H), 3.74 (d, J=10.7 Hz, 1H), 3.86-3.90 (m, 1H), 7.11 (t, J=7.2 Hz, 1H), 7.19 (t, J=7.9 Hz, 2H), 7.27 (d, J=6.9 Hz, 2H), 7.30 (d, J=7.9 Hz, 2H), 7.78 (d, J=8.2 Hz, 2H), 12.78 (s, 2H, OH).

$^{13}$C-NMR (125 MHz, DMSO-d$_6$): δ (ppm)=15.0, 28.0, 30.6, 40.4, 42.2, 57.3, 126.3, 127.8, 127.9, 128.3, 134.3, 141.2, 149.4, 169.0 (CO), 169.6 (CO), 197.3 (CO).

MS (+ESI): m/z=341 (M+H).

1.73. 5-(4-Ethylphenyl)-5-oxo-3-phenylpentanoic acid (PS 217)

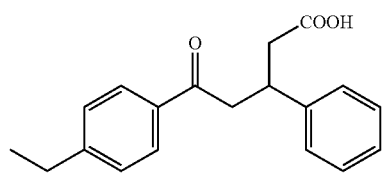 [SMILES: CCc1ccc(C(=O)CC(CC(=O)O)c2ccccc2)cc1]

By a procedure similar to that of example 1.60, starting from 2-[3-(4-ethylphenyl)-3-oxo-1-phenylpropyl]malonic acid, 5-(4-ethylphenyl)-5-oxo-3-phenylpentanoic acid was obtained as colourless solid.

$^1$H-NMR (500 MHz, CDCl$_3$): δ (ppm)=1.24 (t, J=7.6 Hz, 3H), 2.67-2.74 (m, 3H), 2.86 (dd, J=6.6, 6.9 Hz, 1H), 3.33 (d, J=8.2 Hz, 2H), 3.83-3.89 (m, 1H), 7.18-7.20 (m, 1H), 7.28-7.30 (m, 6H), 7.83 (d, J=8.2 Hz, 2H), 10.25 (s, 1H, OH).

$^{13}$C-NMR (125 MHz, CDCl$_3$): δ (ppm)=15.1, 28.9, 37.2, 40.0, 44.4, 126.9, 127.3, 128.1, 128.3, 128.6, 134.5, 143.1, 150.1, 173.5 (CO), 197.7 (CO).

MS (+ESI): m/z=297 (M+H).

1.74. 2-[3-Oxo-3-(4-phenoxyphenyl)-1-phenylpropyl]malonic acid (PS 205)

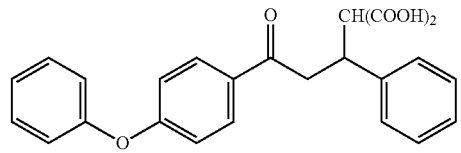

1) 1-(4-Phenoxyphenyl)-3-phenylprop-2-en-1-one

By a procedure similar to that of example 1.59.1, starting from benzaldehyde and 4-phenoxyacetophenone, 1-(4-phenoxyphenyl)-3-phenylprop-2-en-1-one was obtained as yellowish solid.

2) Diethyl 2-[3-oxo-3-(4-phenoxyphenyl)-1-phenylpropyl]malonate

By a procedure similar to that of example 1.59.2, starting from 1-(4-phenoxyphenyl)-3-phenylprop-2-en-1-one and diethyl malonate, diethyl 2-[3-oxo-3-(4-phenoxyphenyl)-1-phenylpropyl]malonate was obtained as colourless solid.

$^1$H-NMR (500 MHz, CDCl$_3$): δ (ppm)=1.01 (t, J=6.9 Hz, 3H), 1.24 (t, J=6.9 Hz, 3H), 3.39 (dd, J=9.1, 9.1 Hz, 1H), 3.49 (dd, J=4.4, 4.4 Hz, 1H), 3.81 (d, J=9.8 Hz, 1H), 3.96 (q, J=7.2 Hz, 2H), 4.14-4.23 (m, 3H), 6.95 (d, J=8.9 Hz, 2H), 7.05 (d, J=8.9 Hz, 1H), 7.15-7.27 (m, 6H), 7.38 (t, J=7.6 Hz, 1H), 7.88 (d, J=9.1 Hz, 2H).

$^{13}$C-NMR (125 MHz, CDCl$_3$): δ (ppm)=13.7, 14.0, 41.0, 42.4, 57.6, 61.3, 61.6, 117.3, 120.1, 124.6, 127.1, 128.2, 128.4, 130.0, 130.4, 131.5, 140.4, 125.5, 161.9, 167.7 (CO), 168.4 (CO), 196.1 (CO).

3) 2-[3-Oxo-3-(4-phenoxyphenyl)-1-phenylpropyl]malonic acid

By a procedure similar to that of example 1.59.3, starting from diethyl 2-[3-oxo-3-(4-phenoxyphenyl)-1-phenylpropyl]malonate, 2-[3-oxo-3-(4-phenoxyphenyl)-1-phenylpropyl]malonic acid was obtained as colourless solid.

$^1$H-NMR (500 MHz, CD$_3$OD): δ (ppm)=3.44 (m, 2H), 3.86 (d, J=10.4 Hz, 1H), 4.05-4.10 (m, 1H), 6.97 (d, J=8.5 Hz, 2H), 7.08 (d J=7.2 Hz, 2H), 7.16 (t, J=7.9 Hz, 1H), 7.20-7.30 (m, 5H), 7.44 (t, J=7.6 Hz, 2H), 7.92 (d, J=8.2 Hz, 2H).

$^{13}$C-NMR (125 MHz, CD$_3$OD): δ (ppm)=42.8, 43.8, 58.9, 118.2, 121.3, 125.8, 128.0, 129.3, 129.6, 131.2, 131.7, 133.0, 142.2, 156.9, 163.6, 171.4 (CO), 171.8 (CO), 199.0 (CO).

MS (+ESI): m/z=405 (M+H).

1.75. 5-Oxo-5-(4-phenoxyphenyl)-3-phenylpentanoic acid (PS 208)

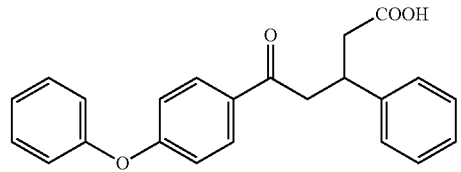 [SMILES: O=C(O)CC(CC(=O)c1ccc(Oc2ccccc2)cc1)c1ccccc1]

By a procedure similar to that of example 1.60, starting from 2-[3-oxo-3-(4-phenoxyphenyl)-1-phenylpropyl]malonic acid, 5-oxo-5-(4-phenoxyphenyl)-3-phenylpentanoic acid was obtained as colourless solid.

$^1$H-NMR (500 MHz, CDCl$_3$): δ (ppm)=2.71 (dd, J=7.9, 7.9 Hz, 1H), 2.86 (dd, J=6.8, 6.8 Hz, 1H), 3.27-3.35 (m, 2H), 3.82-3.88 (m, 1H), 6.96 (d, J=9.1 Hz, 1H), 7.05 (d, J=8.5 Hz, 2H), 7.20 (t, J=7.2 Hz, 2H), 7.25-7.30 (m, 4H), 7.39 (t, J=7.6 Hz, 2H), 7.88 (d, J=8.8 Hz, 2H).

$^{13}$C-NMR (125 MHz, CDCl$_3$): δ (ppm)=37.1, 39.7, 44.0, 117.1, 119.9, 124.4, 126.6, 127.0, 128.4, 129.8, 130.1, 131.3, 142.8, 155.2, 161.8, 175.7 (CO), 196.4 (CO).

MS (+ESI): m/z=361 (M+H).

1.76. 2-[3-(2-Benzyloxyphenyl)-3-oxo-1-phenylpropyl]malonic acid (PS 192)

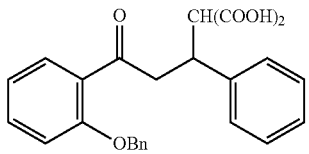

1) 1-(2-Benzyloxyphenyl)-3-phenylprop-2-en-1-one

By a procedure similar to that of example 1.59.1, starting from benzaldehyde and 2-benzyloxyacetophenone, 1-(2-benzyloxyphenyl)-3-phenylprop-2-en-1-one was obtained as yellowish solid.

2) Diethyl 2-[3-(2-benzyloxyphenyl)-3-oxo-1-phenylpropyl]malonate

By a procedure similar to that of example 1.59.2, starting from 1-(2-benzyloxyphenyl)-3-phenylprop-2-en-1-one and diethyl malonate, diethyl 2-[3-(2-benzyloxyphenyl)-3-oxo-1-phenylpropyl]malonate was obtained as colourless solid.

$^1$H-NMR (500 MHz, CDCl$_3$): δ (ppm)=0.98 (t, J=6.9 Hz, 3H), 1.18 (t, J=6.9 Hz, 3H), 3.46-3.59 (m, 2H), 3.65 (d, J=10.1 Hz, 1H), 4.04-4.15 (m, 3H), 5.13 (q, J=11.7 Hz, 2H), 6.92 (t, J=7.6 Hz, 1H), 6.96 (d, J=8.5 Hz, 1H), 7.14-7.18 (m, 6H), 7.36-7.41 (m, 6H), 7.46 (dd, J=7.9, 1.9 Hz, 1H).

$^{13}$C-NMR (125 MHz, CDCl$_3$): δ (ppm)=13.7, 14.0, 40.6, 47.9, 57.8, 61.1, 61.4, 70.7, 112.7, 120.9, 126.8, 127.7, 128.1, 128.2, 128.4, 128.7, 130.4, 133.2, 140.0, 140.9, 153.0, 157.5, 168.2 (CO), 168.3 (CO), 200.0 (CO).

3) 2-[3-(2-Benzyloxyphenyl)-3-oxo-1-phenylpropyl]malonic acid

By a procedure similar to that of example 1.59.3, starting from diethyl 2-[3-(2-benzyloxyphenyl)-3-oxo-1-phenylpropyl]malonate, 2-[3-(2-benzyloxyphenyl)-3-oxo-1-phenylpropyl]-malonic acid was obtained as colourless solid.

$^1$H-NMR (500 MHz, CD$_3$OD): δ (ppm)=3.45 (dd, J=17.1, 4.4 Hz, 1H), 3.58-3.63 (m, 2H), 3.96-4.01 (m, 1H), 5.14-5.2 (m, 2H), 6.90 (t, J=7.2 Hz, 1H), 7.09-7.16 (m, 6H), 7.28 (dd, J=7.6, 1.6 Hz, 1H), 7.35 (t, J=7.2 Hz, 1H), 7.39-7.46 (m, 5H).

$^{13}$C-NMR (125 MHz, CD$_3$OD): δ (ppm)=42.2, 49.7, 59.1, 71.9, 114.4, 121.8, 127.8, 129.1, 129.1, 129.3, 130.0, 130.2, 130.9, 134.6, 138.0, 142.5, 158.9, 171.5 (CO), 171.7 (CO), 202.7 (CO).

1.77. 2-[3-(2-Benzyloxyphenyl)-1-(4-chlorophenyl)-3-oxopropyl]malonic acid (PS 191)

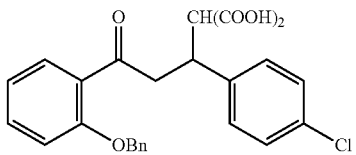

1) 1-(2-Benzyloxyphenyl)-3-(4-chlorophenyl)prop-2-en-1-one

By a procedure similar to that of example 1.59.1, starting from 4-chlorobenzaldehyde and 2-benzyloxyacetophenone, 1-(2-benzyloxyphenyl)-3-(4-chlorophenyl)prop-2-en-1-one was obtained as yellowish solid.

2) Diethyl 2-[3-(2-benzyloxyphenyl)-1-(4-chlorophenyl)-3-oxopropyl]malonate By a procedure similar to that of example 1.59.2, starting from 1-(2-benzyloxyphenyl)-3-(4-chlorophenyl)prop-2-en-1-one and diethyl malonate, diethyl 2-[3-(2-benzyloxyphenyl)-1-(4-chlorophenyl)-3-oxopropyl]malonate was obtained as colourless solid.

$^1$H-NMR (500 MHz, CDCl$_3$): δ (ppm)=1.01 (t, J=7.2 Hz, 3H), 1.19 (t, J=7.2 Hz, 3H), 3.43-3.55 (m, 2H), 3.60 (d, J=9.7 Hz, 1H), 3.93 (q, J=7.2 Hz, 2H), 4.04-4.14 (m, 3H), 5.12 (q, J=11.3 Hz, 2H), 6.94 (t, J=7.6 Hz, 1H), 6.99 (d, J=7.9 Hz, 1H), 7.05 (d, J=8.5 Hz, 2H), 7.12 (d, J=8.5 Hz, 2H), 7.37-7.42 (m, 6H), 7.49 (dd, J=7.6, 1.6 Hz, 1H).

$^{13}$C-NMR (125 MHz, CDCl$_3$): δ (ppm)=13.8, 14.0, 39.8, 47.7, 57.4, 61.2, 61.5, 70.8, 112.7, 121.0, 127.8, 128.2, 128.3, 128.4, 128.7, 129.8, 130.4, 132.5, 133.4, 136.1, 139.6, 167.6 (CO), 167.7 (CO), 199.2 (CO).

3) 2-[3-(2-Benzyloxyphenyl)-1-(4-chlorophenyl)-3-oxopropyl]malonic acid

By a procedure similar to that of example 1.59.3, starting from diethyl 2-[3-(2-benzyloxyphenyl)-1-(4-chlorophenyl)-3-oxopropyl]malonate, 2-[3-(2-benzyloxyphenyl)-1-(4-chlorophenyl)-3-oxopropyl]malonic acid was obtained as colourless solid.

$^1$H-NMR (500 MHz, CD$_3$OD): δ (ppm)=3.44 (dd, J=4.1, 4.1 Hz, 1H), 3.57-3.62 (m, 2H), 3.95-4.00 (m, 1H), 5.15-5.20 (m, 2H), 6.93 (t, J=7.6 Hz, 1H), 7.10-7.15 (m, 5H), 7.33-7.46 (m, 7H).

$^{13}$C-NMR (125 MHz, CD$_3$OD): δ ppm)=41.6, 49.7, 58.8, 71.9, 114.4, 121.9, 130.0, 130.9, 131.4, 133.5, 134.7, 137.9, 141.5, 158.9, 171.3 (CO), 171.5 (CO), 202.3 (CO).

1.78. 2-[3-(2-Naphthalenyl)-3-oxo-1-phenylpropyl] malonic acid (PS 207)

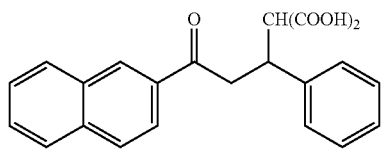

1) 1-(2-Naphthalenyl)-3-phenylprop-2-en-1-one

By a procedure similar to that of example 1.59.1, starting from benzaldehyde and 2-acetylnaphthalene, 1-(2-naphthalenyl)-3-phenylprop-2-en-1-one was obtained as yellowish solid.

2) Diethyl 2-[3-(2-naphthalenyl)-3-oxo-1-phenylpropyl]malonate

By a procedure similar to that of example 1.59.2, starting from 1-(2-naphthalenyl)-3-phenylprop-2-en-1-one and diethyl malonate, diethyl 2-[3-(2-naphthalenyl)-3-oxo-1-phenylpropyl]malonate was obtained as colourless solid.

$^1$H-NMR (500 MHz, CDCl$_3$): δ(ppm)=1.02 (t, J=7.2 Hz, 3H), 1.25 (t, J=7.2 Hz, 3H), 3.60 (dd, J=9.5, 9.5 Hz, 1H), 3.67 (dd, J=4.4, 4.4 Hz, 1H), 3.87 (d, J=9.5 Hz, 1H), 3.97 (q, J=6.9 Hz, 2H), 4.19-4.28 (m, 3H), 7.17 (t, J=7.2 Hz, 1H), 7.23-7.30 (m, 4H), 7.52-7.60 (m, 2H), 7.84 (d, J=8.5 Hz, 2H), 7.93-7.96 (m, 2H), 8.44 (s, 1H).

$^{13}$C-NMR (125 MHz, CDCl$_3$): δ (ppm)=13.7, 14.0, 41.0, 42.7, 57.6, 61.3, 61.6, 123.9, 126.7, 127.1, 127.7, 128.2, 128.4, 128.4, 129.6, 129.8, 132.5, 134.2, 135.5, 140.5, 153.0, 167.6 (CO), 167.8 (CO), 197.5 (CO).

3) 2-[3-(2-Naphthalenyl)-3-oxo-1-phenylpropyl]malonic acid

By a procedure similar to that of example 1.59.3, starting from diethyl 2-[3-(2-naphthalenyl)-3-oxo-1-phenylpropyl]malonate, 2-[3-(2-naphthalenyl)-3-oxo-1-phenylpropyl]-malonic acid was obtained as colourless solid.

$^1$H-NMR (500 MHz, DMSO-d$_6$): δ (ppm)=3.44 (dd, J=3.5, 16.7 Hz, 2H), 3.74-3.80 (m, 2H), 3.93-3.98 (m, 1H), 7.10 (t, J=7.6 Hz, 1H), 7.20 (t, J=7.9 Hz, 2H), 7.31 (d, J=8.5 Hz, 2H), 7.60-7.67 (m, 2H), 7.86 (dd, J=1.9, 8.8 Hz, 1H), 7.96 (dd, J=2.5, 7.9 Hz, 1H), 8.07 (d, J=7.9 Hz, 1H), 8.59 (s, 1H).

$^{13}$C-NMR (125 MHz, DMSO-d$_6$): δ (ppm)=40.6, 42.4, 57.4, 123.3, 126.4, 126.8, 127.5, 127.8, 128.1, 128.3, 128.5, 129.4, 129.6, 132.0, 133.8, 134.8, 141.2, 168.9 (CO), 169.7 (CO), 197.7 (CO).

MS (+ESI): m/z=363 (M+H).

1.79. 2-[3-(6-Methoxy-2-naphthalenyl)-3-oxo-1-phenylpropyl]malonic acid (PS 225)

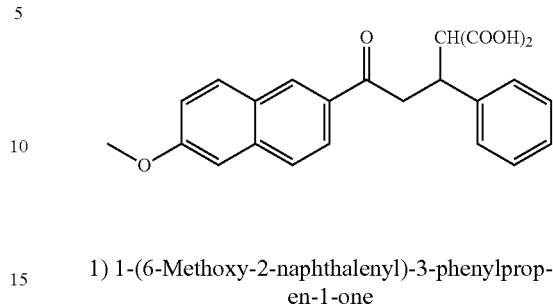

1) 1-(6-Methoxy-2-naphthalenyl)-3-phenylprop-2-en-1-one

By a procedure similar to that of example 1.59.1, starting from benzaldehyde and commercial 2-acetyl-6-methoxynaphthalene, 1-(6-methoxy-2-naphthalenyl)-3-phenylprop-2-en-1-one was obtained as beige coloured solid.

$^1$H-NMR (500 MHz, CDCl$_3$): δ (ppm)=3.95 (s, 3H), 7.18 (d, J=2.2, 1H), 7.22 (dd, J=2.5, 11.3, 1H), 7.43-7.45 (m, 3H), 7.67-7.71 (m, 3H), 7.81 (d, J=8.5 Hz, 1H), 7.86-7.89 (m, 2H), 8.10 (dd, J=1.60, 1.89, 8.5 Hz, 1H), 8.48 (s, 1H).

$^{13}$C-NMR (125 MHz, CDCl$_3$): δ (ppm)=55.4, 105.8, 119.7, 122.1, 125.2, 127.3, 127.9, 128.4, 128.9, 129.8, 130.4, 131.1, 133.5, 135.1, 137.2, 144.3, 159.7, 189.8 (CO).

2) Diethyl 2-[3-(6-methoxy-2-naphthalenyl)-3-oxo-1-phenylpropyl]malonate

By a procedure similar to that of example 1.59.2, starting from 1-(6-methoxy-2-naphthalenyl)-3-phenylprop-2-en-1-one and diethyl malonate, diethyl 2-[3-(6-methoxy-2-naphthalenyl)-3-oxo-1-phenylpropyl]malonate was obtained as beige coloured solid.

$^1$H-NMR (500 MHz, CDCl$_3$): δ (ppm)=1.01 (t, J=7.2 Hz, 3H), 1.25 (t, J=7.2 Hz, 3H), 3.56 (dd, J=9.1 Hz, 1H), 3.64 (dd, J=4.4 Hz, 1H), 3.87 (d, J=9.8 Hz, 1H), 3.94 (s, 3H), 3.96 (q, J=7.2 Hz, 2H), 4.16-4.27 (m, 3H), 7.12-7.30 (m, 7H), 7.71 (d, J=8.8 Hz, 1H), 7.83 (d, J=9.1 Hz, 1H), 7.91 (dd, J=1.9, 8.5 Hz, 1H), 8.37 (d, J=1.6 Hz, 1H).

$^{13}$C-NMR (125 MHz, CDCl$_3$): δ (ppm)=13.7, 14.0, 41.0, 42.5, 55.4, 57.6, 61.3, 61.6, 105.7, 119.6, 124.6, 127.0, 127.1, 127.8, 128.3, 128.4, 129.7, 131.1, 132.2, 137.2, 140.6, 159.7, 167.8 (CO), 168.4 (CO), 197.1 (CO).

3) 2-[3-(6-Methoxy-2-naphthalenyl)-3-oxo-1-phenylpropyl]malonic acid

By a procedure similar to that of example 1.59.3, starting from diethyl 2-[3-(6-methoxy-2-naphthalenyl)-3-oxo-1-phenylpropyl]malonate, 2-[3-(6-methoxy-2-naphthalenyl)-3-oxo-1-phenylpropyl]malonic acid was obtained as yellowish solid.

$^1$H-NMR (500 MHz, DMSO-d$_6$): δ (ppm)=3.38 (dd, J=3.5, 16.7 Hz, 1H), 3.71-3.79 (m, 2H), 3.95 (s, 3H), 3.96 (dt, J=3.5, 10.7 Hz, 1H), 7.10 (t, J=7.2 Hz, 1H), 7.20 (t, J=7.6 Hz, 2H), 7.25 (dd, J=2.2, 8.8 Hz, 1H), 7.31 (d, J=7.2 Hz, 2H), 7.37 (d, J=2.2 Hz, 1H), 7.83 (q, J=8.8 Hz, 2H), 7.98 (d, J=8.8 Hz, 1H), 8.51 (s, 1H), 12.53 (s, OH), 12.92 (s, OH).

$^{13}$C-NMR (125 MHz, DMSO-d$_6$): δ (ppm)=40.6, 42.3, 55.4, 57.5, 106.0, 119.5, 124.0, 126.4, 126.9, 127.3, 127.9, 128.4, 129.6, 131.1, 131.9, 136.8, 141.3, 159.3, 169.1 (CO), 169.8 (CO), 197.3 (CO).

1.80. 5-(6-Hydroxy-2-naphthalenyl)-5-oxo-3-phenyl-pentanoic acid (PS 239)

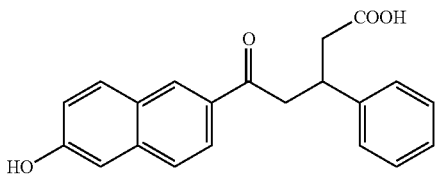 [SMILES: O=C(O)CC(CC(=O)c1ccc2cc(O)ccc2c1)c1ccccc1]

A mixture of 2-(3-(6-methoxynaphthalen-2-yl)-3-oxo-1-phenylpropyl)malonic acid (0.15 g) in acetic acid (5 ml) was treated with 48% aqueous HBr (2 ml) and heated to 150° C. for 2 h. The solvent and acid were removed by distillation and the residue was partitioned between 10% HCl and ethyl acetate. The organic layer was separated, washed with brine, dried over MgSO$_4$, and evaporated to afford a crude, which was purified by flash chromatography on silica gel to give 5-(6-hydroxy-2-naphthalenyl)-5-oxo-3-phenylpentanoic acid (0.1 g) as pale yellow solid.

$^1$H-NMR (500 MHz, DMSO-d$_6$): δ (ppm)=2.59 (dd, J=8.5 Hz, 1H), 2.73 (dd, J=6.3 Hz, 1H), 3.43 (dd, J=6.3 Hz, 1H), 3.52 (dd, J=8.5 Hz, 1H), 3.69-3.74 (m, 1H), 7.12-7.18 (m, 3H), 7.25 (t, J=7.6 Hz, 2H), 7.32 (d, J=8.2 Hz, 2H), 7.71 (d, J=8.8 Hz, 1H), 7.82 (dd, J=1.9, 8.8 Hz, 1H), 7.94 (d, J=9.8 Hz, 1H), 8.51 (d, J=1.6 Hz, 1H), 10.19 (s, OH), 12.20 (s, OH).

$^{13}$C-NMR (125 MHz, DMSO-d$_6$): δ (ppm)=37.3, 40.3, 43.6, 108.6, 119.4, 123.7, 126.1, 126.2, 126.4, 127.4, 128.0, 129.9, 131.1, 131.4, 136.7, 143.9, 157.7, 172.8 (CO), 197.7 (CO).

1.81. 2-[3-Oxo-3-(2-phenanthrenyl)-1-phenylpropyl]malonic acid (PS 224)

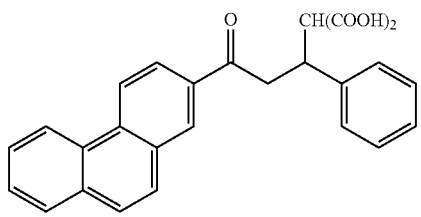

1) 1-(2-Phenanthrenyl)-3-phenylprop-2-en-1-one

By a procedure similar to that of example 1.59.1, starting from benzaldehyde and commercial 2-acetylphenanthrene, 1-(2-phenanthrenyl)-3-phenylprop-2-en-1-one was obtained as yellowish solid.

$^1$H-NMR (500 MHz, CDCl$_3$): δ (ppm)=7.41-7.48 (m, 3H), 7.66-7.74 (m, 5H), 7.84 (q, J=8.8 Hz, 2H), 7.89-7.93 (m, 2H), 8.29 (dd, J=1.89, 8.5 Hz, 1H), 8.57 (d, J=1.89 Hz, 1H), 8.73 (d, J=7.9 Hz, 1H), 8.78 (d, J=8.8 Hz, 1H).

$^{13}$C-NMR (125 MHz, CDCl$_3$): δ (ppm)=122.1, 123.2, 123.3, 125.6, 127.0, 127.3, 127.7, 127.9, 128.5, 128.7, 129.0, 129.7, 130.6, 131.5, 133.0, 133.3, 135.0, 136.0, 144.9, 190.1 (CO).

2) Diethyl 2-[3-oxo-3-(2-phenanthrenyl)-1-phenyl-propyl]malonate

By a procedure similar to that of example 1.59.2, starting from 1-(2-phenanthrenyl)-3-phenylprop-2-en-1-one and diethyl malonate, diethyl 2-[3-oxo-3-(2-phenanthrenyl)-1-phenylpropyl]malonate was obtained as colourless solid.

$^1$H-NMR (500 MHz, CDCl$_3$): δ (ppm)=1.02 (t, J=7.2 Hz, 3H), 1.27 (t, J=7.2 Hz, 3H), 3.62 (dd, J=9.2 Hz, 1H), 3.71 (dd, J=4.4 Hz, 1H), 3.89 (d, J=9.4 Hz, 1H), 3.97 (q, J=7.2 Hz, 2H), 4.18-4.30 (m, 3H), 7.17 (tt, J=1.4, 7.6 Hz, 1H), 7.25 (t, J=7.9 Hz, 2H), 7.31 (dd, J=1.2, 8.2 Hz, 2H), 7.64-7.70 (m, 2H), 7.78 (q, J=8.8 Hz, 2H), 7.91 (dd, J=1.9, 7.2 Hz, 1H), 8.14 (dd, J=1.9, 8.8 Hz, 1H), 8.45 (d, J=1.9 Hz, 1H), 8.68-8.71 (m, 2H).

$^{13}$C-NMR (125 MHz, CDCl$_3$): δ (ppm)=13.8, 14.0, 41.0, 42.8, 57.6, 61.3, 61.7, 123.1, 123.3, 125.1, 127.0, 127.1, 127.4, 127.7, 127.8, 128.3, 128.4, 128.7, 129.5, 129.7, 131.4, 133.0, 133.4, 134.6, 140.5, 167.8 (CO), 168.4 (CO), 197.4 (CO).

3) 2-[3-Oxo-3-(2-phenanthrenyl)-1-phenylpropyl]malonic acid

By a procedure similar to that of example 1.59.3, starting from diethyl 2-[3-oxo-3-(2-phenanthrenyl)-1-phenylpropyl]malonate, 2-[3-oxo-3-(2-phenanthrenyl)-1-phenyl-propyl]malonic acid was obtained as colourless solid.

$^1$H-NMR (500 MHz, DMSO-d$_6$): δ (ppm)=3.49 (dd, J=3.5, 10.9 Hz, 1H), 3.77-3.82 (m, 2H), 3.98 (dt, J=3.5, 10.9 Hz, 1H), 7.11 (t, J=7.2 Hz, 1H), 7.21 (t, J=7.6 Hz, 2H), 7.33 (d, J=7.2 Hz, 2H), 7.70-7.76 (m, 2H), 7.95 (q, J=8.8 Hz, 2H), 8.02-8.39 (m, 1H), 8.07 (dd, J=1.9, 8.8 Hz, 1H), 8.59 (d, J=1.9 Hz, 1H), 8.86-8.90 (m, 2H).

$^{13}$C-NMR (125 MHz, DMSO-d$_6$): δ (ppm)=40.7, 42.6, 57.5, 123.4, 123.6, 124.8, 126.5, 127.2, 127.7, 127.8, 127.9, 128.0, 128.5, 128.6, 129.6, 131.0, 132.1, 132.5, 132.6, 134.5, 141.3, 169.0 (CO), 169.8 (CO), 197.7 (CO).

1.82. 2-[3-(1H-Indol-3-yl)-3-oxo-1-phenylpropyl]malonic acid (PS 240)

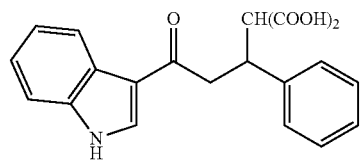

1) 1-(1H-Indol-3-yl)-3-phenylprop-2-en-1-one

By a procedure similar to that of example 1.59.1, starting from benzaldehyde and commercial 3-acetylindole, 1-(1H-indol-3-yl)-3-phenylprop-2-en-1-one was obtained as orange coloured solid.

$^1$H-NMR (500 MHz, DMSO-d$_6$): δ (ppm)=7.21-7.27 (m, 2H), 7.40-7.44 (m, 3H), 7.48 (d, J=7.6, 1H), 7.64 (d, J=15.8, 1H), 7.83-7.86 (m, 3H), 7.83-7.84 (m, 1H), 8.74 (s, 1H), 12.1 (s, NH).

$^{13}$C-NMR (125 MHz, DMSO-d$_6$): δ (ppm)=112.1, 117.7, 121.6, 121.7, 121.8, 123.1, 124.6, 125.9, 128.3, 128.8, 129.7, 135.2, 136.8, 139.5, 183.5 (CO).

2) Diethyl 2-[3-(1H-indol-3-yl)-3-oxo-1-phenylpropyl]malonate

By a procedure similar to that of example 1.59.2, starting from 1-(1H-indol-3-yl)-3-phenylprop-2-en-1-one and diethyl malonate, diethyl 2-[3-(1H-indol-3-yl)-3-oxo-1-phenylpropyl]malonate was obtained as yellowish solid.

¹H-NMR (500 MHz, DMSO-d₆): δ (ppm)=3.10 (dd, J=3.9, 15.7 Hz, 1H), 3.37 (s, 3H), 3.30 (dd, J=10.1 Hz, 1H), 3.67 (s, 3H), 3.96 (d, J=10.4 Hz, 1H), 3.99 (dt, J=3.7, 10.1 Hz, 1H), 7.10-7.13 (m, 2H), 7.18 (dd, J=1.2, 6.9 Hz, 1H), 7.20 (t, J=7.6 Hz, 2H), 7.31 (d, J=8.5 Hz, 2H), 7.42 (d, J=7.9 Hz, 1H), 8.07 (d, J=7.9 Hz, 1H), 8.25 (d, J=3.1 Hz, 1H), 11.9 (s, NH).

¹³C-NMR (125 MHz, DMSO-d₆): δ (ppm)=46.3, 47.7, 57.2, 57.7, 62.2, 117.2, 121.8, 126.5, 126.9, 128.0, 130.4, 131.9, 133.2, 133.5, 139.0, 141.7, 145.9, 173.0 (CO), 173.5 (CO), 197.5 (CO).

3) 2-[3-(1H-Indol-3-yl)-3-oxo-1-phenylpropyl]malonic acid

By a procedure similar to that of example 1.59.3, starting from diethyl 2-[3-(1H-indol-3-yl)-3-oxo-1-phenylpropyl]malonate, 2-[3-(1H-indol-3-yl)-3-oxo-1-phenylpropyl]malonic acid was obtained as yellowish solid.

¹H-NMR (500 MHz, DMSO-d₆): δ (ppm)=3.05 (dd, J=3.5, 15.8 Hz, 1H), 3.47 (dd, J=10.7 Hz, 1H), 3.71 (d, J=10.7 Hz, 1H), 3.94 (dt, J=3.5, 10.7 Hz, 1H), 7.07 (t, J=7.6 Hz, 1H), 7.08-7.12 (m, 4H), 7.30 (d, J=7.7 Hz, 2H), 7.39 (d, J=8.2 Hz, 1H), 8.06 (d, J=7.9 Hz, 1H), 8.23 (d, J=2.8 Hz, 1H), 11.84 (s, NH), 12.51 (s, OH), 12.88 (s, OH).

¹³C-NMR (125 MHz, DMSO-d₆): δ (ppm)=46.3, 47.7, 57.2, 57.7, 62.2, 117.2, 121.8, 126.5, 126.9, 128.0, 130.4, 131.9, 133.2, 133.5, 139.0, 141.7, 145.9, 173.0 (CO), 173.5 (CO), 197.5 (CO).

1.83. Bis(acetoxymethyl) 2-[3-(2-naphthalenyl)-3-oxo-1-phenylpropyl]malonate (PS 222)

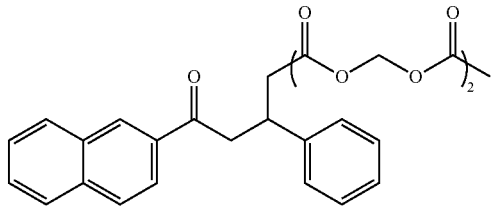

By a procedure similar to that of example 1.62, starting from 2-[3-(2-naphthalenyl)-3-oxo-1-phenylpropyl]malonic acid, bis(acetoxymethyl)2-[3-(2-naphthalenyl)-3-oxo-1-phenylpropyl]malonate was obtained as colourless solid.

¹H-NMR (500 MHz, DMSO-d₆): δ (ppm)=1.97 (s, 3H), 2.10 (s, 3H), 3.61-3.71 (m, 2H), 4.02 (d, J=9.1 Hz, 1H), 4.27-4.32 (m, 1H), 5.58 (q, J=5.7 Hz, 2H), 5.76-5.78 (m, 2H), 7.19 (t, J=7.2 Hz, 1H), 7.24-7.31 (m, 4H), 7.53-7.61 (m, 2H), 7.85 (d, J=8.5 Hz, 2H), 7.92-7.97 (m, 2H), 8.43 (s, 1H).

¹³C-NMR (125 MHz, DMSO-d₆): δ (ppm)=20.5, 20.54, 40.6, 42.2, 56.6, 79.4, 79.8, 123.7, 126.8, 127.4, 127.7, 128.2, 128.4, 128.51, 128.58, 129.6, 129.9, 132.5, 134.0, 135.6, 139.8, 166.1, 166.6, 169.2, 169.3, 197.1.

MS (+ESI): m/z=507 (M+H).

1.84. 5-(2-Naphthalenyl)-5-oxo-3-phenylpentanoic acid (PS 209)

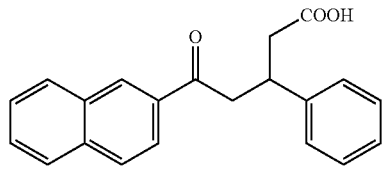 [SMILES: O=C(O)CC(CC(=O)c1ccc2ccccc2c1)c1ccccc1]

By a procedure similar to that of example 1.60, starting from 2-[3-(2-naphthalenyl)-3-oxo-1-phenylpropyl]malonic acid, 5-(2-naphthalenyl)-5-oxo-3-phenylpentanoic acid was obtained as colourless solid.

¹H-NMR (500 MHz, CDCl₃): δ (ppm)=2.77 (dd, J=7.6, 7.9 Hz, 1H), 2.92 (dd, J=6.9, 6.9 Hz, 1H), 3.45-3.55 (m, 2H), 3.91-3.96 (m, 1H), 7.20-7.22 (m, 1H), 7.29-7.31 (m, 4H), 7.52 (t, J=8.2 Hz, 1H), 7.59 (t, J=8.2 Hz, 1H), 7.86 (d, J=8.8 Hz, 1H), 7.92-7.98 (m, 2H), 8.42 (s, 1H).

¹³C-NMR (125 MHz, CDCl₃): δ ppm)=37.4, 40.1, 44.6, 123.8, 126.8, 126.9, 127.4, 127.7, 128.4, 128.5, 128.7, 129.6, 129.8, 132.5, 134.2, 135.6, 143.1, 176.5 (CO), 198.0 (CO).

MS (+ESI): m/z=319 (M+H).

1.85. (Z)-5-(4-Chlorophenyl)-3-phenylpent-2-enoic acid and (E)-5-(4-Chlorophenyl)-3-phenylpent-2-enoic acid (PS 47+PS 48)

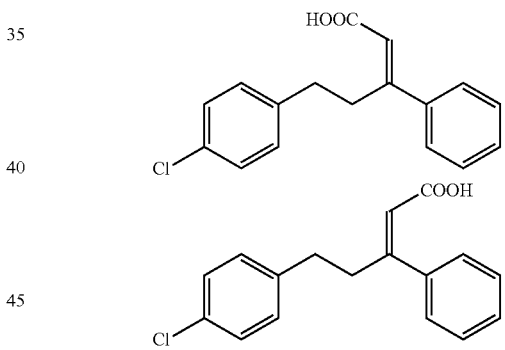

1) 3-(4-Chlorophenyl)-1-phenylprop-2-en-1-one

By a procedure similar to that of example 1.59.1, starting from 4-chlorobenzaldehyde and acetophenone, 3-(4-chlorophenyl)-1-phenylprop-2-en-1-one was obtained as yellowish solid.

2) 3-(4-Chlorophenyl)-1-phenylpropan-1-one

Silica gel (5.26 g) was added to a solution of 3-(4-chlorophenyl)-1-phenylprop-2-en-1-one (0.636 g) and 3,5-bis(ethoxycarbonyl)-1,4-dihydro-2,6-dimethylpyridine (1 g) in toluene (20 ml). The slurry was stirred at 70° C. in the dark for 17 h. After removal of the solvent the residue was purified by flash chromatography on silica gel (petrol ether/ethyl acetate) to provide 3-(4-chlorophenyl)-1-phenylpropan-1-one (0.49 g) as colourless solid.

$^1$H-NMR (500 MHz, CDCl$_3$): δ (ppm)=2.95 (t, J=7.6 Hz, 2H), 3.21 (t, J=7.6 Hz, 2H), 7.17-7.19 (m, 2H), 7.19 (m, 2H), 7.44-7.47 (m, 2H), 7.55-7.58 (m, 1H), 7.94-7.96 (m, 2H).
$^{13}$C-NMR (125 MHz, CDCl$_3$): δ (ppm)=29.6, 40.4, 128.2, 128.9, 129.8, 130.1, 132.1, 133.4, 137.0, 139.0, 199.1.

3) (Z)-Ethyl 5-(4-chlorophenyl)-3-phenylpent-2-enoate and (E)-Ethyl 5-(4-chloro-phenyl)-3-phenyl-pent-2-enoate Triethyl phosphonoacetate (0.96 ml) was added dropwise at rt to a slurry of sodium hydride (60% in mineral oil, 0.17 g) in anhydrous 1,2-dimethoxyethane (15 ml) under nitrogen atmosphere. The reaction mixture was stirred at rt for 1 h and 3-(4-chlorophenyl)-1-phenylpropan-1-one (0.346 g) was added. After stirring at 80° C. for 4 h the solution was poured into ice water (50 ml) and extracted with dichloromethane (3×20 ml). The extract was washed with brine (20 ml), dried (MgSO$_4$) and evaporated in vacuo to afford a crude mixture which was separated by flash chromatography on silica gel (petrol ether/ethyl acetate) to obtain (Z)-ethyl 5-(4-chlorophenyl)-3-phenylpent-2-enoate (0.17 g) and (E)-ethyl 5-(4-chlorophenyl)-3-phenylpent-2-enoate (0.19 g) as colourless oils.

(Z)-Isomer: $^1$H-NMR (500 MHz, CDCl$_3$): δ (ppm)=1.06 (t, J=7.2 Hz, 3H), 2.65-2.68 (m, 2H), 2.69-2.72 (m, 2H), 3.98 (q, J=7.2 Hz, 2H), 5.87 (s, 1H), 7.05 (d, J=8.2 Hz, 2H), 7.17 (d, J=7.8 Hz, 2H), 7.23 (d, J=8.2 Hz, 2H), 7.34-7.37 (m, 3H). $^{13}$C-NMR (125 MHz, CDCl$_3$): δ (ppm)=13.9, 33.1, 41.8, 59.9, 118.1, 127.2, 127.8, 127.9, 128.5, 129.6, 131.9, 139.2, 139.6, 157.8, 164.9. MS (+ESI): m/z=316 (M+H).

(E)-Isomer: $^1$H-NMR (500 MHz, CDCl$_3$): δ (ppm)=1.30 (t, J=7.2 Hz, 3H), 2.68-2.72 (m, 2H), 3.36-3.39 (m, 2H), 4.20 (q, J=7.2 Hz, 2H), 7.12-7.15 (m, 2H), 6.06 (s, 1H), 7.21-7.23 (m, 2H), 7.38-7.40 (m, 3H), 7.42-7.45 (m, 2H). $^{13}$C-NMR (125 MHz, CDCl$_3$): δ (ppm)=14.3, 32.9, 34.4, 59.9, 118.1, 126.7, 128.3, 128.7, 129.0, 129.9, 131.6, 139.9, 140.9, 158.9, 165.9. MS (+ESI): m/z=316 (M+H).

4) (Z)-5-(4-Chlorophenyl)-3-phenylpent-2-enoic acid

A solution of (Z)-ethyl 5-(4-chlorophenyl)-3-phenylpent-2-enoate (139 mg) and 4M NaOH (1.1 ml) in EtOH (10 ml) was stirred at rt for 4 h. The mixture was poured into water (30 ml), acidified to pH 2 with 10% HCl and extracted with ethyl acetate (3×20 ml). The combined organic layers were washed with brine (20 ml), dried (MgSO$_4$) and evaporated to afford a crude, which was purified by crystallisation from hexane/ethylacetate to afford (Z)-5-(4-chlorophenyl)-3-phenylpent-2-enoic acid (93 mg) as colourless solid.

$^1$H-NMR (500 MHz, CDCl$_3$): δ (ppm)=2.64-2.67 (m, 2H), 2.71-2.77 (m, 2H), 5.87 (s, 1H), 7.04 (d, J=8.5 Hz, 2H), 7.18 (m, 2H), 7.24 (d, J=8.5 Hz, 2H), 7.34 (m, 3H).
$^{13}$C-NMR (125 MHz, CDCl$_3$): δ (ppm)=15.9, 32.8, 60.2, 127.1, 127.6, 128.0, 129.7, 131.8, 139.8, 142.4, 145.3, 170.5.
MS (+ESI): m/z=287 (M+H).

5) (E)-5-(4-Chlorophenyl)-3-phenylpent-2-enoic acid

A solution of (E)-ethyl 5-(4-chlorophenyl)-3-phenylpent-2-enoate (160 mg) and 4M NaOH (1.3 ml) in EtOH (10 ml) was stirred at rt for 4 h. The mixture was poured into water (30 ml), acidified to pH 2 with 10% HCl and extracted with ethyl acetate (3×20 ml). The combined organic layers were washed with brine (20 ml), dried (MgSO$_4$) and evaporated to afford a crude, which was purified by crystallisation from hexane/ethylacetate to afford (E)-5-(4-chlorophenyl)-3-phenylpent-2-enoic acid (105 mg) as colourless solid.

$^1$H-NMR (500 MHz, CDCl$_3$): δ (ppm)=2.51-2.56 (m, 2H), 2.79-2.85 (m, 2H), 6.11 (s, 1H), 6.97 (d, J=8.5 Hz, 2H), 7.12 (d, J=8.2 Hz, 2H), 7.31 (t, J=7.6 Hz, 1H), 7.35 (t, J=7.6 Hz, 1H), 7.59 (d, J=8.2 Hz, 2H).
$^{13}$C-NMR (125 MHz, CDCl$_3$): δ (ppm)=17.2, 33.5, 60.2, 126.9, 127.6, 128.0, 128.1, 129.5, 131.2, 141.3, 144.8, 148.8, 180.5.
MS (+ESI): m/z=287 (M+H).

1.86. (Z)-5-(4-Chlorophenyl)-3-(4-fluorophenyl)pent-2-enoic acid and (E)-5-(4-Chlorophenyl)-3-(4-fluorophenyl)pent-2-enoic acid (PS 144)

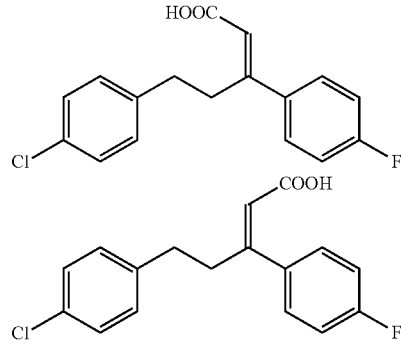

1) 3-(4-Chlorophenyl)-1-(4-fluorophenyl)prop-2-en-1-one

By a procedure similar to that of example 1.59.1, starting from 4-chlorobenzaldehyde and commercial 4-fluoroacetophenone, 3-(4-chlorophenyl)-1-(4-fluorophenyl)prop-2-en-1-one was obtained as yellowish solid.

$^1$H-NMR (500 MHz, CDCl$_3$): δ (ppm)=7.18 (t, J=8.5 Hz, 2H), 7.40 (d, J=8.5 Hz, 2H), 7.47 (d, J=15.4 Hz, 1H), 7.57 (d, J=8.5 Hz, 2H), 7.76 (d, J=15.8 Hz, 1H), 8.06 (d, J=8.5 Hz, 2H).
$^{13}$C-NMR (125 MHz, CDCl$_3$): δ (ppm)=115.8 (d, $^2J_{C\text{-}F}$=22.1 Hz), 121.9, 129.3, 129.6, 131.1 (d, $^3J_{C\text{-}F}$=9.6 Hz), 133.2, 134.4, 136.6, 143.5, 165.6 (d, $^1J_{C\text{-}F}$=255.3 Hz), 188.5.

2) 3-(4-Chlorophenyl)-1-(4-fluorophenyl)propan-1-one

By a procedure similar to that of example 1.85.2, starting from 3-(4-chlorophenyl)-1-(4-fluorophenyl)prop-2-en-1-one, 3-(4-chlorophenyl)-1-(4-fluorophenyl)propan-1-one was obtained as colourless solid.

$^1$H-NMR (500 MHz, CDCl$_3$): δ (ppm)=3.05 (t, J=7.5 Hz, 2H), 3.26 (t, J=7.5 Hz, 2H), 7.13 (d, J=8.5 Hz, 2H), 7.18 (d, J=8.8 Hz, 2H), 7.27 (d, J=8.5 Hz, 2H), 7.98 (t, J=8.8 Hz, 2H).

3) (Z)-Ethyl 5-(4-chlorophenyl)-3-(4-fluorophenyl)pent-2-enoate and (E)-Ethyl 5-(4-chlorophenyl)-3-(4-fluorophenyl)pent-2-enoate By a procedure similar to that of example 1.85.3, starting from 3-(4-chlorophenyl)-1-(4-fluorophenyl)propan-1-one, (Z)-ethyl 5-(4-chlorophenyl)-3-(4-fluorophenyl)pent-2- enoate and (E)-ethyl 5-(4-chlorophenyl)-3-(4-fluorophenyl) pent-2-enoate were obtained as colourless oils.

(Z)-Isomer: $^1$H-NMR (500 MHz, CDCl$_3$): δ (ppm)=1.30 (t, J=7.2 Hz, 3H), 2.67-2.71 (m, 2H), 3.33-3.37 (m, 2H), 4.20 (q, J=7.2 Hz, 2H), 6.01 (s, 1H), 7.06 (t, J=8.5 Hz, 2H), 7.10 (d, J=8.5 Hz, 2H), 7.22 (d, J=8.5 Hz, 2H), 7.39-7.42 (m, 2H). $^{13}$C-NMR (125 MHz, CDCl$_3$): δ (ppm)=14.3, 32.8, 34.3, 60.0, 115.5 (d, $^2J_{C-F}$=22.1 Hz), 118.1, 128.3, 128.5 (d, $^4J_{C-F}$=7.7 Hz), 129.8, 131.7, 136.8 (d, $^3J_{C-F}$=6.7 Hz), 157.8, 163.2 (d, $^1J_{C-F}$=248.5 Hz), 166.1.

(E)-Isomer: $^1$H-NMR (500 MHz, CDCl$_3$): δ (ppm)=1.10 (t, J=6.9 Hz, 3H), 2.63-2.66 (m, 2H), 2.70-2.73 (m, 2H), 3.99 (q, J=6.9 Hz, 2H), 5.87 (s, 1H), 7.02-7.07 (m, 4H), 7.13-7.16 (m, 2H), 7.23 (d, J=8.5 Hz, 2H). $^{13}$C-NMR (125 MHz, CDCl$_3$): δ (ppm)=14.0, 33.1, 41.8, 59.9, 115.0 (d, $^2J_{C-F}$=21.1 Hz), 118.4, 128.6, 129.6 (d, $^3J_{C-F}$=7.7 Hz), 131.9, 135.3, 139.0, 156.8, 164.4 (d, $^1J_{C-F}$=246.6 Hz), 165.7.

4) (Z)-5-(4-Chlorophenyl)-3-(4-fluorophenyl)pent-2-enoic acid

By a procedure similar to that of example 1.85.4, starting from (Z)-ethyl 5-(4-chlorophenyl)-3-(4-fluorophenyl)pent-2-enoate, (Z)-5-(4-chlorophenyl)-3-(4-fluorophenyl)pent-2-enoic acid was obtained as colourless solid.

$^1$H-NMR (500 MHz, CDCl$_3$): δ (ppm)=2.61-2.65 (m, 2H), 2.72-2.75 (m, 2H), 5.85 (s, 1H), 6.98-7.04 (m, 4H), 7.22 (d, J=8.5 Hz, 2H), 7.23-7.27 (m, 2H).

$^{13}$C-NMR (125 MHz, CDCl$_3$): δ (ppm)=33.0, 42.1, 115.1 (d, $^2J_{C-F}$=21.1 Hz), 117.2, 127.7, 128.6 (d, $^3J_{C-F}$=7.7 Hz), 129.1 (d, $^3J_{C-F}$=9.6 Hz), 129.6, 129.8, 138.2, 138.8, 159.8, 164.8 (d, $^1J_{C-F}$=250.5 Hz), 167.6, 169.3.

MS (+ESI): m/z=306 (M+H).

5) (E)-5-(4-Chlorophenyl)-3-(4-fluorophenyl)pent-2-enoic acid

By a procedure similar to that of example 1.85.5, starting from (E)-ethyl 5-(4-chlorophenyl)-3-(4-fluorophenyl)pent-2-enoate, (E)-5-(4-chlorophenyl)-3-(4-fluorophenyl)pent-2-enoic acid was obtained as colourless solid.

$^1$H-NMR (500 MHz, CDCl$_3$): δ (ppm)=2.70-2.72 (m, 2H), 3.35-3.38 (m, 2H), 6.07 (s, 1H), 7.08-7.12 (m, 4H), 7.22 (d, J=8.5 Hz, 2H), 7.42-7.45 (m, 2H).

$^{13}$C-NMR (125 MHz, CDCl$_3$): δ (ppm)=33.1, 34.4, 111.4 (d, $^4J_{C-F}$=2.9 Hz), 113.9, 115.8 (d, $^2J_{C-F}$=21.1 Hz), 128.4, 128.6, 129.8, 131.9, 135.3, 139.5, 143.2, 157.2 (d, $^2J_{C-F}$=250.5 Hz), 162.5, 169.3.

MS (+ESI): m/z=306 (M+H).

1.87. (Z)-5-(4-Chlorophenyl)-3-(3-fluorophenyl)pent-2-enoic acid and (E)-5-(4-Chlorophenyl)-3-(3-fluorophenyl)pent-2-enoic acid (PS 146)

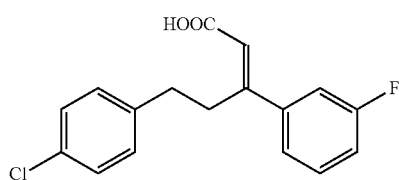

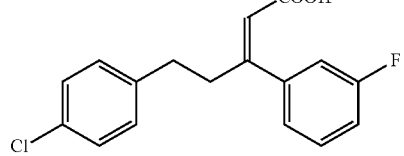

1) 3-(4-Chlorophenyl)-1-(3-fluorophenyl)prop-2-en-1-one

By a procedure similar to that of example 1.59.1, starting from 4-chlorobenzaldehyde and commercial commercial 3-fluoroacetophenone, 3-(4-chlorophenyl)-1-(3-fluorophenyl)prop-2-en-1-one was obtained as yellowish solid.

$^1$H-NMR (500 MHz, CDCl$_3$): δ (ppm)=7.18 (t, J=8.5 Hz, 2H), 7.40 (d, J=8.5 Hz, 2H), 7.47 (d, J=15.4 Hz, 1H), 7.57 (d, J=8.5 Hz, 2H), 7.76 (d, J=15.8 Hz, 1H), 8.06 (d, J=8.5 Hz, 2H);

$^{13}$C-NMR (125 MHz, CDCl$_3$): δ (ppm)=116.5 (d, $^2J_{C-F}$=23.0 Hz), 124.5 (d, $^4J_{C-F}$=3.8 Hz), 126.0 (d, $^3J_{C-F}$=6.7 Hz), 126.9, 129.2, 129.7, 131.0 (d, $^4J_{C-F}$=2.9 Hz), 133.2, 134.1 (d, $^3J_{C-F}$=8.6 Hz), 136.6, 143.2, 161.2 (d, $^1J_{C-F}$=253.3 Hz), 188.7.

2) 3-(4-Chlorophenyl)-1-(3-fluorophenyl)propan-1-one

By a procedure similar to that of example 1.85.2, starting from 3-(4-chlorophenyl)-1-(3-fluorophenyl)prop-2-en-1-one, 3-(4-chlorophenyl)-1-(3-fluorophenyl)propan-1-one was obtained as colourless solid.

$^1$H-NMR (500 MHz, CDCl$_3$): δ (ppm)=3.03 (t, J=7.6 Hz, 2H), 3.23 (t, J=7.6 Hz, 2H), 7.17 (d, J=8.5 Hz, 1H), 7.23-7.28 (m, 3H), 7.40-7.48 (m, 1H), 7.60-7.63 (m, 1H), 7.71 (d, J=7.9 Hz, 1H).

$^{13}$C-NMR (125 MHz, CDCl$_3$): δ (ppm)=29.3, 40.3, 114.7 (d, $^2J_{C-F}$=22.1 Hz), 120.1 (d, $^2J_{C-F}$=21.1 Hz), 123.7, 128.6, 129.8, 130.3 (d, $^3J_{C-F}$=7.7 Hz), 131.9, 138.8 (d, $^3J_{C-F}$=5.8 Hz), 139.4, 162.8 (d, $^1J_{C-F}$=248.5 Hz), 197.5.

3) (Z)-Ethyl 5-(4-chlorophenyl)-3-(3-fluorophenyl)pent-2-enoate and (E)-Ethyl 5-(4-chlorophenyl)-3-(3-fluorophenyl)pent-2-enoate By a procedure similar to that of example 1.85.3, starting from 3-(4-chlorophenyl)-1-(3-fluorophenyl)propan-1-one, (Z)-ethyl 5-(4-chlorophenyl)-3-(3-fluorophenyl)pent-2-enoate and (E)-ethyl 5-(4-chlorophenyl)-3-(3-fluorophenyl) pent-2-enoate were obtained as colourless oils.

(Z)-Isomer: $^1$H-NMR (500 MHz, CDCl$_3$): δ (ppm)=1.07 (t, J=7.2 Hz, 3H), 2.65-2.72 (m, 4H), 3.99 (q, J=7.2 Hz, 2H), 5.88 (s, 1H), 6.87-6.89 (m, 1H), 6.94 (d, J=7.6 Hz, 1H), 7.00-7.01 (m, 1H), 7.04 (d, J=8.5 Hz, 2H), 7.24 (d, J=8.2 Hz, 2H), 7.30-7.35 (m, 1H). $^{13}$C-NMR (125 MHz, CDCl$_3$): δ (ppm)=13.9, 33.0, 41.6, 60.0, 114.4 (d, $^2J_{C-F}$=22.1 Hz), 114.7, 118.7, 123.0 (d, $^4J_{C-F}$=2.9 Hz), 128.6, 129.5, 129.6, 132.0, 156.2 (d, $^4J_{C-F}$=1.9 Hz), 161.4 (d, $^1J_{C-F}$=2465.7 Hz), 162.6, 163.2. 165.5.

(E)-Isomer: $^1$H-NMR (500 MHz, CDCl$_3$): δ (ppm)=1.29 (t, J=7.0 Hz, 3H), 2.69-2.71 (m, 2H), 3.33-3.36 (m, 2H), 4.19 (q, J=7.0 Hz, 2H), 6.05 (s, 1H), 7.04 (t, J=8.5 Hz, 1H), 7.10-7.14 (m, 3H), 7.20-7.23 (m, 3H), 7.33-7.36 (m, 1H). $^{13}$C-NMR (125 MHz, CDCl$_3$): δ (ppm)=14.3, 32.8, 34.3, 60.1, 113.7 (d, $^2J_{C-F}$=23.0 Hz), 115.8 (d, $^2J_{C-F}$=22.1 Hz), 119.0, 122.4 (d, $^4J_{C-F}$=2.9 Hz), 128.3, 129.9, 130.2 (d, $^3J_{C-F}$=8.6 Hz), 131.7, 139.6, 143.2 (d, $^3J_{C-F}$=6.7 Hz), 157.4, 160.0 (d, $^1J_{C-F}$=253.3 Hz), 166.0.

4) (Z)-5-(4-Chlorophenyl)-3-(3-fluorophenyl)pent-2-enoic acid

By a procedure similar to that of example 1.85.4, starting from (Z)-ethyl 5-(4-chlorophenyl)-3-(3-fluorophenyl)pent-2-enoate, (Z)-5-(4-chlorophenyl)-3-(3-fluorophenyl)pent-2-enoic acid was obtained as colourless solid.

$^1$H-NMR (500 MHz, CDCl$_3$): δ (ppm)=2.64-2.67 (m, 2H), 2.71-2.74 (m, 2H), 5.86 (s, 1H), 6.91-7.10 (m, 4H), 7.24-7.27 (m, 3H), 7.31-7.34 (m, 1H).

$^{13}$C-NMR (125 MHz, CDCl$_3$): δ (ppm)=32.9, 41.9, 114.2, 114.9 (d, $^2J_{C-F}$=21.1 Hz), 117.5, 122.9, 128.6, 129.6, 129.7, 131.7, 132.1, 141.1, 143.0, 159.3, 168.3 (d, $^1J_{C-F}$=255.3 Hz).

MS (+ESI): m/z=306 (M+H).

5) (E)-5-(4-Chlorophenyl)-3-(3-fluorophenyl)pent-2-enoic acid

By a procedure similar to that of example 1.85.5, starting from (E)-ethyl 5-(4-chlorophenyl)-3-(3-fluorophenyl)pent-2-enoate, (E)-5-(4-chlorophenyl)-3-(3-fluorophenyl)pent-2-enoic acid was obtained as colourless solid.

$^1$H-NMR (500 MHz, CDCl$_3$): δ (ppm)=2.71-2.74 (m, 2H), 3.34-3.38 (m, 2H), 6.11 (s, 1H), 7.09-7.16 (m, 4H), 7.21-7.24 (m, 3H), 7.36-7.40 (m, 1H).

$^{13}$C-NMR (125 MHz, CDCl$_3$): δ (ppm)=33.1, 34.4, 113.8 (d, $^2J_{C-F}$=22.1 Hz), 116.3 (d, $^2J_{C-F}$=21.1 Hz), 117.9, 122.5 (d, $^4J_{C-F}$=2.9 Hz), 128.5, 129.8, 130.3 (d, $^3J_{C-F}$=8.6 Hz), 131.9, 139.4, 143.0, 160.5, 164.6 (d, $^1J_{C-F}$=261.0 Hz), 170.5.

MS (+ESI): m/z=306 (M+H).

1.88. (Z)-5-(4-Chlorophenyl)-3-(2-fluorophenyl)pent-2-enoic acid and (E)-5-(4-Chlorophenyl)-3-(2-fluorophenyl)pent-2-enoic acid (PS 145)

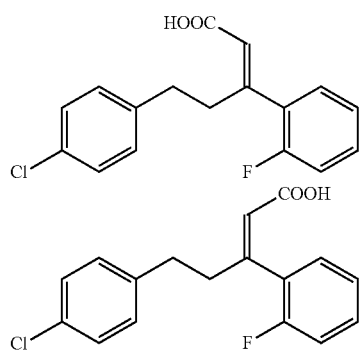

1) 3-(4-Chlorophenyl)-1-(2-fluorophenyl)prop-2-en-1-one

By a procedure similar to that of example 1.59.1, starting from 4-chlorobenzaldehyde and commercial commercial 2-fluoroacetophenone, 3-(4-chlorophenyl)-1-(2-fluorophenyl)prop-2-en-1-one was obtained as yellowish solid.

$^1$H-NMR (500 MHz, CDCl$_3$): δ (ppm)=7.18 (t, J=8.5 Hz, 2H), 7.40 (d, J=8.5 Hz, 2H), 7.47 (d, J=15.4 Hz, 1H), 7.57 (d, J=8.5 Hz, 2H), 7.76 (d, J=15.8 Hz, 1H), 8.06 (d, J=8.5 Hz, 2H).

2) 3-(4-Chlorophenyl)-1-(2-fluorophenyl)propan-1-one

By a procedure similar to that of example 1.85.2, starting from 3-(4-chlorophenyl)-1-(2-fluorophenyl)prop-2-en-1-one, 3-(4-chlorophenyl)-1-(2-fluorophenyl)propan-1-one was obtained as colourless solid.

$^1$H-NMR (500 MHz, CDCl$_3$): δ (ppm)=3.04 (t, J=7.2 Hz, 2H), 3.30 (dt, J=3.1, 7.6 Hz, 2H), 7.12-7.3 (m, 6H), 7.50-7.55 (m, 1H), 7.88 (dd, J=1.6, 8.5 Hz, 1H).

$^{13}$C-NMR (125 MHz, CDCl$_3$): δ (ppm)=29.2, 44.9, 116.6 (d, $^2J_{C-F}$=23.4 Hz), 124.5 (d, $^4J_{C-F}$=2.9 Hz), 125.5 (d, $^3J_{C-F}$=13.4 Hz), 128.5, 129.8, 130.6 (d, $^4J_{C-F}$=2.9 Hz), 131.8, 134.6 (d, $^3J_{C-F}$=9.6 Hz), 139.6, 161.9 (d, $^1J_{C-F}$=254.3 Hz), 197.1.

3) (Z)-Ethyl 5-(4-chlorophenyl)-3-(2-fluorophenyl)pent-2-enoate and (E)-Ethyl 5-(4-chlorophenyl)-3-(2-fluorophenyl)pent-2-enoate By a procedure similar to that of example 1.85.3, starting from 3-(4-chlorophenyl)-1-(2-fluorophenyl)propan-1-one, (Z)-ethyl 5-(4-chlorophenyl)-3-(2-fluorophenyl)pent-2-enoate and (E)-ethyl 5-(4-chlorophenyl)-3-(2-fluorophenyl)pent-2-enoate were obtained as colourless oils.

(Z)-Isomer: $^1$H-NMR (500 MHz, CDCl$_3$): δ (ppm)=1.07 (t, J=7.2 Hz, 3H), 2.69-2.74 (m, 4H), 4.00 (q, J=7.2 Hz, 2H), 5.98 (s, 1H), 7.06-7.14 (m, 5H), 7.23 (d, J=8.5 Hz, 2H), 7.29-7.33 (m, 1H).

(E)-Isomer: $^1$H-NMR (500 MHz, CDCl$_3$): δ (ppm)=1.30 (t, J=7.2 Hz, 3H), 2.66-2.70 (m, 2H), 3.32-3.35 (m, 2H), 4.19 (q, J=7.2 Hz, 2H), 5.94 (s, 1H), 7.07-7.11 (m, 3H), 7.14 (d, J=8.5 Hz, 1H), 7.17-7.21 (m, 3H), 7.31-7.35 (m, 1H). $^{13}$C-NMR (125 MHz, CDCl$_3$): δ (ppm)=14.3, 33.7, 33.9, 60.1, 116.1 (d, $^2J_{C-F}$=23.0 Hz), 117.9, 119.4, 122.0 (d, $^4J_{C-F}$=2.9 Hz), 124.2 (d, $^4J_{C-F}$=3.8 Hz), 128.3, 129.8, 129.9, 130.2, 139.7, 155.1, 167.9 (d, $^{1J}_{C-F}$=250.5 Hz), 169.4.

4) (Z)-5-(4-Chlorophenyl)-3-(2-fluorophenyl)pent-2-enoic acid

By a procedure similar to that of example 1.85.4, starting from (Z)-ethyl 5-(4-chlorophenyl)-3-(2-fluorophenyl)pent-2-enoate, (Z)-5-(4-chlorophenyl)-3-(2-fluorophenyl)pent-2-enoic acid was obtained as colourless solid.

$^1$H-NMR (500 MHz, CDCl$_3$): δ (ppm)=2.60-2.63 (m, 2H), 2.67-2.70 (m, 2H), 5.91 (s, 1H), 6.93-7.10 (m, 4H), 7.17-7.23 (m, 4H).

MS (+ESI): m/z=306 (M+H).

5) (E)-5-(4-Chlorophenyl)-3-(2-fluorophenyl)pent-2-enoic acid

By a procedure similar to that of example 1.85.5, starting from (E)-ethyl 5-(4-chlorophenyl)-3-(2-fluorophenyl)pent-2-enoate, (E)-5-(4-chlorophenyl)-3-(2-fluorophenyl)pent-2-enoic acid was obtained as colourless solid.

$^1$H-NMR (500 MHz, CDCl$_3$): δ (ppm)=2.69-2.72 (m, 2H), 3.34-3.38 (m, 2H), 6.01 (s, 1H), 7.08-7.21 (m, 7H), 7.37-7.38 (m, 1H).

MS (+ESI): m/z=306 (M+H).

1.89. (Z)-5-(4-Chlorophenyl)-3-(4-methoxyphenyl) pent-2-enoic acid and (E)-5-(4-Chlorophenyl)-3-(4-methoxyphenyl)pent-2-enoic acid (PS 250+PS 251)

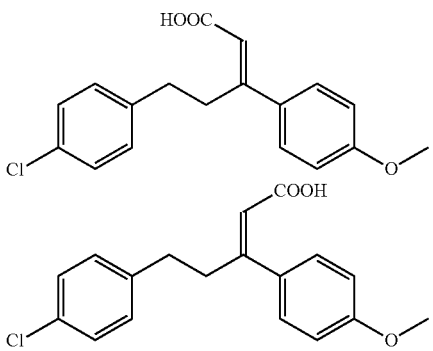

1) 3-(4-Chlorophenyl)-1-(4-methoxyphenyl)prop-2-en-1-one

By a procedure similar to that of example 1.59.1, starting from 4-chlorobenzaldehyde and commercial 4-methoxyacetophenone, 3-(4-chlorophenyl)-1-(4-methoxyphenyl)-prop-2-en-1-one was obtained as yellow solid.

$^1$H-NMR (500 MHz, CDCl$_3$): δ (ppm)=3.87 (s, 3H), 6.96 (d, J=8.5 Hz, 2H), 7.36 (d, J=8.5 Hz, 2H), 7.50 (d, J=15.4 Hz, 1H), 7.54 (d, J=8.2 Hz, 2H), 7.72 (d, J=15.8 Hz, 1H), 8.01 (d, J=8.8 Hz, 2H).

$^{13}$C-NMR (125 MHz, CDCl$_3$): δ (ppm)=55.5, 113.9, 122.3, 129.2, 129.5, 130.8, 130.9, 133.6, 136.2, 142.4, 163.5, 188.4 (CO).

2) 3-(4-Chlorophenyl)-1-(4-methoxyphenyl)propan-1-one

By a procedure similar to that of example 1.85.2, starting from 3-(4-chlorophenyl)-1-(4-methoxyphenyl)-prop-2-en-1-one, 3-(4-chlorophenyl)-1-(4-methoxyphenyl)propan-1-one was obtained as colourless oil.

$^1$H-NMR (500 MHz, CDCl$_3$): δ (ppm)=3.04 (t, J=7.2 Hz, 2H), 3.22 (t, J=7.2 Hz, 2H), 3.86 (s, 3H), 6.92 (d, J=8.8 Hz, 2H), 7.17 (d, J=8.8 Hz, 2H), 7.25 (d, J=8.2 Hz, 2H), 7.93 (d, J=8.8 Hz, 2H).

$^{13}$C-NMR (125 MHz, CDCl$_3$): δ (ppm)=29.6, 39.8, 55.5, 113.8, 128.6, 129.8, 129.9, 130.3, 131.8, 139.9, 163.5, 197.4 (CO).

3) (Z)-Ethyl 5-(4-chlorophenyl)-3-(4-methoxyphenyl)pent-2-enoate and (E)-Ethyl 5-(4-chlorophenyl)-3-(4-methoxyphenyl)pent-2-enoate By a procedure similar to that of example 1.85.3, starting from 3-(4-chlorophenyl)-1-(4-methoxyphenyl)-propan-1-one, (Z)-ethyl 5-(4-chlorophenyl)-3-(4-methoxyphenyl) pent-2-enoate and (E)-ethyl 5-(4-chlorophenyl)-3-(4-methoxyphenyl)pent-2-enoate were obtained as colourless oils.

(Z)-Isomer: $^1$H-NMR (500 MHz, CDCl$_3$): δ (ppm)=1.15 (t, J=7.2 Hz, 3H), 2.63-2.66 (m, 2H), 2.70-2.74 (m, 2H), 3.83 (s, 3H), 4.02 (q, J=7.2 Hz, 2H), 5.82 (s, 1H), 6.89 (d, J=8.8 Hz, 2H), 7.04 (d, J=8.5 Hz, 2H), 7.14 (d, J=8.5 Hz, 2H), 7.23 (d, J=9.1 Hz, 2H). $^{13}$C-NMR (125 MHz, CDCl$_3$): δ (ppm)=14.0, 33.3, 41.8, 55.2, 59.8, 113.4, 117.4, 128.5, 128.8, 129.6, 131.3, 131.8, 139.3, 157.5, 159.4, 166.0 (CO).

(E)-Isomer: $^1$H-NMR (500 MHz, CDCl$_3$): δ (ppm)=1.30 (t, J=7.2 Hz, 3H), 2.69-2.72 (m, 2H), 3.34-3.57 (m, 2H), 3.85 (s, 3H), 4.19 (q, J=7.2 Hz, 2H), 6.04 (s, 1H), 6.91 (d, J=9.1 Hz, 2H), 7.15 (d, J=8.5 Hz, 2H), 7.22 (d, J=8.5 Hz, 2H), 7.41 (d, J=9.1 Hz, 2H). $^{13}$C-NMR (125 MHz, CDCl$_3$): δ (ppm)=14.3, 32.6, 34.6, 55.3, 59.8, 114.0, 116.2, 128.0, 128.3, 129.9, 131.6, 132.9, 140.0, 158.4, 160.5, 166.5 (CO).

4) (Z)-5-(4-Chlorophenyl)-3-(4-methoxyphenyl) pent-2-enoic acid

By a procedure similar to that of example 1.85.4, starting from (Z)-ethyl 5-(4-chlorophenyl)-3-(4-methoxyphenyl) pent-2-enoate, (Z)-5-(4-chlorophenyl)-3-(4-methoxyphenyl) pent-2-enoic acid was obtained as off-white solid.

$^1$H-NMR (500 MHz, CDCl$_3$): δ (ppm)=2.63-2.66 (m, 2H), 3.33-3.36 (m, 2H), 3.85 (s, 3H), 6.10 (s, 1H), 6.91 (d, J=8.8 Hz, 2H), 7.14 (d, J=8.5 Hz, 2H), 7.22 (d, J=8.5 Hz, 2H), 7.44 (d, J=8.8 Hz, 2H).

$^{13}$C-NMR (125 MHz, CDCl$_3$): δ (ppm)=32.9, 34.7, 55.3, 113.5, 114.8, 128.2, 128.5, 128.9, 129.7, 129.8, 130.9, 139.1, 160.2, 170.6 (CO).

5) (E)-5-(4-Chlorophenyl)-3-(4-methoxyphenyl) pent-2-enoic acid

By a procedure similar to that of example 1.85.5, starting from (E)-ethyl 5-(4-chlorophenyl)-3-(4-methoxyphenyl) pent-2-enoate, (E)-5-(4-chlorophenyl)-3-(4-methoxyphenyl) pent-2-enoic acid was obtained as off-white solid.

$^1$H-NMR (500 MHz, CDCl$_3$): δ (ppm)=2.72-2.75 (m, 2H), 3.36-3.39 (m, 2H), 3.86 (s, 3H), 6.10 (s, 1H), 6.94 (d, J=8.8 Hz, 2H), 7.14 (d, J=8.2 Hz, 2H), 7.23 (d, J=8.5 Hz, 2H), 7.45 (d, J=9.1 Hz, 2H).

$^{13}$C-NMR (125 MHz, CDCl$_3$): δ (ppm)=32.9, 34.7, 55.4, 114.1, 114.5, 128.2, 128.4, 129.8, 131.7, 139.9, 156.5, 160.9, 161.5, 170.7 (CO).

1.90. (Z)-5-(4-Chlorophenyl)-3-phenylpent-2-enenitrile and (E)-5-(4-Chlorophenyl)-3-phenylpent-2-enenitrile (PS 104+PS 105)

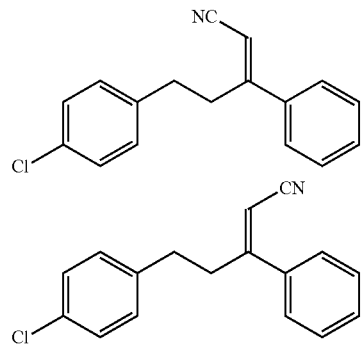

Diethyl cyanomethylphosphonate (0.8 ml) was added dropwise at rt to a slurry of sodium hydride (60% in mineral oil, 0.2 g) in anhydrous 1,2-dimethoxyethane (15 ml) under nitrogen atmosphere. The reaction mixture was stirred at rt for 1 hour and 3-(4-chlorophenyl)-1-phenylpropan-1-one (0.4 g) was added. After stirring at 80° C. for 4 h the resultant solution was poured into ice water (50 ml) and extracted with dichloromethane (3×20 ml). The combined organic layers were washed with brine (20 ml), dried (MgSO$_4$), and evaporated in vacuo. The crude mixture was separated by flash chromatography on silica gel (hexane/ethyl acetate 10:1) to afford (Z)-5-(4-chlorophenyl)-3-phenylpent-2-enenitrile (80 mg) and (E)-5-(4-chlorophenyl)-3-phenylpent-2-enenitrile (284 mg) as colourless oils.

(Z)-Isomer: $^1$H-NMR (500 MHz, CDCl$_3$): δ (ppm)=2.67 (t, J=7.2 Hz, 2H) 2.87 (t, J=7.2 Hz, 2H), 5.30 (s, 1H), 7.01 (d, J=8.5 Hz, 2H), 7.25 (d, J=8.5 Hz, 2H), 7.43-7.48 (m, 5H). $^{13}$C-NMR (125 MHz, CDCl$_3$): δ (ppm)=32.2, 38.6, 95.2, 116.9, 125.3, 126.4, 127.7, 127.8, 128.3, 128.9, 131.2, 135.8, 163.1.

(E)-Isomer: $^1$H-NMR (500 MHz, CDCl$_3$): δ (ppm)=2.75 (t, J=7.7 Hz, 2H) 3.17 (t, J=7.7 Hz, 2H), 5.49 (s, 1H), 7.07 (d, J=8.5 Hz, 2H), 7.24 (d, J=8.5 Hz, 2H), 7.38-7.39 (m, 2H), 7.41-7.47 (m, 3H). $^{13}$C-NMR (125 MHz, CDCl$_3$): δ (ppm)= 33.8, 35.5, 96.7, 117.1, 126.3, 128.6, 129.0, 129.8, 130.2, 132.2, 137.2, 138.3, 163.4.

1.91. (Z)-5-(3-Chlorophenyl)-3-phenylpent-2-enoic acid and (E)-5-(3-Chlorophenyl)-3-phenylpent-2-enoic acid (PS 87+PS 88)

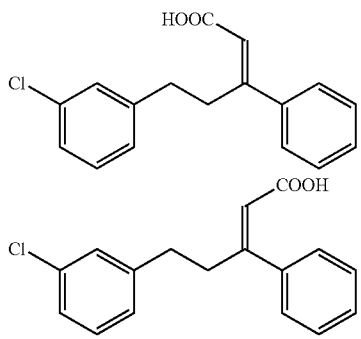

1) 3-(3-Chlorophenyl)-1-phenylprop-2-en-1-one

By a procedure similar to that of example 1.59.1, starting from 3-chlorobenzaldehyde and acetophenone, 3-(3-chlorophenyl)-1-phenylprop-2-en-1-one was obtained as yellowish solid.

2) 3-(3-Chlorophenyl)-1-phenylpropan-1-one

By a procedure similar to that of example 1.85.2, starting from 3-(3-chlorophenyl)-1-phenylprop-2-en-1-one, 3-(3-chlorophenyl)-1-phenylpropan-1-one was obtained as colourless solid.

$^1$H-NMR (500 MHz, CDCl$_3$): δ (ppm)=3.03-3.07 (m, 2H), 3.29-3.32 (m, 2H), 7.27-7.32 (m, 4H), 7.46 (t, J=7.9 Hz, 2H), 7.57 (t, J=7.6 Hz, 1H), 7.96 (d, J=7.9 Hz, 2H).
$^{13}$C-NMR (125 MHz, CDCl$_3$): δ (ppm)=29.7, 40.0, 126.3, 126.7, 128.0, 128.6, 129.7, 133.2, 134.3, 136.8, 143.3, 198.7.

3) (Z)-Ethyl 5-(3-chlorophenyl)-3-phenylpent-2-enoate and (E)-Ethyl 5-(3-chloro-phenyl)-3-phenyl-pent-2-enoate By a procedure similar to that of example 1.85.3, starting from 3-(3-chlorophenyl)-1-phenylpropan-1-one, (Z)-ethyl 5-(3-chloro-phenyl)-3-phenylpent-2-enoate and (E)-ethyl 5-(3-chlorophenyl)-3-phenylpent-2-enoate were obtained as colourless oils.

(Z)-Isomer: $^1$H-NMR (500 MHz, CDCl$_3$): δ (ppm)=1.07 (t, J=7.2 Hz, 3H), 2.66-2.70 (m, 2H), 2.74-2.79 (m, 2H), 3.98 (q, J=7.2 Hz, 2H), 5.88 (s, 1H), 7.05 (d, J=8.2 Hz, 1H), 7.11 (s, 1H), 7.16-7.21 (m, 4H), 7.30-7.37 (m, 3H). $^{13}$C-NMR (125 MHz, CDCl$_3$): δ (ppm)=13.9, 33.5, 41.7, 59.9, 118.0, 126.3, 126.5, 127.8, 128.0, 128.4, 129.7, 134.2, 139.6, 142.8, 157.7, 165.8.

(E)-Isomer: $^1$H-NMR (500 MHz, CDCl$_3$): δ (ppm)=1.32 (t, J=6.9 Hz, 3H), 2.69-2.74 (m, 2H), 3.37-3.41 (m, 2H), 4.21 (q, J=7.2 Hz, 2H), 6.07 (s, 1H), 7.16-7.20 (m, 4H), 7.42-7.46 (m, 5H). $^{13}$C-NMR (125 MHz, CDCl$_3$): δ (ppm)=14.3, 32.7, 34.7, 59.9, 118.1, 126.1, 126.7, 128.6, 128.7, 129.0, 129.5, 133.9, 140.9, 141.3, 143.5, 158.8, 166.3.

4) (Z)-5-(3-Chlorophenyl)-3-phenylpent-2-enoic acid

By a procedure similar to that of example 1.85.4, starting from (Z)-ethyl 5-(3-chlorophenyl)-3-phenylpent-2-enoate, (Z)-5-(3-chlorophenyl)-3-phenylpent-2-enoic acid was obtained as colourless solid.

$^1$H-NMR (500 MHz, CDCl$_3$): δ (ppm)=2.67-2.63 (m, 2H), 2.77-2.74 (m, 2H), 5.85 (s, 1H), 6.99 (d, J=6.9 Hz, 1H), 7.10 (s, 1H), 7.21-7.16 (m, 4H), 7.37-7.33 (m, 3H).
$^{13}$C-NMR (125 MHz, CDCl$_3$): δ (ppm)=33.3, 42.0, 117.0, 126.4, 126.5, 127.2, 128.1, 128.2, 128.4, 129.7, 134.2, 138.9, 142.6, 160.5, 170.3.

5) (E)-5-(3-Chlorophenyl)-3-phenylpent-2-enoic acid

By a procedure similar to that of example 1.85.5, starting from (E)-ethyl 5-(3-chlorophenyl)-3-phenyl-pent-2-enoate, (E)-5-(3-chlorophenyl)-3-phenylpent-2-enoic acid was obtained as colourless solid.

$^1$H-NMR (500 MHz, CDCl$_3$): δ (ppm)=2.72-2.77 (m, 2H), 3.40-3.43 (m, 2H), 6.13 (s, 1H), 7.09 (d, J=7.2 Hz, 1H), 7.15-7.19 (m, 3H), 7.41-7.45 (m, 3H), 7.46-7.50 (m, 2H).
$^{13}$C-NMR (125 MHz, CDCl$_3$): δ (ppm)=33.0, 34.8, 117.0, 126.6, 126.7, 126.8, 128.6, 129.5, 129.6, 134.0, 140.7, 143.3, 162.0, 170.8.

MS (+ESI): m/z=287 (M+H).

1.92. (Z)-5-(4-Fluorophenyl)-3-phenylpent-2-enoic acid and (E)-5-(4-Fluorophenyl)-3-phenylpent-2-enoic acid (PS 136+PS-T3)

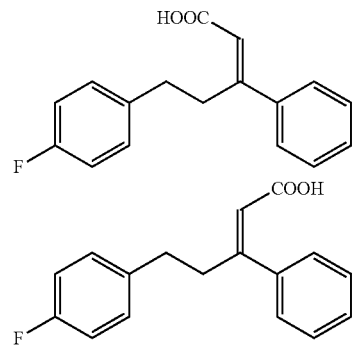

1) 3-(4-Fluorophenyl)-1-phenylprop-2-en-1-one

By a procedure similar to that of example 1.59.1, starting from 4-fluorobenzaldehyde and acetophenone, 3-(4-fluorophenyl)-1-phenylprop-2-en-1-one was obtained as yellow solid.

2) 3-(4-Fluorophenyl)-1-phenylpropan-1-one

By a procedure similar to that of example 1.85.2, starting from 3-(4-fluorophenyl)-1-phenylprop-2-en-1-one, 3-(4-fluorophenyl)-1-phenylpropan-1-one was obtained as yellowish solid.

$^1$H-NMR (500 MHz, CDCl$_3$): δ (ppm)=3.05 (t, J=7.6 Hz, 2H), 3.29 (t, J=7.6, 2H), 6.95-6.99 (m, 2H), 7.19-7.22 (m, 2H), 7.46 (t, J=7.6 Hz, 2H), 7.54-7.58 (m, 1H), 7.95 (d, J=8.5 Hz, 2H).

$^{13}$C-NMR (125 MHz, CDCl$_3$): δ (ppm)=29.2, 40.4, 115.2 (d, $^2J_{C-F}$=21.1 Hz), 127.9, 128.6, 129.8 (d, $^3J_{C-F}$=7.7 Hz), 133.1, 136.7, 136.8, 161.0 (d, $^1J_{C-F}$=243.8 Hz), 198.9.

3) (Z)-Ethyl 5-(4-fluorophenyl)-3-phenylpent-2-enoate and (E)-Ethyl 5-(4-fluorophenyl)-3-phenylpent-2-enoate By a procedure similar to that of example 1.85.3, starting from 3-(4-fluorophenyl)-1-phenylpropan-1-one, (Z)-ethyl 5-(4-fluorophenyl)-3-phenylpent-2-enoate and (E)-ethyl 5-(4-fluorophenyl)-3-phenylpent-2-enoate were obtained as colourless oils.

(Z)-Isomer: $^1$H-NMR (500 MHz, CDCl$_3$): δ (ppm)=1.06 (t, J=7.2 Hz, 3H), 2.65-2.75 (m, 4H), 3.98 (q, J=7.2 Hz, 2H), 5.87 (s, 1H), 6.93-6.97 (m, 2H), 7.06-7.09 (m, 2H), 7.16-7.18 (m, 2H), 7.38-7.31 (m, 3H). $^{13}$C-NMR (125 MHz, CDCl$_3$): δ (ppm)=13.9, 32.9, 42.1, 59.8, 115.0, 115.1 (d, $^2J_{C-F}$=22.1 Hz), 117.9, 127.2, 127.7, 127.8, 127.9, 129.6 (d, $^3J_{C-F}$=7.7 Hz), 136.4, 139.7, 158.0, 161.0 (d, $^1J_{C-F}$=243.8 Hz), 165.8.

(E)-Isomer: $^1$H-NMR (500 MHz, CDCl$_3$): δ (ppm)=1.29 (t, J=7.2 Hz, 3H), 2.69-2.72 (m, 2H), 3.36-3.39 (m, 2H), 4.20 (q, J=7.2 Hz, 2H), 6.06 (s, 1H), 6.92-6.96 (m, 2H), 7.15-7.18 (m, 2H), 7.35-7.46 (m, 5H). $^{13}$C-NMR (125 MHz, CDCl$_3$): δ (ppm)=14.3, 31.0, 34.3, 59.9, 115.0 (d, $^2J_{C-F}$=21.1 Hz), 117.9, 126.7, 128.6, 129.0, 129.8 (d, $^3J_{C-F}$=7.7 Hz), 137.1, 140.9, 159.1, 161.0 (d, $^1J_{C-F}$=243.8 Hz), 166.3.

4) (Z)-5-(4-Fluorophenyl)-3-phenylpent-2-enoic acid

By a procedure similar to that of example 1.85.4, starting from (Z)-ethyl 5-(4-fluorophenyl)-3-phenylpent-2-enoate, (Z)-5-(4-fluorophenyl)-3-phenylpent-2-enoic acid was obtained as colourless solid.

$^1$H-NMR (500 MHz, CDCl$_3$): δ (ppm)=2.63-2.67 (m, 2H), 2.73-2.77 (m, 2H), 5.87 (s, 1H), 6.93-7.07 (m, 2H), 7.16-7.23 (m, 2H), 7.34-7.39 (m, 5H).

$^{13}$C-NMR (125 MHz, CDCl$_3$): δ (ppm)=34.3, 42.4, 116.0 (d, $^2J_{C-F}$=21.1 Hz), 117.9, 127.2, 128.2, 128.6, 129.6, 132.0 (d, $^3J_{C-F}$=7.7 Hz), 141.5, 160.4, 161.5 (d, $^1J_{C-F}$=264.9 Hz), 168.2.

5) (E)-5-(4-Fluorophenyl)-3-phenylpent-2-enoic acid

By a procedure similar to that of example 1.85.5, starting from (E)-ethyl 5-(4-fluorophenyl)-3-phenylpent-2-enoate, (E)-5-(4-fluorophenyl)-3-phenylpent-2-enoic acid was obtained as colourless solid.

$^1$H-NMR (500 MHz, CDCl$_3$): δ (ppm)=2.72-2.75 (m, 2H), 3.38-3.42 (m, 2H), 6.12 (s, 1H), 6.92-6.96 (m, 2H), 7.13-7.16 (m, 2H), 7.41-7.42 (m, 3H), 7.46-7.48 (m, 2H).

$^{13}$C-NMR (125 MHz, CDCl$_3$): δ (ppm)=33.4, 34.4, 115.0 (d, $^2J_{C-F}$=21.1 Hz), 116.9, 126.8, 128.7, 129.4, 129.8 (d, $^3J_{C-F}$=8.6 Hz), 136.9, 140.8, 149.5, 161.0 (d, $^1J_{C-F}$=240.9 Hz), 170.9.

1.93. (Z)-5-(4-Bromophenyl)-3-phenylpent-2-enoic acid and (E)-5-(4-Bromophenyl)-3-phenylpent-2-enoic acid (PS 137+PS-T10)

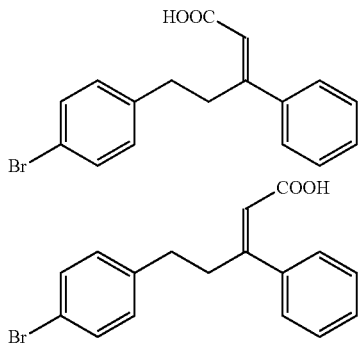

1) 3-(4-Bromophenyl)-1-phenylprop-2-en-1-one

By a procedure similar to that of example 1.59.1, starting from 4-bromobenzaldehyde and acetophenone, 3-(4-bromophenyl)-1-phenylprop-2-en-1-one was obtained as yellow solid.

2) 3-(4-Bromophenyl)-1-phenylpropan-1-one

By a procedure similar to that of example 1.85.2, starting from 3-(4-bromophenyl)-1-phenylprop-2-en-1-one, 3-(4-bromophenyl)-1-phenylpropan-1-one was obtained as yellowish solid.

$^1$H-NMR (500 MHz, CDCl$_3$): δ (ppm)=3.03 (t, J=7.6 Hz, 2H), 3.28 (t, J=7.6, 2H), 7.13 (d, J=8.5 Hz, 2H), 7.30 (d, J=8.5 Hz, 2H), 7.46 (t, J=7.2 Hz, 2H), 7.55-7.58 (m, 1H), 7.94 (dd, J=1.3, 7.2 Hz, 2H).

$^{13}$C-NMR (125 MHz, CDCl$_3$): δ (ppm)=29.4, 40.0, 119.9, 128.0, 128.6, 130.2, 131.5, 133.2, 136.7, 140.2, 198.8.

3) (Z)-Ethyl 5-(4-bromophenyl)-3-phenylpent-2-enoate and (E)-Ethyl 5-(4-bromophenyl)-3-phenylpent-2-enoate By a procedure similar to that of example 1.85.3, starting from 3-(4-bromophenyl)-1-phenylpropan-1-one, (Z)-ethyl 5-(4-bromophenyl)-3-phenylpent-2-enoate and (E)-ethyl 5-(4-bromophenyl)-3-phenylpent-2-enoate were obtained as colourless oils.

(Z)-Isomer: $^1$H-NMR (500 MHz, CDCl$_3$): δ (ppm)=1.06 (t, J=7.2 Hz, 3H), 2.63-2.75 (m, 4H), 3.98 (q, J=7.2 Hz, 2H), 5.87 (s, 1H), 7.00 (d, J=8.5 Hz, 2H), 7.16-7.18 (m, 2H), 7.31-7.40 (m, 5H). $^{13}$C-NMR (125 MHz, CDCl$_3$): δ (ppm)= 13.9, 33.1, 41.8, 59.9, 118.1, 127.2, 127.8, 127.9, 128.5, 129.6, 131.9, 139.2, 139.6, 157.8, 164.9.

(E)-Isomer: $^{1H\text{-}NMR}$ (500 MHz, CDCl$_3$): δ (ppm)=1.30 (t, J=7.2 Hz, 3H), 2.67-2.70 (m, 2H), 3.29-3.36 (m, 2H), 4.20 (q, J=7.2 Hz, 2H), 7.08 (d, J=8.5 Hz, 2H), 7.38-7.45 (m, 7H).

$^{13}$C-NMR (125 MHz, CDCl$_3$): δ (ppm)=12.2, 33.4, 42.0, 60.1, 118.3, 120.2, 127.4, 128.0, 128.2, 130.3, 131.7, 139.8, 140.0, 158.0, 166.1.

4) (Z)-5-(4-Bromophenyl)-3-phenylpent-2-enoic acid

By a procedure similar to that of example 1.85.4, starting from (Z)-ethyl 5-(4-bromophenyl)-3-phenyl-pent-2-enoate, (Z)-5-(4-bromophenyl)-3-phenylpent-2-enoic acid was obtained as colourless solid.

$^1$H-NMR (500 MHz, CDCl$_3$): δ (ppm)=2.62-2.65 (m, 2H), 2.73-2.76 (m, 2H), 5.85 (s, 1H), 6.98 (d, J=8.5 Hz, 2H), 7.11 (d, J=8.5 Hz, 2H), 7.29-7.42 (m, 5H).
$^{13}$C-NMR (125 MHz, CDCl$_3$): δ (ppm)=33.1, 35.7, 116.9, 127.4, 128.5, 130.0, 130.5, 131.6, 133.1, 139.5, 141.4, 160.8, 169.9.

5) (E)-5-(4-Bromophenyl)-3-phenylpent-2-enoic acid

By a procedure similar to that of example 1.85.5, starting from (E)-ethyl 5-(4-bromophenyl)-3-phenyl-pent-2-enoate, (E)-5-(4-bromophenyl)-3-phenylpent-2-enoic acid was obtained as colourless solid.

$^1$H-NMR (500 MHz, CDCl$_3$): δ (ppm)=2.70-2.73 (m, 2H), 3.38-3.40 (m, 2H), 6.12 (s, 1H), 7.07 (d, J=8.2 Hz, 2H), 7.37 (d, J=8.5 Hz, 2H), 7.41-7.45 (m, 3H), 7.45-7.47 (m, 2H).
$^{13}$C-NMR (125 MHz, CDCl$_3$): δ (ppm)=33.1, 34.5, 116.8, 126.8, 128.8, 129.5, 130.2, 131.4, 131.7, 140.2, 140.7, 162.1, 169.9.

1.94. (Z)-5-(4-Ethylphenyl)-3-phenylpent-2-enoic acid and (E)-5-(4-Ethylphenyl)-3-phenylpent-2-enoic acid (PS 129+PS 130)

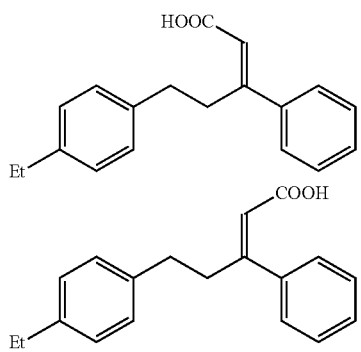

1) 3-(4-Ethylphenyl)-1-phenylprop-2-en-1-one

By a procedure similar to that of example 1.59.1, starting from 4-ethylbenzaldehyde and acetophenone, 3-(4-ethylphenyl)-1-phenylprop-2-en-1-one was obtained as yellow oil.

2) 3-(4-Ethylphenyl)-1-phenylpropan-1-one

By a procedure similar to that of example 1.85.2, starting from 3-(4-ethylphenyl)-1-phenylprop-2-en-1-one, 3-(4-ethylphenyl)-1-phenylpropan-1-one was obtained as yellowish oil.

$^1$H-NMR (500 MHz, CDCl$_3$): δ (ppm)=1.23 (t, J=7.6 Hz, 3H), 2.63 (q, J=7.6 Hz, 2H), 3.05 (t, J=7.6 Hz, 2H), 3.30 (t, J=7.6, 2H), 7.14 (d, J=8.2 Hz, 2H), 7.18 (d, J=8.2 Hz, 2H), 7.46 (t, J=7.2 Hz, 2H), 7.54-7.57 (m, 1H), 7.95-7.98 (m, 2H).
$^{13}$C-NMR (125 MHz, CDCl$_3$): δ (ppm)=15.6, 28.4, 29.7, 40.6, 127.9, 128.0, 128.3, 128.6, 133.0, 136.9, 138.4, 142.0, 199.3.

3) (Z)-Ethyl 5-(4-ethylphenyl)-3-phenylpent-2-enoate and (E)-Ethyl 5-(4-ethylphenyl)-3-phenyl-pent-2-enoate By a procedure similar to that of example 1.85.3, starting from 3-(4-ethylphenyl)-1-phenylpropan-1-one, (Z)-ethyl 5-(4-ethylphenyl)-3-phenylpent-2-enoate and (E)-ethyl 5-(4-ethylphenyl)-3-phenylpent-2-enoate were obtained as colourless oils.

(Z)-Isomer: $^1$H-NMR (500 MHz, CDCl$_3$): δ (ppm)=1.06 (t, J=7.2 Hz, 3H), 1.22 (t, J=7.6 Hz, 3H), 2.60 (q, J=7.6 Hz, 2H), 2.72-2.76 (m, 4H), 3.98 (q, J=7.2 Hz, 2H), 5.90 (s, 1H), 7.05 (d, J=7.9 Hz, 2H), 7.10 (d, J=7.9 Hz, 2H), 7.18-7.20 (m, 2H), 7.30-7.38 (m, 3H). $^{13}$C-NMR (125 MHz, CDCl$_3$): δ (ppm)=13.9, 15.6, 28.4, 33.4, 42.1, 59.8, 117.6, 127.2, 127.7, 127.9, 128.2, 138.1, 139.9, 142.0, 158.6, 166.0.

(E)-Isomer: $^1$H-NMR (500 MHz, CDCl$_3$): δ (ppm)=1.25 (t, J=7.6 Hz, 3H), 1.30 (t, J=7.2 Hz, 3H), 2.61 (q, J=7.6 Hz, 2H), 2.69-2.72 (m, 2H), 3.37-3.40 (m, 2H), 4.21 (q, J=7.2 Hz, 2H), 6.07 (s, 1H), 7.10 (d, J=8.2 Hz, 2H), 7.15 (d, J=8.2 Hz, 2H), 7.38-7.41 (m, 3H), 7.46-7.48 (m, 2H). $^{13}$C-NMR (125 MHz, CDCl$_3$): δ (ppm)=14.3, 15.7, 28.5, 33.3, 34.8, 59.9, 117.8, 126.7, 127.8, 128.4, 128.6, 128.9, 138.8, 141.1, 141.8, 159.5, 166.3.

4) (Z)-5-(4-Ethylphenyl)-3-phenylpent-2-enoic acid

By a procedure similar to that of example 1.85.4, starting from (Z)-ethyl 5-(4-ethylphenyl)-3-phenyl-pent-2-enoate, (Z)-5-(4-ethylphenyl)-3-phenylpent-2-enoic acid was obtained as colourless solid.

$^1$H-NMR (500 MHz, CDCl$_3$): δ (ppm)=1.15 (t, J=7.6 Hz, 3H), 2.54 (q, J=7.6 Hz, 2H), 2.64-2.68 (m, 2H), 3.31-3.34 (m, 2H), 6.05 (s, 1H), 7.03 (d, J=8.2 Hz, 2H), 7.07 (d, J=8.2 Hz, 2H), 7.33-7.35 (m, 3H), 7.41-7.43 (m, 2H).
$^{13}$C-NMR (125 MHz, CDCl$_3$): δ (ppm)=15.7, 28.5, 33.6, 34.8, 116.5, 126.8, 127.8, 128.2, 128.3, 128.7, 129.3, 140.9, 141.9, 162.2, 170.8.

5) (E)-5-(4-Ethylphenyl)-3-phenylpent-2-enoic acid

By a procedure similar to that of example 1.85.5, starting from (E)-ethyl 5-(4-ethylphenyl)-3-phenyl-pent-2-enoate, (E)-5-(4-ethylphenyl)-3-phenylpent-2-enoic acid was obtained as colourless solid.

$^1$H-NMR (500 MHz, CDCl$_3$): δ (ppm)=1.22 (t, J=7.6 Hz, 3H), 2.62 (q, J=7.6 Hz, 2H), 2.72-2.76 (m, 2H), 3.39-3.42 (m, 2H), 6.13 (s, 1H), 7.11 (d, J=8.2 Hz, 2H), 7.15 (d, J=8.2 Hz, 2H), 7.40-7.41 (m, 3H), 7.48-7.50 (m, 2H).

$^{13}$C-NMR (125 MHz, CDCl$_3$): δ (ppm)=15.7, 28.5, 33.6, 34.9, 116.7, 126.8, 127.8, 128.3, 128.7, 129.3, 140.9, 141.9, 145.5, 162.6, 170.8.

1.95. (Z)-3-Phenyl-5-[4-(trifluoromethyl)phenyl] pent-2-enoic acid and (E)-3-Phenyl-5-[4-(trifluoromethyl)phenyl]pent-2-enoic acid (PS 140+PS-T5)

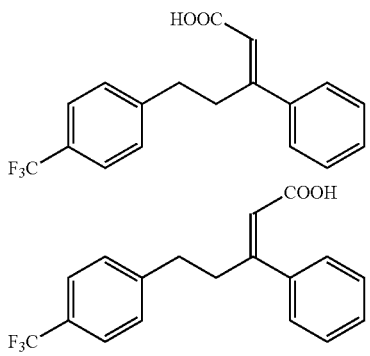

1) 1-Phenyl-3-[4-(trifluoromethyl)phenyl]prop-2-en-1-one

By a procedure similar to that of example 1.59.1, starting from 4-trifluoromethylbenzaldehyde and acetophenone, 1-phenyl-3-[4-(trifluoromethyl)phenyl]prop-2-en-1-one was obtained as yellow solid.

2) 1-Phenyl-3-[4-(trifluoromethyl)phenyl]propan-1-one

By a procedure similar to that of example 1.85.2, starting from 1-phenyl-3-[4-(trifluoromethyl)phenyl]-prop-2-en-1-one, 1-phenyl-3-[4-(trifluoromethyl)phenyl]propan-1-one was obtained as yellowish solid.

$^1$H-NMR (500 MHz, CDCl$_3$): δ (ppm)=3.13 (t, J=7.6 Hz, 2H), 3.32 (t, J=7.6, 2H), 7.37 (d, J=7.9 Hz, 2H), 7.46 (t, J=7.9 Hz, 2H), 7.54-7.56 (m, 3H), 7.95 (d, J=8.2 Hz, 2H).

$^{13}$C-NMR (125 MHz, CDCl$_3$): δ (ppm)=29.0, 39.8, 125.2, 125.4, 127.9, 128.7, 128.8, 133.2, 136.7, 145.1, 145.4, 190.8.

3) (Z)-Ethyl 3-phenyl-5-[4-(trifluoromethyl)phenyl] pent-2-enoate and (E)-Ethyl 3-phenyl-5-[4-(trifluoromethyl)phenyl]pent-2-enoate By a procedure similar to that of example 1.85.3, starting from 1-phenyl-3-[4-(trifluoromethyl)phenyl]-propan-1-one, (Z)-ethyl 3-phenyl-5-[4-(trifluoromethyl)phenyl]pent-2-enoate and (E)-ethyl 3-phenyl-5-[4-(trifluoromethyl)phenyl] pent-2-enoate were obtained as colourless oils.

(Z)-Isomer: $^1$H-NMR (500 MHz, CDCl$_3$): δ (ppm)=1.06 (t, J=7.2 Hz, 3H), 2.73-2.79 (m, 4H), 3.98 (q, J=7.2 Hz, 2H), 5.89 (s, 1H), 7.18 (d, J=8.2 Hz, 2H), 7.23 (d, J=8.2 Hz, 2H), 7.32-7.39 (m, 3H), 7.52 (d, J=7.9 Hz, 2H).

(E)-Isomer: $^1$H-NMR (500 MHz, CDCl$_3$): δ (ppm)=1.30 (t, J=7.2 Hz, 3H), 2.79-2.81 (m, 2H), 3.40-3.44 (m, 2H), 4.20 (q, J=7.2 Hz, 2H), 6.07 (s, 1H), 7.31 (d, J=8.2 Hz, 2H), 7.39-7.45 (m, 5H), 7.50 (d, J=8.2 Hz, 2H). $^{13}$C-NMR (125 MHz, CDCl$_3$): δ (ppm)=14.3, 32.6, 34.9, 59.9, 118.2, 125.0, 125.2, 126.7, 128.4, 128.5, 128.6, 128.8, 129.1, 140.8, 145.5, 158.8, 166.3.

4) (Z)-3-Phenyl-5-[4-(trifluoromethyl)phenyl]pent-2-enoic acid

By a procedure similar to that of example 1.85.4, starting from (Z)-ethyl 3-phenyl-5-[4-(trifluoromethyl)phenyl]pent-2-enoate, (Z)-3-phenyl-5-[4-(trifluoromethyl)phenyl]-pent-2-enoic acid was obtained as colourless solid.

$^1$H-NMR (500 MHz, CDCl$_3$): δ (ppm)=2.70-2.78 (m, 4H), 5.85 (s, 1H), 7.14-7.16 (m, 2H), 7.19-7.29 (m, 2H), 7.30-7.37 (m, 3H), 7.49-7.54 (m, 2H).

$^{13}$C-NMR (125 MHz, CDCl$_3$): δ (ppm)=33.5, 34.9, 125.3, 125.9, 127.2, 127.5, 128.1, 128.5, 128.6, 128.8, 130.0, 133.5, 144.6, 160.6, 170.0.

5) (E)-3-Phenyl-5-[4-(trifluoromethyl)phenyl]pent-2-enoic acid

By a procedure similar to that of example 1.85.5, starting from (E)-ethyl 3-phenyl-5-[4-(trifluoromethyl)phenyl]pent-2-enoate, (E)-3-phenyl-5-[4-(trifluoromethyl)phenyl]-pent-2-enoic acid was obtained as colourless solid.

$^1$H-NMR (500 MHz, CDCl$_3$): δ (ppm)=2.80-2.83 (m, 2H), 3.41-3.45 (m, 2H), 6.13 (s, 1H), 7.30 (d, J=8.2 Hz, 2H), 7.41-7.48 (m, 5H), 7.51 (d, J=8.2 Hz, 2H).

$^{13}$C-NMR (125 MHz, CDCl$_3$): δ (ppm)=32.9, 34.9, 117.0, 125.2, 126.7, 128.3, 128.6, 128.8, 129.1, 129.5, 140.6, 145.3, 162.0, 170.9.

1.96. (Z)-5-[4-(Methylthio)phenyl]-3-phenylpent-2-enoic acid (PS 139) and (E)-5-[4-(Methylthio)phenyl]-3-phenylpent-2-enoic acid

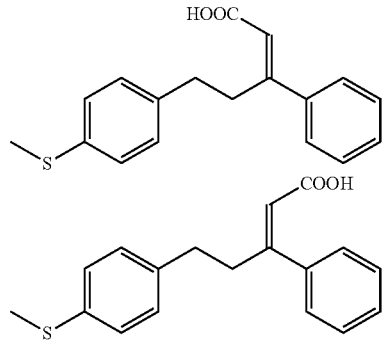

1) 3-[4-(Methylthio)phenyl]-1-phenylprop-2-en-1-one

By a procedure similar to that of example 1.59.1, starting from commercial 4-(methylthio)benzaldehyde and acetophenone, 3-[4-(methylthio)phenyl]-1-phenylprop-2-en-1-one was obtained as yellowish solid.

$^1$H-NMR (500 MHz, CDCl$_3$): δ (ppm)=2.52 (s, 3H), 7.26 (d, J=8.5 Hz, 2H), 7.47-7.52 (m, 3H), 7.55-7.61 (m, 3H), 7.57 (d, J=15.7 Hz, 1H), 8.01 (d, J=8.5 Hz, 2H).

$^{13}$C-NMR (125 MHz, CDCl$_3$): δ (ppm)=15.1, 121.0, 125.9, 128.4, 128.6, 128.8, 131.4, 132.7, 138.3, 142.4, 144.3, 190.4.

2) 3-[4-(Methylthio)phenyl]-1-phenylpropan-1-one

By a procedure similar to that of example 1.85.2, starting from 3-[4-(methylthio)phenyl]-1-phenylprop-2-en-1-one, 3-[4-(methylthio)phenyl]-1-phenylpropan-1-one was obtained as yellowish oil.

¹H-NMR (500 MHz, CDCl₃): δ (ppm)=2.47 (s, 3H), 3.02-3.05 (m, 2H), 3.27-3.29 (m, 2H), 7.19 (q, J=8.5 Hz, 4H), 7.45 (t, J=7.2 Hz, 2H), 7.56 (t, J=7.6 Hz, 1H), 7.95 (d, J=8.2 Hz, 2H).

¹³C-NMR (125 MHz, CDCl₃): δ (ppm)=16.3, 29.5, 40.3, 127.2, 128.0, 128.6, 128.9, 133.1, 135.8, 136.8, 138.3, 199.0.

3) (Z)-Ethyl 5-[4-(methylthio)phenyl]-3-phenylpent-2-enoate and (E)-Ethyl 5-[4-(methylthio)phenyl]-3-phenylpent-2-enoate By a procedure similar to that of example 1.85.3, starting from 3-[4-(methylthio)phenyl]-1-phenylpropan-1-one, (Z)-ethyl 5-[4-(methylthio)phenyl]-3-phenylpent-2-enoate and (E)-ethyl 5-[4-(methylthio)phenyl]-3-phenylpent-2-enoate were obtained as colourless oils.

(Z)-Isomer: ¹H-NMR (500 MHz, CDCl₃): δ (ppm)=1.06 (t, J=7.2 Hz, 3H), 2.46 (s, 3H), 2.64-2.68 (m, 2H), 2.71-2.75 (m, 2H), 4.00 (q, J=7.2 Hz, 2H), 5.88 (s, 1H), 7.05 (d, J=8.5 Hz, 2H), 7.16-7.19 (m, 4H), 7.30-7.38 (m, 3H).

¹³C-NMR (125 MHz, CDCl₃): δ (ppm)=13.9, 16.2, 33.2, 41.9, 59.8, 117.8, 127.1, 127.2, 127.7, 127.9, 128.8, 135.7, 137.9, 139.8, 158.2, 165.9.

(E)-Isomer: ¹H-NMR (500 MHz, CDCl₃): δ (ppm)=1.31 (t, J=7.2 Hz, 3H), 2.46 (s, 3H), 2.68-2.71 (m, 2H), 3.36-3.39 (m, 2H), 4.20 (q, J=7.2 Hz, 2H), 6.06 (s, 1H), 7.16 (q, J=8.5 Hz, 4H), 7.37-7.41 (m, 3H), 7.43-7.46 (m, 2H). ¹³C-NMR (125 MHz, CDCl₃): δ (ppm)=14.3, 16.4, 33.0, 34.6, 59.9, 117.9, 126.7, 127.1, 128.6, 129.0, 129.1, 135.4, 138.7, 141.0, 159.2, 166.3.

4) (Z)-5-[4-(Methylthio)phenyl]-3-phenylpent-2-enoic acid

By a procedure similar to that of example 1.85.4, starting from (Z)-ethyl 5-[4-(methylthio)phenyl]-3-phenylpent-2-enoate, (Z)-5-[4-(methylthio)phenyl]-3-phenylpent-2-enoic acid was obtained as colourless solid.

¹H-NMR (500 MHz, CDCl₃): δ (ppm)=2.46 (s, 3H), 2.64-2.66 (m, 2H), 2.73-2.76 (m, 2H), 5.86 (s, 1H), 7.03 (d, J=8.5 Hz, 2H), 7.17-7.21 (m, 4H), 7.31-7.37 (m, 3H).

¹³C-NMR (125 MHz, CDCl₃): δ (ppm)=16.2, 33.1, 42.3, 116.7, 126.0, 127.1, 127.3, 128.1, 128.2, 128.4, 129.0, 135.9, 139.1, 161.0.

5) (E)-5-[4-(Methylthio)phenyl]-3-phenylpent-2-enoic acid

By a procedure similar to that of example 1.85.5, starting from (E)-ethyl 5-[4-(methylthio)phenyl]-3-phenylpent-2-enoate, (E)-5-[4-(methylthio)phenyl]-3-phenylpent-2-enoic acid was obtained as colourless solid.

¹H-NMR (500 MHz, CDCl₃): δ (ppm)=2.46 (s, 3H), 2.70-2.74 (m, 2H), 3.38-3.41 (m, 2H), 6.12 (s, 1H), 7.15 (q, J=8.5 Hz, 4H), 7.40-7.42 (m, 3H), 7.46-7.49 (m, 2H).

¹³C-NMR (125 MHz, CDCl₃): δ (ppm)=30.9, 33.3, 34.7, 115.1, 116.5, 126.8, 127.1, 128.7, 129.0, 129.4, 135.6, 138.5, 140.8, 169.8.

1.97. (Z)-5-(3,4-Dichlorophenyl)-3-phenylpent-2-enoic acid and (E)-5-(3,4-Dichloro-phenyl)-3-phenylpent-2-enoic acid (PS 131+PS-T7)

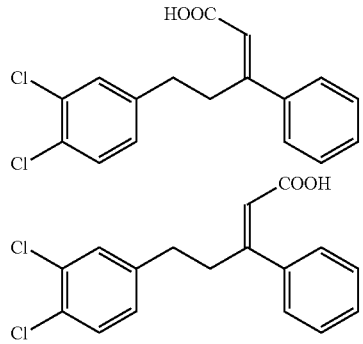

1) 3-(3,4-Dichlorophenyl)-1-phenylprop-2-en-1-one

By a procedure similar to that of example 1.59.1, starting from 3,4-dichlorobenzaldehyde and acetophenone, 3-(3,4-dichlorophenyl)-1-phenylprop-2-en-1-one was obtained as yellowish solid.

2) 3-(3,4-Dichlorophenyl)-1-phenylpropan-1-one

By a procedure similar to that of example 1.85.2, starting from 3-(3,4-dichlorophenyl)-1-phenylprop-2-en-1-one, 3-(3,4-dichlorophenyl)-1-phenylpropan-1-one was obtained as yellowish solid.

¹H-NMR (500 MHz, CDCl₃): δ (ppm)=3.03 (t, J=7.2 Hz, 2H), 3.28 (t, J=7.2 Hz, 2H), 7.09 (dd, J=1.9, 8.5 Hz, 1H), 7.34-7.35 (m, 2H), 7.46 (t, J=7.2 Hz, 2H), 7.55-7.59 (m, 1H), 7.94-7.96 (m, 2H).

¹³C-NMR (125 MHz, CDCl₃): δ (ppm)=29.9, 39.7, 127.9, 128.0, 128.7, 130.0, 130.3, 130.4, 132.3, 133.2, 136.6, 141.5, 198.4.

3) (Z)-Ethyl 5-(3,4-dichlorophenyl)-3-phenylpent-2-enoate and (E)-Ethyl 5-(3,4-dichloro-phenyl)-3-phenylpent-2-enoate By a procedure similar to that of example 1.85.3, starting from 3-(3,4-dichlorophenyl)-1-phenylpropan-1-one, (Z)-ethyl 5-(3,4-dichlorophenyl)-3-phenylpent-2-enoate and (E)-ethyl 5-(3,4-dichlorophenyl)-3-phenylpent-2-enoate were obtained as colourless oils.

(Z)-Isomer: ¹H-NMR (500 MHz, CDCl₃): δ (ppm)=1.01 (t, J=6.9 Hz, 3H), 2.63-2.75 (m, 4H), 3.98 (q, J=6.9 Hz, 2H), 5.87 (s, 1H), 6.96 (dd, J=2.2, 8.2 Hz, 2H), 7.17 (d, J=8.2 Hz, 2H), 7.20 (s, 1H), 7.32-7.38 (m, 4H). ¹³C-NMR (125 MHz, CDCl₃): δ (ppm)=13.9, 32.9, 41.5, 59.9, 118.2, 127.2, 127.8, 127.9, 128.0, 130.1, 130.2, 130.3, 132.3, 139.3, 141.0, 157.3, 165.8.

(E)-Isomer: ¹H-NMR (500 MHz, CDCl₃): δ (ppm)=1.30 (t, J=7.2 Hz, 3H), 2.67-2.71 (m, 2H), 3.36-3.39 (m, 2H), 4.20 (q, J=7.2 Hz, 2H), 6.06 (s, 1H), 7.04 (dd, J=1.9, 8.2 Hz, 1H), 7.28 (d, J=2.2, 8.2 Hz, 1H), 7.30 (d, J=8.2 Hz, 1H), 7.38-7.44 (m, 5H). ¹³C-NMR (125 MHz, CDCl₃): δ (ppm)=14.3, 32.5, 34.1, 60.0, 118.3, 126.7, 128.1, 128.7, 129.1, 129.8, 130.1, 130.5, 132.0, 140.7, 141.6, 158.6, 166.3

4) (Z)-5-(3,4-Dichlorophenyl)-3-phenylpent-2-enoic acid

By a procedure similar to that of example 1.85.4, starting from (Z)-ethyl 5-(3,4-dichlorophenyl)-3-phenylpent-2-enoate, (Z)-5-(3,4-dichlorophenyl)-3-phenylpent-2-enoic acid was obtained as colourless solid.

$^1$H-NMR (500 MHz, CDCl$_3$): δ (ppm)=2.62-2.64 (m, 2H), 2.74-2.77 (m, 2H), 5.86 (s, 1H), 6.93 (dd, J=2.2, 8.2 Hz, 2H), 7.16-7.21 (m, 2H), 7.31-7.39 (m, 4H).

$^{13}$C-NMR (125 MHz, CDCl$_3$): δ (ppm)=32.5, 35.5, 116.8, 125.8, 126.9, 127.5, 127.9, 128.0, 128.2, 130.2, 133.3, 139.9, 140.4, 160.3, 169.9.

5) (E)-5-(3,4-Dichlorophenyl)-3-phenylpent-2-enoic acid

By a procedure similar to that of example 1.85.5, starting from (E)-ethyl 5-(3,4-dichlorophenyl)-3-phenylpent-2-enoate, (E)-5-(3,4-dichlorophenyl)-3-phenylpent-2-enoic acid was obtained as colourless solid.

$^1$H-NMR (500 MHz, CDCl$_3$): δ (ppm)=2.70-2.73 (m, 2H), 3.38-3.41 (m, 2H), 6.13 (s, 1H), 7.02 (dd, J=1.9, 8.2 Hz, 1H), 7.27 (d, J=2.2 Hz, 1H), 7.31 (d, J=8.2 Hz, 1H), 7.41-7.46 (m, 5H).

$^{13}$C-NMR (125 MHz, CDCl$_3$): δ (ppm)=32.8, 34.2, 117.0, 126.7, 128.0, 128.8, 129.6, 130.0, 130.2, 130.4, 132.1, 140.5, 141.4, 170.4, 196.6.

1.98. (Z)-5-(4-Chloro-2-fluorophenyl)-3-phenylpent-2-enoic acid and (E)-5-(4-Chloro-2-fluorophenyl)-3-phenylpent-2-enoic acid (PS 132+PS-T1)

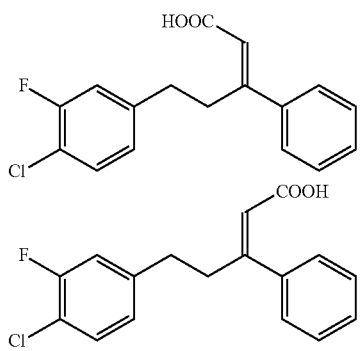

1) 3-(4-Chloro-3-fluorophenyl)-1-phenylprop-2-en-1-one

By a procedure similar to that of example 1.59.1, starting from 4-chloro-3-fluorobenzaldehyde and acetophenone, 3-(4-chloro-3-fluorophenyl)-1-phenylprop-2-en-1-one was obtained as yellow solid.

2) 3-(4-Chloro-3-fluorophenyl)-1-phenylpropan-1-one

By a procedure similar to that of example 1.85.2, starting from 3-(4-chloro-3-fluorophenyl)-1-phenylprop-2-en-1-one, 3-(4-chloro-3-fluorophenyl)-1-phenylpropan-1-one was obtained as colourless oil.

$^1$H-NMR (500 MHz, CDCl$_3$): δ (ppm)=3.05 (t, J=7.2 Hz, 2H), 3.29 (t, J=7.2 Hz, 2H), 6.98 (t, J=8.2 Hz, 1H), 7.05 (t, J=8.2 Hz, 1H), 7.29 (t, J=7.9 Hz, 1H), 7.46 (t, J=7.6 Hz, 2H), 7.57 (t, J=7.2 Hz, 1H), 7.95 (t, J=8.2 Hz, 2H).

$^{13}$C-NMR (125 MHz, CDCl$_3$): δ (ppm)=29.2, 39.8, 116.6 (d, $^2J_{C-F}$=22.1 Hz), 118.0 (d, $^2J_{C-F}$=17.3 Hz), 124.9 (d, $^4J_{C-F}$=2.9 Hz), 127.9, 128.7, 130.4, 133.2, 136.6, 142.2 (d, $^3J_{C-F}$=6.7 Hz), 161.0 (d, $^1J_{C-F}$=251.4 Hz), 198.4.

3) (Z)-Ethyl 5-(4-chloro-3-fluorophenyl)-3-phenylpent-2-enoate and (E)-Ethyl 5-(4-chloro-3-fluorophenyl)-3-phenylpent-2-enoate By a procedure similar to that of example 1.85.3, starting from 3-(4-chloro-3-fluorophenyl)-1-phenylpropan-1-one, (Z)-ethyl 5-(4-chloro-3-fluorophenyl)-3-phenylpent-2-enoate and (E)-ethyl 5-(4-chloro-3-fluorophenyl)-3-phenylpent-2-enoate were obtained as colourless oils.

(Z)-Isomer: $^1$H-NMR (500 MHz, CDCl$_3$): δ (ppm)=1.06 (t, J=6.9 Hz, 3H), 2.65-2.68 (m, 2H), 2.71-2.76 (m, 2H), 3.98 (q, J=6.9 Hz, 2H), 5.87 (s, 1H), 6.83 (dd, J=1.6, 8.2 Hz, 1H), 6.90 (dd, J=1.9, 10.9 Hz, 1H), 7.16 (d, J=8.2 Hz, 2H), 7.28 (d, J=8.2 Hz, 1H), 7.29-7.39 (m, 3H). $^{13}$C-NMR (125 MHz, CDCl$_3$): δ (ppm)=13.9, 33.03, 33.05, 41.4, 59.9, 116.4 (d, $^2J_{C-F}$=20.1 Hz), 118.2, 124.7 (d, $^4J_{C-F}$=3.8 Hz), 127.2, 127.9, 128.0, 130.4, 139.3, 141.7 (d, $^3J_{C-F}$=6.7 Hz), 157.3, 158.0 (d, $^1J_{C-F}$=248.6 Hz), 165.7.

(E)-Isomer: $^1$H-NMR (500 MHz, CDCl$_3$): δ (ppm)=1.31 (t, J=6.9 Hz, 3H), 2.71 (t, J=8.2 Hz, 2H), 3.38 (t, J=8.2 Hz, 2H), 4.20 (q, J=6.9 Hz, 2H), 6.06 (s, 1H), 6.92 (dd, J=1.6, 8.2 Hz, 1H), 7.00 (dd, J=1.9, 10.9 Hz, 1H), 7.23-7.42 (m, 2H), 7.38-7.44 (m, 5H). $^{13}$C-NMR (125 MHz, CDCl$_3$): δ (ppm)=14.3, 32.5, 34.3, 60.0, 116.5 (d, $^2J_{C-F}$=21.1 Hz), 118.3, 125.0 (d, $^4J_{C-F}$=3.8 Hz), 126.7, 128.7, 129.1, 130.2, 140.7, 142.4 (d, $^3J_{C-F}$=6.7 Hz), 158.5 (d, $^1J_{C-F}$=250.5 Hz), 166.2.

4) (Z)-5-(4-Chloro-3-fluorophenyl)-3-phenylpent-2-enoic acid

By a procedure similar to that of example 1.85.4, starting from (Z)-ethyl 5-(4-chloro-3-fluorophenyl)-3-phenyl-pent-2-enoate, (Z)-5-(4-chloro-3-fluorophenyl)-3-phenylpent-2-enoic acid was obtained as colourless solid.

$^1$H-NMR (500 MHz, CDCl$_3$): δ (ppm)=2.57 (t, J=8.3 Hz, 2H), 2.68 (t, J=8.3 Hz, 2H), 5.78 (s, 1H), 6.75 (dd, J=2.2, 8.2 Hz, 1H), 6.82 (dd, J=2.2, 8.2 Hz, 1H), 7.08-7.10 (m, 2H), 7.24-7.33 (m, 5H).

$^{13}$C-NMR (125 MHz, CDCl$_3$): δ (ppm)=32.9, 41.8, 116.5 (d, $^2J_{C-F}$=20.1 Hz), 116.7, 117.0, 124.8 (d, $^4J_{C-F}$=3.8 Hz), 126.0, 128.5, 129.8, 130.5, 133.6, 140.8, 141.3 (d, $^3J_{C-F}$=6.7 Hz), 158.9, 161.0 (d, $^1J_{C-F}$=252.3 Hz).

5) (E)-5-(4-Chloro-3-fluorophenyl)-3-phenylpent-2-enoic acid

By a procedure similar to that of example 1.85.5, starting from (E)-ethyl 5-(4-chloro-3-fluorophenyl)-3-phenylpent-2-enoate, (E)-5-(4-chloro-3-fluorophenyl)-3-phenylpent-2-enoic acid was obtained as colourless solid.

$^1$H-NMR (500 MHz, CDCl$_3$): δ (ppm)=2.73 (t, J=8.3 Hz, 2H), 3.40 (t, J=8.3 Hz, 2H), 6.13 (s, 1H), 6.91 (dd, J=2.2, 8.2 Hz, 1H), 6.98 (dd, J=2.2, 8.2 Hz, 1H), 7.24-7.27 (m, 2H), 7.41-7.46 (m, 5H).

$^{13}$C-NMR (125 MHz, CDCl$_3$): δ (ppm)=32.8, 34.4, 116.6 (d, $^2J_{C-F}$=21.1 Hz), 116.9, 118.3, 124.9 (d, $^4J_{C-F}$=3.8 Hz), 126.7, 128.8, 129.6, 130.3, 140.5, 142.2 (d, $^3J_{C-F}$=6.7 Hz), 161.0 (d, $^1J_{C-F}$=250.5 Hz), 161.8, 169.8.

1.99. (Z)-5-(3,4-Dichlorophenyl)-3-phenylpent-2-enoic acid and (E)-5-(3,4-Dichloro-phenyl)-3-phenylpent-2-enoic acid (PS 135+PS-T9)

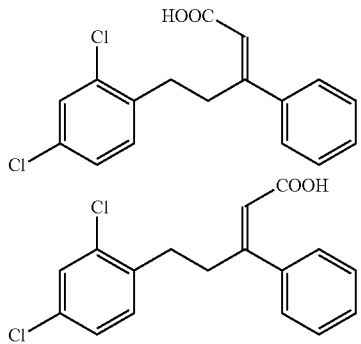

1) 3-(2,4-Dichlorophenyl)-1-phenylprop-2-en-1-one

By a procedure similar to that of example 1.59.1, starting from 2,4-dichlorobenzaldehyde and acetophenone, 3-(2,4-dichlorophenyl)-1-phenylprop-2-en-1-one was obtained as yellow solid.

2) 3-(2,4-Dichlorophenyl)-1-phenylpropan-1-one

By a procedure similar to that of example 1.85.2, starting from 3-(2,4-dichlorophenyl)-1-phenylprop-2-en-1-one, 3-(2,4-dichlorophenyl)-1-phenylpropan-1-one was obtained as pale green oil.

$^1$H-NMR (500 MHz, CDCl$_3$): δ (ppm)=3.15 (t, J=7.6 Hz, 2H), 3.29 (t, J=7.6 Hz, 2H), 7.17 (dd, J=2.2, 8.2 Hz, 1H), 7.26 (d, J=8.2 Hz, 2H), 7.37 (d, J=2.2 Hz, 1H), 7.46 (t, J=7.6 Hz, 2H), 7.54-7.59 (m, 1H), 7.95-7.97 (m, 2H).

$^{13}$C-NMR (125 MHz, CDCl$_3$): δ (ppm)=27.7, 38.1, 127.3, 128.0, 128.6, 129.3, 131.7, 132.7, 133.2, 134.6, 136.6, 137.4, 198.6.

3) (Z)-Ethyl 5-(2,4-dichlorophenyl)-3-phenylpent-2-enoate and (E)-Ethyl 5-(2,4-dichloro-phenyl)-3-phenylpent-2-enoate By a procedure similar to that of example 1.85.3, starting from 3-(2,4-dichlorophenyl)-1-phenylpropan-1-one, (Z)-ethyl 5-(2,4-dichlorophenyl)-3-phenylpent-2-enoate and (E)-ethyl 5-(2,4-dichlorophenyl)-3-phenylpent-2-enoate were obtained as colourless oils.

(Z)-Isomer: $^1$H-NMR (500 MHz, CDCl$_3$): δ (ppm)=1.07 (t, J=7.2 Hz, 3H), 2.70-2.79 (m, 4H), 3.99 (q, J=7.2 Hz, 2H), 5.91 (s, 1H), 7.05 (d, J=8.2 Hz, 1H), 7.15 (dd, J=2.2, 8.2 Hz, 1H), 7.19-7.21 (m, 2H), 7.31-7.38 (m, 4H). $^{13}$C-NMR (125 MHz, CDCl$_3$): δ (ppm)=13.9, 31.4, 39.8, 59.9, 118.0, 127.1, 127.3, 127.9, 128.0, 129.3, 131.1, 132.6, 134.5, 137.0, 139.4, 157.6, 165.9.

(E)-Isomer: $^1$H-NMR (500 MHz, CDCl$_3$): δ (ppm)=1.29 (t, J=7.2 Hz, 3H), 2.83-2.86 (m, 2H), 3.35-3.38 (m, 2H), 4.20 (q, J=7.2 Hz, 2H), 6.10 (s, 1H), 7.14 (dd, J=2.2, 8.2 Hz, 1H), 7.23 (d, J=8.2 Hz, 1H), 7.31 (d, J=2.2 Hz, 1H), 7.37-7.41 (m, 3H), 7.48-7.50 (m, 2H). $^{13}$C-NMR (125 MHz, CDCl$_3$): δ (ppm)=14.3, 30.9, 32.2, 60.0, 118.1, 126.7, 127.0, 128.6, 129.0, 129.1, 131.5, 132.3, 134.4, 137.7, 140.6, 158.6, 166.3.

4) (Z)-5-(2,4-Dichlorophenyl)-3-phenylpent-2-enoic acid

By a procedure similar to that of example 1.85.4, starting from (Z)-ethyl 5-(2,4-dichlorophenyl)-3-phenylpent-2-enoate, (Z)-5-(2,4-dichlorophenyl)-3-phenylpent-2-enoic acid was obtained as colourless solid.

$^1$H-NMR (500 MHz, CDCl$_3$): δ (ppm)=2.67-2.74 (m, 4H), 5.88 (s, 1H), 7.03 (d, J=8.2 Hz, 1H), 7.14 (dd, J=2.2, 8.2 Hz, 1H), 7.19-7.21 (m, 2H), 7.33-7.39 (m, 4H).

$^{13}$C-NMR (125 MHz, CDCl$_3$): δ (ppm)=32.5, 40.2, 116.9, 127.1, 127.3, 128.2, 128.4, 129.4, 131.1, 132.7, 134.5, 138.7, 141.4, 160.5, 176.5.

5) (E)-5-(2,4-Dichlorophenyl)-3-phenylpent-2-enoic acid

By a procedure similar to that of example 1.85.5, starting from (E)-ethyl 5-(2,4-dichlorophenyl)-3-phenyl-pent-2-enoate, (E)-5-(2,4-dichlorophenyl)-3-phenylpent-2-enoic acid was obtained as colourless solid.

$^1$H-NMR (500 MHz, CDCl$_3$): δ (ppm)=2.85-2.89 (m, 2H), 3.40-3.42 (m, 2H), 6.16 (s, 1H), 7.14 (dd, J=2.2, 8.2 Hz, 1H), 7.19 (d, J=8.2 Hz, 1H), 7.32 (d, J=1.9 Hz, 1H), 7.40-7.41 (m, 3H), 7.51-7.53 (m, 2H).

$^{13}$C-NMR (125 MHz, CDCl$_3$): δ (ppm)=31.1, 32.4, 116.8, 125.9, 126.8, 127.1, 128.7, 129.1, 129.6, 131.5, 132.5, 137.1, 137.5, 140.0, 169.9.

1.100. (Z)-5-(4-Bromo-2-fluorophenyl)-3-phenylpent-2-enoic acid and (E)-5-(4-Bromo-2-fluorophenyl)-3-phenylpent-2-enoic acid (PS 133+PS-T8)

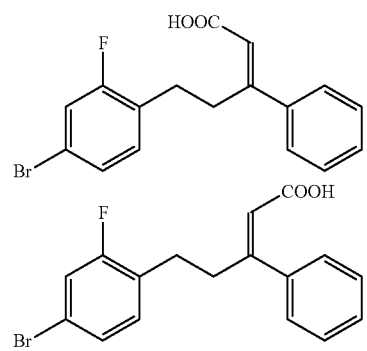

1) 3-(4-Bromo-2-fluorophenyl)-1-phenylprop-2-en-1-one

By a procedure similar to that of example 1.59.1, starting from 4-bromo-2-fluorobenzaldehyde and acetophenone, 3-(4-bromo-2-fluorophenyl)-1-phenylprop-2-en-1-one was obtained as yellow solid.

2) 3-(4-Bromo-2-fluorophenyl)-1-phenylpropan-1-one

By a procedure similar to that of example 1.85.2, starting from 3-(4-bromo-2-fluorophenyl)-1-phenylprop-2-en-1-one, 3-(4-bromo-2-fluorophenyl)-1-phenylpropan-1-one was obtained as pale green oil.

¹H-NMR (500 MHz, CDCl₃): δ (ppm)=3.06 (t, J=7.6 Hz, 2H), 3.28 (t, J=7.6 Hz, 2H), 7.15-7.21 (m, 3H), 7.46 (t, J=7.9 Hz, 2H), 7.54-7.59 (m, 1H), 7.91-7.97 (m, 2H).

¹³C-NMR (125 MHz, CDCl₃): δ (ppm)=23.5, 38.4, 118.8, 119.0, 120, 127.3, 128.0, 128.6, 132.0, 133.2, 136.6, 161.0 (d, $^1J_{C-F}$=249.5 Hz), 198.6.

3) (Z)-Ethyl 5-(4-bromo-2-fluorophenyl)-3-phenylpent-2-enoate and (E)-Ethyl 5-(4-bromo-2-fluorophenyl)-3-phenylpent-2-enoate By a procedure similar to that of example 1.85.3, starting from 3-(4-bromo-2-fluorophenyl)-1-phenylpropan-1-one, (Z)-ethyl 5-(4-bromo-2-fluorophenyl)-3-phenylpent-2-enoate and (E)-ethyl 5-(4-bromo-2-fluorophenyl)-3-phenylpent-2-enoate were obtained as colourless oils.

(Z)-Isomer: ¹H-NMR (500 MHz, CDCl₃): δ (ppm)=1.06 (t, J=7.2 Hz, 3H), 2.66-2.75 (m, 4H), 3.98 (q, J=7.2 Hz, 2H), 5.87 (s, 1H), 6.96 (t, J=8.2 Hz, 1H), 7.18 (d, J=8.8 Hz, 4H), 7.31-7.38 (m, 3H). ¹³C-NMR (125 MHz, CDCl₃): δ (ppm)= 13.9, 27.1, 40.1, 60.0, 118.1, 118.9, 119.0, 119.5, 126.8, 127.1, 127.2, 127.3, 127.9, 131.5, 139.4, 158.5 (d, $^1J_{C-F}$=299.4 Hz), 165.8.

(E)-Isomer: ¹H-NMR (500 MHz, CDCl₃): δ (ppm)=1.30 (t, J=6.9 Hz, 3H), 2.73-2.76 (m, 2H), 3.35-3.38 (m, 2H), 4.19 (q, J=6.9 Hz, 2H), 6.09 (s, 1H), 7.10-7.18 (m, 3H), 7.37-7.39 (m, 3H), 7.45-7.47 (m, 2H). ¹³C-NMR (125 MHz, CDCl₃): δ (ppm)=14.3, 28.0, 31.1, 60.0, 118.2, 118.6, 119.7, 126.7, 127.1, 127.4, 128.6, 129.1, 131.9, 132.0, 140.6, 158.4, 160.5 (d, $^1J_{C-F}$=249.5 Hz).

4) (Z)-5-(4-Bromo-2-fluorophenyl)-3-phenylpent-2-enoic acid

By a procedure similar to that of example 1.85.4, starting from (Z)-ethyl 5-(4-bromo-2-fluorophenyl)-3-phenylpent-2-enoate, (Z)-5-(4-bromo-2-fluorophenyl)-3-phenylpent-2-enoic acid was obtained as colourless solid.

¹H-NMR (500 MHz, CDCl₃): δ (ppm)=2.65-2.68 (m, 2H), 2.74-2.78 (m, 2H), 5.86 (s, 1H), 7.18-7.22 (m, 4H), 7.17-7.38 (m, 4H).

¹³C-NMR (125 MHz, CDCl₃): δ (ppm)=27.0, 28.0, 35.6, 40.5, 116.9, 118.8, 119.2, 120.1, 126.0, 127.5, 128.5, 131.4, 141.4, 161.0 (d, $^1J_{C-F}$=258.4 Hz), 169.8.

5) (E)-5-(4-Bromo-2-fluorophenyl)-3-phenylpent-2-enoic acid

By a procedure similar to that of example 1.85.5, starting from (E)-ethyl 5-(4-bromo-2-fluorophenyl)-3-phenylpent-2-enoate, (E)-5-(4-bromo-2-fluorophenyl)-3-phenylpent-2-enoic acid was obtained as colourless solid.

¹H-NMR (500 MHz, CDCl₃): δ (ppm)=2.76-2.79 (m, 2H), 3.37-3.41 (m, 2H), 6.14 (s, 1H), 7.08 (d, J=8.2 Hz, 1H), 7.14-7.19 (m, 2H), 7.40-7.41 (m, 3H), 7.48-7.50 (m, 2H).

¹³C-NMR (125 MHz, CDCl₃): δ (ppm)=28.1, 31.4, 117.0, 118.7, 118.9, 119.9, 126.7, 127.2, 127.3, 128.7, 129.5, 131.9, 160.9 (d, $^1J_{C-F}$=250.2 Hz), 161.6, 170.9.

1.101. (Z)-5-(Biphenyl-4-yl)-3-phenylpent-2-enoic acid and (E)-5-(Biphenyl-4-yl)-3-phenylpent-2-enoic acid (PS 134+PS-T2)

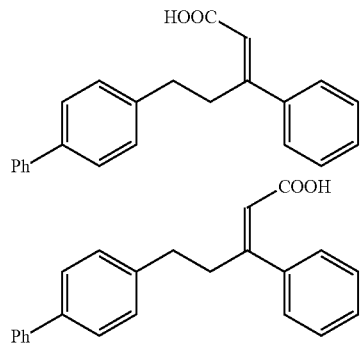

1) 3-(Biphenyl-4-yl)-1-phenylprop-2-en-1-one

By a procedure similar to that of example 1.59.1, starting from 4-biphenylcarboxaldehyde and acetophenone, 3-(biphenyl-4-yl)-1-phenylprop-2-en-1-one was obtained as yellowish solid.

2) 3-(Biphenyl-4-yl)-1-phenylpropan-1-one

By a procedure similar to that of example 1.85.2, starting from 3-(biphenyl-4-yl)-1-phenylprop-2-en-1-one, 3-(biphenyl-4-yl)-1-phenylpropan-1-one was obtained as yellowish solid.

¹H-NMR (500 MHz, CDCl₃): δ (ppm)=3.13 (t, J=7.6 Hz, 2H), 3.35 (t, J=7.6 Hz, 2H), 7.31-7.35 (m, 3H), 7.42-7.48 (m, 4H), 7.55-7.59 (m, 5H), 7.97-8.00 (m, 2H).

¹³C-NMR (125 MHz, CDCl₃): δ (ppm)=29.7, 40.4, 126.9, 127.0, 127.2, 128.0, 128.6, 128.7, 128.9, 133.1, 136.9, 139.1, 140.4, 140.9, 199.1.

3) (Z)-Ethyl 5-(biphenyl-4-yl)-3-phenylpent-2-enoate and (E)-Ethyl 5-(biphenyl-4-yl)-3-phenylpent-2-enoate By a procedure similar to that of example 1.85.3, starting from 3-(biphenyl-4-yl)-1-phenylpropan-1-one, (Z)-ethyl 5-(biphenyl-4-yl)-3-phenylpent-2-enoate and (E)-ethyl 5-(biphenyl-4-yl)-3-phenylpent-2-enoate were obtained as colourless oils.

(Z)-Isomer: ¹H-NMR (500 MHz, CDCl₃): δ (ppm)=1.07 (t, J=7.2 Hz, 3H), 2.73-2.82 (m, 4H), 3.99 (q, J=7.2 Hz, 2H), 5.93 (s, 1H), 7.20-7.22 (m, 4H), 7.31-7.39 (m, 4H), 7.42 (t, J=7.5 Hz, 2H), 7.49-7.51 (m, 2H), 7.56-7.59 (m, 2H). ¹³C-NMR (125 MHz, CDCl₃): δ (ppm)=13.9, 33.4, 42.0, 59.8, 117.8, 127.0, 127.2, 127.3, 127.7, 127.9, 128.7, 138.6, 139.0, 139.8, 139.9, 140.9, 158.3, 166.0.

(E)-Isomer: ¹H-NMR (500 MHz, CDCl₃): δ (ppm)=1.31 (t, J=7.2 Hz, 3H), 2.77-2.81 (m, 2H), 3.42-3.46 (m, 2H), 4.22 (q, J=7.2 Hz, 2H), 6.09 (s, 1H), 7.30-7.37 (m, 3H), 7.38-7.48 (m, 5H), 7.49-7.51 (m, 4H), 7.56-7.59 (m, 2H). ¹³C-NMR (125 MHz, CDCl₃): δ (ppm)=14.3, 33.1, 34.8, 59.9, 117.9, 126.7, 126.9, 127.0, 128.6, 128.7, 128.9, 129.0, 138.9, 140.7, 141.0, 141.1, 159.3, 166.3.

4) (Z)-5-(Biphenyl-4-yl)-3-phenylpent-2-enoic acid

By a procedure similar to that of example 1.85.4, starting from (Z)-ethyl 5-(biphenyl-4-yl)-3-phenylpent-2-enoate, (Z)-5-(biphenyl-4-yl)-3-phenylpent-2-enoic acid was obtained as colourless solid.

$^1$H-NMR (500 MHz, CDCl$_3$): δ (ppm)=2.72-2.75 (m, 2H), 2.78-2.83 (m, 2H), 5.91 (s, 1H), 7.20 (t, J=7.9 Hz, 4H), 7.30-7.39 (m, 4H), 7.42 (t, J=7.9 Hz, 2H), 7.50 (d, J=8.2 Hz, 2H), 7.56-7.58 (m, 2H).

$^{13}$C-NMR (125 MHz, CDCl$_3$): δ (ppm)=33.4, 42.3, 116.6, 127.0, 127.1, 127.2, 128.1, 128.7, 139.1, 139.7, 140.9, 141.5, 160.9, 173.7.

5) (E)-5-(Biphenyl-4-yl)-3-phenylpent-2-enoic acid

By a procedure similar to that of example 1.85.5, starting from (E)-ethyl 5-(biphenyl-4-yl)-3-phenylpent-2-enoate, (E)-5-(biphenyl-4-yl)-3-phenylpent-2-enoic acid was obtained as colourless solid.

$^1$H-NMR (500 MHz, CDCl$_3$): δ (ppm)=2.79-2.83 (m, 2H), 3.44-3.48 (m, 2H), 6.15 (s, 1H), 7.29-7.32 (m, 3H), 7.39-7.44 (m, 5H), 7.50-7.52 (m, 4H), 7.55-7.57 (m, 2H).

$^{13}$C-NMR (125 MHz, CDCl$_3$): δ (ppm)=33.5, 34.9, 116.8, 126.6, 126.8, 127.0, 127.1, 128.7, 128.9, 129.4, 139.0, 140.5, 140.8, 141.1, 162.3, 170.7.

1.102. (Z)-5-(2-Naphthalenyl)-3-phenylpent-2-enoic acid and (E)-5-(2-Naphthalenyl)-3-phenylpent-2-enoic acid (PS 138+PS-T4)

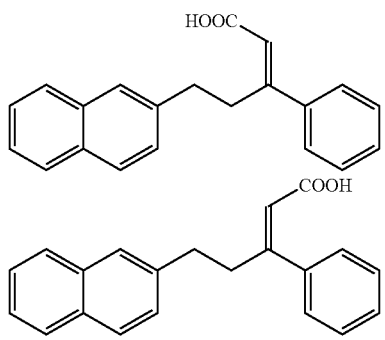

1) 3-(2-Naphthalenyl)-1-phenylprop-2-en-1-one

By a procedure similar to that of example 1.59.1, starting from 2-naphthaldehyde and acetophenone, 3-(2-naphthalenyl)-1-phenylprop-2-en-1-one was obtained as yellowish solid.

2) 3-(2-Naphthalenyl)-1-phenylpropan-1-one

By a procedure similar to that of example 1.85.2, starting from 3-(2-naphthalenyl)-1-phenylprop-2-en-1-one, 3-(2-naphthalenyl)-1-phenylpropan-1-one was obtained as colourless solid.

$^1$H-NMR (500 MHz, CDCl$_3$): δ (ppm)=3.25 (t, J=8.5 Hz, 2H), 3.40 (t, J=8.5 Hz, 2H), 7.39-7.48 (m, 5H), 7.56 (m, 1H), 7.70 (s, 1H), 7.78-7.82 (m, 3H), 7.98 (dd, J=1.3, 8.5 Hz, 2H).

$^{13}$C-NMR (125 MHz, CDCl$_3$): δ (ppm)=30.2, 40.3, 125.3, 126.0, 126.5, 127.1, 127.4, 127.6, 128.0, 128.1, 128.6, 132.1, 133.1, 133.6, 136.9, 138.8, 187.9.

3) (Z)-Ethyl 5-(2-naphthalenyl)-3-phenylpent-2-enoate and (E)-Ethyl 5-(2-naphthalenyl)-3-phenyl-pent-2-enoate By a procedure similar to that of example 1.85.3, starting from 3-(2-naphthalenyl)-1-phenylpropan-1-one, (Z)-ethyl 5-(2-naphthalenyl)-3-phenylpent-2-enoate and (E)-ethyl 5-(2-naphthalenyl)-3-phenylpent-2-enoate were obtained as colourless oils.

(Z)-Isomer: $^1$H-NMR (500 MHz, CDCl$_3$): δ (ppm)=1.06 (t, J=7.2 Hz, 3H), 2.83-2.90 (m, 4H), 3.98 (q, J=7.2 Hz, 2H), 5.94 (s, 1H), 7.21 (dd, J=1.7, 8.2 Hz, 2H), 7.23-7.28 (m, 1H), 7.32-7.47 (m, 5H), 7.56 (s, 1H), 7.76 (d, J=7.9 Hz, 2H), 7.80 (d, J=7.9 Hz, 1H). $^{13}$C-NMR (125 MHz, CDCl$_3$): δ (ppm)= 13.9, 34.0, 41.9, 59.8, 117.8, 125.3, 126.0, 126.4, 127.0, 127.3, 127.4, 127.6, 127.8, 127.9, 128.0, 132.1, 133.6, 138.3, 139.8, 158.4, 165.9.

(E)-Isomer: $^1$H-NMR (500 MHz, CDCl$_3$): δ (ppm)=1.29 (t, J=7.2 Hz, 3H), 2.89-2.92 (m, 2H), 3.48-3.52 (m, 2H), 4.20 (q, J=7.2 Hz, 2H), 6.08 (s, 1H), 7.39-7.50 (m, 8H), 7.63 (s, 1H), 7.75-7.80 (m, 3H). $^{13}$C-NMR (125 MHz, CDCl$_3$): δ (ppm)=14.3, 33.0, 35.3, 59.9, 118.0, 125.1, 125.8, 126.4, 126.8, 127.4, 127.5, 127.6, 127.8, 128.6, 129.0, 132.1, 133.6, 139.1, 141.1, 159.3, 166.4.

4) (Z)-5-(2-Naphthalenyl)-3-phenylpent-2-enoic acid

By a procedure similar to that of example 1.85.4, starting from (Z)-ethyl 5-(2-naphthalenyl)-3-phenylpent-2-enoate, (Z)-5-(2-naphthalenyl)-3-phenylpent-2-enoic acid was obtained as colourless solid.

$^1$H-NMR (500 MHz, CDCl$_3$): δ (ppm)=2.84-2.89 (m, 4H), 5.92 (s, 1H), 7.21 (dd, J=1.7, 8.2 Hz, 2H), 7.27 (m, 1H), 7.30-7.47 (m, 6H), 7.55 (s, 1H), 7.74-7.82 (m, 2H).

$^{13}$C-NMR (125 MHz, CDCl$_3$): δ (ppm)=34.1, 42.5, 116.9, 125.6, 126.3, 126.7, 127.2, 127.5, 127.7, 127.9, 128.3, 128.4, 128.7, 133.8, 138.3, 139.4, 159.8, 173.3.

5) (E)-5-(2-Naphthalenyl)-3-phenylpent-2-enoic acid

By a procedure similar to that of example 1.85.5, starting from (E)-ethyl 5-(2-naphthalenyl)-3-phenylpent-2-enoate, (E)-5-(2-naphthalenyl)-3-phenylpent-2-enoic acid was obtained as colourless solid.

$^1$H-NMR (500 MHz, CDCl$_3$): δ (ppm)=2.91-2.94 (m, 2H), 3.49-3.53 (m, 2H), 6.14 (s, 1H), 7.38-7.44 (m, 6H), 7.51-7.53 (m, 2H), 7.62 (s, 1H), 7.74-7.79 (m, 3H).

$^{13}$C-NMR (125 MHz, CDCl$_3$): δ (ppm)=33.3, 35.4, 116.5, 125.2, 126.5, 126.8, 127.2, 127.4, 127.9, 128.4, 128.7, 129.4, 130.9, 132.1, 138.6, 138.7, 162.4, 170.9.

1.103. (Z)-5-(4-Chlorophenyl)-3-(2-naphthalenyl) pent-2-enoic acid and (E)-5-(4-Chlorophenyl)-3-(2-naphthalenyl)pent-2-enoic acid (PS 246+PS 247)

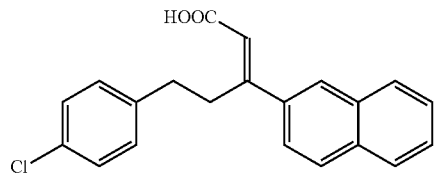

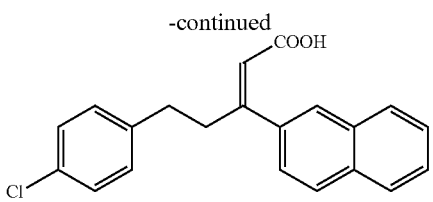

1) 1-(4-Chlorophenyl)-3-(2-naphthalenyl)prop-2-en-1-one

By a procedure similar to that of example 1.59.1, starting from commercial 2-acetylnaphthalene and 4-chlorobenzaldehyde, 1-(4-chlorophenyl)-3-(2-naphthalenyl)prop-2-en-1-one was obtained as yellowish solid.

$^1$H-NMR (500 MHz, CDCl$_3$): δ (ppm)=7.41 (d, J=8.2 Hz, 2H), 7.56-7.63 (m, 4H), 7.67 (d, J=15.8 Hz, 1H), 7.82 (d, J=15.8 Hz, 1H), 7.90 (d, J=8.2 Hz, 1H), 7.94 (d, J=9.8 Hz, 1H), 8.00 (d, J=8.2 Hz, 1H), 8.10 (d, J=8.5 Hz, 1H), 8.53 (s, 1H).
$^{13}$C-NMR (125 MHz, CDCl$_3$): δ (ppm)=122.5, 124.4, 126.8, 127.8, 128.5, 128.6, 129.2, 129.5, 129.6, 129.9, 132.5, 133.5, 135.4, 135.5, 136.4, 143.2, 189.9 (CO).

2) 1-(4-Chlorophenyl)-3-(2-naphthalenyl)propan-1-one

By a procedure similar to that of example 1.85.2, starting from 1-(4-chlorophenyl)-3-(2-naphthalenyl)prop-2-en-1-one, 1-(4-chlorophenyl)-3-(2-naphthalenyl)propan-1-one was obtained as colourless oil.

$^1$H-NMR (500 MHz, CDCl$_3$): δ (ppm)=3.11 (t, J=7.9 Hz, 2H), 3.42 (t, J=7.9 Hz, 2H), 7.22 (d, J=8.5 Hz, 2H), 7.27 (d, J=8.5 Hz, 2H), 7.55 (t, J=7.5 Hz, 1H), 7.59 (t, J=7.5 Hz, 1H), 7.89 (t, J=8.8 Hz, 2H), 7.94 (d, J=8.2 Hz, 1H), 8.01 (dd, J=1.8, 8.5 Hz, 1H), 8.53 (s, 1H).
$^{13}$C-NMR (125 MHz, CDCl$_3$): δ (ppm)=29.5, 40.2, 117.4, 123.8, 127.8, 128.4, 128.5, 128.6, 129.5, 129.6, 129.8, 131.9, 132.5, 134.1, 135.6, 139.8, 198.7 (CO).

3) (Z)-Ethyl 5-(4-chlorophenyl)-3-(2-naphthalenyl)pent-2-enoate and (E)-Ethyl 5-(4-chlorophenyl)-3-(2-naphthalenyl)pent-2-enoate By a procedure similar to that of example 1.85.3, starting from 1-(4-chlorophenyl)-3-(2-naphthalenyl)propan-1-one, (Z)-ethyl 5-(4-chlorophenyl)-3-(2-naphthalenyl)pent-2-enoate and (E)-ethyl 5-(4-chlorophenyl)-3-(2-naphthalenyl)pent-2-enoate were obtained as colourless oils.

(Z)-Isomer: $^1$H-NMR (500 MHz, CDCl$_3$): δ (ppm)=1.00 (t, J=7.2 Hz, 3H), 2.68-2.71 (m, 2H), 2.82-2.86 (m, 2H), 3.97 (q, J=7.2 Hz, 2H), 5.97 (s, 1H), 7.05 (d, J=8.5 Hz, 2H), 7.23 (d, J=8.5 Hz, 2H), 7.30 (dd, J=1.9, 8.5 Hz, 1H), 7.47-7.51 (m, 2H), 7.64 (d, J=1.6 Hz, 1H), 7.82-7.86 (m, 3H). $^{13}$C-NMR (125 MHz, CDCl$_3$): δ (ppm)=13.9, 32.2, 41.9, 59.9, 118.4, 125.9, 126.0, 126.1, 126.2, 127.5, 127.7, 128.1, 128.5, 129.7, 131.9, 132.9, 133.0, 137.1, 139.2, 157.7, 165.8 (CO).

(E)-Isomer: $^1$H-NMR (500 MHz, CDCl$_3$): δ (ppm)=1.33 (t, J=7.2 Hz, 3H), 2.74-2.77 (m, 2H), 3.48-3.52 (m, 2H), 4.22 (q, J=7.2 Hz, 2H), 6.20 (s, 1H), 7.15 (d, J=8.5 Hz, 2H), 7.22 (d, J=8.2 Hz, 2H), 7.51-7.54 (m, 2H), 7.56 (dd, J=1.9, 8.5 Hz, 1H), 7.84-7.88 (m, 3H), 7.90 (d, J=1.6 Hz, 1H). $^{13}$C-NMR (125 MHz, CDCl$_3$): δ (ppm)=14.3, 32.8, 34.5, 60.0, 118.4, 124.3, 126.2, 126.6, 126.8, 127.6, 128.3, 128.4, 128.5, 129.9, 131.7, 133.2, 133.5, 138.1, 139.9, 158.9, 166.3 (CO).

4) (Z)-5-(4-Chlorophenyl)-3-(2-naphthalenyl)pent-2-enoic acid

By a procedure similar to that of example 1.85.4, starting from (Z)-ethyl 5-(4-chlorophenyl)-3-(2-naphthalenyl)pent-2-enoate, (Z)-5-(4-chlorophenyl)-3-(2-naphthalenyl)pent-2-enoic acid was obtained as colourless solid.

$^1$H-NMR (500 MHz, CDCl$_3$): δ (ppm)=2.65-2.68 (m, 2H), 2.82-2.85 (m, 2H), 5.92 (s, 1H), 7.02 (d, J=8.2 Hz, 2H), 7.22 (d, J=8.2 Hz, 2H), 7.42-7.45 (m, 2H), 7.52 (dd, J=1.9, 8.5 Hz, 1H), 7.62 (s, 1H), 7.76-7.78 (m, 3H).
$^{13}$C-NMR (125 MHz, CDCl$_3$): δ (ppm)=33.1, 34.6, 117.1, 117.2, 124.3, 125.9, 126.1, 126.3, 126.4, 127.7, 128.1, 128.6, 129.6, 129.8, 132.0, 133.0, 136.4, 138.9, 160.5 (CO).

5) (E)-5-(4-Chlorophenyl)-3-(2-naphthalenyl)pent-2-enoic acid

By a procedure similar to that of example 1.85.5, starting from (E)-ethyl 5-(4-chlorophenyl)-3-(2-naphthalenyl)pent-2-enoate, (E)-5-(4-chlorophenyl)-3-(2-naphthalenyl)pent-2-enoic acid was obtained as colourless solid.

$^1$H-NMR (500 MHz, CDCl$_3$): δ (ppm)=2.77-2.80 (m, 2H), 3.51-3.54 (m, 2H), 6.27 (s, 1H), 7.15 (d, J=8.5 Hz, 2H), 7.23 (d, J=8.5 Hz, 2H), 7.53-7.56 (m, 2H), 7.58 (dd, J=1.9, 8.5 Hz, 1H), 7.86-7.91 (m, 3H), 7.94 (d, J=1.6 Hz, 1H).
$^{13}$C-NMR (125 MHz, CDCl$_3$): δ (ppm)=33.1, 34.6, 117.1, 117.2, 117.5, 124.2, 126.5, 126.7, 127.0, 127.6, 128.4, 128.5, 129.8, 131.8, 133.1, 133.7, 137.9, 139.7, 162.0 (CO).

1.104. (Z)-5-(4-Chlorophenyl)-3-(1-naphthalenyl)pent-2-enoic acid and (E)-5-(4-Chlorophenyl)-3-(1-naphthalenyl)pent-2-enoic acid (PS 248+PS 249)

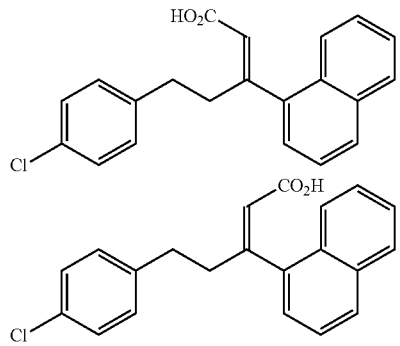

1) 1-(4-Chlorophenyl)-3-(1-naphthalenyl)prop-2-en-1-one

By a procedure similar to that of example 1.59.1, starting from commercial 1-acetylnaphthalene and 4-chlorobenzaldehyde, 1-(4-chlorophenyl)-3-(1-naphthalenyl)prop-2-en-1-one was obtained as yellow solid.

$^1$H-NMR (500 MHz, CDCl$_3$): δ (ppm)=7.35 (d, J=16.1 Hz, 1H), 7.44 (d, J=7.9 Hz, 2H), 7.57 (d, J=7.9 Hz, 2H), 7.59-7.67 (m, 4H), 7.85 (d, J=7.2 Hz, 1H), 7.99 (d, J=7.9 Hz, 1H), 8.08 (d, J=8.2 Hz, 1H), 8.41 (d, J=8.2 Hz, 1H).

<sup>13</sup>C-NMR (125 MHz, CDCl<sub>3</sub>): δ (ppm)=124.4, 125.6, 126.5, 127.2, 127.4, 127.7, 128.4, 129.2, 129.6, 130.4, 131.8, 133.1, 133.8, 136.6, 136.8, 144.2, 195.2 (CO).

2) 1-(4-Chlorophenyl)-3-(1-naphthalenyl)propan-1-one

By a procedure similar to that of example 1.85.2, starting from 1-(4-chlorophenyl)-3-(1-naphthalenyl)prop-2-en-1-one, 1-(4-chlorophenyl)-3-(1-naphthalenyl)propan-1-one was obtained as colourless oil.

<sup>1</sup>H-NMR (500 MHz, CDCl<sub>3</sub>): δ (ppm)=3.07 (t, J=7.2 Hz, 2H), 3.32 (t, J=7.2 Hz, 2H), 7.15 (d, J=7.9 Hz, 2H), 7.22 (d, J=8.2 Hz, 2H), 7.34 (d, J=8.5 Hz, 1H), 7.46-7.53 (m, 2H), 7.77 (dd, J=1.3, 7.2 Hz, 1H), 7.84 (d, J=7.9 Hz, 1H), 7.94 (d, J=8.2 Hz, 1H), 8.50 (dd, J=8.8 Hz, 1H).

3) (Z)-Ethyl 5-(4-chlorophenyl)-3-(1-naphthalenyl)pent-2-enoate and (E)-Ethyl 5-(4-chlorophenyl)-3-(1-naphthalenyl)pent-2-enoate By a procedure similar to that of example 1.85.3, starting from 1-(4-chlorophenyl)-3-(1-naphthalenyl)propan-1-one, (Z)-ethyl 5-(4-chlorophenyl)-3-(1-naphthalenyl)pent-2-enoate and (E)-ethyl 5-(4-chlorophenyl)-3-(1-naphthalenyl)pent-2-enoate were obtained as colourless oils.

(Z)-Isomer: <sup>1</sup>H-NMR (500 MHz, CDCl<sub>3</sub>): δ (ppm)=1.36 (t, J=7.2 Hz, 3H), 2.68-2.71 (m, 2H), 3.40-3.42 (m, 2H), 4.27 (q, J=7.2 Hz, 2H), 5.97 (s, 1H), 7.07 (d, J=8.5 Hz, 2H), 7.17 (d, J=8.5 Hz, 2H), 7.23-7.49 (m, 1H), 7.37-7.53 (m, 3H), 7.80-7.90 (m, 3H). <sup>13</sup>C-NMR (125 MHz, CDCl<sub>3</sub>): δ (ppm)= 14.3, 33.9, 36.0, 60.1, 121.2, 124.8, 125.2, 125.3, 128.3, 128.4, 128.5, 129.8, 130.6, 131.6, 133.7, 134.5, 140.2, 159.9, 166.3 (CO).

(E)-Isomer: <sup>1</sup>H-NMR (500 MHz, CDCl<sub>3</sub>): δ (ppm)=0.78 (t, J=7.2 Hz, 3H), 2.69-2.85 (m, 4H), 3.81 (q, J=7.2 Hz, 2H), 6.21 (s, 1H), 7.05 (d, J=8.5 Hz, 2H), 7.18-7.23 (m, 3H), 7.39-7.49 (m, 3H), 7.72 (d, J=8.2 Hz, 1H), 7.81 (d, J=8.2 Hz, 1H), 7.86 (d, J=8.8 Hz, 1H). <sup>13</sup>C-NMR (125 MHz, CDCl<sub>3</sub>): δ (ppm)=13.5, 33.1, 42.0, 59.7, 120.3, 123.7, 124.8, 125.0, 125.7, 126.0, 127.6, 128.2, 128.5, 129.6, 130.5, 131.8, 133.4, 138.2, 139.2, 156.8, 165.3 (CO).

4) (Z)-5-(4-Chlorophenyl)-3-(1-naphthalenyl)pent-2-enoic acid

By a procedure similar to that of example 1.85.4, starting from (Z)-ethyl 5-(4-chlorophenyl)-3-(1-naphthalenyl)pent-2-enoate, (Z)-5-(4-chlorophenyl)-3-(1-naphthalenyl)pent-2-enoic acid was obtained as colourless solid.

<sup>1</sup>H-NMR (500 MHz, CDCl<sub>3</sub>): δ (ppm)=2.72-2.74 (m, 2H), 3.42-3.45 (m, 2H), 6.05 (s, 1H), 7.06 (d, J=8.5 Hz, 2H), 7.17 (d, J=8.5 Hz, 2H), 7.24-7.31 (m, 2H), 7.51-7.64 (m, 3H), 7.83-7.93 (m, 2H).

<sup>13</sup>C-NMR (125 MHz, CDCl<sub>3</sub>): δ (ppm)=34.0, 36.3, 120.2, 124.7, 125.1, 125.2, 126.1, 126.5, 128.4, 128.5, 128.6, 128.8, 129.8, 133.7, 134.8, 137.0, 139.6, 163.2, 170.2 (CO).

5) (E)-5-(4-Chlorophenyl)-3-(1-naphthalenyl)pent-2-enoic acid

By a procedure similar to that of example 1.85.5, starting from (E)-ethyl 5-(4-chlorophenyl)-3-(1-naphthalenyl)pent-2-enoate, (E)-5-(4-chlorophenyl)-3-(1-naphthalenyl)pent-2-enoic acid was obtained as colourless solid.

<sup>1</sup>H-NMR (500 MHz, CDCl<sub>3</sub>): δ (ppm)=2.81-2.84 (m, 2H), 3.58-3.60 (m, 2H), 6.15 (s, 1H), 7.02 (d, J=8.5 Hz, 2H), 7.20 (d, J=8.5 Hz, 2H), 7.42-7.49 (m, 3H), 7.66 (d, J=8.5 Hz, 1H), 7.80 (d, J=8.2 Hz, 1H), 7.85 (d, J=7.6 Hz, 2H).

<sup>13</sup>C-NMR (125 MHz, CDCl<sub>3</sub>): δ (ppm)=33.1, 42.2, 117.3, 119.2, 123.9, 124.6, 125.0, 125.9, 126.2, 126.3, 127.7, 127.9, 129.6, 131.9, 133.4, 137.4, 138.9, 159.7, 168.4 (CO).

1.105. (Z)-5-(1H-Indol-3-yl)-3-phenylpent-2-enoic acid and (E)-5-(1H-Indol-3-yl)-3-phenylpent-2-enoic acid (PS 158+PS 159)

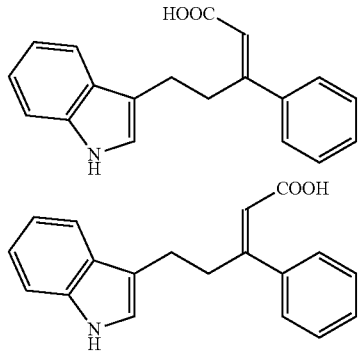

1) 3-(1H-Indol-3-yl)-1-phenylprop-2-en-1-one

By a procedure similar to that of example 1.59.1, starting from commercial 3-indolecarbaldehyde and acetophenone, 3-(1H-indol-3-yl)-1-phenylprop-2-en-1-one was obtained as yellow solid.

2) 3-(1H-Indol-3-yl)-1-phenylpropan-1-one

By a procedure similar to that of example 1.85.2, starting from 3-(1H-indol-3-yl)-1-phenylprop-2-en-1-one, 3-(1H-indol-3-yl)-1-phenylpropan-1-one was obtained as colourless solid.

<sup>1</sup>H-NMR (500 MHz, CDCl<sub>3</sub>): δ (ppm)=3.23 (t, J=7.6 Hz, 2H), 3.39 (t, J=7.6 Hz, 2H), 7.05-7.06 (m, 1H), 7.14 (dt, J=0.9, 7.2 Hz, 1H), 7.21 (dt, J=1.3, 8.2 Hz, 1H), 7.36 (d, J=8.2 Hz, 1H), 7.43-7.47 (m, 2H), 7.53-7.57 (m, 1H), 7.64 (d, J=8.5 Hz, 1H), 7.96-7.99 (m, 2H).

<sup>13</sup>C-NMR (125 MHz, CDCl<sub>3</sub>): δ (ppm)=19.7, 39.3, 111.1, 115.5, 118.7, 119.3, 121.5, 122.0, 127.3, 128.0, 128.5, 132.9, 136.3, 137.0, 199.9.

3) (Z)-Ethyl 5-(1H-indol-3-yl)-3-phenylpent-2-enoate and (E)-Ethyl 5-(1H-indol-3-yl)-3-phenylpent-2-enoate By a procedure similar to that of example 1.85.3, starting from 3-(1H-indol-3-yl)-1-phenylpropan-1-one, (Z)-ethyl 5-(1H-indol-3-yl)-3-phenylpent-2-enoate and (E)-ethyl 5-(1H-indol-3-yl)-3-phenylpent-2-enoate were obtained as light tan oils.

(Z)-Isomer: <sup>1</sup>H-NMR (500 MHz, CDCl<sub>3</sub>): δ (ppm)=1.07 (t, J=6.9 Hz, 3H), 2.82-2.90 (m, 4H), 3.99 (q, J=6.9 Hz, 2H), 5.94 (s, 1H), 6.96 (s, 1H), 7.10 (dt, J=0.9, 7.9 Hz, 1H), 7.19-7.23 (m, 3H), 7.31-7.38 (m, 4H), 7.51 (d, J=7.9 Hz, 1H), 7.93 (s, NH).

(E)-Isomer: <sup>1</sup>H-NMR (500 MHz, CDCl<sub>3</sub>): δ (ppm)=1.29 (t, J=7.2 Hz, 3H), 2.87-2.91 (m, 2H), 3.49-3.52 (m, 2H), 4.19 (q, J=7.2 Hz, 2H), 6.09 (s, 1H), 7.00-7.01 (m, 1H), 7.10 (dt, J=1.3, 8.2 Hz, 1H), 7.17 (dt, J=1.3, 8.2 Hz, 1H), 7.33 (d, J=8.2 Hz, 1H), 7.37-7.41 (m, 3H), 7.48-7.50 (m, 2H), 7.63 (d, J=7.9 Hz, 1H), 7.91 (s, NH).

4) (Z)-5-(1H-Indol-3-yl)-3-phenylpent-2-enoic acid

By a procedure similar to that of example 1.85.4, starting from (Z)-ethyl 5-(1H-indol-3-yl)-3-phenylpent-2-enoate, (Z)-5-(1H-indol-3-yl)-3-phenylpent-2-enoic acid was obtained as colourless solid.

$^1$H-NMR (500 MHz, CD$_3$OD): δ (ppm)=2.68-2.71 (m, 2H), 2.79-2.82 (m, 2H), 5.89 (s, 1H), 6.95 (dt, J=0.9, 7.6 Hz, 1H), 7.05 (dt, J=0.9, 7.6 Hz, 1H), 7.10-7.11 (d, J=2.2 Hz, 1H), 7.23-7.25 (m, 2H), 7.29-7.38 (m, 4H), 7.41 (d, J=7.9 Hz, 1H), 10.78 (s, NH), 11.85 (s, OH).

$^{13}$C-NMR (125 MHz, CD$_3$OD): δ (ppm)=24.6, 42.3, 112.2, 115.1, 118.7, 119.2, 119.5, 122.3, 123.0, 128.5, 128.6, 128.7, 128.9, 138.2, 141.4, 160.7, 169.8.

5) (E)-5-(1H-Indol-3-yl)-3-phenylpent-2-enoic acid

By a procedure similar to that of example 1.85.5, starting from (E)-ethyl 5-(1H-indol-3-yl)-3-phenylpent-2-enoate, (E)-5-(1H-indol-3-yl)-3-phenylpent-2-enoic acid was obtained as colourless solid.

$^1$H-NMR (500 MHz, CD$_3$OD): δ (ppm)=2.72-2.75 (m, 2H), 3.39-3.43 (m, 2H), 6.05 (s, 1H), 6.95 (dt, J=0.9, 8.2 Hz, 1H), 7.05 (dt, J=0.9, 7.9 Hz, 1H), 7.11-7.12 (d, J=2.2 Hz, 1H), 7.31 (d, J=8.2 Hz, 1H), 7.39-7.46 (m, 3H), 7.57-7.60 (m, 3H), 10.76 (s, NH), 12.29 (s, OH).

$^{13}$C-NMR (125 MHz, CD$_3$OD): δ (ppm)=34.3, 40.9, 120.8, 123.6, 127.5, 127.6, 128.0, 130.3, 131.6, 136.1, 136.6, 138.2, 138.5, 145.8, 150.1, 168.0, 176.8.

1.106. (E)-5-(4-Chlorophenyl)-3-(2-pyridinyl)pent-2-enoic acid

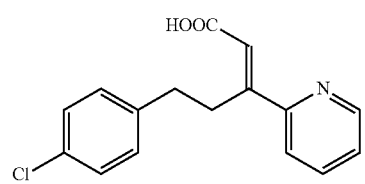 [SMILES: O=C(O)/C=C(\CCc1ccc(Cl)cc1)c1ccccn1]

1) 3-(4-Chlorophenyl)-1-(2-pyridinyl)prop-2-en-1-one

By a procedure similar to that of example 1.59.1, starting from 4-chlorobenzaldehyde and commercial 2-acetylpyridine, 3-(4-chlorophenyl)-1-(2-pyridinyl)prop-2-en-1-one was obtained as yellowish solid.

$^1$H-NMR (500 MHz, CDCl$_3$): δ (ppm)=7.39 (d, J=8.5 Hz, 2H), 7.48-7.51 (m, 1H), 7.66 (d, J=8.8 Hz, 2H), 7.86-7.90 (m, 2H), 8.19 (td, J=0.9, 7.9 Hz, 1H), 8.28 (d, J=16.1 Hz, 1H), 8.73-8.75 (m, 1H).

2) 3-(4-Chlorophenyl)-1-(2-pyridinyl)propan-1-one

By a procedure similar to that of example 1.85.2, starting from 3-(4-chlorophenyl)-1-(2-pyridinyl)prop-2-en-1-one, 3-(4-chlorophenyl)-1-(2-pyridinyl)propan-1-one was obtained as yellowish solid.

$^1$H-NMR (500 MHz, CDCl$_3$): δ (ppm)=3.04 (t, J=7.6 Hz, 2H), 3.55 (t, J=7.6 Hz, 2H), 7.19-7.25 (m, 4H), 7.45-7.48 (m, 1H), 7.82 (dt, J=7.6 Hz, 1H), 8.03 (td, J=1.3, 7.9 Hz, 1H), 8.66-8.70 (m, 1H).

3) (Z)-Ethyl 5-(4-chlorophenyl)-3-(2-pyridinyl)pent-2-enoate and (E)-Ethyl 5-(4-chlorophenyl)-3-(2-pyridinyl)pent-2-enoate By a procedure similar to that of example 1.85.3, starting from 3-(4-chlorophenyl)-1-(2-pyridinyl)propan-1-one, (Z)-ethyl 5-(4-chlorophenyl)-3-(2-pyridinyl)pent-2-enoate and (E)-ethyl 5-(4-chlorophenyl)-3-(2-pyridinyl)pent-2-enoate were obtained as colourless oils.

(Z)-Isomer: $^1$H-NMR (500 MHz, CDCl$_3$): δ (ppm)=1.09 (t, J=7.2 Hz, 3H), 2.77-2.79 (m, 2H), 3.01-3.04 (m, 2H), 4.05 (q, J=7.2 Hz, 2H), 6.30 (s, 1H), 7.06-7.08 (m, 1H), 7.16-7.27 (m, 5H), 7.54 (dt, J=1.6, 7.9 Hz, 1H), 8.49-8.51 (m, 1H).

(E)-Isomer: $^1$H-NMR (500 MHz, CDCl$_3$): δ (ppm)=1.32 (t, J=7.2 Hz, 3H), 2.75-2.79 (m, 2H), 3.47-3.50 (m, 2H), 4.21 (q, J=7.2 Hz, 2H), 6.51 (s, 1H), 7.16-7.21 (m, 4H), 7.22-7.27 (m, 1H), 7.50 (d, J=7.9 Hz, 1H), 7.70 (dt, J=1.6, 7.9 Hz, 1H), 8.65-8.67 (m, 1H).

5) (E)-5-(4-Chlorophenyl)-3-(2-pyridinyl)pent-2-enoic acid

By a procedure similar to that of example 1.85.5, starting from (E)-ethyl 5-(4-chlorophenyl)-3-(2-pyridinyl)pent-2-enoate, (E)-5-(4-chlorophenyl)-3-(2-pyridinyl)pent-2-enoic acid was obtained as yellow solid.

$^1$H-NMR (500 MHz, CDCl$_3$): δ (ppm)=2.76-2.79 (m, 2H), 3.49-3.52 (m, 2H), 6.51 (s, 1H), 7.13 (d, J=8.5 Hz, 2H), 7.20 (d, J=7.9 Hz, 2H), 7.26-7.33 (m, 1H), 7.51 (d, J=7.9 Hz, 1H), 7.74 (dt, J=1.6, 7.9 Hz, 1H), 8.69-8.70 (m, 1H).

$^{13}$C-NMR (125 MHz, CDCl$_3$): δ (ppm)=31.4, 34.6, 118.8, 121.6, 123.9, 128.3, 129.9, 137.0, 139.8, 141.4, 149.4, 157.2, 159.8, 164.2.

MS (+ESI): m/z=288 (M+H).

1.107. (Z)-4-(4-Chlorophenoxy)-3-phenylbut-2-enoic acid and (E)-4-(4-Chlorophenoxy)-3-phenylbut-2-enoic acid (PS 95+PS 97)

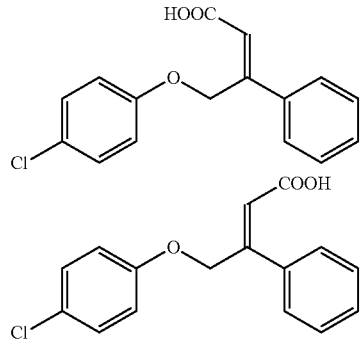

1) 2-(4-Chlorophenoxy)-1-phenylethanone

To a solution of 4-chlorophenol (0.774 g) and phenacyl bromide (1 g) in N,N-dimethyl formamide (10 ml) potassium carbonate (3.5 g) was added. The mixture was refluxed with stirring for 2 h. After cooling the reaction mixture was poured into water (50 ml) and extracted with dichloromethane (3×20 ml). The combined organic layers were washed with water (20 ml) and brine (20 ml), dried (MgSO$_4$), and evaporated. The crude was purified by flash chromatography on silica gel (petrol ether/ethyl acetate 10:1) to give 2-(4-chlorophenoxy)-1-phenylethanone (1.22 g) as pale yellow solid.

$^1$H-NMR (500 MHz, CDCl$_3$): δ (ppm)=5.26 (s, 2H), 6.85-6.89 (m, 2H), 7.22-7.25 (m, 2H), 7.51 (t, J=7.4 Hz, 2H), 7.62 (t, J=8.8 Hz, 1H), 7.97-8.00 (m, 2H).

$^{13}$C-NMR (125 MHz, CDCl$_3$): δ (ppm)=71.0, 116.2, 126.6, 128.0, 128.9, 129.4, 133.9, 134.5, 156.7, 194.1. MS (+ESI): m/z=247 (M+H).

2) (Z)-Ethyl 4-(4-chlorophenoxy)-3-phenylbut-2-enoate and (E)-Ethyl 4-(4-chlorophenoxy)-3-phenyl-but-2-enoate PS-94+PS-96

By a procedure similar to that of example 1.85.3, starting from 2-(4-chlorophenoxy)-1-phenylethanone, (Z)-ethyl 4-(4-chlorophenoxy)-3-phenylbut-2-enoate and (E)-ethyl 4-(4-chlorophenoxy)-3-phenylbut-2-enoate were obtained as colourless oils.

(Z)-Isomer: $^1$H-NMR (500 MHz, CDCl$_3$): δ (ppm)=1.32 (t, J=7.2 Hz, 3H), 4.25 (q, J=7.2 Hz, 2H), 5.56 (s, 2H), 6.25 (s, 1H), 6.81-6.83 (m, 2H), 7.17-7.21 (m, 2H), 7.35-7.38 (m, 3H), 7.46-7.48 (m, 2H). $^{13}$C-NMR (125 MHz, CDCl$_3$): δ (ppm)=14.2, 60.5, 64.4, 116.3, 120.5, 125.9, 127.2, 128.4, 129.2, 129.3, 138.2, 153.5, 157.0, 165.6.

(E)-Isomer: $^1$H-NMR (500 MHz, CDCl$_3$): δ (ppm)=1.01 (t, J=6.9 Hz, 3H), 3.94 (q, J=6.9 Hz, 2H), 4.63 (d, J=1.9 Hz, 2H), 6.19 (t, J=1.9 Hz, 1H), 6.77-6.82 (m, 2H), 7.16-7.20 (m, 4H), 7.28-7.35 (m, 3H). $^{13}$C-NMR (125 MHz, CDCl$_3$): δ (ppm)=13.9, 60.1, 71.1, 116.1, 117.4, 126.4, 127.5, 128.2, 128.4, 129.5, 136.6, 152.4, 156.5, 165.6.

3) (Z)-4-(4-Chlorophenoxy)-3-phenylbut-2-enoic acid

By a procedure similar to that of example 1.85.4, starting from (Z)-ethyl 4-(4-chlorophenoxy)-3-phenylbut-2-enoate, (Z)-4-(4-chlorophenoxy)-3-phenylbut-2-enoic acid was obtained as colourless solid.

$^1$H-NMR (500 MHz, CDCl$_3$): δ (ppm)=3.59 (s, 2H), 6.79 (s, 1H), 6.90 (d, J=8.8 Hz, 2H), 7.20-7.16 (m, 4H), 7.28-7.23 (m, 3H).

$^{13}$C-NMR (125 MHz, CDCl$_3$): δ (ppm)=64.5, 116.3, 119.2, 126.1, 127.3, 128.5, 129.3, 129.7, 137.8, 156.7, 156.9, 170.4.

4) (E)-4-(4-Chlorophenoxy)-3-phenylbut-2-enoic acid

By a procedure similar to that of example 1.85.5, starting from (E)-ethyl 4-(4-chlorophenoxy)-3-phenylbut-2-enoate, (E)-4-(4-chlorophenoxy)-3-phenylbut-2-enoic acid was obtained as colourless solid.

$^1$H-NMR (500 MHz, CDCl$_3$): δ (ppm)=5.48 (s, 2H), 6.21 (s, 1H), 6.71-6.74 (m, 2H), 7.10-7.13 (m, 2H), 7.28-7.33 (m, 3H), 7.38-7.42 (m, 2H).

$^{13}$C-NMR (125 MHz, CDCl$_3$): δ (ppm)=64.5, 116.3, 119.2, 126.1, 127.3, 128.5, 129.3, 129.7, 137.8, 156.7, 156.9, 170.4.

1.108. (E)-4-(4-Chlorophenylthio)-3-phenylbut-2-enoic acid (PS 99)

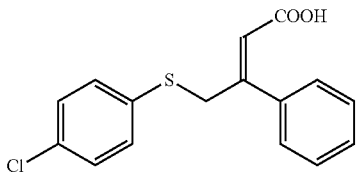 [SMILES: O=C(O)/C=C(/CSc1ccc(Cl)cc1)c1ccccc1]

1) 2-(4-Chlorophenylthio)-1-phenylethanone

To a solution of phenacyl bromide (1 g), 4-chlorothiophenol (1.37 g), and benzyl triethyl ammonium chloride (78 mg) in dichloromethane (20 ml) NaOH (0.61 g) in water (2 ml) was added. The mixture was stirred vigorously at rt for 16 h. After dilution with water (50 ml) the organic layer was separated, washed with brine (20 ml), dried (MgSO$_4$), and evaporated. The crude was purified by column chromatography on silica gel (petrol ether/ethyl acetate 12:1) to provide 2-(4-chlorophenylthio)-1-phenylethanone (0.74 g) as pale yellow solid.

$^1$H-NMR (500 MHz, CDCl$_3$): δ (ppm)=4.26 (s, 2H), 7.24-7.28 (m, 2H), 7.31-7.34 (m, 2H), 7.46-7.50 (m, 2H), 7.58-7.62 (m, 1H), 7.92-7.97 (m, 2H).

2) (E)-Ethyl 4-(4-chlorophenylthio)-3-phenylbut-2-enoate

By a procedure similar to that of example 1.85.3, starting from 2-(4-chlorophenylthio)-1-phenylethanone, (E)-ethyl 4-(4-chlorophenylthio)-3-phenylbut-2-enoate was obtained as yellowish oil. Only (E)-isomer is formed.

$^1$H-NMR (500 MHz, CDCl$_3$): δ (ppm)=1.23 (t, J=7.2 Hz, 3H), 3.77 (s, 2H), 4.14 (q, J=7.2 Hz, 2H), 6.69 (s, 1H), 7.27-7.31 (m, 3H), 7.32-7.36 (m, 4H), 7.38-7.42 (m, 2H).

$^{13}$C-NMR (125 MHz, CDCl$_3$): δ (ppm)=14.1, 27.8, 61.0, 124.8, 125.8, 127.7, 128.6, 129.2, 130.5, 132.6, 134.3, 136.1, 140.1, 170.3.

3) (E)-4-(4-Chlorophenylthio)-3-phenylbut-2-enoic acid

By a procedure similar to that of example 1.85.5, starting from (E)-ethyl 4-(4-chlorophenylthio)-3-phenylbut-2-enoate, (E)-4-(4-chlorophenylthio)-3-phenylbut-2-enoic acid was obtained as colourless solid.

$^1$H-NMR (500 MHz, CDCl$_3$): δ (ppm)=3.76 (s, 2H), 6.66 (s, 1H), 6.71-6.74 (m, 2H), 7.20-7.35 (m, 9H).

$^{13}$C-NMR (125 MHz, CDCl$_3$): δ (ppm)=37.3, 125.6, 125.7, 127.9, 128.7, 129.3, 130.7, 133.1, 134.0, 134.8, 139.7, 176.2.

1.109. (E/Z)-3-(5-Chloro-2-benzofuranyl)-3-phenylacrylic acid (PS 101)

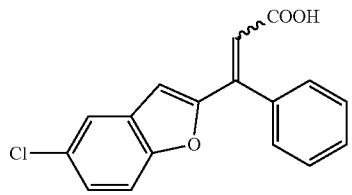 [SMILES: O=C(O)C=C(c1ccccc1)c1cc2cc(Cl)ccc2o1]

1) 2-Benzoyl-5-chlorobenzofuran

To a solution of 5-chloro-2-hydroxybenzaldehyde (2 g) and phenacyl bromide (1.85 g) in ethanol (10 ml) potassium carbonate (3.53 g) was added. The mixture was stirred at 80° C. for 1 h. Then the reaction mixture was poured into water (50 ml) and extracted with dichloromethane (3×20 ml). The combined organic layers were washed with brine (20 ml), dried (MgSO$_4$), and concentrated under reduced pressure. The crude was purified by flash chromatography on silica gel (hexane/ethyl acetate 12:1) to give 2-benzoyl-5-chlorobenzofuran (1.85 g) as colourless solid.

$^1$H-NMR (500 MHz, CDCl$_3$): δ (ppm)=7.44-7.48 (m, 2H), 7.53-7.58 (m, 3H), 7.64-7.68 (m, 1H), 7.70 (d, J=2.2 Hz, 1H), 8.03-8.06 (m, 2H).

$^{13}$C-NMR (125 MHz, CDCl$_3$): δ (ppm)=113.7, 115.4, 122.6, 126.5, 128.2, 128.6, 128.7, 129.5, 129.6, 133.2, 136.9, 154.2, 184.1.

2) (E/Z)-Ethyl 3-(5-chloro-2-benzofuranyl)-3-phenylacrylate PS 100

By a procedure similar to that of example 1.85.3, starting from 2-benzoyl-5-chlorobenzofuran, a mixture of (Z)-ethyl 3-(5-chloro-2-benzofuranyl)-3-phenylacrylate and (E)-ethyl 3-(5-chloro-2-benzofuranyl)-3-phenylacrylate was obtained as yellowish oil.

3) (E/Z)-3-(5-Chloro-2-benzofuranyl)-3-phenylacrylic acid

By a procedure similar to that of example 1.85.4, starting from a mixture of (Z)-ethyl 3-(5-chloro-2-benzofuranyl)-3-phenylacrylate and (E)-ethyl 3-(5-chloro-2-benzofuranyl)-3-phenylacrylate, a mixture of (Z)-3-(5-chloro-2-benzofuranyl)-3-phenylacrylic acid and (E)-3-(5-chloro-2-benzofuranyl)-3-phenylacrylic acid was obtained as yellowish solid.

1.110. (E/Z)-3-(5-Methyl-2-benzofuranyl)-3-phenylacrylic acid (PS 103)

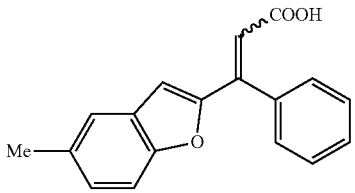 [SMILES: Cc1ccc2oc(C(=CC(=O)O)c3ccccc3)cc2c1]

1) 2-Benzoyl-5-methylbenzofuran

To a solution of 2-hydroxy-5-methylbenzaldehyde (1 g) and phenacyl bromide (1.06 g) in ethanol (10 ml) potassium carbonate (2.03 g) was added. The mixture was stirred at 80° C. for 1 h. Then the reaction mixture was poured into water (50 ml) and extracted with dichloromethane (3×20 ml). The combined organic layers were washed with brine (20 ml), dried (MgSO$_4$), and concentrated under reduced pressure. The crude was purified by flash chromatography on silica gel (hexane/ethyl acetate 12:1) to give 2-benzoyl-5-methylbenzofuran (1.1 g) as yellowish solid.

$^1$H-NMR (500 MHz, CDCl$_3$): δ (ppm)=2.47 (s, 3H), 7.31 (dd, J=1.9, 8.2 Hz, 1H), 7.46 (s, 1H), 7.49-7.55 (m, 4H), 7.61-7.66 (m, 1H), 8.03-8.06 (m, 2H).

$^{13}$C-NMR (125 MHz, CDCl$_3$): δ (ppm)=21.3, 112.1, 116.4, 122.7, 128.5, 129.4, 130.0, 132.8, 133.6, 137.3, 152.4, 154.6, 184.4.

2) (E/Z)-Ethyl 3-(5-methyl-2-benzofuranyl)-3-phenylacrylate

By a procedure similar to that of example 1.85.3, starting from 2-benzoyl-5-methylbenzofuran, a mixture of (Z)-ethyl 3-(5-methyl-2-benzofuranyl)-3-phenylacrylate and (E)-ethyl 3-(5-methyl-2-benzofuranyl)-3-phenylacrylate was obtained as yellowish oil.

3) (E/Z)-3-(5-Methyl-2-benzofuranyl)-3-phenylacrylic acid

By a procedure similar to that of example 1.85.4, starting from a mixture of (Z)-ethyl 3-(5-methyl-2-benzofuranyl)-3-phenylacrylate and (E)-ethyl 3-(5-methyl-2-benzofuranyl)-3-phenylacrylate, a mixture of (Z)-3-(5-methyl-2-benzofuranyl)-3-phenylacrylic acid and (E)-3-(5-methyl-2-benzofuranyl)-3-phenylacrylic acid was obtained as yellowish solid.

1.111. (Z)-3-(5-Chloro-2-benzothiophenyl)-3-phenylacrylic acid and (E)-3-(5-Chloro-2-benzothiophenyl)-3-phenylacrylic acid (PS 118+PS 119)

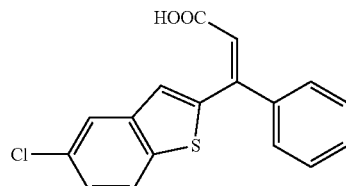

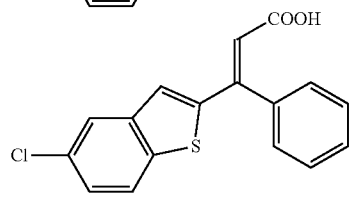

1) 2-Benzoyl-5-chlorobenzothiophene

To an ice-cold mixture of 5-chloro-2-nitro-benzaldehyde (0.2 g) and potassium carbonate (0.221 g) in N,N-dimethyl formamide a solution of α'-thioacetophenone (0.243 g) in N,N-dimethyl formamide was added with stirring. Stirring was continued while allowing the mixture to reach rt in the course of 3 h. Then the mixture was poured into water and extracted with dichloromethane. The organic layer was dried (MgSO$_4$) and concentrated under reduced pressure. The residue was purified by flash chromatography on silica gel (petrol ether/ethyl acetate 10:1) to give 2-benzoyl-5-chlorobenzothiophene (0.31 g) as yellowish solid.

$^1$H-NMR (500 MHz, CDCl$_3$): δ (ppm)=7.45 (dd, J=1.9, 8.8 Hz, 1H), 7.53-7.56 (m, 2H), 7.63-7.67 (m, 1H), 7.79 (s, 1H), 7.83-7.86 (m, 2H), 7.91-7.94 (m, 2H).

$^{13}$C-NMR (125 MHz, CDCl$_3$): δ (ppm)=124.0, 124.9, 125.3, 126.7, 127.9, 128.6, 129.3, 130.9, 131.3, 132.7, 137.5, 144.9, 189.3.

2) (Z)-Ethyl 3-(5-chloro-2-benzothiophenyl)-3-phenylacrylate and (E)-Ethyl 3-(5-chloro-2-benzothiophenyl)-3-phenylacrylate By a procedure similar to that of example 1.85.3, starting from 2-benzoyl-5-chlorobenzothiophene, (Z)-ethyl 3-(5-chloro-2-benzothiophenyl)-3-phenylacrylate and (E)-ethyl 3-(5-chloro-2-benzothiophenyl)-3-phenylacrylate were obtained as yellowish oils.

(Z)-Isomer: $^1$H-NMR (500 MHz, CDCl$_3$): δ (ppm)=1.11 (t, J=6.9 Hz, 3H), 4.04 (q, J=6.9 Hz, 2H), 6.46 (s, 1H), 6.90 (s, 1H), 7.29-7.31 (m, 2H), 7.35-7.46 (m, 3H), 7.59 (d, J=1.9 Hz, 1H), 7.69 (d, J=8.5 Hz, 1H). $^{13}$C-NMR (125 MHz, CDCl$_3$): δ (ppm)=13.9, 60.2, 118.0, 123.3, 123.8, 126.3, 126.9, 128.0, 128.4, 128.6, 135.0, 137.4, 138.0, 140.7, 146.5, 156.8, 165.3.

(E)-Isomer: $^1$H-NMR (500 MHz, CDCl$_3$): δ (ppm)=1.17 (t, J=6.9 Hz, 3H), 4.14 (q, J=6.9 Hz, 2H), 6.39 (s, 1H), 7.27 (s, 1H), 7.27-7.32 (m, 2H), 7.34-7.41 (m, 5H), 7.71-7.74 (m, 2H). $^{13}$C-NMR (125 MHz, CDCl$_3$): δ (ppm)=14.0, 60.5, 120.4, 123.2, 123.4, 125.2, 125.4, 128.2, 128.5, 128.7, 130.6, 138.8, 139.0, 140.4, 141.9, 147.9, 165.5.

3)(Z)-3-(5-Chloro-2-benzothiophenyl)-3-phenylacrylic acid

By a procedure similar to that of example 1.85.4, starting from (Z)-ethyl 3-(5-chloro-2-benzothiophenyl)-3-phenylacrylate, (Z)-3-(5-chloro-2-benzothiophenyl)-3-phenylacrylic acid was obtained as yellowish solid.

$^1$H-NMR (500 MHz, CDCl$_3$): δ (ppm)=6.43 (s, 1H), 6.85 (s, 1H), 7.26-7.30 (m, 3H), 7.36-7.39 (m, 3H), 7.54 (s, 1H), 7.65 (dd, J=8.2, 2.5 Hz, 1H).

$^{13}$C-NMR (125 MHz, CDCl$_3$): δ (ppm)=117.8, 120.5, 123.2, 123.7, 126.2, 126.3, 126.9, 127.9, 128.3, 128.6, 130.8, 138.0, 145.6, 146.5, 172.8.

4) (E)-3-(5-Chloro-2-benzothiophenyl)-3-phenylacrylic acid

By a procedure similar to that of example 1.85.5, starting from (E)-ethyl 3-(5-chloro-2-benzothiophenyl)-3-phenylacrylate, (E)-3-(5-chloro-2-benzothiophenyl)-3-phenylacrylic acid was obtained as yellowish solid.

$^1$H-NMR (500 MHz, CDCl$_3$): δ (ppm)=6.26 (s, 1H), 7.15-7.17 (m, 2H), 7.21-7.28 (m, 5H), 7.59 (d, J=19.1 Hz, 1H), 7.61 (s, 1H).

$^{13}$C-NMR (125 MHz, CDCl$_3$): δ (ppm)=120.4, 122.9, 123.1, 124.8, 125.1, 128.0, 128.2, 129.5, 130.3, 138.9, 140.0, 140.2, 141.7, 147.6, 167.4.

1.112. 3-(5-Chloro-2-benzofuranyl)-3-phenylpropanoic acid (PS 124)

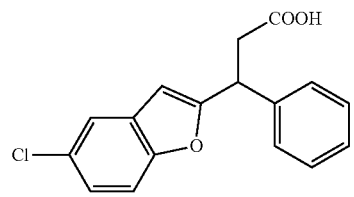 [SMILES: O=C(O)CC(c1ccccc1)c1cc2cc(Cl)ccc2o1]

1) Ethyl 3-(5-chloro-2-benzofuranyl)-3-phenylpropanoate

To a solution of (Z/E)-ethyl 3-(benzo-2-furanyl)-3-phenylacrylate (0.4 g) in ethanol (10 ml) was added 10% Pd/C (0.13 g) and a solution of sodium hypophosphite (0.194 g) in 7 ml of water. The mixture was stirred at 50° C. for 1.5 h. Then the catalyst was removed by filtration and the filtrate was diluted with water (50 ml). The aqueous layer was extracted with dichloromethane (3×20 ml) and the combined organic layers were dried over MgSO$_4$. After evaporation of the solvent the residue was purified by flash chromatography on silica gel (hexane/ethyl acetate 3:2+3% formic acid) to afford ethyl 3-(5-chloro-2-benzofuranyl)-3-phenylpropanoate (0.249 g) as yellowish oil.

$^1$H-NMR (500 MHz, CDCl$_3$): δ (ppm)=1.16 (t, J=7.2 Hz, 3H), 2.95-3.01 (m, 1H), 3.17-3.24 (m, 1H), 4.03-4.13 (m, 2H), 4.69 (t, J=7.9 Hz, 1H), 6.45 (s, 1H), 7.16-7.32 (m, 4H), 7.38-7.49 (m, 4H).

$^{13}$C-NMR (125 MHz, CDCl$_3$): δ (ppm)=14.1, 41.8, 60.6, 102.8, 111.0, 120.6, 122.6, 123.9, 127.4, 127.8, 128.2, 128.7, 129.8, 140.4, 153.2, 159.3, 171.0.

2) 3-(5-Chloro-2-benzofuranyl)-3-phenylpropanoic acid

By hydrolysis similar to the procedure of example 1.85.4, starting from ethyl 3-(5-chloro-2-benzofuranyl)-3-phenylpropanoate, 3-(5-chloro-2-benzofuranyl)-3-phenylpropanoic acid was obtained as colourless solid.

$^1$H-NMR (500 MHz, CDCl$_3$): δ (ppm)=3.03-3.06 (m, 1H), 3.25-3.29 (m, 1H), 4.67 (t, J=7.6 Hz, 1H), 6.45 (s, 1H), 7.15-7.30 (m, 4H), 7.39-7.47 (m, 4H).

$^{13}$C-NMR (125 MHz, CDCl$_3$): δ (ppm)=38.9, 41.4, 102.9, 112.0, 117.8, 120.6, 122.7, 123.8, 127.4, 127.7, 127.8, 128.4, 128.9, 154.8, 160.5.

1.113. 3-(5-Methyl-2-benzofuranyl)-3-phenylpropanoic acid (PS 120)

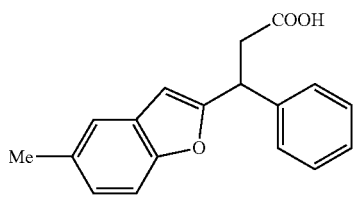 [SMILES: Cc1ccc2oc(C(CC(=O)O)c3ccccc3)cc2c1]

1) Ethyl 3-(5-methyl-2-benzofuranyl)-3-phenylpropanoate

By hydrogenation similar to the procedure of example 1.112.1, starting from (E/Z)-ethyl 3-(5-methyl-2-benzofuranyl)-3-phenylacrylate, ethyl 3-(5-methyl-2-benzofuranyl)-3-phenylpropanoate was obtained as colourless oil.

$^1$H-NMR (500 MHz, CDCl$_3$): δ (ppm)=1.15 (t, J=7.2 Hz, 3H), 2.40 (s, 3H), 2.95-3.00 (m, 1H), 3.17-3.22 (m, 1H), 4.02-4.12 (m, 2H), 4.67 (t, J=7.9 Hz, 1H), 6.37 (s, 1H), 7.02 (dd, J=1.6, 9.1 Hz, 1H), 7.23-7.33 (m, 7H).

$^{13}$C-NMR (125 MHz, CDCl$_3$): δ (ppm)=14.1, 21.2, 39.5, 41.8, 60.6, 102.6, 110.5, 120.5, 124.8, 127.2, 127.9, 128.5, 128.6, 132.0, 140.4, 153.2, 159.4, 171.1.

2) 3-(5-Methyl-2-benzofuranyl)-3-phenylpropanoic acid

By hydrolysis similar to the procedure of example 1.85.4, starting from ethyl 3-(5-methyl-2-benzofuranyl)-3-phenylpropanoate, 3-(5-methyl-2-benzofuranyl)-3-phenyl-propanoic acid was obtained as colourless solid.

$^1$H-NMR (500 MHz, CDCl$_3$): δ (ppm)=2.40 (s, 3H), 2.99-3.04 (m, 1H), 3.23-3.28 (m, 1H), 4.64 (t, J=8.2 Hz, 1H), 6.37 (s, 1H), 7.01 (dd, J=1.6, 8.8 Hz, 1H), 7.23-7.33 (m, 7H).

$^{13}$C-NMR (125 MHz, CDCl$_3$): δ (ppm)=21.3, 38.8, 41.5, 102.7, 110.6, 120.1, 120.5, 124.9, 125.7, 127.3, 127.8, 128.5, 128.8, 132.1, 153.3, 158.9, 175.6.

1.114. 3-(5-Chloro-2-benzimidazolyl)-3-(4-chlorophenyl)propanoic acid HCl (PS 232)

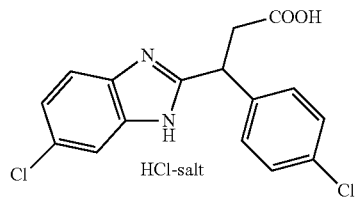 [SMILES: O=C(O)CC(c1ccc(Cl)cc1)c1nc2ccc(Cl)cc2[nH]1]

To a solution of 4-monoethyl p-chlorophenylsuccinate (0.83 g) and three drops of N,N-dimethylformamide in dichloromethane (4 ml) oxalyl chloride (0.55 ml) was added with stirring at rt. The solution was stirred further 10 min at rt and 10 min under reflux. Then all volatiles were removed at the water aspirator and the oily residue was redissolved in dichloromethane (10 ml). This solution was added dropwise in the course of 10 min to the stirred ice-cold solution of 4-chloro-1,2-phenylenediamine (0.46 g) and triethylamine (0.46 ml) in dichloromethane (10 ml). The cooling bath was removed and the redbrown solution stirred at rt for 1 h. The organic layer was washed with water (20 ml) and saturated sodium carbonate solution (10 ml) and dried (sodium sulfate). After filtration and removal of solvent a crude (1.15 g) was obtained which was triturated with diethyl ether to give a mixture of regioisomeric p-chlorophenylsuccinic monoamides (0.5 g) as beige coloured solid.

The mixture of monoamides was dissolved in acetic acid (3 ml) and 4M HCl in 1,4-dioxane (1 ml) was added. The solution was heated to reflux for 1 h. Then all volatiles were removed at the water aspirator and the residue was dissolved in ethyl acetate (20 ml). The organic layer was washed with 1M sodium hydroxide (2×10 ml), dried (sodium sulphate), and evaporated to give a crude which was recrystallised from few ethyl acetate to afford ethyl 3-(5-chloro-2-benzimidazolyl)-3-(4-chlorophenyl)propanoate (0.32 g) as light beige solid.

The ester (135 mg) was dissolved in a mixture of acetic acid (2 ml) and conc. HCl (1 ml) and heated under reflux for 1 h. All volatiles are removed at the water aspirator and the residue was precipitated from acetone solution with ethyl acetate to give 3-(5-chloro-2-benzimidazolyl)-3-(4-chlorophenyl)propanoic acid HCl (130 mg) as colourless solid.

$^1$H-NMR (500 MHz, DMSO-d$_6$): δ (ppm)=3.23 (dd, J=17.3, 6.6 Hz, 1H), 3.71 (dd, J=17.3, 9.2 Hz, 1H), 5.00 (dd, J=9.1, 6.7 Hz, 1H), 7.44 (d, J=8.6 Hz, 2H), 7.50 (dd, J=8.7, 1.9 Hz, 1H), 7.56 (d, J=8.6 Hz, 2H), 7.75 (d, J=8.8 Hz, 1H), 7.82 (d, J=1.8 Hz, 1H).

$^{13}$C-NMR and DEPT (125 MHz, DMSO-d$_6$): δ (ppm)= 37.18 (CH$_2$), 39.11 (CH), 113.81 (CH), 115.50 (CH), 125.36 (CH), 128.88 (2CH), 129.37 (C), 129.81 (2CH), 130.81 (br, C), 132.64 (C), 132.78 (br, C), 136.56 (C), 155.80 (C), 171.57 (CO).

1.115. N-((4-Chlorophenylacetyl)-N-phenylglycine (PS 72)

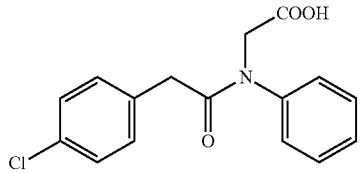 [SMILES: O=C(O)CN(C(=O)Cc1ccc(Cl)cc1)c1ccccc1]

1) Ethyl N-(4-chlorophenylacetyl)-N-phenylglycinate (PS 71)

Commercial 4-chloro-phenylacetyl chloride (0.95 g) was added dropwise to a stirred solution of commercial ethyl N-phenylglycinate (1 g) and dry pyridine (3 ml) in dichloromethane (20 ml) under nitrogen atmosphere at rt. After stirring for 72 h the mixture was poured into 10% HCl solution and extracted with ethyl acetate. The organic layer was washed with saturated NaCl solution, dried over MgSO$_4$, and concentrated. The residue was purified by flash chromatography on silica gel (hexane/ethyl acetate 4:1) to give ethyl N-(4-chlorophenylacetyl)-N-phenylglycinate (0.95 g) as colourless oil.

$^1$H-NMR (CDCl$_3$, 500 MHz): δ=1, 13 (t, J=7.2 Hz, 3H), 3.36 (s, 2H), 4.07 (q, J=7.2 Hz, 2H), 4.23 (s, 2H), 6, 88 (d, J=7.8 Hz, 2H), 7.08 (d, J=7.8 Hz, 2H), 7.15 (m, 2H), 7.26 (m, 3H).

$^{13}$C-NMR (CDCl$_3$, 125 MHz): δ=14.3, 40.2, 51.8, 61.5, 128.5, 128.7, 128.72, 129.9, 130.7, 132.8, 133.7, 142.9, 169.2, 171.1.

2) N-((4-Chlorophenylacetyl)-N-phenylglycine

A solution of ethyl N-(4-chloro-phenylacetyl)-N-phenylglycinate (0.4 g) and 5M NaOH (2.4 ml) in EtOH (12 ml) was refluxed for 2 h. After cooling to rt the mixture was poured into water (30 ml), acidified to pH 2 with 10% HCl and extracted with ethyl acetate (3×20 ml). The combined organic layers were washed with brine (20 ml), dried over MgSO$_4$, and evaporated. The crude was purified by flash chromatography on silica gel (hexane/ethyl acetate 3:2+3% formic acid) to afford N-((4-chlorophenylacetyl)-N-phenylglycine (0.1 g) as colourless solid.

$^1$H-NMR (CDCl$_3$, 500 MHz): =3.49 (s, 2H), 4.41 (s, 2H), 6, 75 (d, J=8.3 Hz, 2H), 7.19 (d, J=8.3 Hz, 2H), 7.28 (d, J=9.4 Hz, 2H), 7.41 (m, 3H), 8.25 (m, 1H, OH).

$^{13}$C-NMR (CDCl$_3$, 125 MHz): δ=39.7, 51.3, 127.8, 128.3, 128.5, 129.7, 130.2, 132.4, 132.8, 141.9, 164.1, 173.2.

MS (+ESI): m/z=302 (M+H).

1.116. 3-[2-(4-Chlorophenyl)-N-phenylacetamido]propanoic acid (PS 74)

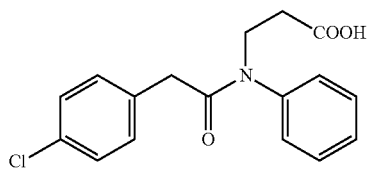 [SMILES: O=C(O)CCN(C(=O)Cc1ccc(Cl)cc1)c1ccccc1]

1) Ethyl N-phenyl-3-aminopropionate

A mixture of aniline (1.4 ml), ethyl acrylate (3.4 ml), and conc. HCl (1.6 ml) in ethanol (17 ml) was heated to reflux for 24 h. Then the solvent was removed and the residue partitioned between an excess of ammonia solution and dichloromethane. The organic layer was separated, washed with brine, dried (MgSO$_4$), and evaporated. The residue was purified by flash chromatography on silica gel (hexane/ethyl acetate 2:1) to provide ethyl N-(4-chlorophenyl)-3-aminopropionate (1.27 g) as yellowish oil.

2) Ethyl 3-[2-(4-chlorophenyl)-N-phenylacetamido]propanoate (PS 75)

By a procedure similar to that of example 1.115.1, starting from 4-chlorophenylacetyl chloride and ethyl N-phenyl-3-aminopropionate, ethyl 3-[2-(4-chlorophenyl)-N-phenylacetamido]propanoate was obtained as light tan oil.

$^1$H-NMR (500 MHz, CDCl$_3$): (ppm)=1, 17 (t, J=6.9 Hz, 3H), 2, 57 (t, J=7.2 Hz, 2H), 3, 38 (s, 2H), 4.03 (m, 4H), 6, 95 (d, J=8.5 Hz, 2H), 7.09 (d, J=6.6 Hz, 2H), 7.18 (d, J=8.5 Hz, 2H), 7.39 (m, 3H).

$^{13}$C-NMR (125 MHz, CDCl$_3$): δ (ppm)=13.8, 32.5, 40.2, 45.3, 60.2, 128.11, 128.12, 128.2, 129.5, 130.1, 132.2, 133.4, 141.6, 170.1, 171.0.

3) 3-[2-(4-Chlorophenyl)-N-phenylacetamido]propanoic acid

By hydrolysis similar to the procedure of example 1.115.2, starting from ethyl 3-[2-(4-chlorophenyl)-N-phenylacetamido]propanoate, 3-[2-(4-chlorophenyl)-N-phenylacetamido]propanoic acid was obtained as colourless solid.

$^1$H-NMR (500 MHz, CDCl$_3$): δ (ppm)=2.59 (t, J=7.2 Hz, 2H), 3.38 (s, 2H), 3.95 (t, J=7.2 Hz, 2H), 6.76 (d, J=8.5 Hz, 2H), 7.15 (d, J=6.3 Hz, 2H), 7.19 (d, J=8.5 Hz, 2H), 7.40 (m, 3H).

$^{13}$C-NMR (125 MHz, CDCl$_3$): δ (ppm)=32.7, 40.7, 45.7, 128.6, 128.9, 130.1, 130.6, 130.9, 132.8, 133.6, 141.9, 171.5, 176.4.

MS (+ESI): m/z=318 (M+H).

1.117. 3-[2-(4-Methylphenyl)-N-phenylacetamido]propanoic acid

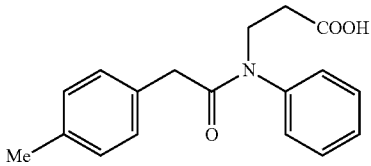 [SMILES: Cc1ccc(CC(=O)N(CCC(=O)O)c2ccccc2)cc1]

1) Ethyl 3-[2-(4-methylphenyl)-N-phenylacetamido]propanoate

By a procedure similar to that of example 1.115.1, starting from 4-methylphenylacetyl chloride and ethyl N-phenyl-3-aminopropionate, ethyl 3-[2-(4-methylphenyl)-N-phenylacetamido]propanoate was obtained as yellowish oil.

$^1$H-NMR (500 MHz, CDCl$_3$): δ (ppm)=1, 18 (t, J=7.1 Hz, 3H), 2, 29 (s, 3H), 2, 58 (t, J=7.4 Hz, 2H), 3.36 (s, 2H), 4.02 (m, 4H), 6, 91 (d, J=8.1 Hz, 2H), 7.03 (d, J=7.0 Hz, 2H), 7.09 (d, J=7.0 Hz, 2H), 7.38 (m, 3H).

$^{13}$C-NMR (125 MHz, CDCl$_3$): δ (ppm)=14.1, 21.0, 32.9, 39.5, 40.7, 45.6, 60.5, 128.2, 128.6, 128.8, 129.0, 129.7, 136.1, 142.1, 171.0, 171.4, 174.1.

2) 3-[2-(4-Methylphenyl)-N-phenylacetamido]propanoic acid

By hydrolysis similar to the procedure of example 1.115.2, starting from ethyl 3-[2-(4-methylphenyl)-N-phenylacetamido]propanoate, 3-[2-(4-methylphenyl)-N-phenylacetamido]propanoic acid was obtained as colourless solid.

$^1$H-NMR (500 MHz, CDCl$_3$): δ (ppm)=2.29 (s, 3H), 2, 62 (t, J=7.1 Hz, 2H), 3.38 (s, 2H), 3.99 (t, J=7.3 Hz, 2H), 6, 89 (d, J=7.9 Hz, 2H), 7.02 (d, J=7.9 Hz, 2H), 7.11 (d, J=7.6 Hz, 2H), 7.39 (m, 3H).

$^{13}$C-NMR (125 MHz, CDCl$_3$): δ (ppm)=21.0, 32.6, 40.7, 45.5, 128.4, 128.4, 128.8, 129.0, 129.8, 131.8, 136.2, 141.9, 171.8, 175.5.

MS (+ESI): m/z=298 (M+H).

1.118. 3-[2-(3,4-Dichlorophenyl)-N-phenylacetamido]propanoic acid (PS 106)

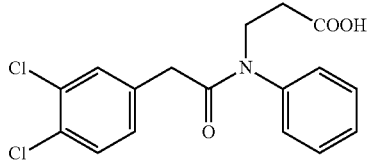 [SMILES: O=C(O)CCN(C(=O)Cc1ccc(Cl)c(Cl)c1)c1ccccc1]

1) Ethyl 3-[2-(3,4-dichlorophenyl)-N-phenylacetamido]propanoate

By a procedure similar to that of example 1.115.1, starting from 3,4-dichlorophenylacetyl chloride and ethyl N-phenyl-3-aminopropionate, ethyl 3-[2-(3,4-dichlorophenyl)-N-phenyl-acetamido]propanoate was obtained as yellowish oil.

$^1$H-NMR (500 MHz, CDCl$_3$): δ (ppm)=1.18 (t, J=7.1 Hz, 3H), 2.56 (t, J=7.2 Hz, 2H), 3.35 (s, 2H), 4.02 (m, 4H), 6, 88 (d, J=8.2 Hz, 1H), 7.09 (m, 3H), 7.29 (d, J=8.2 Hz, 1H), 7.42 (m, 3H).

$^{13}$C-NMR (125 MHz, CDCl$_3$): δ (ppm)=14.0, 32.8, 40.2, 45.6, 60.6, 128.5, 128.5, 128.5, 129.9, 130.1, 130.8, 131.1, 132.1, 135.3, 142.7, 169.7, 171.2.

2) 3-[2-(3,4-Dichlorophenyl)-N-phenylacetamido]propanoic acid

By hydrolysis similar to the procedure of example 1.115.2, starting from ethyl 3-[2-(3,4-dichlorophenyl)-N-phenylacetamido]propanoate, 3-[2-(3,4-dichlorophenyl)-N-phenylacetamido]propanoic acid was obtained as colourless solid.

$^1$H-NMR (500 MHz, CDCl$_3$): δ (ppm)=2, 62 (t, J=7.3 Hz, 2H), 3.36 (s, 2H), 4.0 (t, J=7.3 Hz, 2H), 6, 89 (d, J=8.2 Hz, 1H), 7.07 (s, 1H), 7.12 (d, J=6.3 Hz, 2H), 7.30 (d, J=8.2 Hz, 1H), 7.43 (m, 3H).

$^{13}$C-NMR (125 MHz, CDCl$_3$): δ (ppm)=32.4, 40.2, 45.5, 128.4, 128.5, 128.7, 130.0, 130.2, 130.9, 131.1, 132.2, 135.1, 141.5, 170.5, 175.8.

MS (+ESI): m/z=352 (M+H).

1.119. 3-[2-(2,4-Dichlorophenyl)-N-phenylacetamido]propanoic acid (PS 107)

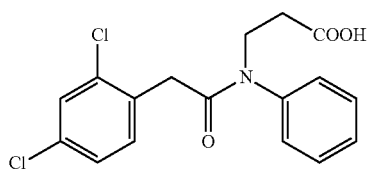 [SMILES: O=C(O)CCN(C(=O)Cc1ccc(Cl)cc1Cl)c1ccccc1]

1) Ethyl 3-[2-(2,4-dichlorophenyl)-N-phenylacetamido]propanoate

By a procedure similar to that of example 1.115.1, starting from 2,4-dichlorophenylacetyl chloride and ethyl N-phenyl-3-aminopropionate, ethyl 3-[2-(2,4-dichlorophenyl)-N-phenyl-acetamido]propanoate was obtained as yellowish oil.

$^1$H-NMR (500 MHz, CDCl$_3$): δ (ppm)=1, 18 (t, J=7.1 Hz, 3H), 2, 60 (t, J=7.4 Hz, 2H), 3.45 (s, 2H), 4.04 (m, 4H), 7.16 (m, 2H), 7.20 (d, J=8.2 Hz, 2H), 7.30 (s, 1H), 7.41 (m, 3H).

$^{13}$C-NMR (125 MHz, CDCl$_3$): δ ppm)=14.1, 32.9, 38.8, 45.6, 60.5, 127.0, 128.2, 128.4, 129.0, 129.9, 132.2, 132.4, 133.2, 134.8, 141.8, 169.3, 171.3.

2) 3-[2-(2,4-Dichlorophenyl)-N-phenylacetamido]propanoic acid

By hydrolysis similar to the procedure of example 1.115.2, starting from ethyl 3-[2-(2,4-di-chlorophenyl)-N-phenylacetamido]propanoate, 3-[2-(2,4-dichlorophenyl)-N-phenylacetamido]propanoic acid was obtained as colourless solid.

$^1$H-NMR (500 MHz, CDCl$_3$): δ (ppm)=2, 63 (t, J=7.1 Hz, 2H), 3.46 (s, 2H), 4.02 (t, J=7.3 Hz, 2H), 7.15 (s, 2H), 7.21 (d, J=6.9 Hz, 2H), 7.30 (s, 1H), 7.41 (m, 3H).

$^{13}$C-NMR (125 MHz, CDCl$_3$): δ (ppm)=32.5, 38.8, 45.5, 127.0, 128.1, 128.6, 129.0, 130.1, 132.2, 133.3, 134.8, 141.6, 169.9, 176.0.

MS (+ESI): m/z=352 (M+H).

1.120. 3-[2-(4-Chlorophenyl)-N-(4-chlorophenyl)acetamido]propanoic acid (PS 108)

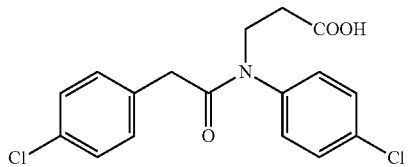 [SMILES: O=C(O)CCN(C(=O)Cc1ccc(Cl)cc1)c1ccc(Cl)cc1]

1) Ethyl N-(4-chlorophenyl)-3-aminopropionate

By a procedure similar to that of example 1.116.1, starting from 4-chloroaniline and ethyl acrylate, ethyl N-(4-chlorophenyl)-3-aminopropionate was obtained as light tan oil.

2) Ethyl 3-[2-(4-chlorophenyl)-N-(4-chlorophenyl)acetamido]propanoate

By a procedure similar to that of example 1.115.1, starting from 4-chlorophenylacetyl chloride and ethyl N-(4-chlorophenyl)-3-aminopropionate, ethyl 3-[2-(4-chloro-phenyl)-N-(4-chlorophenyl)acetamido]-propanoate was obtained as yellowish oil.

$^1$H-NMR (500 MHz, CDCl$_3$): δ (ppm)=1, 18 (t, J=7.1 Hz, 3H), 2, 54 (t, J=7.1 Hz, 2H), 3.36 (s, 2H), 3.96 (t, J=7.1 Hz, 2H), 4.03 (q, J=7.1 Hz, 2H), 6, 96 (d, J=8.2 Hz, 2H), 7.03 (d, J=8.5 Hz, 2H), 7.20 (d, J=8.5 Hz, 2H), 7.37 (d, J=8.8 Hz, 2H).

$^{13}$C-NMR (125 MHz, CDCl$_3$): δ (ppm)=14.0, 32.7, 40.5, 45.6, 60.6, 128.5, 129.8, 129.9, 130.2, 132.6, 133.3, 134.3, 140.4, 170.2, 171.2.

3) 3-[2-(4-Chlorophenyl)-N-(4-chlorophenyl)acetamido]propanoic acid

By hydrolysis similar to the procedure of example 1.115.2, starting from ethyl 3-[2-(4-chlorophenyl)-N-(4-chlorophenyl)acetamido]propanoate, 3-[2-(4-chlorophenyl)-N-(4-chlorophenyl)acetamido]propanoic acid was obtained as colourless solid.

$^1$H-NMR (500 MHz, CDCl$_3$): δ (ppm)=2, 59 (t, J=6.9 Hz, 2H), 3.38 (s, 2H), 3.97 (t, J=7.1 Hz, 2H), 6.95 (d, J=8.5 Hz, 2H), 7.05 (d, J=8.8 Hz, 2H), 7.20 (d, J=8.5 Hz, 2H), 7.38 (d, J=8.8 Hz, 2H).

$^{13}$C-NMR (125 MHz, CDCl$_3$): δ (ppm)=32.4, 40.5, 45.6, 128.6, 129.8, 130.1, 130.3, 132.8, 133.1, 134.6, 140.2, 170.8, 175.6.

MS (+ESI): m/z=352 (M+H).

1.121. 4-(2-Benzimidazolyl)-3-(2-naphthyl)butanoic acid•HCl (PS 510)

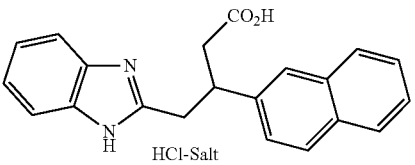 [SMILES: O=C(O)CC(Cc1nc2ccccc2[nH]1)c1ccc2ccccc2c1]

1,2-Phenylenediamine (54 mg) and 3-(2-naphthyl)glutaric anhydride (120 mg) were dissolved in dichloromethane (2 ml) with heating. The solution was stirred at rt for 1 h. The precipitate formed was collected by suction filtration, washed with dichloromethane, and dried to give a mixture of regioisomeric amides (131 mg) as colourless solid. This solid was dissolved in 1,4-dioxane (1 ml) with heating, and 4M HCl in 1,4-dioxane (1 ml) was added. The solution was heated to reflux for 1 h. After removal of the solvent the residue was triturated with acetone to give 4-(2-benzimidazolyl)-3-(2-naphthyl)butanoic acid HCl (100 mg) as colourless solid.

$^1$H-NMR (500 MHz, DMSO-$d_6$)): δ (ppm)=2.84 (dd, J=16.1, 8.3 Hz, 1H), 2.91 (dd, J=16.2, 6.4 Hz, 1H), 3.57 (dd, J=14.9, 9.2 Hz, 1H), 3.64 (dd, J=15.0, 6.9 Hz, 1H), 4.05 (m, 1H), 7.41-7.47 (m, 4H), 7.52 (dd, J=8.6, 1.8 Hz, 1H), 7.67-7.71 (m, 2H), 7.80-7.86 (m, 4H).

$^{13}$C-NMR and DEPT (125 MHz, DMSO-$d_6$): δ (ppm)= 32.64 (CH$_2$), 39.93 (CH$_2$), 39.96 (CH), 89.44 (C), 115.64 (CH), 121.99 (CH), 125.53 (CH), 125.60 (CH), 125.70 (CH), 126.06 (CH), 127.34 (CH), 127.48 (CH), 128.01 (CH), 130.49 (C), 131.96 (C), 132.57 (C), 132.75 (C), 133.67 (CH), 139.23 (C), 152.73 (C), 172.25 (CO).

1.122. 4-(5-Chloro-2-benzimidazolyl)-3-(2-naphthyl)butanoic acid•HCl (PS 524)

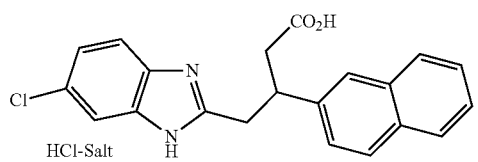 [SMILES: O=C(O)CC(Cc1nc2ccc(Cl)cc2[nH]1)c1ccc2ccccc2c1]

4-Chloro-1,2-phenylenediamine (143 mg) and 3-(2-naphthyl)glutaric anhydride (240 mg) were dissolved in dichloromethane (3 ml) with heating. The dark solution was stirred at rt for 1 h. The precipitate formed was collected by suction filtration, washed with dichloromethane, and dried in vacuo to give a mixture of regioisomeric amides (0.32 g) as brownish solid. This solid was dissolved in 4M HCl in 1,4-dioxane (4 ml) and the dark solution was heated to reflux for 1 h. After removal of the solvent in vacuo the residue was taken up in acetic acid (5 ml), treated with charcoal, and filtered. From the filtrate the solvent was removed and the residue triturated with acetone to give 4-(5-chloro-2-benzimidazolyl)-3-(2-naphthyl)butanoic acid HCl (138 mg) as colourless solid.

$^1$H-NMR (500 MHz, DMSO-$d_6$)): δ (ppm)=2.84 (dd, J=16.2, 7.8 Hz, 1H), 2.91 (dd, J=16.2, 6.3 Hz, 1H), 3.56 (dd, J=14.9, 9.1 Hz, 1H), 3.63 (dd, J=15.0, 7.0 Hz, 1H), 4.01 (m, 1H), 7.42-7.48 (m, 3H), 7.51 (dd, J=8.6, 1.7 Hz, 1H), 7.70 (d, J=8.8, 1H), 7.80 (d, J=2.0 Hz, 1H), 7.81-7.84 (m, 4H).

$^{13}$C-NMR and DEPT (125 MHz, DMSO-$d_6$): δ (ppm)= 32.82 (CH$_2$), 39.91 (CH$_2$), 39.99 (CH), 113.54 (CH), 115.21 (CH), 125.39 (CH), 125.51 (CH), 125.59 (CH), 125.68 (CH), 126.05 (CH), 127.34 (CH), 127.46 (CH), 128.00 (CH), 129.45 (C), 130.08 (C), 131.95 (C), 132.05 (C), 132.75 (CH), 139.28 (C), 153.55 (C), 172.27 (CO).

1.123. 4-(5-Fluoro-2-benzimidazolyl)-3-(2-naphthyl) butanoic acid•HCl (PS 511)

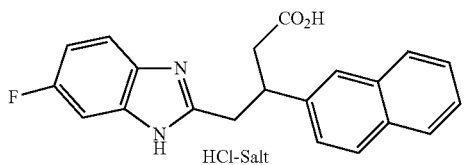 [SMILES: O=C(O)CC(Cc1nc2ccc(F)cc2[nH]1)c1ccc2ccccc2c1]

By a procedure similar to that of example 1.121, starting from 4-fluoro-1,2-phenylenediamine and 3-(2-naphthyl)glutaric anhydride, 4-(5-fluoro-2-benzimidazolyl)-3-(2-naphthyl)butanoic acid HCl was obtained as greyish solid.

$^1$H-NMR (500 MHz, DMSO-$d_6$)): δ (ppm)=2.84 (dd, J=16.1, 8.4 Hz, 1H), 2.91 (dd, J=16.2, 6.4 Hz, 1H), 3.57 (dd, J=15.0, 9.2 Hz, 1H), 3.64 (dd, J=15.0, 6.9 Hz, 1H), 4.01 (m, 1H), 7.31 (dt, J=9.3, 2.5 Hz, 1H), 7.42-7.48 (m, 2H), 7.51 (dd, J=8.6, 1.8 Hz, 1H), 7.58 (dd, J=8.6, 2.4 Hz, 1H), 7.72 (dd, J=8.6, 4.1 Hz, 1H), 7.81-7.84 (m, 4H).

1.123. 4-(5-Methyl-2-benzimidazolyl)-3-(2-naphthyl)butanoic acid•HCl (PS 513)

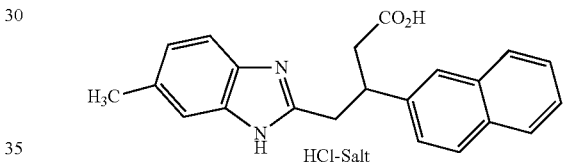

By a procedure similar to that of example 1.121, starting from 4-methyl-1,2-phenylenediamine and 3-(2-naphthyl) glutaric anhydride, 4-(5-methyl-2-benzimidazolyl)-3-(2-naphthyl)butanoic acid HCl was obtained as colourless solid.

$^1$H-NMR (500 MHz, DMSO-$d_6$)): δ (ppm)=2.40 (s, 3H), 2.84 (dd, J=16.1, 7.8 Hz, 1H), 2.90 (dd, J=16.1, 6.4 Hz, 1H), 3.58 (dd, J=15.0, 9.5 Hz, 1H), 3.65 (dd, J=14.9, 6.7 Hz, 1H), 4.03 (m, 1H), 7.25 (ddd, J=8.4, 1.5, 0.6 Hz, 1H), 7.41-7.47 (m, 3H), 7.51 (dd, J=8.5, 1.8 Hz, 1H), 7.55 (d, J=8.4 Hz, 1H), 7.79-7.82 (m, 3H), 7.84 (d, J=1.6 Hz, 1H).

$^{13}$C-NMR and DEPT (125 MHz, DMSO-$d_6$): δ (ppm)= 20.95 (CH$_3$), 32.53 (CH$_2$), 40.05 (CH), 40.12 (CH$_2$), 113.09 (CH), 113.21 (CH), 125.58 (CH), 125.71 (CH), 125.75 (CH), 126.12 (CH), 126.78 (CH), 127.41 (CH), 127.53 (CH), 128.05 (CH), 128.71 (C), 130.91 (C), 132.02 (C), 132.81 (C), 135.35 (C), 139.25 (C), 151.58 (C), 172.31 (CO).

1.124. 4-(4,5-Dimethyl-2-benzimidazolyl)-3-(2-naphthyl)butanoic acid•HCl (PS 515)

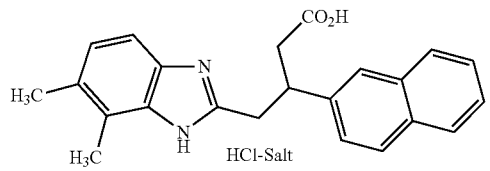 [SMILES: Cc1ccc2nc(CC(CC(=O)O)c3ccc4ccccc4c3)[nH]c2c1C]

By a procedure similar to that of example 1.121, starting from 3,4-dimethyl-1,2-phenylenediamine and 3-(2-naphthyl)glutaric anhydride, 4-(4,5-dimethyl-2-benzimidazolyl)-3-(2-naphthyl)butanoic acid HCl was obtained as tan solid.

¹H-NMR (500 MHz, DMSO-d₆)): δ (ppm)=2.30 (s, 3H), 2.45 (s, 3H), 2.84 (dd, J=16.0, 8.2 Hz, 1H), 2.88 (dd, J=16.2, 6.5 Hz, 1H), 3.62 (dd, J=14.8, 9.1 Hz, 1H), 3.65 (dd, J=14.9, 7.3 Hz, 1H), 4.08 (m, 1H), 7.23 (d, J=8.4 Hz, 1H), 7.37 (d, J=8.3 Hz, 1H), 7.44 (m, 2H), 7.53 (dd, J=8.6, 1.8 Hz, 1H), 7.80-7.85 (m, 3H), 7.86 (d, J=1.4 Hz, 1H).

¹³C-NMR and DEPT (125 MHz, DMSO-d₆): δ (ppm)= 13.61 (CH₃), 18.68 (CH₃), 32.33 (CH₂), 40.13 (CH₂), 110.15 (CH), 121.75 (C), 125.59 (CH), 125.62 (CH), 125.67 (CH), 126.04 (CH), 127.34 (CH), 127.48 (CH), 127.98 (CH), 128.70 (C), 130.82 (C), 131.95 (C), 132.77 (C), 133.275 (C), 139.29 (C), 151.51 (C), 172.24 (CO).

1.125. 4-(2-Naphtho[1,2-b]imidazolyl)-3-(2-naphthyl)butanoic acid•HCl (PS 516)

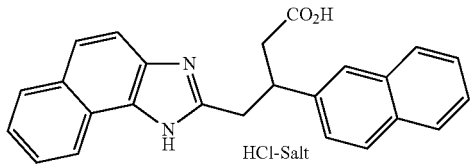 [SMILES: O=C(O)CC(Cc1nc2ccc3ccccc3c2[nH]1)c1ccc2ccccc2c1]

By a procedure similar to that of example 1.121, starting from 1,2-naphthylenediamine and 3-(2-naphthyl)glutaric anhydride, 4-(2-naphtho[1,2-b]imidazolyl)-3-(2-naphthyl) butanoic acid HCl was obtained as light red solid.

¹H-NMR (500 MHz, DMSO-d₆)): δ (ppm)=2.88 (dd, J=16.1, 8.4 Hz, 1H), 2.94 (dd, J=16.2, 9.8 Hz, 1H), 3.70 (dd, J=14.9, 8.8 Hz, 1H), 3.74 (dd, J=14.9, 7.6 Hz, 1H), 4.15 (m, 1H), 7.43 (m, 2H), 7.57 (dd, J=8.6, 1.8 Hz, 1H), 7.63 (dt, J=7.0, 1.2 Hz, 1H), 7.75 (dt, J=7.0, 1.2 Hz, 1H), 7.77 (d, J=8.9 Hz, 1H), 7.79-7.84 (m, 3H), 7.90 (d, J=1.6 Hz, 1H), 7.94 (d, J=8.8 Hz, 1H), 8.10 (d, J=8.2 Hz, 1H), 8.63 (dd, J=8.3, 1.1 Hz, 1H).

¹³C-NMR and DEPT (125 MHz, DMSO-d₆): δ (ppm)= 32.61 (CH₂), 40.10 (CH₂), 40.28 (CH), 112.72 (CH), 121.69 (CH), 125.69 (CH), 125.72 (CH), 125.73 (CH), 126.11 (CH), 126.06 (CH), 126.39 (CH), 127.48 (CH), 126.59 (CH), 126.64 (?C), 127.41 (CH), 127.55 (CH), 127.76 (CH), 127.93 (CH), 128.08 (CH), 128.94 (CH), 130.49 (C), 132.03 (C), 132.86 (C), 139.47 (C), 149.78 (C), 172.25 (CO).

1.126. 4-(4-Methyl-2-benzimidazolyl)-3-(2-naphthyl)butanoic acid•HCl (PS 512)

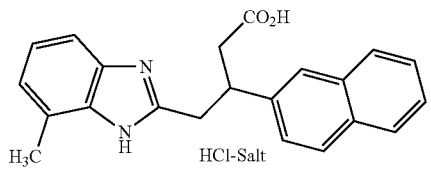 [SMILES: Cc1cccc2nc(CC(CC(=O)O)c3ccc4ccccc4c3)[nH]c12]

3-Methyl-1,2-phenylenediamine (61 mg) and 3-(2-naphthyl)glutaric anhydride (120 mg) were dissolved in dichloromethane (2 ml) with heating. The solution was stirred at rt for 1 h. The solvent was removed and the residue was dissolved in 1,4-dioxane (1 ml) with heating. 4M HCl in 1,4-dioxane (1 ml) was added and the solution was heated to reflux for 1 h. The precipitate formed was isolated by suction filtration, washed with 1,4-dioxane, and dried to give 4-(4-methyl-2-benzimidazolyl)-3-(2-naphthyl)butanoic acid HCl (162 mg) as beige coloured solid.

¹H-NMR (500 MHz, DMSO-d₆)): δ (ppm)=2.55 (s, 3H), 2.85 (dd, J=16.1, 8.3 Hz, 1H), 2.89 (dd, J=16.1, 6.5 Hz, 1H), 3.62 (dd, J=14.9, 8.9 Hz, 1H), 3.66 (dd, J=14.9, 7.4 Hz, 1H), 4.09 (m, 1H), 7.24 (d, J=7.4 Hz, 1H), 7.33 (t, J=7.8 Hz, 1H), 7.42-7.50 (m, 3H), 7.54 (dd, J=8.6, 1.8 Hz, 1H), 7.81-7.84 (m, 3H), 7.87 (d, J=1.1 Hz, 1H).

¹³C-NMR and DEPT (125 MHz, DMSO-d₆): δ (ppm)= 16.50 (CH₃), 32.41 (CH₂), 39.97 (CH), 40.03 (CH₂), 110.82 (CH), 123.95 (C), 125.37 (CH), 125.60 (CH), 125.62 (CH), 125.69 (CH), 125.74 (CH), 126.06 (CH), 127.35 (CH), 127.48 (CH), 128.00 (CH), 130.36 (C), 130.47 (C), 131.97 (C), 132.78 (C), 139.32 (C), 151.83 (C), 172.26 (CO).

1.127. 4-(5-Trifluormethyl-2-benzimidazolyl)-3-(2-naphthyl)butanoic acid•HCl (PS 514)

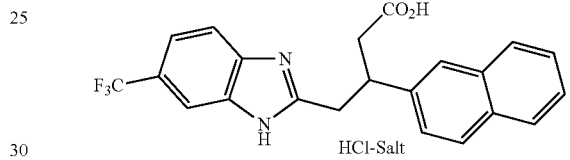

By a procedure similar to that of example 1.126, starting from 4-trifluormethyl-1,2-phenylenediamine and 3-(2-naphthyl)glutaric anhydride, 4-(5-trifluormethyl-2-benzimidazolyl)-3-(2-naphthyl)butanoic acid HCl was obtained as colourless solid.

¹H-NMR (500 MHz, DMSO-d₆)): δ (ppm)=2.85 (dd, J=16.1, 8.4 Hz, 1H), 2.93 (dd, J=16.2, 6.3 Hz, 1H), 3.60 (dd, J=14.9, 8.8 Hz, 1H), 3.66 (dd, J=14.9, 7.2 Hz, 1H), 4.04 (m, 1H), 7.45 (m, 2H), 7.53 (dd, J=8.6, 1.7 Hz, 1H), 7.73 (dd, J=8.6, 1.3 Hz, 1H), 7.81-7.83 (m, 3H), 7.85 (d, J=1.5 Hz, 1H), 7.89 (d, J=8.6 Hz, 1H), 8.05 (m, 1H).

¹³C-NMR and DEPT (125 MHz, DMSO-d₆): δ (ppm)= 33.11 (CH₂), 39.92 (CH₂), 40.03 (CH), 111.70 (CH, ³J$_{C-F}$=4.0 Hz), 114.95 (CH), 121.48 (CH, ³J$_{C-F}$=3.7 Hz), 123.03 (C), 125.19 (C), 125.59 (CH), 125.62 (CH), 125.69 (CH), 126.06 (CH), 127.36 (CH), 127.49 (CH), 128.01 (CH), 131.65 (br, C), 131.98 (C), 132.79 (C), 134.14 (br, C), 139.42 (C), 155.18 (C), 172.34 (CO).

1.128. 4-(2-Naphtho[2,3-b]imidazolyl)-3-(2-naphthyl)butanoic acid•HCl (PS 517)

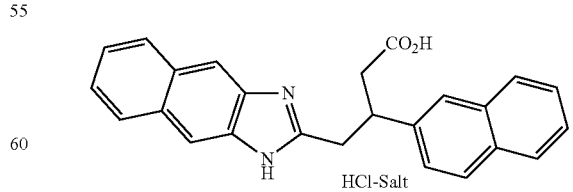

By a procedure similar to that of example 1.126, starting from 2,3-naphthylenediamine and 3-(2-naphthyl)glutaric anhydride, 4-(2-naphtho[2,3-b]imidazolyl)-3-(2-naphthyl) butanoic acid HCl was obtained as colourless solid.

¹H-NMR (500 MHz, DMSO-d₆)): δ (ppm)=2.88 (dd, J=16.1, 8.4 Hz, 1H), 2.96 (dd, J=16.2, 6.3 Hz, 1H), 3.60 (dd, J=15.1, 9.1 Hz, 1H), 3.69 (dd, J=14.9, 7.0 Hz, 1H), 4.09 (m, 1H), 7.43 (m, 2H), 7.49 (m, 2H), 7.54 (dd, J=8.6, 1.8 Hz, 1H), 7.79-7.83 (m, 3H), 7.81 (d, J=1.5 Hz, 1H), 8.07 (m, 2H), 8.19 (s, 2H).

¹³C-NMR and DEPT (125 MHz, DMSO-d₆): δ (ppm)= 33.50 (CH₂), 40.03 (CH), 110.33 (2CH), 125.08 (2CH), 125.61 (CH), 125.65 (CH), 126.03 (CH), 127.33 (CH), 127.46 (CH), 127.86 (2CH), 127.96 (CH), 130.34 (C), 131.84 (C), 131.94 (C), 132.77 (C), 139.49 (C), 156.91 (C), 172.36 (CO).

1.129. 3-(5-Chloro-2-benzimidazolyl)-2-(4-chlorophenyl)propanoic acid•HCl (PS 509)

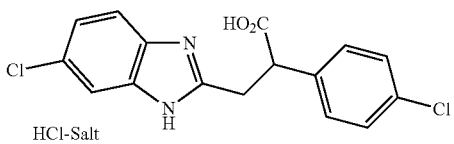 [SMILES: O=C(O)C(Cc1nc2ccc(Cl)cc2[nH]1)c1ccc(Cl)cc1]

4-Chloro-1,2-phenylenediamine (285 mg) and 2-(4-chlorophenyl)maleic anhydride (420 mg) were dissolved in dichloromethane (4 ml) with heating. The dark solution was stirred at rt for 1 h. The solvent was removed in vacuo and the residue was dissolved in 1M HCl in acetic acid (4 ml). The solution was heated to reflux for 1 h, treated with charcoal, and filtered. From the filtrate the solvent was removed and the residue crystallised from acetone/ethyl acetate to give 3-(5-chloro-2-benzimidazolyl)-2-(4-chlorophenyl)propanoic acid HCl (130 mg) as light orange solid.

¹H-NMR (500 MHz, DMSO-d₆)): δ (ppm)=3.49 (dd, J=15.5, 7.7 Hz, 1H), 3.73 (dd, J=15.4, 8.4 Hz, 1H), 4.60 (t, J=8.1 Hz, 1H), 7.39 (m, 4H), 7.44 (dd, J=8.7, 2.0 Hz, 1H), 7.70 (dd, J=8.7, 0.6 Hz, 1H), 7.78 (dd, J=2.0, 0.6 Hz, 1H).

¹³C-NMR and DEPT (125 MHz, DMSO-d₆): δ (ppm)= 30.23 (CH₂), 47.52 (CH), 113.72 (CH), 115.28 (CH), 124.84 (CH), 128.68 (2CH), 129.57 (2CH), 131.24 (C), 132.19 (C), 133.32 (C), 136.61 (C), 153.26 (C), 172.69 (CO).

1.130. 4-(2-Benzothiazolyl)-3-(4-chlorophenyl)butanoic acid (PS 507)

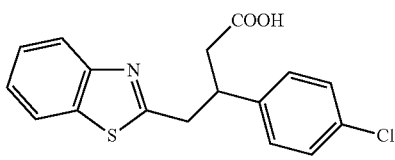 [SMILES: O=C(O)CC(Cc1nc2ccccc2s1)c1ccc(Cl)cc1]

By a procedure similar to that of example 1.55, starting from 2-aminothiophenol and 3-(4-chlorophenyl)glutaric anhydride, 4-(2-benzothiazolyl)-3-(4-chlorophenyl)-butanoic acid was obtained as colourless solid.

¹H-NMR (500 MHz, DMSO-d₆): δ (ppm)=2.65 (dd, J=16.0, 8.6 Hz, 1H), 2.80 (dd, J=16.0, 6.1 Hz, 1H), 3.43 (dd, J=14.9, 9.3 Hz, 1H), 3.51 (dd, J=14.9, 5.9 Hz, 1H), 3.64 (m, 1H), 7.29 (d, J=8.6 Hz, 2H), 7.34 (d, J=8.7 Hz, 2H), 7.37 (dd, J=8.1, 1.1 Hz, 1H), 7.45 (dt, J=8.2, 1.3 Hz, 1H), 7.90 (d, J=8.1 Hz, 1H), 7.98 (d, J=8.0 Hz, 1H).

¹³C-NMR and DEPT (125 MHz, DMSO-d₆): δ (ppm)= 39.24 (CH₂), 40.08 (CH₂), 41.21 (CH), 121.90 (CH), 122.10 (CH), 124.71 (CH), 125.86 (CH), 128.09 (2CH), 129.54 (2CH), 131.07 (C), 134.56 (C), 141.58 (C), 152.47 (C), 169.12 (C), 172.46 (CO).

1.131. 4-(5-Trifluoromethyl-2-benzothiazolyl)-3-(4-chlorophenyl)butanoic acid (PS 508)

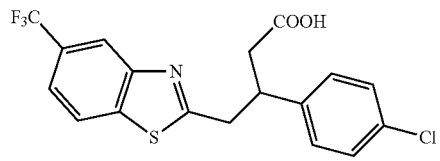 [SMILES: O=C(O)CC(Cc1nc2cc(C(F)(F)F)ccc2s1)c1ccc(Cl)cc1]

By a procedure similar to that of example 1.55, starting from 2-amino-4-trifluoromethylthiophenol and 3-(4-chlorophenyl)glutaric anhydride, 4-(5-trifluoromethyl-2-benzothiazolyl)-3-(4-chlorophenyl)butanoic acid was obtained as colourless solid.

¹H-NMR (500 MHz, DMSO-d₆): δ (ppm)=2.67 (dd, J=16.1, 8.5 Hz, 1H), 2.82 (dd, J=16.1, 6.2 Hz, 1H), 3.50 (dd, J=14.8, 9.4 Hz, 1H), 3.57 (dd, J=14.8, 5.8 Hz, 1H), 3.65 (m, 1H), 7.30 (d, J=8.6 Hz, 2H), 7.40 (d, J=8.6 Hz, 2H), 7.69 (dd, J=8.4, 1.6 Hz, 1H), 8.24-8.27 (m, 2H).

1.132. N-[(1,3-Dioxo-2-isondolinyl)methyl]-N-(4-chlorophenyl)glycine (PS 501)

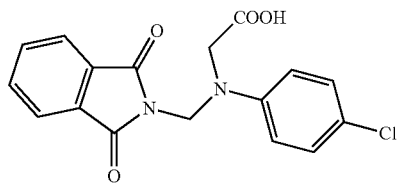 [SMILES: O=C(O)CN(CN1C(=O)c2ccccc2C1=O)c1ccc(Cl)cc1]

By a procedure similar to that of example 1.57.3, starting from phthalimide and N-(4-chlorophenyl)glycine, N-[(1,3-dioxo-2-isondolinyl)methyl]-N-(4-chlorophenyl)-glycine was obtained as light yellow solid.

¹H-NMR (500 MHz, DMSO-d₆): δ (ppm)=4.28 (s, 2H), 5.24 (s, 2H), 6.98 (m, 2H), 7.22 (m, 2H), 7.87 (m, 4H).

¹³C-NMR and DEPT (125 MHz, DMSO-d₆): δ (ppm)= 51.84 (CH₂), 54.55 (CH₂), 114.32 (2CH), 121.61 (C), 123.25 (2CH), 128.43 (2CH), 131.39 (C), 134.63 (2CH), 145.37 (C), 168.25 (2CO), 171.53 (CO).

1.133. 3-(4-Chlorophenyl)-4-(4-hydroxy-2-quinazolinyl)butanoic acid (PS 451)

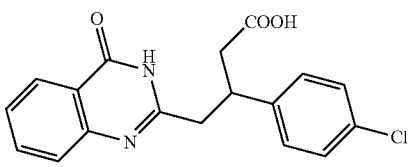 [SMILES: O=C(O)CC(Cc1nc2ccccc2c(=O)[nH]1)c1ccc(Cl)cc1]

The solution of 3-(4-chlorophenyl)glutaric anhydride (449 mg) and anthranilamide (272 mg) in toluene (8 ml) was heated to reflux for 4 h. After removal of the solvent the residue was dried in vacuo. The off-white solid was dissolved in 2M sodium hydroxide (3 ml) and stirred under reflux for 2 h. After cooling to room temperature acetic acid (0.5 ml) was added with stirring. The precipitate formed was isolated by suction filtration, washed, and dried in vacuo to give 3-(4-chlorophenyl)-4-(4-hydroxy-2-quinazolinyl)butanoic acid (0.57 g) as colourless solid.

$^1$H-NMR (500 MHz, DMSO-$d_6$)): δ (ppm)=2.62 (dd, J=16.0, 9.3 Hz, 1H), 2.74 (dd, J=16.0, 5.6 Hz, 1H), 2.86 (dd, J=14.4, 7.7 Hz, 1H), 2.93 (dd, J=14.4, 7.8 Hz, 1H), 3.74 (m, 1H), 7.32 (m, 4H), 7.44 (dt, J=8.0, 1.1 Hz, 1H), 7.59 (d, J=8.0, 1H), 7.76 (dt, J=7.7, 1.6 Hz, 1H), 8.04 (dd, J=7.9, 1.2 Hz, 1H), 12.10 (s, br, 1H), 12.20 (s, br, 1H).

$^{13}$C-NMR and DEPT (125 MHz, DMSO-$d_6$): δ (ppm)= 38.82 (CH), 39.37 (CH$_2$), 40.75 (CH), 120.70 (C), 125.56 (CH), 125.98 (CH), 126.75 (CH), 128.07 (CH), 129.33 (CH), 130.90 (C), 134.19 (C), 142.22 (C), 148.59 (C), 155.17 (C), 161.59 (CO), 172.55 (CO).

1.134. 3-(4-Chlorophenyl)-4-(6-chloro-4-hydroxy-2-quinazolinyl)butanoic acid (PS 452)

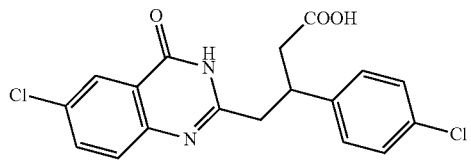 [SMILES: O=C(O)CC(Cc1nc2ccc(Cl)cc2c(=O)[nH]1)c1ccc(Cl)cc1]

By a procedure similar to that of 1.133, starting from 3-(4-chlorophenyl)glutaric anhydride and 5-chloroanthranil-amide, 3-(4-chlorophenyl)-4-(6-chloro-4-hydroxy-2-quinazolinyl)butanoic acid was obtained as colourless solid.

$^1$H-NMR (500 MHz, DMSO-$d_6$)): δ (ppm)=2.60 (dd, J=15.9, 9.0 Hz, 1H), 2.73 (dd, J=15.9, 5.8 Hz, 1H), 2.86 (dd, J=14.3, 7.6 Hz, 1H), 2.94 (dd, J=14.4, 7.8 Hz, 1H), 3.72 (m, 1H), 7.31 (s, 4H), 7.61 (d, J=8.7 Hz, 1H), 7.78 (dd, J=8.7, 2.6 Hz, 1H), 7.97 (d, J=2.5 Hz, 1H).

$^{13}$C-NMR and DEPT (125 MHz, DMSO-$d_6$): δ (ppm)= 38.82 (CH$_2$), 39.93 (CH$_2$), 40.77 (CH$_2$), 121.95 (C), 124.54 (CH), 128.04 (2CH), 128.94 (CH), 129.28 (2CH), 130.19 (CH), 130.88 (C), 134.25 (CH), 142.22 (C), 147.25 (C), 155.91 (C), 160.64 (CO), 172.55 (CO).

1.135. 5-Oxo-5-(2-phenanthrenyl)-3-phenylpentanoic acid (PS 255)

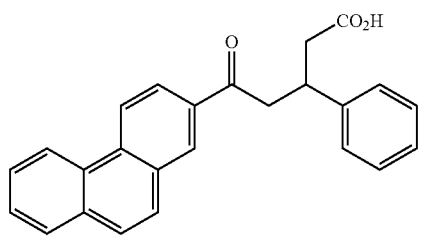 [SMILES: O=C(O)CC(CC(=O)c1ccc2c(ccc3ccccc32)c1)c1ccccc1]

By a procedure similar to that of example 1.60, starting from 2-[3-oxo-3-(2-phenanthrenyl)-1-phenylpropyl]malonic acid, 5-oxo-5-(2-phenanthrenyl)-3-phenylpentanoic acid was obtained as colourless solid.

$^1$H-NMR (500 MHz, (DMSO-$d_6$): δ (ppm)=2.62 (dd, J=8.5 Hz, 1H), 2.76 (dd, J=6.6 Hz, 1H), 3.58 (dd, J=6.6 Hz, 1H), 3.64 (dd, J=7.6 Hz, 1H), 3.73-3.79 (m, 1H), 7.15 (t, J=7.6 Hz, 1H), 7.26 (t, J=7.9 Hz, 2H), 7.35 (d, J=8.2 Hz, 2H), 7.71-7.76 (m, 2H), 7.96 (q, J=8.8 Hz, 2H), 8.01-8.04 (m, 1H), 8.13 (dd, J=1.9, 8.8 Hz, 1H), 8.66 (ds, J=1.9 Hz, 1H), 8.87 (d, J=9.1 Hz, 1H), 8.90 (d, J=8.8 Hz, 1H), 12.15 (s, OH).

$^{13}$C-NMR (125 MHz, (DMSO-$d_6$): δ (ppm)=37.2, 40.4, 44.1, 116.2, 123.3, 123.5, 124.8, 126.1, 127.1, 127.2, 127.5, 127.6, 127.9, 128.1, 128.5, 129.0, 129.4, 131.0, 132.4, 132.6, 134.5, 143.9, 198.2.

1.136. Methyl 2-cyano-5-(6-methoxynaphthalen-2-yl)-5-oxo-3-phenylpentanoate (PS 471)

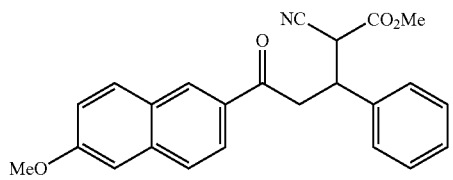 [SMILES: COC(=O)C(C#N)C(CC(=O)c1ccc2cc(OC)ccc2c1)c1ccccc1]

To a solution of 1-(6-methoxy-2-naphthalenyl)-3-phenyl-prop-2-en-1-one (1 g) and ethyl cyanoacetate (0.41 ml) in methanol, a catalytic amount of sodium hydride was added. The solution was stirred under reflux for 2 h. After cooling to room temperature water was added. The mixture was extracted with dichloromethane and the separated organic layer was washed with brine and dried (magnesium sulphate). After removal of the solvent the crude was recrystallised from dichloromethane/hexanes mixture to afford methyl 2-cyano-5-(6-methoxy-2-naphthalenyl)-5-oxo-3-phenylpentanoate as light yellow solid (mixture of diastereomers).

$^1$H-NMR (500 MHz, CDCl$_3$): δ (ppm)=3.64 (dd, J=4.7, 18.0 Hz, 1H), 3.66 (s, 3H), 3.75 (s, 1.8H), 3.78-3.80 (m, 1.5H), 3.82 (dd, J=9.5, 18.0 Hz, 3H), 3.95 (s, 1.8H), 3.95 (s, 3H); 3.97 (d, J=4.72 Hz, 0.6H), 4.19-4.27 (m, 1.7H), 4.40 (d, J=5.36 Hz, 1H), 3.87 (d, J=9.8 Hz, 1H), 3.94 (s, 3H), 3.96 (q, J=7.2 Hz, 2H), 4.16-4.27 (m, 3H), 7.12-7.30 (m, 7H), 7.15-7.18 (m, 1.7H), 7.21-7.23 (m, 1.7H), 7.27-7.45 (m, 8.6H), 7.77 (m, 1.7H); 7.85-7.88 (m, 1.6H), 7.97 (dd, J=1.9, 8.8 Hz, 0.7H), 7.99 (dd, J=1.9, 8.8 Hz, 1H), 8.42-8.43 (m, 1.6H).

$^{13}$C-NMR (125 MHz, CDCl$_3$): δ (ppm)=40.3, 40.8, 41.3, 43.3, 44.1, 53.2, 53.5, 55.4, 119.9, 120.0, 121.6, 121.64, 124.3, 124.4, 127.2, 127.3, 127.6, 127.8, 128.0, 128.1, 128.3, 128.9, 129.0, 129.8, 131.2, 131.23, 131.6, 137.6, 138.5, 160.0, 160.1, 165.5, 196.7, 196.8.

1.137. Ethyl 5-(6-methoxy-2-naphthalenyl)-2-nitro-5-oxo-3-phenylpentanoate (PS 472)

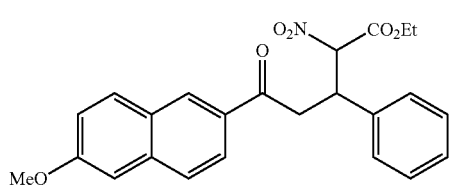 [SMILES: CCOC(=O)C(C(CC(=O)c1ccc2cc(OC)ccc2c1)c1ccccc1)[N+](=O)[O-]]

1-(6-methoxynaphthalen-2-yl)-3-phenylprop-2-en-1-one (0.3 g) and ethyl 2-nitroacetate (0.19 ml) were dissolved in ethanol and diethyl amine (0.02 ml) was added dropwise at 0°. The solution was stirred for 3 h at room temperature. The reaction was quenched by addition of water and the aqueous layer was extracted with dichloromethane. The organic layer was dried over MgSO$_4$ and concentrated and the residue was crystallised from ethanol to provide ethyl 5-(6-methoxy-2-naphthalenyl)-2-nitro-5-oxo-3-phenylpentanoate (0.29 g) as pale yellow solid (mixture of diastereomers).

$^1$H-NMR (500 MHz, (DMSO-d$_6$): δ (ppm)=0.91 (t, J=7.2 Hz, 2.5H), 1.09 (t, J=7.2 Hz, 3H), 3.50 (dd, J=3.7, 17.6 Hz, 1H), 3.67-3.78 (m, 2.1H), 3.91 (s, 5.3H), 3.94-4.15 (m, 4.2H), 4.20-4.27 (m, 1.1H), 4.27-4.38 (m, 1.8H), 6.07 (d, J=8.8 Hz, 0.7H), 6.14 (d, J=10.7 Hz, 1H), 7.21 (t, J=7.2 Hz, 1.7H), 7.25-7.30 (m, 5.4H), 7.39-7.41 (m, 3.4H), 7.45 (d, J=7.2 Hz, 2.1H), 7.85-7.87 (m, 1.4H), 7.88 (s, 2.1H), 8.02 (d, J=9.1 Hz, 1.8H), 8.53 (s, 1.7H).

$^{13}$C-NMR (125 MHz, (DMSO-d$_6$): δ (ppm)=13.2, 13.3, 40.5, 41.3, 41.5, 55.3, 62.3, 62.9, 80.3, 119.5, 119.6, 123.9, 126.9, 127.0, 127.2, 127.5, 128.2, 128.3, 128.4, 128.7, 129.7, 131.1, 131.2, 131.3, 131.5, 136.9, 137.1, 138.7, 158.4, 159.4, 163.6, 164.4, 165.1, 169.8, 171.7, 196.0, 196.2.

1.138. 2-(3-(4-Bromophenyl)-1-(4-chlorophenyl)-3-oxopropyl)malonic acid (PS 427)

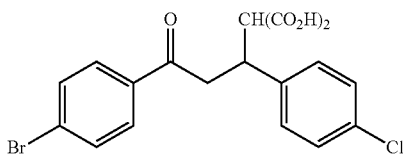

1) 1-(4-Bromophenyl)-3-(4-chlorophenyl)prop-2-en-1-one

By a procedure similar to that of example 1.59.1, starting from 4-chlorobenzaldehyde and 4-bromoacetophenone, 1-(4-bromophenyl)-3-(4-chlorophenyl)prop-2-en-1-one was obtained as yellowish solid.

$^1$H-NMR (500 MHz, CDCl$_3$): δ (ppm)=7.39 (d, J=8.5 Hz, 2H), 7.44 (d, J=15.5 Hz, 1H), 7.57 (d, J=8.5 Hz, 2H), 7.65 (d, J=8.5 Hz, 2H), 7.76 (d, J=15.5 Hz, 1H), 7.88 (d, J=8.5 Hz, 2H).

$^{13}$C-NMR (125 MHz, CDCl$_3$): δ (ppm)=121.9, 128.0, 129.3, 129.6, 130.0, 132.0, 133.2, 136.7, 136.8, 143.8, 189.0 (CO).

2) Dimethyl 2-(3-(4-bromophenyl)-1-(4-chlorophenyl)-3-oxopropyl)malonate

By a procedure similar to that of example 1.59.2, starting from 1-(4-bromophenyl)-3-(4-chlorophenyl)prop-2-en-1-one and dimethyl malonate, dimethyl 2-(3-(4-bromophenyl)-1-(4-chlorophenyl)-3-oxopropyl)malonate was obtained as colourless solid.

$^1$H-NMR (500 MHz, CDCl$_3$): δ (ppm)=3.39 (dd, J=9.1 Hz, 1H), 3.50 (dd, J=4.7 Hz, 1H), 3.53 (s, 3H), 3.73 (s, 3H), 3.80 (d, J=9.1 Hz, 1H), 4.11-4.16 (m, 1H), 7.21 (q, J=8.5 Hz, 4H), 7.57 (d, J=8.5 Hz, 2H), 7.75 (d, J=8.8 Hz, 2H).

$^{13}$C-NMR (125 MHz, CDCl$_3$): δ (ppm)=40.1, 42.1, 52.5, 52.7, 56.9, 128.4, 128.7, 129.4, 129.6, 131.9, 133.1, 135.3, 138.7, 167.9 (CO), 168.5 (CO), 196.2 (CO).

3) 2-(3-(4-Bromophenyl)-1-(4-chlorophenyl)-3-oxopropyl)malonic acid

By a procedure similar to that of example 1.59.3, starting from dimethyl 2-(3-(4-bromophenyl)-1-(4-chlorophenyl)-3-oxopropyl)malonate, 2-(3-(4-bromophenyl)-1-(4-chlorophenyl)-3-oxopropyl)malonic acid was obtained as colourless solid.

$^1$H-NMR (500 MHz, (DMSO-d$_6$): δ (ppm)=3.32 (dd, J=3.5, 17.3 Hz, 1H), 3.62 (dd, J=10.1 Hz, 1H), 3.74 (d, J=10.7 Hz, 1H), 3.82 (dt, J=3.8, 10.4 Hz, 1H), 7.26 (d, J=8.5 Hz, 2H), 7.31 (d, J=8.5 Hz, 2H), 7.70 (d, J=8.8 Hz, 2H), 7.79 (d, J=8.8 Hz, 2H), 12.60 (s, OH), 13.00 (s, OH).

$^{13}$C-NMR (125 MHz, (DMSO-d$_6$): δ (ppm)=30.6, 42.2, 57.0, 127.3, 127.8, 129.74, 130.3, 131.1, 131.7, 135.4, 140.1, 168.9 (CO), 169.4 (CO), 197.0 (CO).

1.139. Bis(acetoxymethyl)2-(3-(4-bromophenyl)-1-(4-chlorophenyl)-3-oxopropyl)-malonate (PS 446)

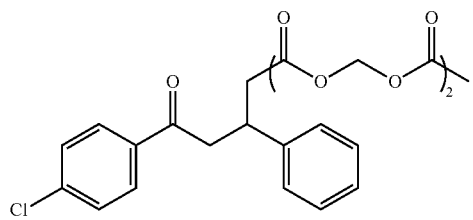

By a procedure similar to that of example 1.62, starting from 2-(3-(4-bromophenyl)-1-(4-chlorophenyl)-3-oxopropyl)malonic acid, bis(acetoxymethyl)2-(3-(4-bromophenyl)-1-(4-chlorophenyl)-3-oxopropyl)-malonate was obtained as colourless solid.

$^1$H-NMR (500 MHz, CDCl$_3$): δ (ppm)=2.00 (s, 3H), 2.08 (s, 3H), 3.41 (dd, J=9.1, 17.0 Hz, 1H), 3.51 (dd, J=4.7, 17.0 Hz, 1H), 3.91 (d, J=9.1 Hz, 1H), 4.13-4.17 (m, 1H), 5.57 (q, J=5.7 Hz, 2H), 5.75 (q, J=5.7 Hz, 2H), 7.21 (q, J=8.5 Hz, 4H), 7.58 (d, J=8.5 Hz, 2H), 7.74 (d, J=8.5 Hz, 2H).

$^{13}$C-NMR (125 MHz, CDCl$_3$): δ (ppm)=20.4, 20.5, 39.8, 41.9, 56.3, 79.5, 79.9, 128.8, 129.6, 129.7, 132.0, 132.8, 133.3, 134.4, 138.1, 165.9, 166.3, 168.9, 169.3, 195.9.

1.140. 2-(3-(4-Iodophenyl)-1-(2-naphthalenyl)-3-oxopropyl)malonic acid (PS 259)

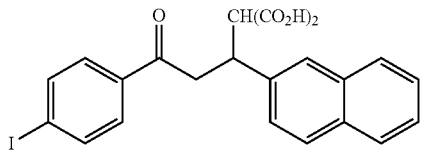

1) 1-(4-Iodophenyl)-3-(2-naphthalenyl)prop-2-en-1-one

By a procedure similar to that of example 1.59.1, starting from 2-naphthaldehyde and 4-iodoacetophenone, 1-(4-iodophenyl)-3-(2-naphthalenyl)prop-2-en-1-one was obtained as yellowish solid.

$^1$H-NMR (500 MHz, CDCl$_3$): δ (ppm)=7.51-7.56 (m, 2H), 7.58 (d, J=15.6 Hz, 1H), 7.76 (d, J=8.5 Hz, 2H), 7.76-7.80 (m, 1H), 7.82-7.89 (m, 3H), 7.88 (d, J=8.5 Hz, 2H), 7.98 (d, J=15.6 Hz, 1H), 8.04 (s, 1H).

2) Dimethyl 2-(3-(4-iodophenyl)-1-(2-naphthalenyl)-3-oxopropyl)malonate

By a procedure similar to that of example 1.59.2, starting from 1-(4-iodophenyl)-3-(2-naphthalenyl)prop-2-en-1-one and dimethyl malonate, dimethyl dimethyl 2-(3-(4-iodophenyl)-1-(2-naphthalenyl)-3-oxopropyl)malonate was obtained as yellowish solid.

$^1$H-NMR (500 MHz, CDCl$_3$): δ (ppm)=3.47 (s, 3H), 3.53 (dd, J=8.8, 16.9 Hz, 1H), 3.59 (dd, J=4.7, 16.9 Hz, 1H), 3.73 (s, 3H), 3.95 (d, J=9.1 Hz, 1H), 4.31-4.36 (m, 1H), 7.39 (dd, J=1.9, 8.5 Hz, 1H), 7.41-7.45 (m, 2H), 7.60 (d, J=8.5 Hz, 2H), 7.67 (ds, J=1.26 Hz, 1H), 7.74-7.77 (m, 3H), 7.78 (d, J=8.5 Hz, 2H).

$^{13}$C-NMR (125 MHz, CDCl$_3$): δ (ppm)=40.8, 42.2, 52.4, 52.7, 57.2, 101.1, 125.9, 126.0, 126.1, 127.6, 127.8, 128.3, 129.5, 132.6, 133.3, 136.0, 137.8, 137.9, 168.0 (CO), 168.7 (CO), 196.5 (CO).

3) 2-(3-(4-Iodophenyl)-1-(2-naphthalenyl)-3-oxopropyl)malonic acid

By a procedure similar to that of example 1.59.3, starting from dimethyl 2-(3-(4-iodophenyl)-1-(2-naphthalenyl)-3-oxopropyl)malonate, 2-(3-(4-iodophenyl)-1-(2-naphthalenyl)-3-oxopropyl)malonic acid was obtained as colourless solid.

$^1$H-NMR (500 MHz, (DMSO-d$_6$): δ (ppm)=3.41 (dd, J=3.5, 17.02 Hz, 1H), 3.71 (dd, J=10.4 Hz, 1H), 3.85 (d, J=10.7 Hz, 1H), 4.02 (dt, J=3.8, 10.4 Hz, 1H), 7.41-7.46 (m, 2H), 7.50 (dd, J=1.6, 8.5 Hz, 1H), 7.74-7.77 (m, 2H), 7.79-7.82 (m, 2H), 7.86 (d, J=8.5 Hz, 21H), 12.84 (s, 2OH).

$^{13}$C-NMR (125 MHz, (DMSO-d$_6$): δ (ppm)=40.2, 40.5, 57.3, 101.7, 125.5, 125.8, 126.7, 126.9, 127.2, 127.3, 127.4, 129.5, 131.8, 132.6, 134.4, 135.7, 137.5, 138.7, 168.9 (CO), 169.6, (CO), 192.4 (CO).

1.141. Bis(acetoxymethyl)2-(3-(4-iodophenyl)-1-(2-naphthalenyl)-3-oxopropyl)-malonate (PS 411)

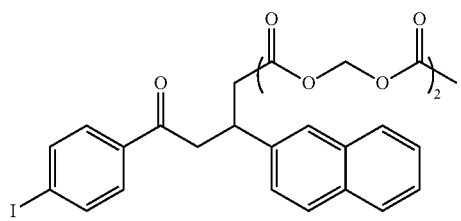

By a procedure similar to that of example 1.62, starting from 2-(3-(4-iodophenyl)-1-(2-naphthalenyl)-3-oxopropyl) malonic acid, bis(acetoxymethyl)2-(3-(4-iodophenyl)-1-(2-naphthalenyl)-3-oxopropyl)malonate was obtained as colourless solid.

$^1$H-NMR (500 MHz, CDCl$_3$): δ (ppm)=1.67 (s, 3H), 2.03 (s, 3H), 3.53 (dd, J=8.5, 17.0 Hz, 1H), 3.56 (dd, J=5.0, 17.0 Hz, 1H), 4.07 (d, J=9.1 Hz, 1H), 4.33-4.37 (m, 1H), 5.52 (q, J=5.8 Hz, 2H), 5.76 (q, J=5.8 Hz, 2H), 7.40 (dd, J=1.6, 8.5 Hz, 1H), 7.44-7.46 (m, 2H), 7.59 (d, J=8.8 Hz, 2H), 7.68 (ds, J=1.3 Hz, 1H), 7.75-7.77 (m, 3H), 7.78 (d, J=8.8 Hz, 2H).

$^{13}$C-NMR (125 MHz, CDCl$_3$): δ (ppm)=20.0, 40.5, 42.2, 56.5, 79.3, 79.8, 101.1, 101.2, 125.9, 126.0, 126.1, 126.2, 127.2, 127.6, 128.0, 128.4, 129.5, 132.6, 133.2, 135.8, 137.9, 166.1, 166.5, 169.2, 169.3, 196.5.

1.142. 2-(1-(4-Chlorophenyl)-3-(4-ethylphenyl)-3-oxopropyl)malonic acid (PS 424)

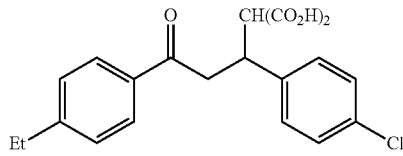

1) 3-(4-Chlorophenyl)-1-(4-ethylphenyl)prop-2-en-1-one

By a procedure similar to that of example 1.59.1, starting from 4-chlorobenzaldehyde and 4-ethylacetophenone, 3-(4-chlorophenyl)-1-(4-ethylphenyl)prop-2-en-1-one was obtained as pale yellowish solid.

$^1$H-NMR (500 MHz, CDCl$_3$): δ (ppm)=1.28 (t, J=7.9 Hz, 3H), 2.73 (q, J=7.9 Hz, 2H), 7.33 (d, J=8.2 Hz, 2H), 7.39 (d, J=8.5 Hz, 2H), 7.50 (d, J=15.8 Hz, 1H), 7.57 (d, J=8.8 Hz, 2H), 7.75 (d, J=15.8 Hz, 1H), 7.95 (d, J=8.2 Hz, 2H).

$^{13}$C-NMR (125 MHz, CDCl$_3$): δ (ppm)=15.2, 29.0, 122.6, 128.2, 128.7, 129.2, 129.5, 133.5, 135.7, 136.3, 142.1, 150.0, 189.7 (CO).

2) Dimethyl 2-(1-(4-chlorophenyl)-3-(4-ethylphenyl)-3-oxopropyl)malonate

By a procedure similar to that of example 1.59.2, starting from 3-(4-chlorophenyl)-1-(4-ethylphenyl)prop-2-en-1-one and dimethyl malonate, dimethyl 2-(1-(4-chlorophenyl)-3-(4-ethylphenyl)-3-oxopropyl)malonate was obtained as pale yellowish solid.

$^1$H-NMR (500 MHz, CDCl$_3$): δ (ppm)=1.24 (t, J=7.8 Hz, 3H), 2.69 (q, J=7.8 Hz, 2H), 3.42 (dd, J=8.8, 16.7 Hz, 1H), 3.48 (dd, J=4.7, 16.7 Hz, 1H), 3.53 (s, 3H), 3.73 (s, 3H), 3.82 (d, J=9.5 Hz, 1H), 4.14-4.19 (m, 1H), 7.19-7.23 (m, 4H), 7.25 (d, J=8.5 Hz, 2H), 7.81 (d, J=8.2 Hz, 2H).

$^{13}$C-NMR (125 MHz, CDCl$_3$): δ (ppm)=15.1, 28.9, 40.2, 42.0, 52.5, 52.7, 57.1, 128.1, 128.3, 128.6, 129.5, 132.9, 134.4, 139.1, 150.2, 168.0 (CO), 168.5 (CO), 196.8 (CO).

3) 2-(1-(4-Chlorophenyl)-3-(4-ethylphenyl)-3-oxopropyl)malonic acid

By a procedure similar to that of example 1.59.3, starting from dimethyl 2-(1-(4-chlorophenyl)-3-(4-ethylphenyl)-3-oxopropyl)malonate, 2-(1-(4-chlorophenyl)-3-(4-ethylphenyl)-3-oxopropyl)malonic acid was obtained as colourless solid.

$^1$H-NMR (500 MHz, (DMSO-d$_6$): δ (ppm)=1.17 (t, J=7.6 Hz, 3H), 2.65 (q, J=7.6 Hz, 2H), 3.28 (dd, J=3.5, 16.7 Hz, 1H), 3.60 (dd, J=10.4, 16.7 Hz, 1H), 3.75 (d, J=10.7 Hz, 1H), 3.86 (dt, J=3.5, 10.4 Hz, 1H), 7.26 (d, J=8.5 Hz, 2H), 7.30-7.32 (m, 4H), 7.79 (d, J=8.2 Hz, 2H), 12.80 (s, 2OH).

$^{13}$C-NMR (125 MHz, (DMSO-d$_6$): δ (ppm)=15.0, 28.0, 42.1, 46.4, 57.1, 127.7, 127.9, 128.0, 132.3, 131.0, 134.2, 140.2, 149.5, 168.9, 169.5, 197.2.

1.143. Bis(acetoxymethyl)2-(1-(4-chlorophenyl)-3-(4-ethylphenyl)-3-oxopropyl)-malonate (PS 445)

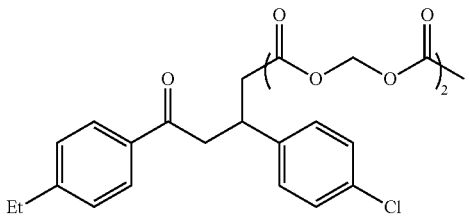

By a procedure similar to that of example 1.62, starting from 2-(1-(4-chlorophenyl)-3-(4-ethylphenyl)-3-oxopropyl) malonic acid, bis(acetoxymethyl)2-(1-(4-chlorophenyl)-3-(4-ethylphenyl)-3-oxopropyl)malonate was obtained as colourless solid.

$^1$H-NMR (500 MHz, CDCl$_3$): δ (ppm)=1.28 (t, J=7.6 Hz, 3H), 2.03 (s, 3H), 2.11 (s, 3H), 2.72 (q, J=7.6 Hz, 2H), 3.47 (dd, J=8.8, 17.1 Hz, 1H), 3.56 (dd, J=4.7, 17.1 Hz, 1H), 3.97 (d, J=9.5 Hz, 1H), 4.21-4.24 (m, 1H), 5.61 (q, J=5.7 Hz, 2H), 5.79 (q, J=5.7 Hz, 2H), 7.26-7.30 (m, 6H), 7.83 (d, J=8.2 Hz, 2H).

$^{13}$C-NMR (125 MHz, CDCl$_3$): δ (ppm)=15.1, 20.4, 20.5, 28.9, 39.8, 41.9, 56.4, 79.4, 79.8, 128.1, 128.2, 128.7, 129.7, 133.1, 134.3, 138.4, 150.3, 166.0, 166.4, 169.2, 169.3, 196.5.

1.144. 2-(1-(4-Chlorophenyl)-3-oxo-3-(4-(trifluoromethyl)phenyl)propyl)malonic acid (PS 449)

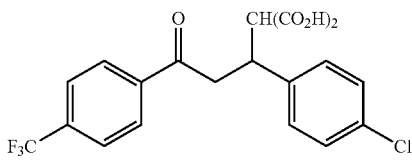

1) 3-(4-Chlorophenyl)-1-(4-(trifluoromethyl)phenyl)prop-2-en-1-one

By a procedure similar to that of example 1.59.1, starting from 4-chlorobenzaldehyde and p-(trifluoromethyl)acetophenone, 3-(4-chlorophenyl)-1-(4-(trifluoromethyl)-phenyl)prop-2-en-1-one was obtained as beige coloured solid.

$^1$H-NMR (500 MHz, CDCl$_3$): δ (ppm)=7.41 (d, J=8.5 Hz, 2H), 7.46 (d, J=15.8 Hz, 1H), 7.58 (q, J=8.5 Hz, 2H), 7.77 (d, J=8.2 Hz, 2H), 7.78 (d, J=15.8 Hz, 1H), 8.10 (d, J=8.2 Hz, 2H).

$^{13}$C-NMR (125 MHz, CDCl$_3$): δ (ppm)=122.0, 123.7 (q, $^1$J$_{C-F}$=273.1 Hz), 125.7 (q, $^3$J$_{C-F}$=3.7 Hz), 128.8, 129.4, 129.7, 133.0, 134.3, 136.9, 140.9, 144.5, 189.3 (CO).

2) Dimethyl 2-(1-(4-chlorophenyl)-3-oxo-3-(4-(trifluoromethyl)phenyl)propyl)-malonate By a procedure similar to that of example 1.59.2, starting from 3-(4-chlorophenyl)-1-(4-(trifluoromethyl)-phenyl)prop-2-en-1-one and dimethyl malonate, dimethyl 2-(1-(4-chlorophenyl)-3-oxo-3-(4-(trifluoromethyl)phenyl)-propyl)malonate was obtained as colourless solid.

$^1$H-NMR (500 MHz, CDCl$_3$): δ (ppm)=3.45 (dd, J=9.1, 17.0 Hz, 1H), 3.54 (s, 3H), 3.59 (dd, J=4.4, 17.0 Hz, 1H), 3.74 (s, 3H), 3.81 (d, J=9.1 Hz, 1H), 4.13-4.17 (m, 1H), 7.18-7.24 (q, J=8.5 Hz, 4H), 7.70 (d, J=8.2 Hz, 2H), 7.99 (d, J=8.2 Hz, 2H).

$^{13}$C-NMR (125 MHz, CDCl$_3$): δ (ppm)=40.0, 42.4, 52.6, 52.8, 56.9, 122.4, 125.7 (q, $^3$J$_{C-F}$=3.7 Hz), 128.4, 128.8, 129.4, 133.2, 134.7, 138.6, 139.2, 167.8 (CO), 168.5 (CO), 196.4 (CO).

3) 2-(1-(4-Chlorophenyl)-3-oxo-3-(4-(trifluoromethyl)phenyl)propyl) malonic acid By a procedure similar to that of example 1.59.3, starting from dimethyl 2-(1-(4-chlorophenyl)-3-oxo-3-(4-(trifluoromethyl)phenyl)propyl)malonate, 2-(1-(4-chlorophenyl)-3-oxo-3-(4-(trifluoromethyl)phenyl)propyl) malonic acid was obtained as colourless solid.

$^1$H-NMR (500 MHz, (DMSO-d$_6$): δ (ppm)=3.49 (dd, J=3.8, 17.9 Hz, 1H), 3.67 (dd, J=3.8, 9.8 Hz, 1H), 3.76 (d, J=10.7 Hz, 1H), 3.85 (dt, J=3.8, 10.4 Hz, 1H), 7.30 (q, J=8.5 Hz, 4H), 7.87 (d, J=8.5 Hz, 2H), 8.05 (d, J=8.5 Hz, 2H).

$^{13}$C-NMR (125 MHz, (DMSO-d$_6$): δ (ppm)=40.0, 42.6, 57.0, 124.0 (q, $^1$J$_{C-F}$=272.9 Hz), 125.7 (q, $^3$J$_{C-F}$=4.3 Hz), 127.8, 128.6, 130.3, 131.1, 139.5, 140.0, 140.7, 168.9, 169.5, 197.4.

1.145. 3-(4-Chlorophenyl)-5-oxo-5-(4-(trifluoromethyl)phenyl)pentanoic acid (PS 522)

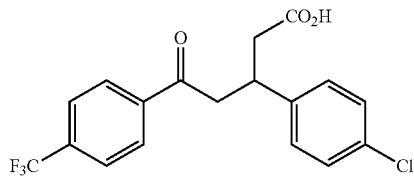

By a procedure similar to that of example 1.60, starting from 2-(1-(4-chlorophenyl)-3-oxo-3-(4-(trifluoromethyl)phenyl)propyl)malonic acid, 3-(4-chlorophenyl)-5-oxo-5-(4-(trifluoromethyl)phenyl)pentanoic acid was obtained as colourless solid.

$^1$H-NMR (500 MHz, (DMSO-d$_6$): δ (ppm)=2.70 (dd, J=7.4, 16.1 Hz, 1H), 2.85 (dd, J=7.4, 16.1 Hz, 1H), 3.34 (dd, J=7.0, 17.1 Hz, 1H), 3.40 (dd, J=7.0, 17.1 Hz, 1H), 3.82-3.88 (m, 1H), 7.20 (d, J=8.5 Hz, 2H), 7.27 (d, J=8.5 Hz, 2H), 7.70 (d, J=8.2 Hz, 2H), 7.99 (d, J=8.2 Hz, 2H).

$^{13}$C-NMR (125 MHz, (DMSO-d$_6$): δ (ppm)=36.5, 39.8, 44.6, 122.4, 125.7 (q, $^3$J$_{C-F}$=4.3 Hz), 128.3, 128.7, 128.72, 128.9, 132.8, 139.3, 141.1, 175.4, 196.8.

1.146. Bis(acetoxymethyl)2-(1-(4-chlorophenyl)-3-oxo-3-(4-(trifluoromethyl)-phenyl)propyl)malonate (PS 450)

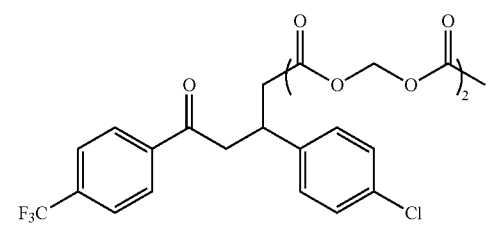

By a procedure similar to that of example 1.62, starting from 2-(1-(4-chlorophenyl)-3-oxo-3-(4-(trifluoromethyl)phenyl)propyl)malonic acid, bis-(acetoxymethyl)2-(1-(4-chlorophenyl)-3-oxo-3-(4-(trifluoromethyl)phenyl)propyl)-malonate was obtained as colourless solid.

$^1$H-NMR (500 MHz, CDCl$_3$): δ (ppm)=2.00 (s, 3H), 2.09 (s, 3H), 3.47 (dd, J=9.1, 17.2 Hz 1H), 3.58 (dd, J=4.2, 17.2 Hz, 1H), 3.92 (d, J=9.4 Hz, 1H), 4.14-4.18 (m, 1H), 5.58 (q, J=5.8 Hz, 2H), 5.75 (q, J=5.8, Hz, 2H), 7.22 (q, J=8.8 Hz, 4H), 7.71 (d, J=8.2 Hz, 2H), 7.99 (d, J=8.2 Hz, 2H).

$^{13}$C-NMR (125 MHz, CDCl$_3$): δ (ppm)=20.4, 20.5, 39.7, 42.3, 56.3, 79.5, 79.9, 123.1, 125.7 (q, $^3J_{C-F}$=4.3 Hz), 128.4, 128.8, 129.6, 133.4, 137.9, 139.1, 165.4, 165.9, 166.3, 168.1, 169.2 (CO), 169.3 (CO).

1.147. 2-(3-Oxo-1-(4-phenylthiophen-2-yl)-3-(4-(trifluoromethyl)phenyl)propyl)-malonic acid (PS 467)

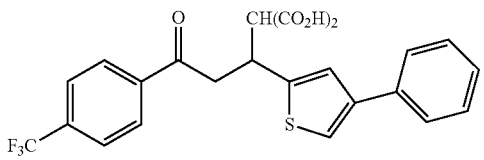

1) 3-(4-Phenylthiophen-2-yl)-1-(4-(trifluoromethyl)phenyl)prop-2-en-1-one

By a procedure similar to that of example 1.59.1, starting from 4-phenylthiophene-2-carbaldehyde and p-(trifluoromethyl)acetophenone, 3-(4-phenylthiophen-2-yl)-1-(4-(trifluoromethyl)phenyl)prop-2-en-1-one was obtained as yellow solid.

$^1$H-NMR (500 MHz, CDCl$_3$): δ (ppm)=7.31 (d, J=15.3, 1H), 7.34 (tt, J=1.3, 7.6, 1H), 7.43 (t, J=7.9, 2H), 7.58 (dt, J=8.2, 3H), 7.66 (ds, J=1.3 Hz, 1H), 7.78 (d, J=8.2 Hz, 2H), 7.99 (d, J=15.3 Hz, 1H), 8.10 (d, J=7.9 Hz, 2H).

2) Diethyl 2-(3-oxo-1-(4-phenylthiophen-2-yl)-3-(4-(trifluoromethyl)phenyl)-propyl)malonate By a procedure similar to that of example 1.59.2, starting from 3-(4-phenylthiophen-2-yl)-1-(4-(trifluoromethyl)phenyl)prop-2-en-1-one and diethyl malonate, diethyl 2-(3-oxo-1-(4-phenylthiophen-2-yl)-3-(4-(trifluoromethyl)-phenyl)propyl)malonate was obtained as yellow oil.

$^1$H-NMR (500 MHz, DMSO-d$_6$): δ (ppm)=0.99 (t, J=7.1 Hz, 3H), 1.16 (t, J=7.1 Hz, 3H), 3.31 (s, 3H), 3.56 (dd, J=4.1, 17.8 Hz, 1H), 3.80 (dd, J=9.5, 17.8 Hz, 1H), 3.95-3.98 (m, 2H), 3.99 (m, 2H), 4.12-4.18 (m, 2H), 4.27 (dt, J=4.1, 9.1 Hz, 1H), 7.26 (tt, J=1.3, 7.3 Hz, 1H), 7.37 (t, J=7.6 Hz, 2H), 7.45 (ds, J=1.3 Hz, 1H), 7.60 (dd, J=1.3, 8.2 Hz, 2H), 7.62 (ds, J=1.6 Hz, 1H), 7.89 (d, J=8.5 Hz, 2H), 8.13 (d, J=8.5 Hz, 2H).

$^{13}$C-NMR (125 MHz, DMSO-d$_6$): δ (ppm)=13.5, 13.7, 35.4, 43.1, 57.0, 60.9, 61.3, 119.4, 122.5, 124.6, 125.61, 125.63, 125.7, 126.9, 128.7, 128.71, 135.0, 138.5, 140.4, 144.0, 167.0 (CO), 167.4 (CO), 196.9 (CO).

3) 2-(3-Oxo-1-(4-phenylthiophen-2-yl)-3-(4-(trifluoromethyl)phenyl)propyl)malonic acid By a procedure similar to that of example 1.59.3, starting from diethyl 2-(3-oxo-1-(4-phenylthiophen-2-yl)-3-(4-(trifluoromethyl)phenyl)propyl)malonate, 2-(3-oxo-1-(4-phenylthiophen-2-yl)-3-(4-(trifluoromethyl)phenyl)propyl)malonic acid was obtained as colourless solid.

$^1$H-NMR (500 MHz, (DMSO-d$_6$): δ (ppm)=3.53 (dd, J=3.8, 17.3 Hz, 1H), 3.79 (dd, J=9.5, 17.3 Hz, 1H), 3.80 (d, J=9.8 Hz, 1H), 4.20 (dt, J=4.1, 9.5 Hz, 1H), 7.26 (t, J=7.3 Hz, 1H), 7.37 (t, J=7.6 Hz, 2H), 7.41 (ds, J=1.3 Hz, 1H), 7.58-7.60 (m, 3H), 7.88 (d, J=8.2 Hz, 2H), 8.12 (d, J=8.2 Hz, 2H), 12.92 (s, 2OH).

$^{13}$C-NMR (125 MHz, (DMSO-d$_6$): δ (ppm)=35.5, 43.3, 57.7, 119.2, 124.3, 125.6, 126.9, 128.6, 128.7, 135.0, 138.9, 140.3, 144.8, 168.9, 169.2, 175.0, 183.1, 194.0, 194.2, 197.1.

1.148. 2-(1,3-Di(2-naphthalenyl)-3-oxopropyl)malonic acid (PS 257)

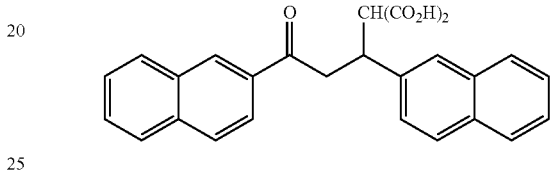

1) 1,3-Di(2-naphthalenyl)prop-2-en-1-one

By a procedure similar to that of example 1.59.1, starting from 2-naphthaldehyde and 2-acetylnaphthalene, 1,3-di-(2-naphthalenyl)prop-2-en-1-one was obtained as yellow solid.

$^1$H-NMR (500 MHz, CDCl$_3$): δ (ppm)=7.52-7.55 (m, 2H), 7.56-7.65 (m, 2H), 7.82 (d, J=15.8 Hz, 1H), 7.86-7.92 (m, 5H), 7.97 (d, J=8.8 Hz, 1H), 8.02-8.07 (m, 2H), 8.08 (s, 1H), 8.14 (dd, J=1.6, 8.5 Hz, 1H), 8.59 (s, 1H).

$^{13}$C-NMR (125 MHz, CDCl$_3$): δ (ppm)=117.7, 122.2, 123.7, 124.5, 126.8, 127.4, 127.81, 127.84, 128.4, 128.6, 128.7, 128.8, 129.5, 129.9, 130.7, 132.5, 132.6, 133.4, 134.4, 35.5, 135.7, 144.9, 190.2.

2) Diethyl 2-(1,3-di(2-naphthalenyl)-3-oxopropyl)malonate

By a procedure similar to that of example 1.59.2, starting from 1,3-di(2-naphthalenyl)prop-2-en-1-one and diethyl malonate, diethyl 2-(1,3-di(2-naphthalenyl)-3-oxopropyl)malonate was obtained as colourless solid.

$^1$H-NMR (500 MHz, CDCl$_3$): δ (ppm)=0.95 (t, J=7.1 Hz, 3H), 1.25 (t, J=7.1 Hz, 3H), 3.72 (dd, J=9.1, 16.7 Hz, 1H), 3.77 (dd, J=4.9, 16.7 Hz, 1H), 3.90-3.96 (m, 2H), 3.98 (d, J=9.7 Hz, 1H), 4.18-4.27 (m, 2H), 4.41-4.46 (m, 1H), 7.39-7.44 (m, 2H), 7.47 (dd, J=1.5, 8.5 Hz, 1H), 7.53 (t, J=7.9 Hz, 1H), 7.58 (t, J=8.2 Hz, 1H), 7.73-7.77 (m, 4H), 7.83-7.85 (m, 2H), 7.93-7.95 (m, 2H), 8.47 (s, 1H).

3) 2-(1,3-Di(2-naphthalenyl)-3-oxopropyl)malonic acid

By a procedure similar to that of example 1.59.3, starting from diethyl 2-(1,3-di(2-naphthalenyl)-3-oxopropyl)malonate, 2-(1,3-di(2-naphthalenyl)-3-oxopropyl)malonic acid was obtained as colourless solid.

$^1$H-NMR (500 MHz, DMSO-d$_6$): δ (ppm)=3.61 (dd, J=3.8, 16.85 Hz, 1H), 3.85 (dd, J=9.8, 16.85 Hz, 1H), 3.92 (d, J=10.4 Hz, 1H), 4.17 (dt, J=3.8, 10.1 Hz, 1H), 7.39-7.45 (m, 2H), 7.53 (dd, J=1.9, 8.5 Hz, 1H), 7.59 (dt, J=1.3, 8.2, 1H), 7.64 (dt, J=1.3, 8.2 Hz, 1H), 7.76 (d, J=8.5 Hz, 1H), 7.78-7.80

(m, 3H), 7.86 (dd, J=1.6, 8.8 Hz, 1H), 7.93-7.95 (m, 2H), 8.06 (d, J=8.2 Hz, 1H), 8.58 (s, 1H), 12.78 (s, 2OH).

1.149. 3,5-Di(2-naphthalenyl)-5-oxopentanoic acid (PS 262)

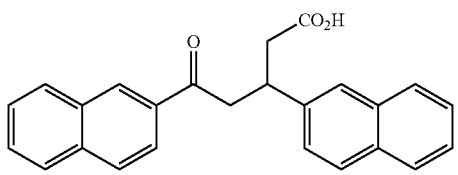 [SMILES: O=C(O)CC(CC(=O)c1ccc2ccccc2c1)c1ccc2ccccc2c1]

By a procedure similar to that of example 1.60, starting from 2-(1,3-di(2-naphthalenyl)-3-oxopropyl)malonic acid, 3,5-di(2-naphthalenyl)-5-oxopentanoic acid was obtained as beige coloured solid.

$^1$H-NMR (500 MHz, CDCl$_3$): δ (ppm)=2.86 (dd, J=7.9, 16.1 Hz, 1H), 2.99 (dd, J=6.9, 16.1 Hz, 1H), 3.53-3.63 (m, 2H), 4.08-4.13 (m, 1H), 7.39-7.46 (m, 3H), 7.53 (dt, J=0.9, 8.2 Hz, 1H), 7.59 (dt, J=1.3, 8.4 Hz, 1H), 7.74 (ds, J=1.3 Hz, 1H), 7.76-7.79 (m, 3H), 7.84 (d, J=8.8 Hz, 2H), 7.91 (d, J=8.2 Hz, 1H), 7.96 (dd, J=1.9, 8.8 Hz, 1H), 8.43 (s, 1H).

$^{13}$C-NMR (125 MHz, CDCl$_3$): δ (ppm)=37.4, 40.2, 44.6, 123.8, 125.6, 125.7, 125.9, 126.1, 126.7, 126.8, 127.6, 127.73, 127.75, 128.45, 128.48, 129.6, 129.8, 132.4, 132.5, 133.5, 134.1, 135.6, 140.5, 176.8, 198.0.

1.150. 2-(3-(9H-Carbazol-2-yl)-3-oxo-1-phenylpropyl)malonic acid (PS 470)

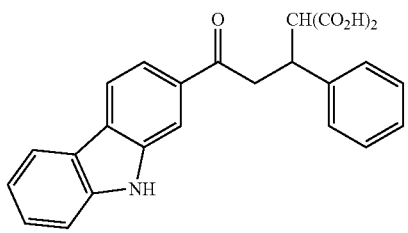

1) 1-(9H-Carbazol-2-yl)-3-phenylprop-2-en-1-one

By a procedure similar to that of example 1.59.1, starting from benzaldehyde and 2-acetylcarbazole, 1-(9H-carbazol-2-yl)-3-phenylprop-2-en-1-one was obtained as yellow solid.

$^1$H-NMR (500 MHz, CDCl$_3$): δ (ppm)=7.22 (t, J=7.9 Hz, 1H), 7.45-7.51 (m, 4H), 7.58 (d, J=8.2 Hz, 1H), 7.78 (d, J=15.6 Hz, 1H), 7.91-7.93 (m, 2H), 8.01 (dd, J=1.6, 8.2 Hz, 1H), 8.06 (d, J=15.6 Hz, 1H), 8.23 (d, J=7.9 Hz, 1H), 8.27-8.30 (m, 2H), 11.55 (s, NH).

$^{13}$C-NMR (125 MHz, CDCl$_3$): δ (ppm)=111.3, 111.6, 119.1, 120.11, 120.13, 121.1, 121.5, 122.6, 126.2, 127.0, 128.7, 128.9, 130.4, 134.7, 134.8, 139.2, 141.3, 143.3, 189.1.

2) Dimethyl 2-(3-(9H-carbazol-2-yl)-3-oxo-1-phenylpropyl)malonate

By a procedure similar to that of example 1.59.2, starting from 1-(9H-carbazol-2-yl)-3-phenylprop-2-en-1-one and dimethyl malonate, dimethyl 2-(3-(9H-carbazol-2-yl)-3-oxo-1-phenylpropyl)malonate was obtained as colourless solid.

$^1$H-NMR (500 MHz, (DMSO-d$_6$): δ (ppm)=3.37 (s, 3H), 3.46 (dd, J=3.6, 17.1 Hz, 1H), 3.69 (s, 3H), 3.77 (dd, J=9.1 Hz, 1H), 4.00-4.08 (m, 2H), 7.13 (t, J=7.3 Hz, 1H), 7.19-7.24 (m, 3H), 7.32 (d, J=7.3 Hz, 2H), 7.46 (d, J=8.2 Hz, 1H), 7.54 (d, J=8.2 Hz, 1H), 7.72 (dd, J=1.5, 8.2 Hz, 1H), 8.90 (s, 1H), 8.19 (t, J=7.9 Hz, 2H), 11.5 (s, NH).

3) 2-(3-(9H-Carbazol-2-yl)-3-oxo-1-phenylpropyl)malonic acid

By a procedure similar to that of example 1.59.3, starting from dimethyl 2-(3-(9H-carbazol-2-yl)-3-oxo-1-phenylpropyl)malonate, 2-(3-(9H-carbazol-2-yl)-3-oxo-1-phenylpropyl)-malonic acid was obtained as colourless solid.

$^1$H-NMR (500 MHz, (DMSO-d$_6$): δ (ppm)=3.40 (dd, J=3.3, 16.75 Hz, 1H), 3.74 (dd, J=10.3, 16.75 Hz, 1H), 3.81 (d, J=10.3 Hz, 1H), 3.96 (dt, J=3.0, 10.7 Hz, 1H), 7.11 (t, J=7.3 Hz, 1H), 7.19-7.22 (m, 3H), 7.32 (d, J=7.3 Hz, 2H), 7.46 (d, J=7.9 Hz, 1H), 7.53 (d, J=7.9 Hz, 1H), 7.71 (dd, J=1.2, 7.9 Hz, 1H), 7.99 (ds, J=0.6 Hz, 1H), 8.17-8.20 (m, 2H), 11.5 (s, NH), 12.71 (s, 2OH).

1.151. 5-Oxo-3-phenyl-5-(4-(trifluoromethyl)phenyl)pentanoic acid (PS 519)

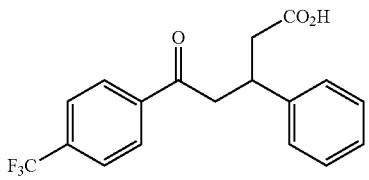 [SMILES: O=C(O)CC(CC(=O)c1ccc(C(F)(F)F)cc1)c1ccccc1]

By a procedure similar to that of example 1.60, starting from 2-(3-oxo-1-phenyl-3-(4-(trifluoromethyl)phenyl)propyl)malonic acid, 5-oxo-3-phenyl-5-(4-(trifluoromethyl)phenyl)pentanoic acid was obtained as colourless solid.

$^1$H-NMR (500 MHz, CDCl$_3$): δ (ppm)=2.75 (dd, J=7.0, 16.1 Hz, 1H), 2.87 (dd, J=7.0, 16.1 Hz, 1H), 3.36 (dd, J=6.8, 17.0 Hz, 1H), 3.42 (dd, J=6.8, 17.0 Hz, 1H), 3.83-3.89 (m, 1H), 7.20 (tt, J=1.6, 6.9 Hz, 1H), 7.22-7.31 (m, 4H), 7.69 (d, J=8.2 Hz, 2H), 7.90 (d, J=8.2 Hz, 2H).

$^{13}$C-NMR (125 MHz, CDCl$_3$): δ (ppm)=37.2, 39.9, 44.8, 114.8, 115.3, 116.0, 116.5, 125.7 (q, $^3J_{C-F}$=3.7 Hz), 127.1, 127.3, 128.4, 128.8, 175.6, 199.4.

1.152. Bis(acetoxymethyl)2-(3-oxo-1-phenyl-3-(4(trifluoromethyl)phenyl)propyl)-malonate (PS 423)

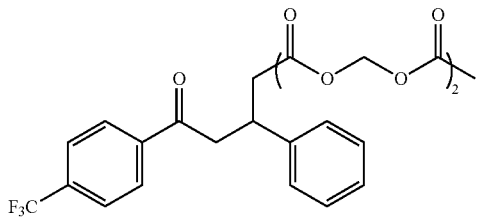

By a procedure similar to that of example 1.62, starting from 2-(3-oxo-1-phenyl-3-(4-(trifluoromethyl)phenyl)propyl)malonic acid, bis-(acetoxymethyl)2-(3-oxo-1-phenyl-3-(4(trifluoromethyl)phenyl)propyl)malonate was obtained as colourless solid.

¹H-NMR (500 MHz, CD₃OD): δ (ppm)=1.98 (s, 3H), 2.09 (s, 3H), 3.50 (dd, J=8.8 Hz, 1H), 3.60 (dd, J=4.2 Hz, 1H), 3.96 (d, J=9.1 Hz, 1H), 4.17-4.21 (m, 1H), 5.55 (q, J=5.7 Hz, 2H), 5.76 (d, J=5.7 Hz, 2H), 7.18-7.21 (m, 1H), 7.23-7.28 (m, 4H), 7.69 (d, J=8.2 Hz, 2H), 7.98.

¹³C-NMR (125 MHz, CD₃OD): δ (ppm)=20.5, 20.6, 40.4, 40.5, 56.5, 79.4, 79.8, 118.0, 125.6 (q, ³J$_{C-F}$=4.6 Hz), 127.6, 128.1, 128.4, 128.7, 164.9, 165.8, 166.0, 166.5, 169.2, 169.3, 196.4.

1.153. Bis(acetoxymethyl)2-(3-oxo-3-(4-phenoxyphenyl)-1-phenylpropyl)malonate (PS 426)

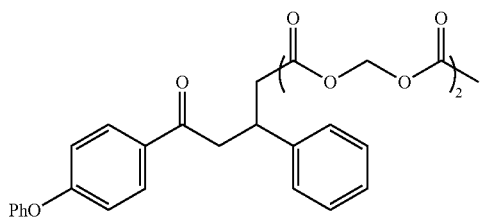

By a procedure similar to that of example 1.62, starting from 2-(3-oxo-3-(4-phenoxyphenyl)-1-phenylpropyl)malonic acid, bis(acetoxymethyl)2-(3-oxo-3-(4-phenoxyphenyl)-1-phenylpropyl)malonate was obtained as colourless solid.

¹H-NMR (500 MHz, CD₃OD): δ (ppm)=1.98 (s, 3H), 2.08 (s, 3H), 3.42 (dd, J=8.0 Hz, 1H), 3.96 (d, J=9.1 Hz, 1H), 4.17-4.21 (m, 1H), 5.55 (q, J=5.7 Hz, 2H), 5.76 (d, J=5.7 Hz, 2H), 6.96 (d, J=8.8 Hz, 2H), 7.05 (d, J=8.5 Hz, 2H), 7.18-7.21 (m, 2H), 7.23-7.27 (m, 4H), 7.38 (t, J=7.6 Hz, 2H), 7.86 (d, J=8.8 Hz, 2H).

¹³C-NMR (125 MHz, CD₃OD): δ (ppm)=20.51, 20.54, 40.5, 41.9, 56.6, 79.4, 79.8, 117.0, 117.3, 120.0, 124.6, 127.4, 128.2, 128.5, 130.0, 130.3, 139.8, 144.4, 155.4, 162.0, 166.1, 169.2, 169.3, 195.7.

1.154. Bis(acetoxymethyl)2-(1-(4-chlorophenyl)-3-(4-iodophenyl)-3-oxopropyl)-malonate (PS 425)

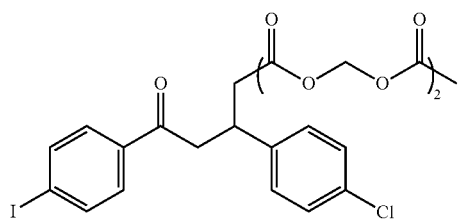

By a procedure similar to that of example 1.62, starting from 2-(1-(4-chlorophenyl)-3-(4-iodophenyl)-3-oxopropyl) malonic acid, bis(acetoxymethyl)2-(1-(4-chlorophenyl)-3-(4-iodophenyl)-3-oxopropyl)malonate was obtained as colourless solid.

¹H-NMR (500 MHz, CD₃OD): δ (ppm)=1.98 (s, 3H), 2.08 (s, 3H), 3.40 (dd, J=9.1 Hz, 1H), 3.50 (d, J=4.7 Hz, 1H), 3.90 (d, J=9.1 Hz, 1H), 4.12-4.17 (m, 1H), 5.57 (q, J=5.7 Hz, 2H), 5.74 (d, J=5.7 Hz, 2H), 7.21 (q, J=8.8 Hz, 4H), 7.58 (d, J=8.5 Hz, 2H), 7.80 (d, J=7.6 Hz, 2H).

¹³C-NMR (125 MHz, CD₃OD): δ (ppm)=20.4, 20.5, 39.8, 41.9, 56.3, 79.4, 79.9, 101.4, 128.8, 129.4, 129.6, 133.3, 135.7, 138.0, 138.1, 165.3, 165.9, 168.0, 169.2, 196.2.

1.155. Bis(acetoxymethyl)2-(3-(6-methoxy-2-naphthalenyl)-3-oxo-1-phenyl-propyl)malonate (PS 389)

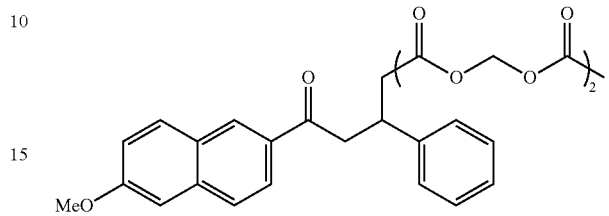

By a procedure similar to that of example 1.62, starting from 2-(3-(6-methoxy-2-naphthalenyl)-3-oxo-1-phenylpropyl)malonic acid, bis(acetoxymethyl)2-(3-(6-methoxy-2-naphthalenyl)-3-oxo-1-phenylpropyl)malonate was obtained as colourless solid.

¹H-NMR (500 MHz, CD₃OD): δ (ppm)=1.97 (s, 3H), 2.06 (s, 3H), 3.60 (dd, J=6.0 Hz, 1H), 3.68 (d, J=5.4 Hz, 1H), 3.94 (m, 3H), 4.01 (d, J=9.1 Hz, 1H), 4.25-4.29 (m, 1H), 5.57 (q, J=5.7 Hz, 2H), 5.76 (s, 2H), 7.13 (ds, J=2.2 Hz, 1H), 7.16-7.18 (m, 2H), 7.23-7.27 (m, 2H), 7.30 (d, J=6.9 Hz, 2H), 7.72 (d, J=8.8 Hz, 1H), 7.84 (d, J=9.1 Hz, 1H), 7.90 (dd, J=1.6, 8.8 Hz, 1H), 8.35 (ds, J=1.6 Hz, 1H).

¹³C-NMR (125 MHz, CD₃OD): δ (ppm)=20.51, 20.54, 40.6, 42.0, 55.4, 56.7, 79.4, 79.8, 105.7, 119.7, 124.5, 127.1, 127.3, 127.8, 128.2, 128.6, 129.7, 131.1, 131.2, 132.2, 137.3, 139.9, 159.8, 166.2, 166.6, 169.2, 169.3, 196.7.

1.156. 2-(3-(4-Iodophenyl)-3-oxo-1-phenylpropyl)malonic acid (PS 505)

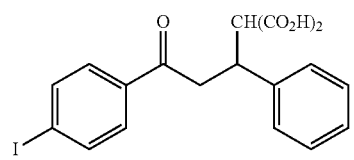

1) 1-(4-Iodophenyl)-3-phenylprop-2-en-1-one

By a procedure similar to that of example 1.59.1, starting from benzaldehyde and p-iodoacetophenone, 1-(4-iodophenyl)-3-phenylprop-2-en-1-one was obtained as beige coloured solid.

¹H-NMR (500 MHz, CDCl₃): δ (ppm)=7.42-7.44 (m, 3H), 7.46 (d, J=15.5 Hz, 1H), 7.62-7.67 (m, 2H), 7.73 (d, J=8.2 Hz, 2H), 7.82 (d, J=15.5 Hz, 1H), 7.87 (d, J=8.5 Hz, 2H).

2) Dimethyl 2-(3-(4-iodophenyl)-3-oxo-1-phenylpropyl)malonate

By a procedure similar to that of example 1.59.2, starting from 1-(4-iodophenyl)-3-phenylprop-2-en-1-one and dimethyl malonate, dimethyl 2-(3-(4-iodophenyl)-3-oxo-1-phenylpropyl)malonate was obtained as yellowish solid.

¹H-NMR (500 MHz, CDCl₃): δ (ppm)=3.41 (dd, J=4.8, 16.7 Hz, 1H), 3.50 (s, 3H), 3.52 (dd, J=4.8, 16.7 Hz, 1H), 3.72

(s, 3H), 3.83 (d, J=9.4 Hz, 1H), 4.12-4.17 (m, 1H), 7.16-7.20 (m, 1H), 7.21-7.27 (m, 4H), 7.60 (d, J=8.5 Hz, 2H), 7.79 (d, J=8.5 Hz, 2H).

$^{13}$C-NMR (125 MHz, CDCl$_3$): δ (ppm)=40.8, 42.2, 52.4, 52.7, 57.2, 127.9, 128.5, 129.5, 137.9, 140.2, 142.8, 145.1, 158.8, 177.0, 177.3, 199.6.

3) 2-(3-(4-Iodophenyl)-3-oxo-1-phenylpropyl)malonic acid

By a procedure similar to that of example 1.59.3, starting from dimethyl 2-(3-(4-iodophenyl)-3-oxo-1-phenylpropyl)malonate, 2-(3-(4-iodophenyl)-3-oxo-1-phenylpropyl)malonic acid was obtained as colourless solid.

$^1$H-NMR (500 MHz, (DMSO-d$_6$): δ (ppm)=3.28 (dd, J=3.6, 17.1 Hz, 1H), 3.58 (dd, J=10.5 Hz, 1H), 3.73 (d, J=10.7 Hz, 1H), 3.84 (dt, J=3.6, 10.3 Hz, 1H), 7.11 (t, J=7.3 Hz, 1H), 7.19 (t, J=7.9 Hz, 2H), 7.26 (d, J=7.3 Hz, 2H), 7.61 (d, J=8.5 Hz, 2H), 7.87 (d, J=8.5 Hz, 2H), 12.61 (s, OH), 12.90 (s, OH).

1.157. 5-(4-Iodophenyl)-5-oxo-3-phenylpentanoic acid (PS 520)

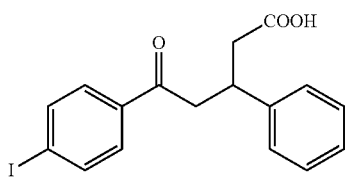 [SMILES: O=C(O)CC(CC(=O)c1ccc(I)cc1)c1ccccc1]

By a procedure similar to that of example 1.60, starting from 2-(3-(4-iodophenyl)-3-oxo-1-phenylpropyl)malonic acid, 5-(4-iodophenyl)-5-oxo-3-phenylpentanoic acid was obtained as colourless solid.

$^1$H-NMR (500 MHz, CDCl$_3$): δ (ppm)=2.73 (dd, J=7.3, 16.0 Hz, 1H), 2.85 (dd, J=7.3, 16.0 Hz, 1H), 3.28 (dd, J=7.2, 16.7 Hz, 1H), 3.34 (dd, J=7.2, 16.7 Hz, 1H), 3.81-3.87 (m, 1H), 7.20 (tt, J=1.3, 7.2 Hz, 1H), 7.24-7.31 (m, 4H), 7.59 (d, J=8.6 Hz, 2H), 7.79 (d, J=8.6 Hz, 2H).

1.158. 2-(3-(4-Iodophenyl)-3-oxo-1-phenylpropyl)malononitrile (PS 523)

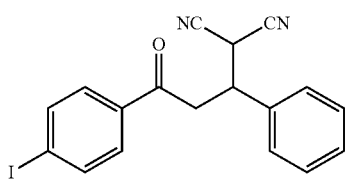 [SMILES: N#CC(C#N)C(CC(=O)c1ccc(I)cc1)c1ccccc1]

By a procedure similar to that of example 1.59.2, starting from 1-(4-iodophenyl)-3-phenylprop-2-en-1-one and malononitrile, 2-(3-(4-iodophenyl)-3-oxo-1-phenylpropyl)malononitrile was obtained as colourless solid.

$^1$H-NMR (500 MHz, CD$_3$OD): δ (ppm)=3.58 (dd, J=5.4, 12.9 Hz, 1H), 3.65 (dd, J=8.2, 18.3 Hz, 1H), 3.92-3.97 (m, 1H), 4.60 (d, J=5.4 Hz, 1H), 7.38-7.44 (m, 5H), 7.66 (d, J=8.5 Hz, 2H), 7.87 (d, J=8.5 Hz, 2H).

$^{13}$C-NMR (125 MHz, CD$_3$OD): δ (ppm)=28.7, 40.0, 41.1, 102.4, 111.6, 127.9, 129.2, 129.3, 129.4, 135.0, 136.3, 138.3, 195.9.

1.159. 5-(3-Oxo-3-(4-phenoxyphenyl)-1-phenylpropyl)pyrimidine-2,4,6-(1H,3H,5H)-trione (PS 376)

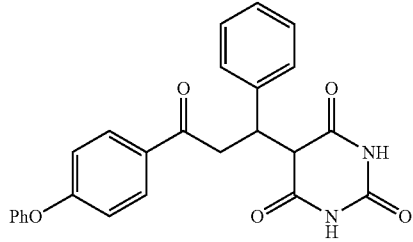 [SMILES: O=C1NC(=O)C(C(CC(=O)c2ccc(Oc3ccccc3)cc2)c2ccccc2)C(=O)N1]

By a procedure similar to that of example 1.59.2, starting from 1-(4-phenoxyphenyl)-3-phenylprop-2-en-1-one and barbituric acid, 5-(3-oxo-3-(4-phenoxyphenyl)-1-phenylpropyl)pyrimidine-2,4,6(1H,3H,5H)-trione was obtained as yellow solid.

$^1$H-NMR (500 MHz, (DMSO-d$_6$): δ (ppm)=3.57 (dd, J=6.6 Hz, 1H), 3.80 (d, J=3.8 Hz, 1H), 3.99 (dd, J=8.2 Hz, 1H), 4.15-4.19 (m, 1H), 7.06 (d, J=8.8 Hz, 2H), 7.12 (dd, J=0.9, 8.8 Hz, 2H), 7.17 (d, J=8.5 Hz, 2H), 7.21-7.30 (m, 4H), 7.46 (t, J=8.5 Hz, 2H), 8.01 (d, J=9.1 Hz, 2H), 11.02 (s, NH), 11.07 (s, NH).

$^{13}$C-NMR (125 MHz, (DMSO-d$_6$): δ (ppm)=40.3, 41.5, 51.6, 117.1, 119.8, 124.6, 127.1, 127.7, 128.1, 128.3, 130.2, 130.3, 131.4, 139.5, 150.3, 154.9, 161.2, 169.7, 170.0, 196.6.

1.160. 2-(1-(4-Chlorophenyl)-3-(4-hydroxyphenyl)-3-oxopropyl)malonic acid (PS 502)

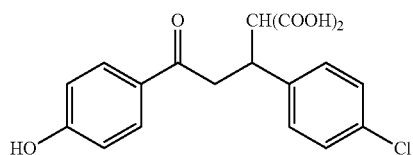

1) p-Methoxymethoxyacetophenone

Bromomethyl-methylether (0.87 ml) was added dropwise to a stirred suspension of p-hydroxyacetophenone (1 g) and sodium hydride (0.44 g) at 0° C. under nitrogen. The mixture was stirred for 1 h at room temperature. Then water was added and the mixture was extracted with ethylacetate. The organic layer was dried over magnesium sulphate and concentrated in vacuo to leave p-methoxymethoxyacetophenone (1.4 g) as yellow solid which was processed without further purification.

2) 3-(4-Chlorophenyl)-1-(4-methoxymethoxyphenyl)prop-2-en-1-one

By a procedure similar to that of example 1.59.1, starting from 4-chlorobenzaldehyde and p-methoxymethoxyacetophenone, 3-(4-chlorophenyl)-1-(4-methoxymethoxyphenyl)prop-2-en-1-one was obtained as yellowish solid.

¹H-NMR (500 MHz, CDCl₃): δ (ppm)=3.50 (s, 3H), 5.26 (s, 2H), 7.12 (d, J=8.8 Hz, 2H), 7.39 (d, J=8.2 Hz, 2H), 7.50 (d, J=15.5 Hz, 1H), 7.57 (d, J=8.2 Hz, 2H), 7.74 (d, J=15.5 Hz, 1H), 8.02 (d, J=8.8 Hz, 2H).

3) Dimethyl 2-(1-(4-chlorophenyl)-3-(4-(methoxymethoxy)phenyl)-3-oxopropyl)-malonate By a procedure similar to that of example 1.59.2, starting from 3-(4-chlorophenyl)-1-(4-methoxymethoxy-phenyl) prop-2-en-1-one and dimethyl malonate, dimethyl 2-(1-(4-chlorophenyl)-3-(4-(methoxymethoxy)phenyl)-3-oxopropyl)malonate was obtained as colourless solid.

¹H-NMR (500 MHz, CDCl₃): δ (ppm)=3.38 (dd, J=9.1 Hz, 1H), 3.46 (d, J=4.7 Hz, 1H), 3.47 (s, 3H), 3.52 (s, 3H), 3.72 (s, 3H), 3.82 (d, J=9.1 Hz, 1H), 4.13-4.17 (m, 1H), 5.21 (s, 2H), 7.04 (d, J=8.8 Hz, 2H), 7.19-7.27 (m, 4H), 7.86 (d, J=8.8 Hz, 2H).

4) Dimethyl 2-(1-(4-chlorophenyl)-3-(4-hydroxyphenyl)-3-oxopropyl)malonate

A solution of dimethyl 2-(1-(4-chlorophenyl)-3-(4-(methoxymethoxy)phenyl)-3-oxopropyl)malonate (0.3 g) in methanol (10 ml) was treated with 10% HCl (2 ml) and the resulting mixture was refluxed for 2 h. After cooling to room temperature the solvent was removed, the residue was extracted with ethyl acetate, and dried (magnesium sulphate). After concentration the crude (0.3 g yellow oil) was used for the next step without further purification.

¹H-NMR (500 MHz, CDCl₃): δ (ppm)=3.37 (dd, J=9.1 Hz, 1H), 3.46 (d, J=4.6 Hz, 1H), 3.53 (s, 3H), 3.73 (s, 3H), 3.81 (d, J=9.1 Hz, 1H), 4.14-4.17 (m, 2H), 6.82 (d, J=8.8 Hz, 2H), 7.18-7.22 (m, 4H), 7.82 (d, J=8.8 Hz, 2H).

5) 2-(1-(4-Chlorophenyl)-3-(4-hydroxyphenyl)-3-oxopropyl)malonic acid

By a procedure similar to that of example 1.59.3, starting from dimethyl 2-(1-(4-chlorophenyl)-3-(4-hydroxyphenyl)-3-oxopropyl)malonate, 2-(1-(4-chlorophenyl)-3-(4-hydroxyphenyl)-3-oxopropyl)malonic acid was obtained as colourless solid.

1.161. (Z)-3-(Biphenyl-4-yl)-5-(4-chlorophenyl) pent-2-enoic acid and (E)-3-(Biphenyl-4-yl)-5-(4-chlorophenyl)pent-2-enoic acid (PS 315+PS 314)

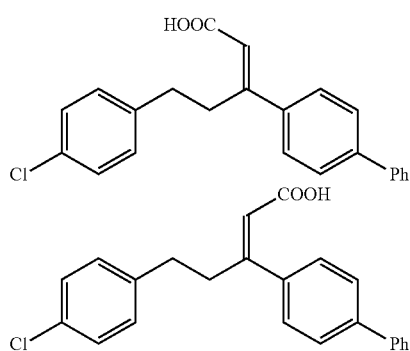

1) 1-(Biphenyl-4-yl)-3-(4-chlorophenyl)prop-2-en-1-one

Synthesised according to example 1.59.1 using 4-chlorobenzaldehyde (3.58 g, 25.48 mmol) and 1-(biphenyl-4-yl)ethanone (5.00 g, 25.48 mmol); pale yellow solid; yield: 7.74 g (95%);

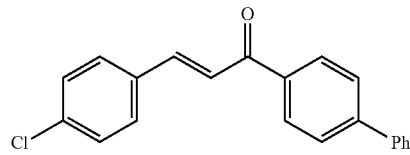 [SMILES: O=C(/C=C/c1ccc(Cl)cc1)c1ccc(-c2ccccc2)cc1]

¹H-NMR (500 MHz, CDCl₃): δ (ppm)=7.41 (t, J=8.2 Hz, 3H), 7.49 (t, J=7.9 Hz, 2H), 7.56 (d, J=15.5 Hz, 1H), 7.60 (d, J=8.8 Hz, 2H), 7.66 (d, J=8.2 Hz, 2H), 7.74 (d, J=8.5 Hz, 2H), 7.80 (d, J=15.5 Hz, 1H), 7.81 (d, J=8.5 Hz, 2H).
¹³C-NMR (125 MHz, CDCl₃): δ (ppm)=122.4, 127.3, 127.31, 128.2, 129.0, 129.1, 129.2, 129.6, 133.4, 136.4, 136.7, 139.9, 143.2, 145.7, 189.6.

2) 1-(Biphenyl-4-yl)-3-(4-chlorophenyl)propan-1-one

Synthesised according to example 1.85.2 using 1-(biphenyl-4-yl)-3-(4-chlorophenyl)prop-2-en-1-one; colourless oil; yield: 90%;

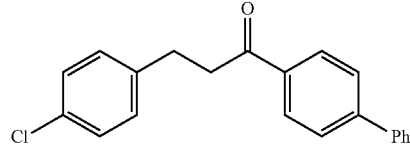 [SMILES: O=C(CCc1ccc(Cl)cc1)c1ccc(-c2ccccc2)cc1]

¹H-NMR (500 MHz, CDCl₃): δ (ppm)=3.07 (t, J=7.4 Hz, 2H), 3.31 (t, J=7.4 Hz, 2H), 7.20 (d, J=8.5 Hz, 2H), 7.27 (d, J=8.5 Hz, 2H), 7.40 (t, J=7.6 Hz, 1H), 7.47 (t, J=6.9 Hz, 2H), 7.62 (t, J=6.9 Hz, 2H), 7.68 (d, J=8.5 Hz, 2H), 8.02 (d, J=8.5 Hz, 2H).
¹³C-NMR (125 MHz, CDCl₃): δ (ppm)=29.4, 40.2, 127.2, 127.3, 128.2, 128.6, 128.9, 129.8, 131.9, 135.4, 139.7, 139.8, 145.8, 198.4.

3) (E,Z)-Ethyl 3-(biphenyl-4-yl)-5-(4-chlorophenyl) pent-2-enoate

Synthesised according to Method 1.85.3, using 1-(biphenyl-4-yl)-3-(4-chlorophenyl)propan-1-one (1.5 g, 4.67 mmol), NaH (0.56 g, 14.00 mmol) and triethyl phosphonoacetate (2.89 mL, 14.47 mmol);

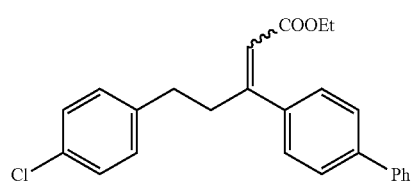 [SMILES: CCOC(=O)C=C(CCc1ccc(Cl)cc1)c1ccc(-c2ccccc2)cc1]

E: colourless oil; yield: 0.85 g (47%);
¹H-NMR (500 MHz, CDCl₃): δ (ppm)=1.32 (t, J=7.3 Hz, 3H), 2.74-2.77 (m, 2H), 3.41-3.44 (m, 2H), 4.21 (q, J=7.0 Hz, 2H), 6.14 (s, 1H), 7.17 (d, J=8.5 Hz, 2H), 7.24 (d, J=8.5 Hz, 2H), 7.38 (t, J=7.3 Hz, 1H), 7.47 (d, J=7.3 Hz, 2H), 7.53 (d, J=8.2 Hz, 2H), 7.63 (d, J=7.9 Hz, 4H).

$^{13}$C-NMR (125 MHz, CDCl$_3$): δ (ppm)=14.3, 32.7, 34.5, 59.9, 117.8, 127.0, 127.2, 127.3, 127.7, 128.3, 128.9, 129.9, 131.6, 139.6, 139.9, 140.2, 141.9, 146.7, 158.4, 166.3.

Z: colourless oil; yield: 0.89 g (49%);

$^1$H-NMR (500 MHz, CDCl$_3$): δ (ppm)=1.09 (t, J=7.1 Hz, 3H), 2.69-2.73 (m, 2H), 2.77-2.86 (m, 2H), 4.02 (q, J=7.1 Hz, 2H), 5.91 (s, 1H), 7.26 (d, J=8.2 Hz, 4H), 7.36 (t, J=7.3 Hz, 2H), 7.46 (t, J=1.9, 8.5 Hz, 1H), 7.61 (d, J=8.2 Hz, 2H), 7.64 (d, J=7.3 Hz, 2H).

$^{13}$C-NMR (125 MHz, CDCl$_3$): δ (ppm)=13.9, 33.2, 41.8, 59.9, 118.0, 126.6, 127.0, 127.3, 127.8, 128.5, 128.7, 129.7, 131.8, 138.4, 139.2, 140.6, 157.5, 165.9.

4) (E)-3-(Biphenyl-4-yl)-5-(4-chlorophenyl)pent-2-enoic acid (PS 314)

Synthesised according to example 1.85.5, using (E)-ethyl 3-(biphenyl-4-yl)-5-(4-chlorophenyl)pent-2-enoate (0.6 g, 1.53 mmol) and NaOH$_{aq}$ (1.50 mL, 4.60 mmol); white solid; yield: 0.45 g (81%);

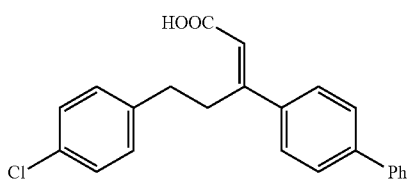 [SMILES: O=C(O)/C=C(\CCc1ccc(Cl)cc1)c1ccc(-c2ccccc2)cc1]

$^1$H-NMR (500 MHz, CDCl$_3$): δ (ppm)=2.77-2.81 (m, 2H), 3.43-3.46 (m, 2H), 6.21 (s, 1H), 7.16 (d, J=8.2 Hz, 2H), 7.25 (d, J=8.5 Hz, 2H), 7.39 (t, J=7.2 Hz, 1H), 7.48 (t, J=7.2 Hz, 1H), 7.56 (d, J=8.2 Hz, 2H), 7.65 (d, J=8.2 Hz, 4H).

$^{13}$C-NMR (125 MHz, CDCl$_3$): δ (ppm)=33.1, 34.6, 116.7, 127.1, 127.2, 127.4, 127.8, 128.5, 128.9, 131.8, 139.4, 139.7, 140.1, 142.4, 161.6, 171.2.

5) (Z)-3-(Biphenyl-4-yl)-5-(4-chlorophenyl)pent-2-enoic acid (PS 315)

Synthesised according to example 1.85.4 using (Z)-ethyl 3-(biphenyl-4-yl)-5-(4-chlorophenyl)pent-2-enoate (0.6 g, 1.53 mmol) and NaOH$_{aq}$ (1.50 mL, 4.60 mmol); white solid; yield: 0.40 g (72%);

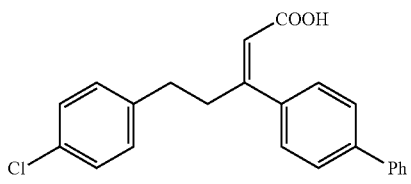 [SMILES: O=C(O)/C=C(/CCc1ccc(Cl)cc1)c1ccc(-c2ccccc2)cc1]

$^1$H-NMR (500 MHz, CDCl$_3$): δ (ppm)=2.67-2.70 (m, 2H), 2.77-2.80 (m, 2H), 5.88 (s, 1H), 7.05 (d, J=8.8 Hz, 2H), 7.24 (d, J=8.5 Hz, 2H), 7.25 (d, J=8.2 Hz, 2H), 7.35 (d, J=7.9 Hz, 2H), 7.44 (t, J=7.9 Hz, 2H), 7.58 (d, J=7.58 Hz, 2H), 7.61 (t, J=7.9 Hz, 2H).

$^{13}$C-NMR (125 MHz, CDCl$_3$): δ (ppm)=33.2, 42.1, 126.8, 127.1, 127.5, 127.8, 128.6, 128.7, 129.7, 132.0, 137.7, 138.9, 139.0, 141.4, 161.0, 166.5.

1.162. (Z)-3,5-Di(naphthalen-2-yl)pent-2-enoic acid and (E)-3,5-Di(naphthalen-2-yl)pent-2-enoic acid (PS 261+PS 260)

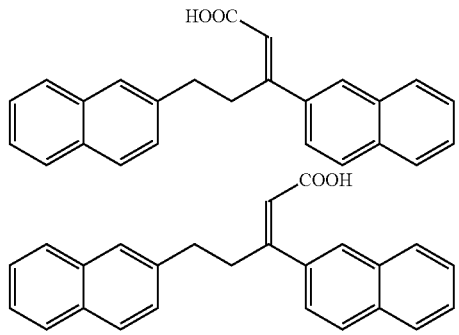

1) 1,3-Di(naphthalen-2-yl)prop-2-en-1-one

Synthesised according to example 1.59.1, using 2-naphthaldehyde (10.9 g, 64.03 mmol) and 1-(naphthalen-2-yl)ethanone (11.9 g, 64.03 mmol); yellow solid; yield: 18.8 g (95%);

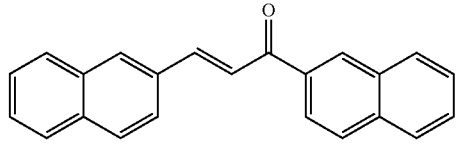

$^1$H-NMR (500 MHz, CDCl$_3$): δ (ppm)=7.52-7.55 (m, 2H), 7.56-7.65 (m, 2H), 7.82 (d, J=15.8 Hz, 1H), 7.86-7.92 (m, 5H), 7.97 (d, J=8.8 Hz, 1H), 8.02-8.07 (m, 2H), 8.08 (s, 1H), 8.14 (dd, J=1.6, 8.5 Hz, 1H), 8.59 (s, 1H).

$^{13}$C-NMR (125 MHz, CDCl$_3$): δ (ppm)=117.7, 122.2, 123.7, 124.5, 126.8, 127.4, 127.81, 127.84, 128.4, 128.6, 128.7, 128.8, 129.5, 129.9, 130.7, 132.5, 132.6, 133.4, 134.4, 35.5, 135.7, 144.9, 190.2.

2) 1,3-Di(naphthalen-2-yl)propan-1-one

Synthesised according to example 1.85.2 using 1,3-di(naphthalen-2-yl)prop-2-en-1-one; colourless oil; yield: 62%;

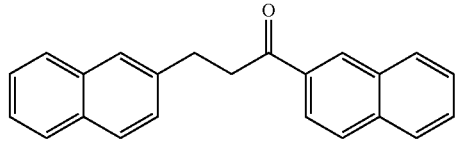

$^1$H-NMR (500 MHz, CDCl$_3$): δ (ppm)=3.30 (t, J=7.6 Hz, 2H), 3.54 (t, J=7.6 Hz, 2H), 7.41-7.48 (m, 3H), 7.54 (t, J=6.9 Hz, 1H), 7.60 (t, J=7.9 Hz, 1H), 7.74 (s, 1H), 7.79-7.83 (m, 3H), 7.87-7.91 (m, 2H), 7.94 (d, J=8.2 Hz, 1H), 8.06 (dd, J=1.9, 8.8 Hz, 1H), 8.48 (s, 1H), ¹³C NMR (CDCl₃, 125 MHz): δ (ppm)=30.4, 40.5, 123.8, 125.3, 126.0, 126.5, 126.8, 127.2, 127.22, 127.4, 127.8, 128.2, 128.4, 128.5, 129.5, 129.7, 132.1, 132.5, 134.2, 135.6, 138.8, 146.7, 199.1.

3) (E,Z)-Ethyl 3,5-di(naphthalen-2-yl)pent-2-enoate

Synthesised according to example 1.85.3 using 1-(biphenyl-4-yl)-3-(4-chlorophenyl)propan-1-one (1.0 g, 3.22 mmol), NaH (0.39 g, 9.66 mmol) and triethyl phosphonoacetate (2.00 mL, 9.98 mmol);

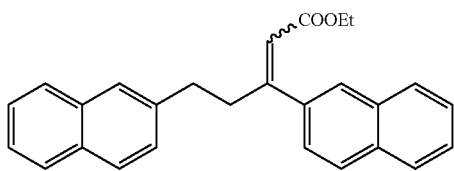 [SMILES: CCOC(=O)C=C(CCc1ccc2ccccc2c1)c1ccc2ccccc2c1]

E: colourless oil; yield: 0.56 g (46%);
¹H-NMR (500 MHz, CDCl₃): δ (ppm)=1.32 (t, J=7.3 Hz, 3H), 2.98-3.01 (m, 2H), 3.64-3.66 (m, 2H), 4.25 (q, J=6.9 Hz, 2H), 7.59-7.61 (m, 3H), 7.50-7.54 (m, 2H), 7.59 (dd, J=1.9, 8.2 Hz, 1H), 7.65 (s, 1H), 7.75-7.80 (m, 3H), 7.84-7.87 (m, 3H), 7.95 (ds, J=1.9, 1H).
¹³C NMR (CDCl₃, 125 MHz): δ (ppm)=14.3, 33.0, 35.4, 59.9, 118.6, 124.5, 125.1, 125.8, 126.3, 126.5, 126.6, 126.7, 127.4, 127.5, 127.6, 127.6, 127.9, 128.3, 128.5, 132.3, 133.4, 133.7, 133.8, 138.6, 139.2, 159.0, 166.3.

Z: colourless oil; yield: 0.61 g (50%);
¹H-NMR (500 MHz, CDCl₃): δ (ppm)=0.99 (t, J=7.3 Hz, 3H), 2.91-2.94 (m, 2H), 2.96-2.99 (m, 2H), 3.96 (q, J=7.3 Hz, 2H), 7.27 (dd, J=1.9, 8.2 Hz, 1H), 7.35 (dd, J=1.6, 8.2 Hz, 1H), 7.40-7.46 (m, 2H), 7.46-7.50 (m, 2H), 7.56 (s, 1H), 7.68 (s, 1H), 7.73-7.76 (m, 2H), 7.79 (d, J=9.2 Hz, 1H), 7.81-7.86 (m, 3H).
¹³C NMR (CDCl₃, 125 MHz): δ (ppm)=13.9, 34.3, 41.9, 59.8, 118.6, 125.3, 126.0, 126.02, 126.1, 126.2, 126.22, 126.6, 127.0, 127.5, 127.5, 127.7, 127.8, 128.1, 128.2, 132.4, 133.1, 133.3, 133.8, 137.6, 138.5, 157.8, 165.9.

4) (E)-3,5-Di(naphthalen-2-yl)pent-2-enoic acid (PS 260)

Synthesised according to example 1.85.5 using (E)-ethyl 3,5-di(naphthalen-2-yl)pent-2-enoate (0.50 g, 1.31 mmol) and NaOH_aq (1.32 mL, 3.94 mmol); white solid; yield: 0.20 g (43%);

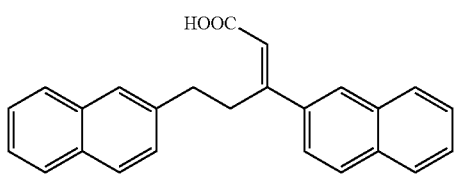 [SMILES: O=C(O)/C=C(\CCc1ccc2ccccc2c1)c1ccc2ccccc2c1]

¹H-NMR (500 MHz, CDCl₃): δ (ppm)=2.98-3.01 (m, 2H), 3.63-3.67 (m, 2H), 6.30 (s, 1H), 7.40-7.45 (m, 3H), 7.53-7.57 (m, 2H), 7.63 (dd, J=1.9, 8.2 Hz, 2H), 7.75-7.79 (m, 3H), 7.87-7.91 (m, 3H), 7.99 (ds, J=1.3 Hz, 1H).
¹³C NMR (CDCl₃, 125 MHz): δ (ppm)=33.3, 35.5, 117.3, 124.4, 125.2, 125.9, 126.5, 126.6, 126.6, 126.9, 127.3, 127.5, 127.6, 128.0, 128.5, 128.6, 133.2, 133.6, 138.1, 138.9, 162.4, 171.0, 178.9.

5) (Z)-3,5-Di(naphthalen-2-yl)pent-2-enoic acid (PS 261)

Synthesised according to example 1.85.4 using (Z)-ethyl 3,5-di(naphthalen-2-yl)pent-2-enoate (0.55 g, 1.44 mmol) and NaOH_aq (1.44 mL, 4.32 mmol); white solid; yield: 0.22 g (51%);

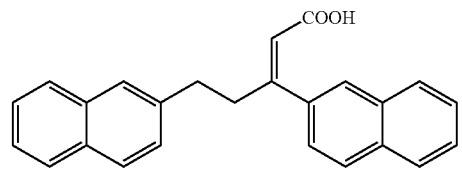 [SMILES: O=C(O)/C=C(/CCc1ccc2ccccc2c1)c1ccc2ccccc2c1]

¹H-NMR (500 MHz, CDCl₃): δ (ppm)=2.86-2.89 (m, 2H), 2.95-2.98 (m, 2H), 6.00 (s, 1H), 7.25 (dd, J=1.5, 8.5 Hz, 1H), 7.32 (dd, J=1.6, 8.5 Hz, 1H), 7.41-7.46 (m, 3H), 7.47-7.50 (m, 1H), 7.53 (s, 1H), 7.58 (dd, J=1.3, 8.8 Hz, 1H), 7.70 (s, 1H), 7.76 (d, J=8.8 Hz, 1H), 7.78-7.85 (m, 4H).
¹³C NMR (CDCl₃, 125 MHz): δ (ppm)=34.0, 35.7, 117.1, 124.4, 124.7, 125.4, 125.8, 126.3, 126.9, 127.2, 127.7, 128.1, 128.2, 131.7, 132.2, 133.4, 133.5, 133.7, 136.7, 137.4, 138.0, 138.8, 161.3, 169.8, 176.5.

1.163. (Z)-5-(Biphenyl-4-yl)-3-(naphthalen-2-yl)pent-2-enoic acid and (E)-5-(Biphenyl-4-yl)-3-(naphthalen-2-yl)pent-2-enoic acid (PS 470+PS 469)

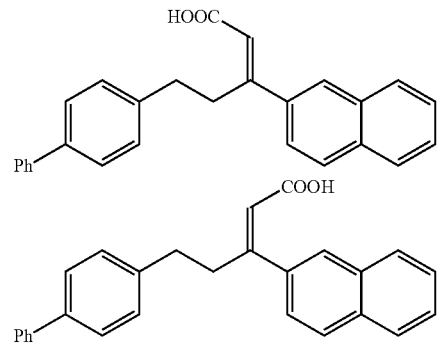

1) 3-(Biphenyl-4-yl)-1-(naphthalen-2-yl)prop-2-en-1-one

Synthesised according to example 1.59.1 using biphenyl-4-carbaldehyde (5.0 g, 29.3 mmol) and 1-(naphthalen-2-yl)ethanone (5.35 g, 29.3 mmol); yellow solid; yield: 7.80 g (79%);

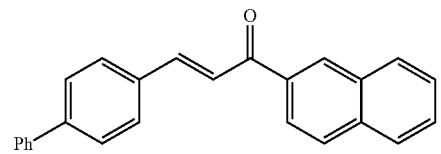 [SMILES: O=C(/C=C/c1ccc(-c2ccccc2)cc1)c1ccc2ccccc2c1]

¹H-NMR (500 MHz, CDCl₃): δ (ppm)=7.40 (t, J=7.6 Hz, 1H), 7.48 (t, J=7.9 Hz, 2H), 7.52-7.55 (m, 2H), 7.57-7.66 (m, 3H), 7.68 (d, J=8.2 Hz, 2H), 7.73 (d, J=15.7 Hz, 1H), 7.76 (t, J=8.2 Hz, 2H), 7.93 (q, J=9.1 Hz, 2H), 8.02 (d, J=7.9 Hz, 1H), 8.13 (d, J=8.5 Hz, 1H), 8.57 (s, 1H).

2) 3-(Biphenyl-4-yl)-1-(naphthalen-2-yl)propan-1-one

Synthesised according to example 1.85.2 using 3-(biphenyl-4-yl)-1-(naphthalen-2-yl)prop-2-en-1-one; colourless oil; yield: 86%;

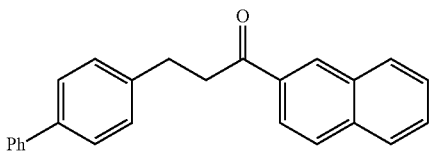 [SMILES: O=C(CCc1ccc(-c2ccccc2)cc1)c1ccc2ccccc2c1]

$^1$H NMR (CDCl$_3$, 500 MHz): δ (ppm)=8.49 (s, 1H), 8.07 (dd, 1H), 7.95 (d, J=8.2 Hz, 1H), 7.90 (t, 2H), 7.62-7.54 (m, 6H), 7.44 (t, J=7.3 Hz, 2H), 7.38 (d, J=8.5 Hz, 2H), 7.34 (tt, J=7.3 Hz, 1H), 3.49 (t, J=7.3 Hz, 2H), 3.19 (t, J=7.9 Hz, 2H).

$^{13}$C NMR (CDCl$_3$, 125 MHz): δ (ppm)=199.1, 180.0, 141.0, 140.4, 139.2, 135.6, 134.2, 132.5, 129.7, 129.5, 128.9, 128.7, 128.5, 128.4, 127.8, 127.3, 127.1, 127.0, 126.8, 126.8, 40.5, 29.9

3) (E,Z)-Ethyl 5-(biphenyl-4-yl)-3-(naphthalen-2-yl)pent-2-enoate

Synthesised according to example 1.85.3 using 3-(biphenyl-4-yl)-1-(naphthalen-2-yl)propan-1-one (1.5 g, 4.46 mmol), NaH (0.54 g, 12.93 mmol), and triethyl phosphonoacetate (2.68 mL, 13.4 mmol);

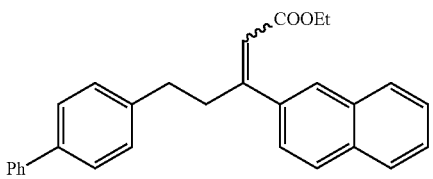 [SMILES: CCOC(=O)C=C(CCc1ccc(-c2ccccc2)cc1)c1ccc2ccccc2c1]

E: colourless oil; yield: 0.85 g (47%);

$^1$H NMR (CDCl$_3$, 500 MHz): δ (ppm)=1.35 (t, J=7.3 Hz, 5H), 2.82-2.86 (m, 2H), 3.54-3.58 (m, 2H), 4.24 (q, J=7.3 Hz, 2H), 7.31-7.34 (m, 3H), 7.42 (t, J=7.9 Hz, 2H), 7.49-7.53 (m, 4H), 7.56 (dd, J=1.9, 8.8 Hz, 2H), 7.60 (dd, J=1.9, 8.8 Hz, 2H), 7.83-7.89 (m, 3H), 7.94 (ds, J=1.6 Hz, 1H).

$^{13}$C NMR (CDCl$_3$, 125 MHz): δ (ppm)=14.4, 33.1, 35.0, 60.0, 118.3, 122.9, 123.4, 124.0, 124.4, 126.3, 126.5, 126.7, 127.0, 127.02, 127.6, 128.3, 128.5, 128.7, 128.9, 133.1, 133.2, 133.5, 139.0, 140.7, 141.2, 149.6, 153.5.

Z: colourless oil; yield: 0.83 g (46%);

$^1$H NMR (CDCl$_3$, 500 MHz): δ (ppm)=1.01 (t, J=7.3 Hz, 3H), 2.77-2.80 (m, 2H), 2.89-2.93 (m, 2H), 3.97 (q, J=7.3 Hz, 2H), 6.03 (s, 1H), 7.21 (d, J=8.2 Hz, 2H), 7.32-7.36 (m, 2H), 7.41 (t, J=7.9 Hz, 2H), 7.48-7.52 (m, 4H), 7.57 (t, J=7.9 Hz, 2H), 7.68 (s, 1H), 7.87-7.83 (m, 3H).

$^{13}$C NMR (CDCl$_3$, 125 MHz): δ (ppm)=13.9, 33.6, 42.1, 59.9, 126.0, 126.1, 126.12, 127.0, 127.1, 127.2, 127.4, 127.7, 128.1, 128.7, 128.7, 132.9, 133.0, 137.3, 139.0, 139.9, 140.9, 158.2, 166.0.

4) (E)-5-(Biphenyl-4-yl)-3-(naphthalen-2-yl)pent-2-enoic acid (PS 469)

Synthesised according to example 1.85.5 using (E)-ethyl 5-(biphenyl-4-yl)-3-(naphthalen-2-yl)pent-2-enoate (0.60 g, 1.47 mmol) and NaOH$_{aq}$ (1.5 mL, 4.41 mmol); white solid; yield: 0.37 g (63%);

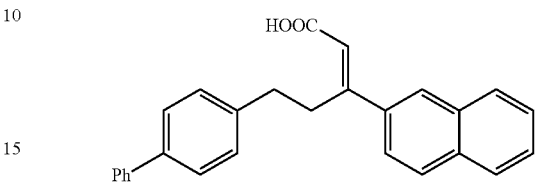

$^1$H NMR (CDCl$_3$, 500 MHz): δ (ppm)=2.87-2.90 (m, 2H), 3.57-3.61 (m, 2H), 6.30 (s, 1H), 7.32 (t, J=8.2 Hz, 3H), 7.40 (t, J=7.9 Hz, 2H), 7.52 (t, J=8.2 Hz, 2H), 7.53-7.57 (m, 4H), 7.63 (dd, J=1.6, 8.5 Hz, 1H), 7.88-7.91 (m, 3H), 7.99 (s, 1H).

5) (Z)-5-(Biphenyl-4-yl)-3-(naphthalen-2-yl)pent-2-enoic acid (PS 470)

Synthesised according to example 1.85.4 using (Z)-ethyl 5-(biphenyl-4-yl)-3-(naphthalen-2-yl)pent-2-enoate (0.60 g, 1.47 mmol) and NaOH$_{aq}$ (1.5 mL, 4.41 mmol); white solid; yield: 0.42 g (72%);

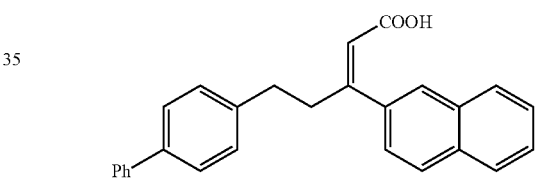

$^1$H NMR (CDCl$_3$, 500 MHz): δ (ppm)=2.73-2.76 (m, 2H), 2.89-2.91 (m, 2H), 5.98 (s, 1H), 7.18 (d, J=8.2 Hz, 2H), 7.30-7.34 (m, 2H), 7.42 (t, J=7.3 Hz, 2H), 7.47-7.51 (m, 4H), 7.55 (dd, J=0.9, 8.23 Hz, 2H), 7.66 (s, 1H), 7.80-7.85 (m, 3H).

1.164. (Z)-5-(4-phenoxyphenyl)-3-phenylpent-2-enoic acid and (E)-5-(4-phenoxyphenyl)-3-phenyl-pent-2-enoic acid (PS 370+PS 371)

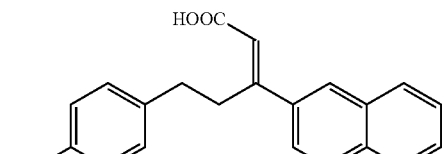

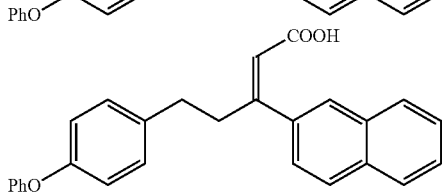

1) 3-(4-Phenoxyphenyl)-1-phenylprop-2-en-1-one

Synthesised according to example 1.59.1 using 4-phenoxybenzaldehyde (3.0 g, 15.1 mmol) and 1-(naphthalen-2-yl)ethanone (2.58 g, 15.1 mmol); pale yellow solid; yield: 4.70 g (89%);

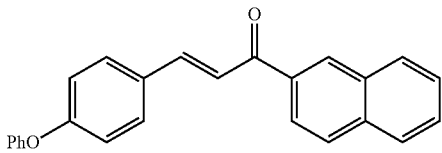 [SMILES: O=C(/C=C/c1ccc(Oc2ccccc2)cc1)c1ccc2ccccc2c1]

$^1$H-NMR (CDCl$_3$, 500 MHz): δ (ppm)=7.05 (d, J=7.6 Hz, 2H), 7.08 (d, J=7.6 Hz, 2H), 7.19 (t, J=7.3 Hz, 1H), 7.40 (t, J=7.6 Hz, 2H), 7.63-7.55 (m, 3H), 7.67 (d, J=8.8 Hz, 2H), 7.87 (t, J=15.5 Hz, 1H), 7.90 (d, J=8.5 Hz, 1H), 7.94 (d, J=8.5 Hz, 1H), 8.00 (d, J=7.9 Hz, 1H), 8.11 (dd, J=1.5, 8.8 Hz, 1H), 8.54 (s, 1H).

$^{13}$C NMR (CDCl$_3$, 125 MHz): δ (ppm)=118.4, 119.7, 120.8, 124.2, 124.5, 126.7, 127.8, 128.3, 128.5, 129.5, 129.7, 129.8, 129.9, 130.2, 132.5, 135.4, 135.6, 144.1, 156.0, 159.8, 190.1.

2) 3-(4-Phenoxyphenyl)-1-phenylpropan-1-one

Synthesised according to example 1.85.2 using 3-(4-phenoxyphenyl)-1-phenylprop-2-en-1-one; colourless oil; yield: 77%;

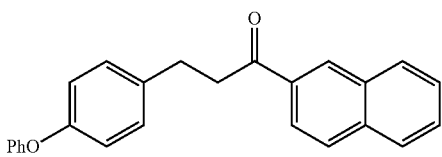 [SMILES: O=C(CCc1ccc(Oc2ccccc2)cc1)c1ccc2ccccc2c1]

$^1$H-NMR (CDCl$_3$, 500 MHz): δ (ppm)=3.13 (t, J=7.4 Hz, 2H), 3.44 (t, J=7.4 Hz, 2H), 6.86 (d, J=8.5 Hz, 2H), 6.99 (d, J=8.8 Hz, 2H), 7.08 (t, J=7.3 Hz, 1H), 7.25 (d, J=8.5 Hz, 2H), 7.32 (t, J=8.5 Hz, 2H), 7.56 (dt, J=1.3, 8.2 Hz, 1H), 7.61 (dt, J=6.9, 8.1 Hz, 1H), 7.89 (t, J=8.5 Hz, 2H), 7.95 (d, J=7.9 Hz, 1H), 8.05 (dd, J=1.6, 8.8 Hz, 1H), 8.47 (s, 1H).

$^{13}$C NMR (CDCl$_3$, 125 MHz): δ (ppm)=29.6, 40.6, 118.6, 119.2, 123.0, 123.8, 126.8, 127.8, 128.4, 128.5, 129.5, 129.6, 129.71, 129.77, 132.5, 134.2, 135.6, 136.3, 155.5, 157.5, 199.2.

3) (E,Z)-Ethyl 5-(4-phenoxyphenyl)-3-phenylpent-2-enoate

Synthesised according to example 1.85.3 using 3-(4-phenoxyphenyl)-1-phenylpropan-1-one (1.40 g, 3.97 mmol), NaH (0.48 g, 12.31 mmol) and triethyl phosphonoacetate (2.46 mL, 12-31 mmol);

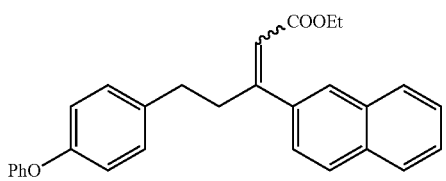 [SMILES: CCOC(=O)C=C(CCc1ccc(Oc2ccccc2)cc1)c1ccc2ccccc2c1]

E: colourless oil; yield: 0.78 g (52%);

$^1$H NMR (CDCl$_3$, 500 MHz): δ (ppm)=1.34 (t, J=6.7 Hz, 3H), 2.78-2.81 (m, 2H), 3.52-3.55 (m, 2H), 4.25 (q, J=6.7 Hz, 2H), 6.23 (s, 1H), 6.93 (d, J=7.9 Hz, 2H), 6.96 (d, J=8.2 Hz, 2H), 7.08 (t, J=7.3 Hz, 1H), 7.21 (d, J=7.9 Hz, 2H), 7.31 (t, J=7.6, 2H), 7.55-7.51 (m, 2H), 7.58 (d, J=8.5 Hz, 1H), 7.89-7.86 (m, 3H), 7.93 (s, 1H).

$^{13}$C NMR (CDCl$_3$, 125 MHz): δ (ppm)=14.4, 33.1, 34.6, 59.9, 118.3, 118.4, 119.0, 122.8, 124.4, 126.3, 126.5, 126.7, 127.6, 128.3, 128.4, 129.6, 129.7, 133.2, 133.5, 136.6, 138.3, 155.2, 157.7, 159.2, 166, 3.

Z: colourless oil; yield: 0.69 g (47%);

$^1$H NMR (CDCl$_3$, 500 MHz): δ (ppm)=1.02 (t, J=7.3 Hz, 3H), 2.72-2.75 (m, 2H), 2.86-2.89 (m, 2H), 4.03 (q, J=7.3 Hz, 2H), 6.00 (s, 1H), 6.94 (d, J=8.5 Hz, 2H), 6.99 (d, J=8.8 Hz, 2H), 7.07-11 (m, 3H), 7.30-7.35 (m, 3H), 7.47-7.51 (m, 2H), 7.67 (ds, J=1.5 Hz, 1H), 7.87-7.83 (m, 3H).

$^{13}$C NMR (CDCl$_3$, 125 MHz): δ (ppm)=13.9, 33.2, 42.2, 59.8, 118.2, 118.6, 119.0, 119.2, 123.0, 126.0, 126.1, 126.1, 127.4, 127.4, 127.7, 128.1, 129.5, 129.7, 133.0, 135.7, 137.3, 139.2, 155.4, 157.5, 158.1, 166.9.

4) (E)-5-(4-Phenoxyphenyl)-3-phenylpent-2-enoic acid (PS 371)

Synthesised according to example 1.85.5 using (E)-ethyl 5-(4-phenoxyphenyl)-3-phenylpent-2-enoate (0.60 g, 1.42 mmol) and NaOH$_{aq}$ (1.6 mL, 4.83 mmol); white solid; yield: 0.40 g (71%);

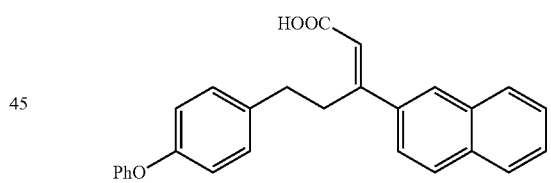

$^1$H-NMR (CDCl$_3$, 500 MHz): δ (ppm)=2.79-2.83 (m, 2H), 3.53-3.56 (m, 2H), 6.27 (s, 1H), 6.91 (d, J=8.5 Hz, 2H), 6.94 (d, J=8.5 Hz, 2H), 7.06 (tt, J=1.3, 7.3 Hz, 1H), 7.18 (d, J=8.8 Hz, 2H), 7.27-7.32 (m, 2H), 7.52-7.56 (m, 2H), 7.59 (dd, J=1.2, 8.5 Hz, 1H), 7.86-7.90 (m, 3H), 7.95 (ds, J=1.6 Hz, 1H).

$^{13}$C NMR (CDCl$_3$, 500 MHz): δ (ppm)=33.4, 34.6, 117.1, 118.5, 119.0, 122.9, 124.3, 126.5, 126.7, 127.2, 126.9, 127.6, 128.4, 128.6, 129.6, 129.7, 133.2, 133.7, 136.3, 138.1, 155.3, 157.6, 162.4.

5) (Z)-5-(4-Phenoxyphenyl)-3-phenylpent-2-enoic acid (PS 370)

Synthesised according to example 1.85.4 using (Z)-ethyl 5-(4-phenoxyphenyl)-3-phenylpent-2-enoate (0.50 g, 1.18 mmol) and NaOH$_{aq}$ (1.8 mL, 5.37 mmol); white solid; yield: 0.41 g (88%);

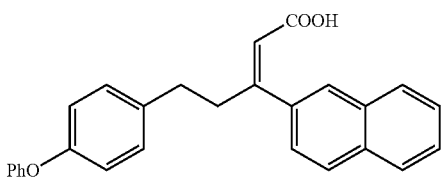 [SMILES: O=C(O)/C=C(/CCc1ccc(Oc2ccccc2)cc1)c1ccc2ccccc2c1]

¹H-NMR (CDCl₃, 500 MHz): δ (ppm)=2.67-2.70 (m, 2H), 2.84-2.87 (m, 2H), 5.92 (s, 1H), 6.90 (d, J=8.5 Hz, 2H), 6.98-6.95 (m, 2H), 7.05-7.09 (m, 3H), 7.27-7.33 (m, 3H), 7.46-7.51 (m, 2H), 7.64 (ds, J=1.6 Hz, 1H), 7.78-7.85 (m, 3H).

¹³C NMR (CDCl₃, 500 MHz): δ (ppm)=33.1, 42.6, 117.1, 118.6, 119.0, 123.0, 125.7, 126.1, 126.2, 126.3, 127.6, 127.7, 128.2, 129.5, 129.7, 132.9, 133.0, 135.5, 136.6, 155.4, 157.5, 160.8, 169.8.

1.165. (Z)-3-(Naphthalen-2-yl)-5-(quinolin-2-yl)pent-2-enoic acid and (E)-3-(Naphthalen-2-yl)-5-(quinolin-2-yl)pent-2-enoic acid (PS 387+PS 386)

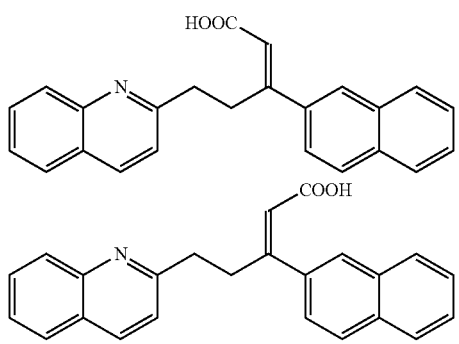

1) 1-(Naphthalen-2-yl)-3-(quinolin-2-yl)prop-2-en-1-one

Synthesised according to example 1.59.1 using quinoline-2-carbaldehyde (3.0 g, 19.09 mmol) and 1-(naphthalen-2-yl)ethanone (3.25 g, 19.09 mmol); yellow solid; yield: 4.95 g (84%);

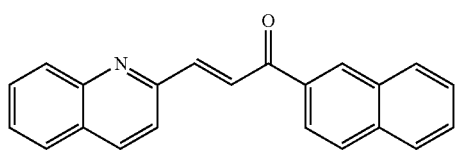 [SMILES: O=C(/C=C/c1ccc2ccccc2n1)c1ccc2ccccc2c1]

2) 1-(Naphthalen-2-yl)-3-(quinolin-2-yl)propan-1-one

Synthesised according to example 1.85.2 using 1-(naphthalen-2-yl)-3-(quinolin-2-yl)prop-2-en-1-one; colourless oil; yield: 63%;

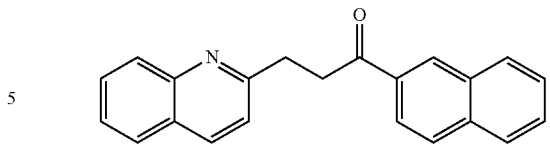

¹H-NMR (500 MHz, CDCl₃): δ (ppm)=3.51 (t, J=7.3 Hz, 2H), 3.77 (t, J=7.3 Hz, 2H), 7.43 (d, J=8.5 Hz, 1H), 7.48 (t, J=7.9 Hz, 1H), 7.54 (t, J=7.9 Hz, 1H), 7.58 (t, J=8.2 Hz, 1H), 7.66 (t, J=8.5 Hz, 1H), 7.78 (d, J=9.1 Hz, 1H), 7.87-7.91 (m, 2H), 7.97 (t, J=9.1 Hz, 2H), 8.07-8.10 (m, 2H), 8.57 (s, 1H).

¹³C NMR (CDCl₃, 125 MHz): δ (ppm)=32.9, 37.5, 121.9, 124.0, 125.8, 126.7, 126.9, 127.5, 127.7, 128.3, 128.4, 128.8, 129.3, 129.6, 129.7, 132.6, 134.4, 135.6, 136.2, 147.9, 161.2, 199.3.

3) (E,Z)-Ethyl 3-(naphthalen-2-yl)-5-(quinolin-2-yl)pent-2-enoate

Synthesised according to example 1.85.3 using 1-(naphthalen-2-yl)-3-(quinolin-2-yl)propan-1-one (0.90 g, 2.89 mmol), NaH (0.35 g, 8.67 mmol) and triethyl phosphonoacetate (1.79 mL, 8.96 mmol);

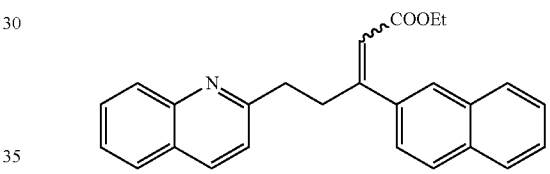

E: yellow oil; yield: 0.53 g (48%);

¹H-NMR (500 MHz, CDCl₃): δ (ppm)=1.32 (t, J=6.9 Hz, 3H), 3.18-3.21 (m, 2H), 3.72-3.75 (m, 2H), 4.23 (t, J=6.9 Hz, 2H), 6.25 (s, 1H), 7.42 (d, J=8.5 Hz, 1H), 7.45-7.51 (m, 3H), 7.62 (dd, J=1.9, 8.5 Hz, 1H), 7.66 (dt, J=1.6, 8.5 Hz, 1H), 7.74 (dd, J=1.3, 8.2 Hz, 1H), 7.81-7.83 (m, 3H), 7.97 (ds, J=1.9 Hz, 1H), 8.01-8.04 (m, 2H). ¹³C (CDCl₃, 125 MHz): δ (ppm)=14.3, 31.2, 38.5, 60.0, 118.3, 121.6, 124.4, 125.7, 126.4, 126.5, 126.6, 126.8, 127.4, 127.5, 128.3, 128.4, 128.9, 129.2, 133.2, 133.5, 136.1, 138.2, 147.9, 159.4, 161, 7, 166.4.

Z: yellow oil; yield: 0.49 g (44%);

¹H-NMR (500 MHz, CDCl₃): δ (ppm)=0.99 (t, J=7.0 Hz, 3H), 3.10-3.17 (m, 4H), 3.95 (t, J=7.0 Hz, 2H), 6.06 (s, 1H), 7.19 (d, J=8.5 Hz, 1H), 7.35 (d, J=8.5 Hz, 1H), 7.36-7.50 (m, 3H), 7.67-7.70 (m, 2H), 7.75 (d, J=8.5 Hz, 1H), 7.79-7.85 (m, 3H), 8.01-8.04 (m, 2H).

¹³C NMR (CDCl₃, 125 MHz): δ (ppm)=13.9, 36.9, 39.8, 59.8, 118.2, 121.3, 124.5, 125.9, 126.0, 126.1, 126.11, 126.9, 127.0, 127.4, 127.5, 127.7, 128.1, 128.9, 129.4, 133.0, 136.3, 137.4, 148.0, 158.2, 160.8, 165.9.

4) (E)-3-(Naphthalen-2-yl)-5-(quinolin-2-yl)pent-2-enoic acid (PS 386)

Synthesised according to example 1.85.5 using (E)-ethyl 3-(naphthalen-2-yl)-5-(quinolin-2-yl)pent-2-enoate (0.45 g, 1.18 mmol) and NaOH$_{aq}$ (1.20 mL, 3.53 mmol); white solid; yield: 0.20 g (48%);

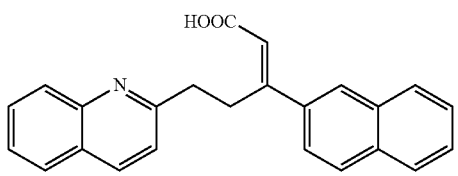 [SMILES: O=C(O)/C=C(\CCc1ccc2ccccc2n1)c1ccc2ccccc2c1]

¹H-NMR (500 MHz, (CD₃)₂SO): δ (ppm)=3.03-3.06 (m, 2H), 3.67-3.71 (m, 2H), 6.22 (s, 1H), 7.42 (d, J=8.5 Hz, 1H), 7.51-7.56 (m, 3H), 7.69-7.23 (m, 2H), 7.89 (dd, J=1.3, 8.2 Hz, 1H), 7.91-7.98 (m, 4H), 8.14 (ds, J=1.6 Hz, 1H), 8.23 (d, J=8.2 Hz, 1H).
¹³C NMR (125 MHz, (CD₃)₂SO): δ (ppm)=29.4, 37.4, 121.3, 124.3, 125.6, 126.0, 126.3, 126.6, 127.3, 127.6, 128.1, 128.2, 128.3, 129.2, 132, 7, 132.9, 136.0, 137.6, 141.2, 147.1, 161.1, 167.1, 170.1.

5) (Z)-3-(Naphthalen-2-yl)-5-(quinolin-2-yl)pent-2-enoic acid (PS 387)

Synthesised according to example 1.85.4 using (Z)-ethyl 3-(naphthalen-2-yl)-5-(quinolin-2-yl)pent-2-enoate (0.40 g, 1.05 mmol) and NaOH$_{aq}$ (1.00 mL, 3.16 mmol); white solid; yield: 0.15 g (36%);

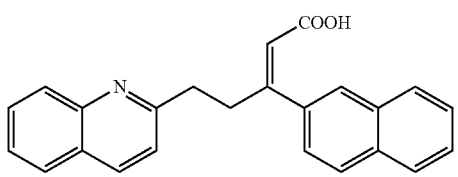 [SMILES: O=C(O)/C=C(/CCc1ccc2ccccc2n1)c1ccc2ccccc2c1]

¹H-NMR (500 MHz, (CD₃)₂SO): δ (ppm)=2.99-3.03 (m, 2H), 3.03-3.08 (m, 2H), 6.00 (s, 1H), 7.38 (dd, J=1.6, 8.5 Hz, 1H), 7.41 (d, J=8.5 Hz, 1H), 7.50-7.55 (m, 3H), 7.71 (dt, J=1.6, 8.2 Hz, 1H), 7.78 (s, 1H), 7.88 (d, J=8.2 Hz, 1H), 7.89-7.94 (m, 4H), 8.24 (d, J=8.2 Hz, 1H).

1.166. (Z)-Ethyl 5-(6-hydroxynaphthalen-2-yl)-3-(naphthalen-2-yl)pent-2-enoate and (E)-Ethyl 5-(6-hydroxynaphthalen-2-yl)-3-(naphthalen-2-yl)pent-2-enoate (PS 504+PS 503)

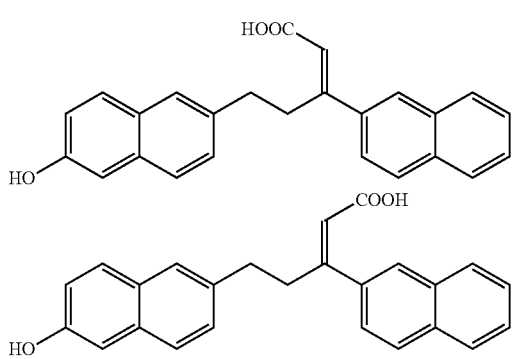

1) 6-(Methoxymethoxy)-2-naphthaldehyde

Bromomethyl-methylether (1.50 mL, 18.3 mmol) was added dropwise to a stirred suspension of 6-hydroxy-2-naphthaldehyde (2.1 g, 12.2 mmol) and sodium hydride (0.73 g, 18.3 mmol) in dimethoxyethane at 0° C. The mixture was stirred for 1 h at room temperature. After the complete addition water was carefully added and it was entracte with ethylacetate (3×), dried over MgSO₄ and concentrated in vacuo; yellow solid; yield: 2.64 g (91%);

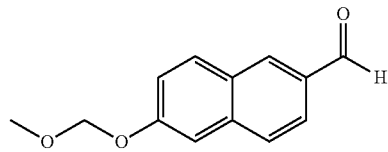 [SMILES: COCOc1ccc2cc(C=O)ccc2c1]

¹H-NMR (500 MHz, CDCl₃): δ (ppm)=3.53 (s, 3H), 5.33 (s, 2H), 7.31 (d, J=8.8 Hz, 1H), 7.44 (s, 1H), 7.73-7.82 (m, 1H), 7, 91 (ds., J=1.9 Hz, 2H), 8.26 (s, 1H), 10.10 (s. 1H).
¹³C-NMR (125 MHz, CDCl₃): δ (ppm)=56.3, 94.4, 110.0, 120.1, 123.5, 128.1, 128.4, 131.2, 132.7, 134.2, 138.0, 157.6, 192.0.

2) 3-(6-(Methoxymethoxy)naphthalen-2-yl)-1-(naphthalen-2-yl)prop-2-en-1-one

Synthesised according to example 1.59.1 using 6-(methoxymethoxy)-2-naphthaldehyde (2.0 g, 9.25 mmol) and 1-(naphthalen-2-yl)ethanone (1.57 g, 9.25 mmol); yellow solid; yield: 1.90 g (56%);

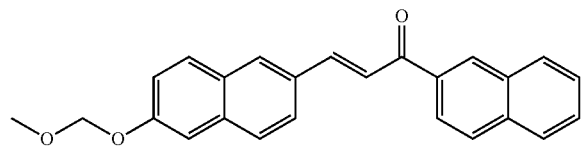 [SMILES: COCOc1ccc2cc(/C=C/C(=O)c3ccc4ccccc4c3)ccc2c1]

¹H-NMR (500 MHz, CD₃Cl): δ (ppm)=3.54 (s, 3H), 5.32 (s, 2H), 7.27 (dd, J=1.9, 8.8 Hz, 1H), 7.42 (ds, J=2.2 Hz, 1H), 7.56-7.63 (m, 2H), 7.76-7.84 (m, 4H), 7.91 (d, J=7.9 Hz, 1H), 7.95 (d, J=8.8 Hz, 1H), 8.04-8.01 (m, 3H), 8.14 (dd, J=1.6, 8.2 Hz, 1H), 8.58 (s, 1H).
¹³C NMR (125 MHz, CDCl₃): δ (ppm)=56.2, 94.5, 110.0, 119.7, 121.4, 124.4, 124.6, 126.7, 127.8, 127.8, 128.3, 128.5, 129.3, 129.5, 129.8, 130.3, 130.5, 130.8, 132.6, 135.7, 135.7, 135.8, 145.0, 156.4, 190.2.

3) 6-(Methoxymethoxy)naphthalen-2-yl)-1-(naphthalen-2-yl)propan-1-one

Synthesised according to example 1.85.2 using 3-(6-(methoxymethoxy)-naphthalen-2-yl)-1-(naphthalen-2-yl) prop-2-en-1-one; colourless oil; yield: 73%;

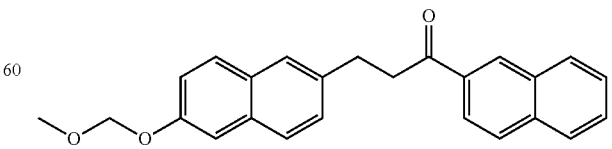

¹H-NMR (500 MHz, CD₃Cl): δ (ppm)=3.26 (t, J=7.9 Hz, 2H), 3.51 (t, J=7.9 Hz, 2H) 3.53 (s, 3H), 5.29 (s, 2H), 7.21 (dd, J=2.4, 8.8 Hz, 1H), 7.38-7.41 (m, 2H), 7.54 (t, J=7.9 Hz, 1H), 7.59 (d, J=8.2 Hz, 1H), 7.67 (s, 1H), 7.70-7.73 (m, 2H), 7.89 (t, J=7.9 Hz, 2H), 7.94 (d, J=8.8 Hz, 1H), 8.06 (dd, J=1.5, 8.2 Hz, 1H), 8.48 (s, 1H).

$^{13}$C NMR (125 MHz, CDCl$_3$): δ (ppm)=30.3, 40.5, 56.0, 94.6, 109.9, 123.8, 126.3, 126.7, 127.3, 127.7, 127.8, 128.4, 128.5, 129.0, 129.5, 129.7, 132.5, 133.0, 134.2, 135.6, 136.9, 154.7, 199.1.

4) (Z)-Ethyl 5-(6-(methoxymethoxy)naphthalen-2-yl)-3-(naphthalen-2-yl)pent-2-enoate Synthesised according to example 1.85.3 using 6-(methoxymethoxy)naphthalen-2-yl)-1-(naphthalen-2-yl)propan-1-one (0.8 g, 2.16 mmol), NaH (0.25 g, 6.26 mmol) and triethyl phosphonoacetate (1.30 mL, 6.26 mmol);

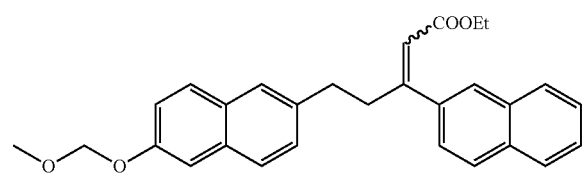 [SMILES: CCOC(=O)C=C(CCc1ccc2cc(OCOC)ccc2c1)c1ccc2ccccc2c1]

E: colourless oil; yield: 0.45 g (47%);

$^1$H-NMR (500 MHz, CD$_3$Cl): δ (ppm)=1.30 (t, J=7.0 Hz, 3H), 2.90-2.93 (m, 2H), 3.53 (s, 3H), 3.58-3.61 (m, 2H), 4.22 (q, J=7.0 Hz, 2H), 5.29 (s, 2H), 6.21 (s, 1H), 7.18 (dd, J=2.5, 8.8 Hz, 1H), 7.35-7.38 (m, 2H), 7.51-7.54 (m, 2H), 7.56 (s, 1H), 7.60 (dd, J=2.5, 8.5 Hz, 1H), 7.65-7.69 (m, 2H), 7.84-7.88 (m, 3H), 7.93 (ds, J=1.6 Hz, 1H).

$^{13}$C NMR (CDCl$_3$, 125 MHz): δ (ppm)=14.3, 33.0, 35.2, 56.0, 59.9, 94.6, 109.9, 116.8, 188.3, 118.8, 124.4, 126.3, 126.5, 126.7, 127.0, 127.6, 127.9, 128.3, 128.5, 129.0, 129.6, 133.2, 137.2, 138.4, 154.6, 159.2, 166.4.

Z: colourless oil; yield: 0.46 g (48%);

$^1$H-NMR (500 MHz, CD$_3$Cl): δ (ppm)=1.01 (t, J=7.2 Hz, 3H), 2.85-2.89 (m, 2H), 2.92-2.96 (m, 2H), 3.52 (s, 3H), 3.96 (q, J=7.2 Hz, 2H), 5.29 (s, 2H), 6.01 (s, 1H), 7.19 (dd, J=2.5, 8.8 Hz, 1H), 7.20 (dd, J=2.5, 8.5 Hz, 1H), 7.33-7.36 (m, 2H), 7.47-7.50 (m, 3H), 7.65-7.68 (m, 3H), 7.82-7.86 (m, 3H).

$^{13}$C NMR (CDCl$_3$, 125 MHz): δ (ppm)=13.9, 33.9, 42.1, 56.0, 59.8, 94.6, 109.9, 118.2, 119.0, 125.9, 126.0, 126.1, 126.3, 127.2, 127.4, 127.5, 127.7, 128.1, 129.6, 132.9, 133.0, 133.02, 136.4, 137.3, 154.7, 158.3, 165.9.

5) (E)-Ethyl 5-(6-hydroxynaphthalen-2-yl)-3-(naphthalen-2-yl)pent-2-enoate

A solution of (E)-ethyl 5-(6-(methoxymethoxy)naphthalen-2-yl)-3-(naphthalen-2-yl)pent-2-enoate (0.25 g, 0.57 mmol) in methanol (10 mL) was treated with 10% HCl (2 mL) and the resulting mixture was refluxed for 2 h. After cooling the solvent was removed, the residue was extracted with ethyl acetate (3×) and dried with MgSO$_4$. Then the crude product was concentrated to obtain the product; yellow oil; yield: 0.095 g (quant, without further purification);

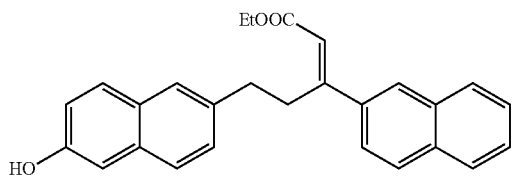 [SMILES: CCOC(=O)/C=C(\CCc1ccc2cc(O)ccc2c1)c1ccc2ccccc2c1]

$^1$H-NMR (500 MHz, CD$_3$Cl): δ (ppm)=1.31 (t, J=7.0 Hz, 3H), 2.89-2.93 (m, 2H), 3.58-3.621 (m, 2H), 4.23 (q, J=7.0 Hz, 2H), 5.15 (s, OH), 6.21 (s, 1H), 7.06 (dd, J=2.5, 8.5 Hz, 1H), 7.10 (ds, J=1.6 Hz, 1H), 7.35 (dd, J=1.6, 8.2 Hz, 1H), 7.52-7.61 (m, 5H), 7.63 (d, J=8.8 Hz, 1H), 7.85-7.88 (m, 3H), 7.94 (ds, J=1.6 Hz, 1H).

6) (Z)-Ethyl 5-(6-hydroxynaphthalen-2-yl)-3-(naphthalen-2-yl)pent-2-enoate

A solution of ((Z)-ethyl 5-(6-(methoxymethoxy)naphthalen-2-yl)-3-(naphthalen-2-yl)pent-2-enoate (0.35 g, 0.80 mmol) in methanol (10 mL) was treated with 10% HCl (2 mL) and the resulting mixture was refluxed for 2 h. After cooling the solvent was removed, the residue was extracted with ethyl acetate (3×) and dried with MgSO$_4$. Then the crude product was concentrated to obtain the product; yellow oil; yield: 0.32 g (quant, without further purification);

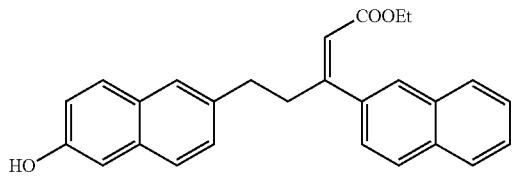

$^1$H-NMR (500 MHz, CD$_3$Cl): δ (ppm)=1.01 (t, J=7.0 Hz, 3H), 2.83-2.86 (m, 2H), 2.92-2.96 (m, 2H), 4.11 (q, J=7.0 Hz, 2H), 6.02 (s, 1H), 7.04 (dd, J=2.4, 8.8 Hz, 1H), 7.08 (ds, J=2.4 Hz, 1H), 7.21 (dd, J=1.9, 8.2 Hz, 1H), 7.32-7.35 (m, 1H), 7.47-7.50 (m, 3H), 7.58 (d, J=8.5 Hz, 1H), 7.63 (d, J=8.8 Hz, 1H), 7.68 (s, 1H), 7.82-7.86 (m, 3H).

7) (E)-5-(6-Hydroxynaphthalen-2-yl)-3-(naphthalen-2-yl)pent-2-enoic acid (PS 503)

Synthesised according to example 1.85.5 using (E)-ethyl 5-(6-hydroxynaphthalen-2-yl)-3-(naphthalen-2-yl)pent-2-enoate (0.07 g, 0.18 mmol) and NaOH$_{aq}$ (0.2 mL, 0.53 mmol); white solid; yield: 0.55 g (83%);

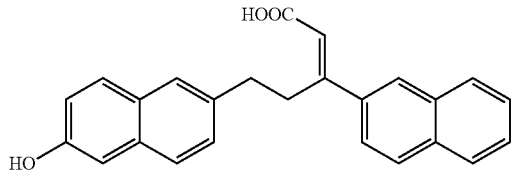 [SMILES: O=C(O)/C=C(\CCc1ccc2cc(O)ccc2c1)c1ccc2ccccc2c1]

$^1$H-NMR (500 MHz, (CD$_3$)$_2$SO): δ (ppm)=2.75-2.77 (m, 2H), 3.48-3.52 (m, 2H), 6.17 (s, 1H), 6.21 (s, 1H), 6.99 (dd, J=2.4, 8.5 Hz, 1H), 7.02 (ds, J=2.1 Hz, 1H), 7.28 (dd, J=1.5, 8.5 Hz, 1H), 7.52-7.57 (m, 4H), 7.62 (d, J=8.8 Hz, 1H), 7.69 (dd, J=1.5, 8.2 Hz, 1H), 7.91-7.95 (m, 2H), 7.98-8.00 (m, 1H), 8.13 (s, 1H), 9.57 (s, OH).

8) (Z)-5-(6-Hydroxynaphthalen-2-yl)-3-(naphthalen-2-yl)pent-2-enoic acid (PS 504)

Synthesised according to example 1.85.4 using (Z)-ethyl 5-(6-hydroxynaphthalen-2-yl)-3-(naphthalen-2-yl)pent-2-enoate (0.30 g, 0.76 mmol) and NaOH$_{aq}$ (1.30 mL, 3.78 mmol); white solid; yield: 0.16 g (57%);

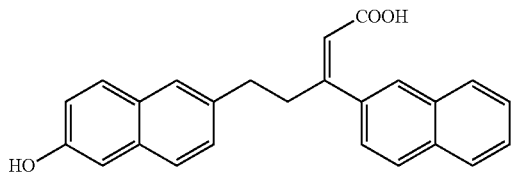 [SMILES: O=C(O)/C=C(/CCc1ccc2cc(O)ccc2c1)c1ccc2ccccc2c1]

$^1$H-NMR (500 MHz, (CD$_3$)$_2$SO): δ (ppm)=2.72-2.75 (m, 2H), 2.90-2.93 (m, 2H), 5.97 (s, 1H), 7.02-7.09 (m, 2H), 7.24 (dd, J=1.5, 8.2 Hz, 1H), 7.37 (dd, J=1.9, 8.5 Hz, 1H), 7.51-7.53 (m, 3H), 7.58 (d, J=8.5 Hz, 1H), 7.65 (d, J=8.8 Hz, 1H), 7.78 (s, 1H), 7.88-7.93 (m, 3H), 9.59 (s, OH), 11.94 (s, OH).

Example 2

Activation or Inhibition of Different Protein Kinases of the AGC Family

Principle of the cell-free kinase activity assay: In general, the activity of the compounds as protein kinase inhibitors or activators may be assayed in vitro (cell free assay is meant here), in vivo or in a cell line. In vitro assays include assays that determine inhibition or activation of either the phosphorylation activity or ATPase activity of the activated protein kinase. Alternate in vitro assays quantitate the ability of the inhibitor to bind to the protein kinase. Compound binding may be measured by radiolabelling the compound prior to binding, isolating the inhibitor or activator/protein kinase complex and determining the amount of radiolabel bound. Alternatively, inhibitor or activator binding may be determined by running a competition experiment where new compounds are incubated with the protein kinase bound to known radioligands. Newer methods comprise fluorescence polarisation assays and surface plasmon resonance dependent techniques. Modulation of PDK1 activity may be tested as following: A compound of interest is tested for its ability to activate or inhibit GST-PDK1 full length or truncated mutants of PDK1. The activity and modulation of activity is measured using a standard ATPgamma[$^{32}$P] assay as described earlier. The assay is performed in 20l containing 50 mM TRIS (pH 7.5), 10 mM MgCl$_2$, 100 µM ATP, 0.5 mM DTT. The concentration of T308tide is 1 mM and the amount of PDK1 used is 200 ng. Reactions are carried out at room temperature. Reaction is started by addition of ATP-Mg mix and stopped with phosphoric acid after 30 min. Stopped reactions were spotted on to phosphocellulose paper (P81, Whatman) and washed. After drying, the radioactivity associated to the band was quantified. As non limiting examples, results for two selected AGC kinases, PDK1 and PKCzeta are summarized in Tables 1 and 2. Importantly, it is demonstrated in these tables that the example compounds are selectively affecting the catalytic activities of only the respective target protein, PDK1 or PKCzeta. Thus, despite bearing common, conserved properties, the differences in amino acid side chains, shape, size and overall geometry of the hydrophobic PIF pockets of the different AGC kinases are sufficient to enable the development of small molecules which are selectively binding to only a given AGC kinase or a small subset of AGC kinases. This selectivity, as demonstrated in Tables 1 and 2 for different structural classes of our compounds, is an important general advantage over ATP-competitive compounds.

TABLE 1

Examples for compounds which selectivity activate PDK1.

| PS- | Compounds Structure | PDK1 200 µM | PDK1 50 µM | PKCζ 200 µM | PKCζ 50 µM | SGK 200 µM | SGK 50 µM | PRK2 200 µM | PRK2 50 µM | S6K 200 µM | S6K 50 µM | PKBβ 200 µM | PKBβ 50 µM | PKA 200 µM | PKA 50 µM |
|---|---|---|---|---|---|---|---|---|---|---|---|---|---|---|---|
| 114 | (structure: COOH, 4-chlorophenyl, 5-chlorobenzimidazole) | 500% | 400% | 30% | no effect | no effect | no effect | no effect | no effect | 75% | no effect | 80% | 85% | no effect | no effect |
| 141 | (structure: COOH, 4-chlorophenyl, chloroisoindoline amide) | 400% | 300% | 30-40% | 80% | ~70-80% | no effect | no effect | no effect | ~80% | no effect | no effect | no effect | no effect | no effect |
| 152 | (structure: COOH, 4-chlorophenyl, chlorotetrahydroisoquinoline amide) | 310% | 240% | no effect | no effect | ~60% | no effect | no effect | no effect | ~80% | no effect | no effect | no effect | no effect | no effect |
| 163 | (structure: CO₂H, phenyl, 5,6-dichlorobenzimidazole) HCl-salt | >250% | ~250% | 50% | no effect | no effect | no effect | no effect | no effect | ~50% | no effect | no effect | no effect | no effect | no effect |

TABLE 1-continued

Examples for compounds which selectivity activate PDK1.

| Compounds | | PDK1 | | PKCζ | | SGK | | PRK2 | | S6K | | PKBβ | | PKA | |
|---|---|---|---|---|---|---|---|---|---|---|---|---|---|---|---|
| PS- | Structure | 200 µM | 50 µM | 200 µM | 50 µM | 200 µM | 50 µM | 200 µM | 50 µM | 200 µM | 50 µM | 200 µM | 50 µM | 200 µM | 50 µM |
| T10 | 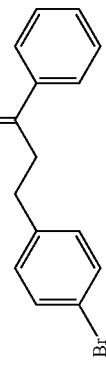 | 450% | 400% | — | — | no effect | no effect | no effect | no effect | no effect | no effect | ~70-80% | no effect | no effect | no effect |

Values are given as percent of catalytic activity of the Kinase in the presence of compound as compared to the solvent control (DMSO), which was set 100%.

TABLE 2

Examples for compounds which selectivity inhibit PKCzeta.

| Compounds | | PKCζ | | SGK | | PRK2 | | S6K | | PKBβ | | PKA | | PDK1 | |
|---|---|---|---|---|---|---|---|---|---|---|---|---|---|---|---|
| PS- | Structure | 200 μM | 50 μM | 200 μM | 50 μM | 200 μM | 50 μM | 200 μM | 50 μM | 200 μM | 50 μM | 200 μM | 50 μM | 200 μM | 50 μM |
| 87 | *structure with COOH, phenyl, Cl* | 3% | 45% | 60% | no effect | no effect | no effect | 65% | 90% | ~60% | ~80% | — | — | 150% | 150% |
| 102 | *indene structure with COOH, Cl* | 2% | 45% | 50% | 112% | 110% | no effect | 55% | 90% | ~60-70% | ~80-90% | — | — | 180% | — |
| 118 | *benzothiophene structure with HOOC, phenyl, Cl* | 0% | 10-20% | ~20% | no effect | no effect | no effect | 25% | 85% | 25% | 90% | no effect | no effect | no effect | no effect |
| 145 | *structure with HOOC, F, Cl* | 0% | 50% | ~40% | ~80% | — | — | ~80% | no effect | ~70% | no effect | ~60% | no effect | ~120% | — |

TABLE 2-continued

Examples for compounds which selectivity inhibit PKCzeta.

| Compounds | Structure | PKCζ 200 μM | PKCζ 50 μM | SGK 200 μM | SGK 50 μM | PRK2 200 μM | PRK2 50 μM | S6K 200 μM | S6K 50 μM | PKBβ 200 μM | PKBβ 50 μM | PKA 200 μM | PKA 50 μM | PDK1 200 μM | PDK1 50 μM |
|---|---|---|---|---|---|---|---|---|---|---|---|---|---|---|---|
| PS-171 HCl-salt | (structure: 4,6-dichlorobenzimidazole with CH₂-CH(4-chlorophenyl)-CH₂-CO₂H) | 0% | ~40% | ~70% | no effect | no effect | no effect | ~50% | weak inhib. | ~70% | no effect | ~80-90% | no effect | ~200% | — |
| T5 | (structure: 4-CF₃-phenyl-CH₂-CH₂-C(phenyl)=CH-COOH) | ~0% | ~0% | ~20% | weak inhib. | no effect | no effect | ~60% | no effect | ~80% | no effect | ~60% | no effect | >250% | >250% |

Values are given as percent of catalytic activity of the Kinase in the presence of compound as compared to the solvent control (DMSO), which was set 100%.

Example 3

For PS 48, which represents one example compound according to the invention, it is demonstrated in FIG. 1 that the target binding site is the PIF pocket of the protein kinase PDK1. A kinase activity assay employing T308tide as substrate peptide was performed to measure the effect of compound PS48 on the PDK1 catalytic activity. Compound PS 48 was found to increase PDK1 activity to a similar extent as did the original compound PS 46 (which is not part of the present invention), despite being even smaller (4.3-fold activation, $AC_{50}=19.3$ μM). In the next step, we corroborated that this activatory effect is exerted via binding of PS 48 to the PIF pocket; for this purpose, some amino acid residues lining the PIF pocket were replaced using site directed mutagenesis. As depicted in FIG. 1, the ability of PS 48 (and of PS 46) to activate PDK1 was lost towards the PDK1$^{V127T}$ mutant, indicating that the compound's binding site in wild type PDK1 is indeed the PIF pocket. As a control, the same mutant could still be activated by the so called PIFtide, a 22 residue peptide derived from the C-terminus of PRK-2, which acts as natural PIF pocket ligand. Thus, the mutations did not affect the allosteric mechanism itself nor the overall activity of the kinase. These data confirmed that PS48 was targeting the PIF pocket of PDK1. The mutant PDK1$^{L155S}$, in which the character of the PIF pocket is completely changed, could not be activated anymore even by PIFtide, proving again the target site specificity of the tested effectors.

Example 4

Allosteric Activation of the Protein Kinase PDK1 with Structure-Dependent Potency Small compounds developed to modulate conformational changes in proteins can lead in cells to different effects as observed in vitro, mainly by influencing protein-protein interactions (also intramolecularly) and subcellular localizations, which are essential for proper functioning and regulation of the protein kinase. Thus, compounds which prompt a particular conformation of a protein (e.g. activate an enzyme) in vitro may act in the opposite manner (e.g. as "inhibitors") in vivo. Alternatively, compounds which prompt a particular phosphorylation-dependent conformation on a protein (e.g. considered to "inhibit" an enzyme) may act in the opposite manner in vivo. We describe that one reason for this unexpected result is that the compounds may affect the level of phosphorylation of the protein target. It was also shown that the conformational transition which activates an enzyme in vitro may act as an inhibitor of the activity of the enzyme in two ways. Firstly, the compound will be an inhibitor if the drug target pocket is required for the docking of a substrate. Thus, if the substrate binding site is occupied by the compound, the substrate phosphorylation will be inhibited even if the compound mimics an activated protein conformation on the target protein. Alternatively, depending on the specific molecular mechanisms that take place in cells, compounds which activate an enzyme in vitro may displace an intramolecular polypeptide interaction from the compound binding site. In this scenario, even if the target enzyme is activated in vitro, the displacement of the intramolecular polypeptide interaction may prompt in vivo the phosphorylation or dephosphorylation of the polypeptide and transduce a physiological message different from activation. The invention also contemplates that the binding of a compound that triggers a phosphorylation-dephosphorylation conformational transition can prompt the proteolysis of the target protein in vivo, independent of the possible effect of the compound in vitro. In a particular case, the above finding is applicable to protein kinases which are targets for numerous disorders, including cancer, neurodegenerative disorders, diabetes, inflammation, fungal infections, parasitic infections, etc. In a more specific case, the examples refer to protein kinases from the AGC group of protein kinases. Protein kinases are enzymes that catalyze the transfer of the γ-phosphate group of ATP to serine, threonine or tyrosine residues in proteins or peptides (called substrates) in order to alter their properties. Protein phosphorylation is the most general regulatory mechanism in eukaryotic cells and regulates most fundamental as well as specialized cellular processes. Humans contain about 500 different protein kinases. In the case of PDK1 as a target, small molecules activating PDK1 in a cell free assay—which are, however, not part of the present invention—were able to inhibit the activation of S6K and SGK in intact cells (Engel et al., EMBO J. 2006, Vol. 25, pp. 5469-5480).

Table 3 shows examples of 3,5-diarylpentenoic acids and derivatives according to the present invention, and their differential ability to allosterically activate PDK1. The most potent compound shown here was PS-T4 which activated PDK1 in the low μM range ($AC_{50}=4$ μM) more than 4 fold.

TABLE 3

Allosteric activators of PDK1 according to the present invention.

| PS No. | Ar | Z/E | max. activation of PDK1 (fold)[1] | $AC_{50}$ PDK1 (μM) |
|---|---|---|---|---|
| 48 | | Z | 4.3 | 19.3 |
| 47 | 4-Cl-phenyl | E | 2 | >100 |

TABLE 3-continued

Allosteric activators of PDK1 according to the present invention.

| | | | | |
|---|---|---|---|---|
| 87 | 3-Cl-phenyl | Z | 4.1 | 11.6 |
| 88 | | E | 2 | >100 |
| T3 | 4-F-phenyl | Z | 3.3 | 41 |
| 136 | | E | 1.3 | >100 |
| T10 | 4-Br-phenyl | Z | 4.1 | 14.5 |
| 137 | | E | 2 | >100 |
| T5 | 4-CF₃-phenyl | Z | 4.7 | 13.8 |
| 140 | | E | n.e. | n.e. |
| T7 | 3,4-diCl-phenyl | Z | 3.4 | 8.0 |
| 131 | | E | 2 | >100 |
| T9 | 2,4-diCl-phenyl | Z | 2.2 | 9.4 |
| 135 | | E | n.e. | n.e. |
| T8 | 4-Br-2-F-phenyl | Z | 3.2 | 10.0 |
| 133 | | E | 1.5 | >100 |
| 130 | 4-ethyl-phenyl | Z | 1.4 | >30 |
| 129 | | E | 1.5 | >100 |
| T2 | biphenyl | Z | 3.3 | 15.4 |
| 134 | | E | 2.6 | >100 |
| T4 | 2-naphthyl | Z | 4.2 | 4 |
| 138 | | E | 3.1 | 27.1 |

TABLE 3-continued
Allosteric activators of PDK1 according to the present invention.
| | | | | |
|---|---|---|---|---|
| 159 | 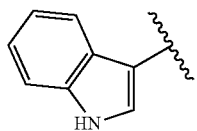 [SMILES: *c1c[nH]c2ccccc12] | Z | 3.7 | 9.3 |
| 158 | | E | 2.9 | 34.6 |
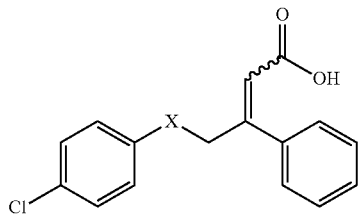
| | X | Z/E | | |
|---|---|---|---|---|
| 97 | O | E | 3.0 | 22.8 |
| 95 | O | Z | 2.7 | >60 |
| 99 | S | E | 2.6 | 22.8 |
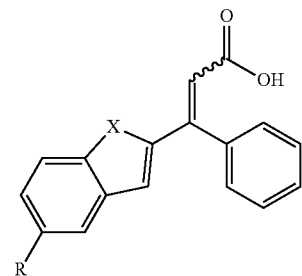
| | R | X | Z/E | | |
|---|---|---|---|---|---|
| 101 | Cl | O | E | 3.2 | 31.6 |
| 103 | Me | O | E | 3.1 | 41.3 |
| 119 | Cl | S | E | 3.1 | 13.2 |
| 118 | Cl | S | Z | n.e. | n.e. |
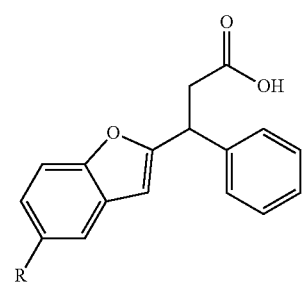
| | R | | |
|---|---|---|---|
| 124 | Cl | 2.9 | 19.0 |
| 120 | Me | 2.7 | 29.1 |

TABLE 3-continued

Allosteric activators of PDK1 according to the present invention.

| 102 | 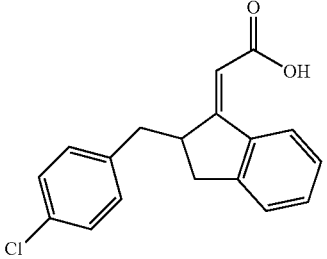 | 1.8 | 30 |

[1] As a particularity for compounds with activatory properties, it was necessary to indicate the maximum activation that was achievable with a compound, as compared to the basal activity of PDK1 (set to 100%).
Where possible, AC50 values and max. activation were measured. AC50 indicates the concentration of the compound required to activate half maximally; n.e.: no effect.

Example 5

Compound PS 99 Inhibits the Proliferation of/or Induces Cell Death of PC3 Prostate Carcinoma Cells To measure the potency of selected compounds to inhibit growth of a cancer cell line, the widely established MTT assay was used. The assay principle relies on the formation of a purple formazan dye from MTT which has been added to the cultured cells due to mitochondrial reductase activity in intact cells. After 3-4 hours of cell incubation with MTT, formazan crystals develop in living and early apoptotic cells but not in dead cells. MTT is suitable for measuring cell proliferation and cell viability.

PC3 prostate cancer cells were chosen as a test system, because they display strongly enhanced PI3K/PDK1 signalling due to a deletion of PTEN. Thus the cell's viability critically relies on high activities of this pathway but on the other hand it requires highly efficient inhibitors to hit the cells.

Results: the example compound PS99 significantly reduced the number of the PC3 cells as compared to the DMSO-treated control. Effects were detectable at 10-20 µM of PS-99, while the very potent drug rapamycin used as a control displayed an EC50 of about 1 µM (FIG. 2).

Example 6

Compounds According to the Invention Sensitize Cells for a Stronger Insulin Response Test principle: cells are deprived of glucose, test compounds or DMSO is added, then $^3$H-labelled 2-Desoxyglucose is added (50 µM) in the presence of buffered saline (Mg2+, Ca2+), uptake of glucose is triggered by the addition of suboptimal concentrations of insulin (0.3 nM), cells are washed 4 times, the relative amount of 2-DG taken up by the cells is quantified by β-counting. Detailed procedure: 70% Confluent Huh7 cells (hepatocellular carcinoma cell line) were starved in DMEM containing 0.1% FCS for 16 h, in the presence of normal glucose (5.6 mM). Then the cells were washed 3× by PBS/BSA and incubated for 30 min with HBSS (Hank's balanced salt solution+glucose) containing the test compounds (50 µM), or DMSO as a control, respectively. Then $^3$H-labelled 2-Desoxyglucose was added (to 50 µM final concentration) and glucose uptake triggered by addition of 0.3 nM Insulin for 10 min. The reaction was then stopped by the addition of cold 2-deoxyglucose in excess, the cells washed 4× with ice cold PBS/BSA, 250 µl 0.5 M NaOH/0.1% SDS were added to lyse the cells, and the relative amount of radioactive 2-deoxyglucose taken up by the cells was quantified using liquid scintillation β-counting. Values were generated as triplicates at least. As shown in FIG. 3, compounds according to the invention were effective in increasing the uptake of radiolabeled 2-deoxyglucose. Several were superior to the compound lipoic acid, which was reported to have insulin-sensitizing activity and was included here for comparison in the same concentration.

The compound structures as disclosed under "example 1". Preparation of AGC Kinase and Aurora kinase modulators" above are identified by their numbers with the prefix "PS". Compounds according to the invention such as those shown in the present example are useful for the treatment of insulin resistance and diabetes type-2.

Example 7

Binding of the compound PS 48 to the PIF pocket, produces local changes at the target site (the PIF-binding pocket) and also changes at the ATP binding site and a further site distant from the PIF pocket: We found this in the co-crystal structure of PDK1 bound to PS 48, a compound according to the invention (see FIG. 4). (The crystal structure is part of a different pending patent application). In addition, we followed the conformational change induced by activating compounds in solution by monitoring the changes in fluorescence intensity of an ATP analogue and by performing deuterium exchange experiments (FIG. 5).

To obtain PDK1 protein crystals capable of accepting a small PIF-pocket binding molecule, a set of mutants of PDK1 disrupted in the crystallographic contacts along the PIF-binding pocket was prepared. PDK1 50-359[Tyr288Gly; Gln192Ala] crystallised in a different crystal packing (now termed crystal packing II), that exposed the PIF-binding pocket.

The crystal structure of PDK1 bound to low molecular weight compounds was obtained from co-crystallization trials set in the presence of ATP and PS48 and also by soaking experiments on crystal packing II, with similar results. The model structure of the PDK1 complex with ATP and PS48 (obtained from a crystal soaked with PS48) was solved to 1.9 Å resolution.

The overall structure in the presence of compound differed slightly from the apoPDK1 structure described above (FIG. 4A), mainly within the PIF-binding pocket and its associated phosphate-binding site, the ATP binding site and the activation loop. The mode of interaction of PS48 with the PIF pocket is reminiscent of the mode of binding of PKA C-terminus to its own pocket (Knighton et al, 1991) (Suppl FIG. 2). Remarkably, the phenyl rings in PS48 mimicked the positioning of the two Phe aromatic side chains, each occupying one of the two sub-pockets like it is seen in PKA. As a major difference to all other PDK1 crystal structures described so far, the low molecular weight compound induced an important movement on Phe157, which is found in a different conformation, pointing inwards instead of occupying the base of the pocket (FIGS. 4B and 4C). The conformational change enlarged the depth of the pocket and allowed the ring closer to the carboxylate group from PS48 to enter the pocket. In the presence of PS48, Lys76 and Arg131 moved to interact with the carboxylate from PS48 (FIGS. 4D and 4E). Altogether, the crystallography derived structural data confirmed that the small activating compound PS48 indeed bound to the PIF-binding pocket displacing Phe157 and providing crystallographic evidence for the stabilization of the putative phosphate binding site residues by the interaction with the carboxylate from PS48. This result further reinforced the idea that the carboxylate from small compounds binds to residues forming part of the phosphate-binding site.

In the presence of PS48, the bound ATP adopts the same conformation as in the apo-structure. However, we observed a movement of Lys111 which approached α-C-helix residue Glu130. This displacement can be due to the conformational change of the PIF-binding pocket Phe157 residue described above, as (Cγ and Cδ atoms) the aliphatic chain of Lys111 formed hydrophobic interactions with (Cδ1 and Cε1) the aromatic ring of Phe157. Since it is well established that the equivalent Lys-Glu pair coordinates the ATP molecule in other protein kinases, the small but significant movements of both residues (distance of 3.1 Å in the apo PDK1 structure and 2.7 Å in the complex) could reflect an allosteric effect on the ATP binding site upon binding of compounds to the PIF-binding pocket. Compared to the apo structure, in the complex with PS48, there is also a significant change at the top of the ATP binding site, along the glycine-rich loop. Here, the side chain of Phe93 rotated approximately 110° (χ1 angle= −60° versus +53°) suggesting that a glycine-rich loop residue can also transduce allosteric effects from the PIF-binding pocket to the ATP binding site (FIGS. 4F and 4G). Phe93 conformation is also affected upon binding of ATP competitive inhibitors such as staurosporine, and thus, the glycine-rich loop appears as a sensor of both PIF-binding pocket and ATP binding site occupancy by activators and inhibitors. However, perhaps the most striking overall feature that differs between the apo and PS48 complex structure lied in the ordering of the activation loop in the presence of compound (FIGS. 4F and 4G). In the apoPDK1 structure, residues 233 to 236 were disordered. In addition to ordering of the activation loop, there was also some degree of movement. Thus, in the apoPDK1 the amine group of Lys228 and phospho-Ser241 were at a distance of 2.9 Å whereas in the complex they were 4 Å apart. Lys228 amine group displacement (1.5 Å) also triggered a new interaction with Arg129 via an ordered water molecule (<B-factor>=36.9 Å$^2$) that was absent in apoPDK1. The new location of Lys228 also enabled it to interact with Gln236 from the activation loop via another water molecule (<B-factor>=29.6 Å$^2$) (FIG. 2H). Overall, the data showed that the binding of PS48 allosterically affected the ATP binding site and the activation loop.

Probing the Conformational Change Induced by HM-Polypeptides and Allosteric Compounds by Use of the Fluorescent ATP Analogue TNP-ATP:

In order to shed further light on the conformational change induced by the binding of small compounds to the PIF-binding pocket of PDK1, we developed a method to probe the ATP binding site conformation in solution with the use of a fluorescent ATP analogue, trinitrophenyl-ATP (TNP-ATP; FIG. 5A). The fluorescence intensity of TNP-ATP increased with the addition of PDK1 (FIG. 5B) and was competed with the addition of excess of ATP, indicating that the TNP-ATP fluorescence intensity increased upon binding to the ATP binding site on PDK1. Interestingly, the TNP-ATP fluorescence intensity decreased with the subsequent addition of PIFtide or phosphorylated HM polypeptides (not shown). Similarly, low molecular weight compound activators of PDK1, represented by PS08 (=PS-T-8), produced a concentration-dependent decrease in TNP-ATP fluorescence in the presence of PDK1 (FIG. 5C), while they had no effect on TNP-ATP fluorescence in the absence of the kinase. In the same assay, the E-isomer of PS08 (=PS-T-8), PS133, did not affect the fluorescence intensity of TNP-ATP in the presence of PDK1, indicating that the effect produced by PS08 was highly specific (FIG. 5D). Altogether, the results showed that the binding of activating molecules targeting the PIF-binding pocket of PDK1 produced a significant allosteric effect which could be sensed at the ATP-binding site. Since the decrease in fluorescence intensity was also measured with phosphorylated HM polypeptides and PIFtide, it is likely that the ATP-binding site conformational change measured was actually related to the equivalent events that activate PDK1 by low molecular weight compounds and HM-polypeptides.

Allosteric Effects of Small Compounds Upon Binding to the PIF-Binding Pocket on PDK1 Revealed by Amide Hydrogen/Deuterium ($^1$H/$^2$H) Exchange and Mass Spectrometry:

We also analyzed the effect of compound binding and the possible conformational changes induced by polypeptides and small compounds on PDK1 by studying their ability to protect or expose regions of the protein to hydrogen/deuterium ($^1$H/$^2$H) exchange. PDK1 50-359[Tyr288Gly; Gln192Ala] was incubated in the presence or absence of PIFtide or small compounds in buffer containing $^2$H$_2$O for different incubation times, the exchange process was stopped with addition of TFA and incubation on ice and the PDK1 mass evaluated by mass-spectrometry. The mass of PDK1 increased along the time of incubation in $^2$H$_2$O buffer indicating that $^2$H was incorporated into the protein. The incubation of PDK1 with the polypeptide PIFtide (0.625 mM) prompted a significantly lower increase in PDK1 mass along time, equivalent to 20 $^2$H less incorporated/PDK1 molecule after 45 minutes, indicating a large protection on the overall $^1$H/$^2$H exchange. A similar global exchange protection was also observed when PDK1 was incubated with PS48 (500 µM) or PS08 (=PS-T-8) (250 µM), although to a lower degree (10-12 $^2$H/PDK1 molecule). Under the conditions tested, only the backbone amide group can exchange its $^1$H for $^2$H, giving rise to a maximum of one $^2$H exchanged per aminoacid (except proline). Thus, the global exchange analysis suggested that low molecular weight compounds activators protected between 10 and 12 aminoacids from $^2$H exchange after 45 minutes incubation.

In order to identify the PDK1 sequences that were affected by the interaction of compounds to the PIF-binding pocket, we repeated the $^1$H/$^2$H exchange experiments at different incubation times, digested PDK1 at each time point with pepsin and subjected the polypeptides to liquid chromatography followed by tandem mass-spectrometry (LC-MS/MS). After pepsin digestion, we could identify and analyze 36 polypeptides with overlapping regions (see Materials and Methods), covering 84.5% of PDK1 50-359[Tyr288Gly; Gln192Ala] sequence. In the presence of low molecular weight compounds, a strong protection was observed in peptides corresponding to the aminoacid sequences 108-121

(FIG. 6B), 108-134 (FIG. 6C),108-130 (not shown), covering the α-B and α-C helices and 146-155 (FIG. 6D) spanning the β-5 strand, all limiting the PIF-binding pocket (FIG. 6A). In addition to the protection at the PIF-binding pocket, we observed protection from $^1$H/$^2$H exchange at sites distinct from the compound binding site. Thus, peptides 49-93 (FIG. 6F) and 52-93 (FIG. 6G), but not the shorter peptide 49-66 (FIG. 6H) were strongly protected by low molecular weight compounds. The protected aminoacid sequence (67-93) spans the β-1 strand and Gly-rich loop, at the top of the ATP binding site. This finding correlates well with the conformational change of Gly-rich loop Phe93 observed in the crystal.

As expected, the polypeptides spanning the activation loop (218-247 and 225-247; FIGS. 6I and J) readily exchanged $^1$H for $^2$H with most protection on 218-247, suggesting that the most significant protection occurred between aminoacid 218 and 224. Interestingly, this region does not correspond to the activation loop but rather to the β-8 sheet and up to the DFG motif (Phe224) located within the ATP binding site. The above results allow to pin-point the regions corresponding to the Gly-rich loop and β-8/DFG motif within the ATP binding site as key sites allosterically protected from $^1$H/$^2$H exchange by low molecular weight compounds in solution.

Unexpectedly, all low molecular weight compounds tested also triggered protection from $^1$H/$^2$H exchange at a distal region, on three polypeptides (276-291, 292-311 and 292-316) spanning the α-G-helix within the large lobe of the catalytic domain. Interestingly, the overlapping peptides (298-311 and 302-311) were not protected in the presence of compounds, thus defining the region undergoing the protection between residues 292 and 298 in the α-G-helix.

Altogether, the results from the $^1$H/$^2$H exchange experiments supported the biochemical and crystallographic identification of the PIF-binding pocket as the target of the small compounds. In addition, the data provided support for the crystallographic and fluorescent data that suggested that the ATP binding site was a target of the allosteric effect prompted by the binding of low molecular weight compounds to PIF-binding pocket. Finally, the $^1$H/$^2$H exchange data uncovered a further allosteric effect on the α-G-helix on the large lobe of the kinase, suggesting that binding of small compounds to the PIF-binding pocket can prompt conformational changes unrelated to the activation of the catalytic domain.

FIG. 4 shows the crystal structure of apoPDK1 and PS48 bound PDK1 in the crystal form II. (A) Superimposition of PDK1-ATP and PDK1-ATP-PS48. Superimposition was performed by fixing the backbone atoms of the large, C-terminal lobe. (B,C) Binding of PS48 to the PIF-pocket triggers a conformational change in residues Phe157 and the ion pair Lys111-Glu130. (D,E) The PIF-binding pocket and phosphate-binding site in PDK1-ATP and PDK1-ATP-PS48 structures. (F,G) Effect of PS48 on the activation loop. In the PDK1-ATP-PS48 structure the activation loop is ordered.

FIG. 5 shows the modulation of PDK1 conformation by small compounds, notably the effect of PS08 (=PS-T-8) and PS133 on the emission fluorescence of trinitrophenyl-ATP (TNP-ATP)/PDK1. (A) TNP-ATP formulae. (B, C and D) Fluorescence intensities are expressed as % of the maximal fluorescence intensity of TNP-ATP obtained with addition of 15 μM PDK1 CD. (B) Effect of PDK1 addition on TNP-ATP fluorescence. (C) Addition of PS08 to the TNP-ATP-PDK1 mixture triggered a concentration dependent decrease of the fluorescence intensity. At 167 μM PS08 (=PS-T-8), the maximum fluorescence intensity was 60%, similar to TNP-ATP alone. (D) Effect of 167 μM PS133, the isomer compound PS08 to the TNP-ATP-PDK1.

FIG. 6 shows the deuterium incorporation levels along time in presence or absence of PS08 (=PS-T-8). PDK1 50-359 was incubated in a deuterium solution in the presence or absence of PS08 (=PS-T-8), an analogue of PS48, and the exchange of hydrogen ($^1$H) for deuterium ($^2$H) analyzed by mass spectrometry after protease cleavage. We identified polypeptides covering 84.5% of the PDK1 50-359 sequence. A subset of polypeptides were protected from $^1$H/$^2$H exchange upon compound treatment. (A) Catalytic domain of PDK1 bound to PS48, indicating the location of polypeptides which were protected from $^1$H/$^2$H exchange. (B,C,D,E,F,G,H,I,J) Deuterium incorporation at 1, 5, 15 and 45 min in the indicated peptides from PDK1 samples incubated in the absence (open circles) or presence of PS08 (closed circles).

The invention claimed is:

1. A compound of formula I:

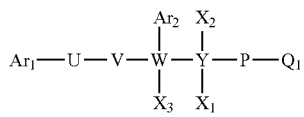

wherein,

Y is C;

W is C;

$X_1$ taken together with $X_3$ forms a double bond between Y and W;

$X_2$ is $Q_2$;

$X_3$ taken together with $X_1$ forms a double bond between W and Y;

$Q_2$ H;

$Q_1$ is COOH or $COOR^1$;

P is absent and $Q_1$ is bonded to Y by a single bond;

V is $CH_2$;

U is $CH_2$;

$R^1$, $R^2$, $R^3$, $R^4$, $R^5$, $R^6$, $R^7$, $R^8$, $R^9$, $R^{10}$ and $R^{11}$ are at each occurrence in the compound of formula I $C_{1-6}$alkyl, $C_{2-6}$alkenyl, $C_{2-6}$alkynyl, $C_{3-6}$cycloalkyl, $C_{3-6}$cycloalkenyl, optionally substituted heteroaryl or optionally substituted aryl;

$Ar_2$ is a phenyl ring, a naphthyl ring, or an indenyl ring carrying 0-4 substituents $R^{12}$;

$Ar_1$ is an aryl or a heteroaryl group selected from the group consisting of phenyl, naphthyl, indolyl, benzofuranyl, benzothiophenyl, isoindolyl, indazolyl, benzo[d]isothiazolyl, benzimidazolyl, benzoxazolyl, benzothiazolyl, isoquinolinyl, quinolinyl, phthalazinyl, quinoxalinyl, quinazolinyl, cinnolinyl, and naphthoimidazolyl, wherein the aryl group or the heteroaryl group carry 1-4 substituents $R^{12}$, and wherein any stable S or N ring atom of said heteroaryl group may be substituted with oxo;

$R^{12}$ is at each occurrence in the compound of formula I selected from the group consisting of hydrogen, $C_{1-6}$alkyl, $C_{2-6}$alkenyl, $C_{2-6}$alkynyl, $C_{3-6}$cycloalkyl, $C_{3-6}$cycloalkenyl, optionally substituted heterocyclyl, optionally substituted heteroaryl, optionally substituted aryl, —F, —Cl, —Br, —I, —$CF_3$, —Z—$OR^{13}$, —Z—$NO_2$, —Z—$NR^{13}OOR^{14}$, —Z—$NR^{13}R^{14}$, —Z—$SR^{13}$, —Z—$COOR^{13}$, —Z—$CONR^{13}R^{14}$, —Z—C(O)$SR^{13}$, —Z—C(O)$NR^{13}OR^{14}$, —Z—CN, —Z—$COR^{13}$, —Z—$COOCH_2C(O)$ $R^{13}$, —Z—$COOCH_2C(O)NR^{13}R^{14}$, —Z—$SOR^{13}$, —Z—$SO_2R^{13}$, —Z—$SO_2NR^{13}R^{14}$, —Z—P(O)($OR^{13}$)$OR^{14}$ and —Z-tetrazol-5-yl;

Z is a single bond or a bivalent spacer group;

$R^{13}$ and $R^{14}$ are at each occurrence in the compound of formula I independently selected from the group consisting of hydrogen, $C_{1-6}$alkyl, $C_{2-6}$alkenyl, $C_{2-6}$alkynyl, $C_{3-6}$cycloalkyl, $C_{3-6}$cycloalkenyl, optionally substituted heteroaryl and optionally substituted aryl, or a pharmaceutically acceptable salt, solvate, diastereomer, enantiomer, tautomer or racemate thereof.

2. The compound of claim 1, wherein, in $R^{12}$ the heterocyclyl group of the optionally substituted heterocyclyl is a 5-membered unsaturated, partly unsaturated, or saturated monocyclic ring with 1 or 2 hetero ring atoms selected from the group consisting of N, O and S, or a 6-membered unsaturated, partly unsaturated, or saturated monocyclic ring with 1 to 3 hetero ring atoms selected from the group consisting of N, O and S;

Z is a single bond, an optionally substituted methylene, an optionally substituted ethylene, an optionally substituted ethenylene, or an ethynylene group;

the number of substituents of the optionally substituted heterocyclyl, optionally substituted heteroaryl, and optionally substituted aryl is 1 to 10 wherein said substituents are at each occurrence in the compound of formula I are independently selected from the group consisting of —F, —Cl, —Br, —I, —$CF_3$, —$OR^{15}$, —$NO_2$, —$NR^{15}R^{16}$, —$SR^{15}$, —$CH_2OR^{15}$, —$CH_2NR^{15}R^{16}$, —$COOR^{15}$, —$CONR^{15}R^{16}$, —C(O)$SR^{15}$, —C(O)$NR^{15}OR^{16}$, —CN, —$COR^{15}$, —$SOR^{15}$, —$SO_2R^{15}$, and —$SO_2NR^{15}R^{16}$, wherein $R^{15}$ and $R^{16}$ can be the same or different and are at each occurrence in the compound of formula I independently selected from the group consisting of hydrogen, branched or linear $C_{1-6}$alkyl, branched or linear $C_{2-6}$alkenyl, branched or linear $C_{2-6}$alkynyl, $C_{3-6}$cycloalkyl, and $C_{3-6}$cycloalkenyl;

the number of substituents of the optionally substituted methylene, optionally substituted ethylene, and optionally substituted ethenylene is 1 to 4, wherein said substituents are at each occurrence in the compound of formula I are independently selected from the group consisting of —F, $CF_3$, $NO_2$, —$COOR^{17}$, —$CONR^{17}R^{18}$, —CN, —$COR^{17}$, —$SOR^{17}$, —$SO_2R^{17}$, —$SO_2NR^{17}R^{18}$, and —P(O)($OR^{17}$)$OR^{18}$, wherein $R^{17}$ and $R^{18}$ can be the same or different and are at each occurrence in the compound of formula I independently selected from the group consisting of hydrogen, branched or linear $C_{1-6}$alkyl, branched or linear $C_{2-6}$alkenyl, branched or linear $C_{2-6}$alkynyl, $C_{3-6}$cycloalkyl, and $C_{3-6}$cycloalkenyl.

3. The compound of claim 1, which is selected from the group consisting of:

(Z)-5-(4-Chlorophenyl)-3-phenylpent-2-enoic acid and (E)-5-(4-Chlorophenyl)-3-phenylpent-2-enoic acid (PS 47+PS 48)

(Z)-5-(4-Chlorophenyl)-3-(4-fluorophenyl)pent-2-enoic acid and (E)-5-(4-Chlorophenyl)-3-(4-fluorophenyl)pent-2-enoic acid (PS 144)

(Z)- 5-(4-Chlorophenyl)-3-(3-fluorophenyl)pent-2-enoic acid and (E)-5-(4-Chlorophenyl)-3-(3-fluorophenyl)pent-2-enoic acid (PS 146)

(Z)-5-(4-Chlorophenyl)-3-(2-fluorophenyl)pent-2-enoic acid and (E)-5-(4-Chlorophenyl)-3-(2-fluorophenyl)pent-2-enoic acid (PS 145)

(Z)-5-(4-Chlorophenyl)-3-(4-methoxyphenyl)pent-2-enoic acid and (E)-5-(4-Chlorophenyl)-3-(4-methoxyphenyl)pent-2-enoic acid (PS 250+PS 251)

(Z)-5-(4-Chlorophenyl)-3-phenylpent-2-enenitrile and (E)-5-(4-Chlorophenyl)-3-phenylpent-2-enenitrile (PS 104+PS 105)

(Z)-5-(3-Chlorophenyl)-3-phenylpent-2-enoic acid and (E)-5-(3-Chlorophenyl)-3-phenylpent-2-enoic acid (PS 87+PS 88)

(Z)-5-(4-Fluorophenyl)-3-phenylpent-2-enoic acid and (E)-5-(4-Fluorophenyl)-3-phenylpent-2-enoic acid (PS 136+PS-T3)

(Z)-5-(4-Bromophenyl)-3-phenylpent-2-enoic acid and (E)-5-(4-Bromophenyl)-3-phenylpent-2-enoic acid (PS 137+PS-T10)

(Z)-5-(4-Ethylphenyl)-3-phenylpent-2-enoic acid and (E)-5-(4-Ethylphenyl)-3-phenylpent-2-enoic acid (PS 129+PS 130)

(Z)-3-Phenyl-5-[4-(trifluoromethyl)phenyl]pent-2-enoic acid and (E)-3-Phenyl-5-[4-(trifluoromethyl)phenyl]pent-2-enoic acid (PS 140+PS-T5)

(Z)-5-[4-(Methylthio)phenyl]-3-phenylpent-2-enoic acid (PS 139) and (E)-5-[4-(Methylthio)phenyl]-3-phenyl-pent-2-enoic acid (Z)-5-(3,4-Dichlorophenyl)-3-phenylpent-2-enoic acid and (E)-5-(3,4-Dichloro-phenyl)-3-phenylpent-2-enoic acid (PS 131+PS-T7)

(Z)-5-(4-Chloro-2-fluorophenyl)-3-phenylpent-2-enoic acid and (E)-5-(4-Chloro-2-fluorophenyl)-3-phenyl-pent-2-enoic acid (PS 132+PS-T1)

(Z)-5-(3,4-Dichlorophenyl)-3-phenylpent-2-enoic acid and (E)-5-(3,4-Dichloro-phenyl)-3-phenylpent-2-enoic acid (PS 135+PS-T9)

(Z)-5-(4-Bromo-2-fluorophenyl)-3-phenylpent-2-enoic acid and (E)-5-(4-Bromo-2-fluorophenyl)-3-phenyl-pent-2-enoic acid (PS 133+PS-T8)

(Z)-5-(Biphenyl-4-yl)-3-phenylpent-2-enoic acid and (E)-5-(Biphenyl-4-yl)-3-phenylpent-2-enoic acid (PS 134+PS-T2)

(Z)-5-(2-Naphthalenyl)-3-phenylpent-2-enoic acid and (E)-5-(2-Naphthalenyl)-3-phenylpent-2-enoic acid (PS 138+PS-T4)

(Z)-5-(4-Chlorophenyl)-3-(2-naphthalenyl)pent-2-enoic acid and (E)-5-(4-Chlorophenyl)-3-(2-naphthalenyl)pent-2-enoic acid (PS 246+PS 247)

(Z)-5-(4-Chlorophenyl)-3-(1-naphthalenyl)pent-2-enoic acid and (E)-5-(4-Chlorophenyl)-3-(1-naphthalenyl)pent-2-enoic acid (PS 248+PS 249)

(E)-5-(4-Chlorophenyl)-3-(2-pyridinyl)pent-2-enoic acid (Z)-4-(4-Chlorophenoxy)-3-phenylbut-2-enoic acid and (E)-4-(4-Chlorophenoxy)-3-phenylbut-2-enoic acid (PS 95+PS 97)

(E)-4-(4-Chlorophenylthio)-3-phenylbut-2-enoic acid (PS 99)

(Z)-3-(Biphenyl-4-yl)-5-(4-chlorophenyl)pent-2-enoic acid and (E)-3-(Biphenyl-4-yl)-5-(4-chlorophenyl)pent-2-enoic acid (PS 315+PS 314)

(Z)-5-(Biphenyl-4-yl)-3-(naphthalen-2-yl)pent-2-enoic acid and (E)-5-(Biphenyl-4-yl)-3-(naphthalen-2-yl)pent-2-enoic acid (PS 470+PS 469)

(Z)-5-(4-phenoxyphenyl)-3-phenylpent-2-enoic acid and (E)-5-(4-phenoxyphenyl)-3-phenylpent-2-enoic acid (PS 370+PS 371)

(Z)-Ethyl 5-(6-hydroxynaphthalen-2-yl)-3-(naphthalen-2-yl)pent-2-enoate and (E)-Ethyl 5-(6-hydroxynaphthalen-2-yl)-3-(naphthalen-2-yl)pent-2-enoate (PS 504+PS 503)

or a pharmaceutically acceptable salt thereof.

4. A pharmaceutical composition or medicament comprising a compound according to claim 1 and a pharmaceutically acceptable carrier.

5. The compound of claim 1, wherein Z is a single bond, an optionally substituted methylene, an optionally substituted ethylene, an optionally substituted ethenylene, or an ethynylene group.

\* \* \* \* \*

SEQUENCE LISTING

```
<160> NUMBER OF SEQ ID NOS: 7

<210> SEQ ID NO 1
<211> LENGTH: 50
<212> TYPE: PRT
<213> ORGANISM: Homo sapiens

<400> SEQUENCE: 1

Lys Ile Leu Glu Lys Arg His Ile Ile Lys Glu Asn Lys Val Pro Tyr
1               5                   10                  15

Val Thr Arg Glu Arg Asp Val Met Ser Arg Leu Asp His Pro Phe Phe
                20                  25                  30

Val Lys Leu Tyr Phe Thr Phe Gln Asp Asp Glu Lys Leu Tyr Phe Gly
            35                  40                  45

Leu Ser
    50

<210> SEQ ID NO 2
<211> LENGTH: 5
<212> TYPE: PRT
<213> ORGANISM: Artificial
<220> FEATURE:
```

```
<223> OTHER INFORMATION: hydrophobic pocket
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)
<223> OTHER INFORMATION: Xaa is an acidic amino acid

<400> SEQUENCE: 2

Phe Xaa Xaa Phe Xaa
1               5

<210> SEQ ID NO 3
<211> LENGTH: 5
<212> TYPE: PRT
<213> ORGANISM: Artificial
<220> FEATURE:
<223> OTHER INFORMATION: hydrophobic pocket
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)
<223> OTHER INFORMATION: Xaa is an acidic amino acid

<400> SEQUENCE: 3

Phe Xaa Xaa Tyr Xaa
1               5

<210> SEQ ID NO 4
<211> LENGTH: 5
<212> TYPE: PRT
<213> ORGANISM: Artificial
<220> FEATURE:
<223> OTHER INFORMATION: hydrophobic pocket
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)
<223> OTHER INFORMATION: Xaa is an acidic amino acid

<400> SEQUENCE: 4

Tyr Xaa Xaa Phe Xaa
1               5

<210> SEQ ID NO 5
<211> LENGTH: 5
<212> TYPE: PRT
<213> ORGANISM: Artificial
<220> FEATURE:
<223> OTHER INFORMATION: hydrophobic pocket
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)
<223> OTHER INFORMATION: Xaa is an acidic amino acid

<400> SEQUENCE: 5

Tyr Xaa Xaa Tyr Xaa
1               5
```

```
<210> SEQ ID NO 6
<211> LENGTH: 6
<212> TYPE: PRT
<213> ORGANISM: Artificial
<220> FEATURE:
<223> OTHER INFORMATION: hydrophobic pocket
<220> FEATURE:
<221> NAME/KEY: misc_feature
<222> LOCATION: (1), (4) and (6)
<223> OTHER INFORMATION: Xaa is Phe or Tyr
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)
<223> OTHER INFORMATION: Xaa is an acidic amino acid

<400> SEQUENCE: 6

Xaa Xaa Xaa Xaa Xaa Xaa
1               5

<210> SEQ ID NO 7
<211> LENGTH: 255
<212> TYPE: PRT
<213> ORGANISM: Homo sapiens

<400> SEQUENCE: 7
```

| | | | | | | | | | | | | | | |
|---|---|---|---|---|---|---|---|---|---|---|---|---|---|---|
| Phe | Glu | Arg | Ile | Lys | Thr | Leu | Gly | Thr | Gly | Ser | Phe | Gly | Arg | Val | Met |
| 1 | | | | 5 | | | | | 10 | | | | | 15 | |
| Leu | Val | Lys | His | Lys | Glu | Thr | Gly | Asn | His | Tyr | Ala | Met | Lys | Ile | Leu |
| | | | 20 | | | | | 25 | | | | | 30 | | |
| Asp | Lys | Gln | Lys | Val | Val | Lys | Leu | Lys | Gln | Ile | Glu | His | Thr | Leu | Asn |
| | | 35 | | | | | 40 | | | | | 45 | | | |
| Glu | Lys | Arg | Ile | Leu | Gln | Ala | Val | Asn | Phe | Pro | Phe | Leu | Val | Lys | Leu |
| 50 | | | | | 55 | | | | | 60 | | | | | |
| Glu | Phe | Ser | Phe | Lys | Asp | Asn | Ser | Asn | Leu | Tyr | Met | Val | Met | Glu | Tyr |
| 65 | | | | 70 | | | | | 75 | | | | | 80 | |
| Val | Pro | Gly | Gly | Glu | Met | Phe | Ser | His | Leu | Arg | Arg | Ile | Gly | Arg | Phe |
| | | | | 85 | | | | | 90 | | | | | 95 | |
| Ser | Glu | Pro | His | Ala | Arg | Phe | Tyr | Ala | Ala | Gln | Ile | Val | Leu | Thr | Phe |
| | | | 100 | | | | | 105 | | | | | 110 | | |
| Glu | Tyr | Leu | His | Ser | Leu | Asp | Leu | Ile | Tyr | Arg | Asp | Leu | Lys | Pro | Glu |
| | | 115 | | | | | 120 | | | | | 125 | | | |
| Asn | Leu | Leu | Ile | Asp | Gln | Gln | Gly | Tyr | Ile | Gln | Val | Thr | Asp | Phe | Gly |
| 130 | | | | | 135 | | | | | 140 | | | | | |
| Phe | Ala | Lys | Arg | Val | Lys | Gly | Arg | Thr | Trp | Thr | Leu | Cys | Gly | Thr | Pro |
| 145 | | | | 150 | | | | | 155 | | | | | 160 | |
| Glu | Tyr | Leu | Ala | Pro | Glu | Ile | Ile | Leu | Ser | Lys | Gly | Tyr | Asn | Lys | Ala |
| | | | | 165 | | | | | 170 | | | | | 175 | |
| Val | Asp | Trp | Trp | Ala | Leu | Gly | Val | Leu | Ile | Tyr | Glu | Met | Ala | Ala | Gly |
| | | | 180 | | | | | 185 | | | | | 190 | | |
| Tyr | Pro | Pro | Phe | Phe | Ala | Asp | Gln | Pro | Ile | Gln | Ile | Tyr | Glu | Lys | Ile |
| | | 195 | | | | | 200 | | | | | 205 | | | |
| Val | Ser | Gly | Lys | Val | Arg | Phe | Pro | Ser | His | Phe | Ser | Ser | Asp | Leu | Lys |
| 210 | | | | | 215 | | | | | 220 | | | | | |
| Asp | Leu | Leu | Arg | Asn | Leu | Leu | Gln | Val | Asp | Leu | Thr | Lys | Arg | Phe | Gly |
| 225 | | | | 230 | | | | | 235 | | | | | 240 | |
| Asn | Leu | Lys | Asn | Gly | Val | Asn | Asp | Ile | Lys | Asn | His | Lys | Trp | Phe | |
| | | | | 245 | | | | | 250 | | | | | 255 | |